US010894953B2

(12) United States Patent
Shumaker et al.

(10) Patent No.: US 10,894,953 B2
(45) **Date of Patent: *Jan. 19, 2021**

(54) ENZYME VARIANTS WITH IMPROVED ESTER SYNTHASE PROPERTIES

(71) Applicant: Genomatica, Inc., San Diego, CA (US)

(72) Inventors: Andrew M. Shumaker, South San Francisco, CA (US); Bernardo M. da Costa, South San Francisco, CA (US); Kevin Holden, South San Francisco, CA (US); Louis G. Hom, South San Francisco, CA (US); Tarah S. Baron, South San Francisco, CA (US); Noah Helman, South San Francisco, CA (US)

(73) Assignee: Genomatica, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/873,977

(22) Filed: Jan. 18, 2018

(65) Prior Publication Data

US 2018/0327728 A1 Nov. 15, 2018

Related U.S. Application Data

(63) Continuation of application No. 14/424,387, filed as application No. PCT/US2013/032564 on Mar. 15, 2013, now Pat. No. 9,879,239.

(60) Provisional application No. 61/701,191, filed on Sep. 14, 2012, provisional application No. 61/708,424, filed on Oct. 1, 2012.

(51) Int. Cl.

*C12N 9/18* (2006.01)
*C12N 9/10* (2006.01)
*C12P 7/64* (2006.01)

(52) U.S. Cl.

CPC ............. *C12N 9/18* (2013.01); *C12N 9/1007* (2013.01); *C12P 7/6436* (2013.01); *C12Y 201/01015* (2013.01)

(58) Field of Classification Search

None

See application file for complete search history.

(56) References Cited

U.S. PATENT DOCUMENTS

| | | | |
|---|---|---|---|
| 7,169,588 B2 | 1/2007 | Burch et al. | |
| 7,897,369 B2 | 3/2011 | Schmidt-Dannert et al. | |
| 2009/0117629 A1 | 5/2009 | Schmidt-Dannert et al. | |
| 2010/0154293 A1 | 6/2010 | Hom et al. | |
| 2011/0072714 A1* | 3/2011 | Gaertner | C10L 1/026 44/388 |
| 2011/0244532 A1 | 10/2011 | Hu et al. | |
| 2013/0078684 A1 | 3/2013 | Holtzapple et al. | |

FOREIGN PATENT DOCUMENTS

| | | | |
|---|---|---|---|
| JP | 2008-506381 A | 3/2008 | |
| JP | 2011-103863 A | 6/2011 | |
| WO | WO-91/16427 | 10/1991 | |
| WO | WO-2004/074476 | 9/2004 | |
| WO | WO-2006/008508 | 1/2006 | |
| WO | WO-2010/042664 A1 | 4/2010 | |

OTHER PUBLICATIONS

Arnold, F.H. 2001 Nature 409: 253-257. (Year: 2001).*
Altschul et al., "Basic Local Alignment Search Tool," Journal of Molecular Biology 215(3): 403-410 (1990).
Antunes et al. Uniprot, Accession No. U2ELE7, Nov. 13, 2013.
Arkin et al. "An algorithm for protein engineering: Simulations of recursive ensemble mutagenesis," Proc. Natl. Acad. Sci. USA. 89: 7811-7815 (1992).
Barrick et al., "Quantitative analysis of ribosome binding sites in e-coli," Nucleic Acids Res., 1994, vol. 22, No. 7: 1287-1295.
Cadwell et al., "Randomization of Genes by PCR Mutagenesis," PCR Methods Applic. 2: 28-33 (1992).
Currie, "Source Apportionment of Atmospnenc particles," Characterization of Environmental Particles, vol. 1 of the IUPAC Environmental Analytical Chemistry Series, pp. 3-74 (1992).
Database UniProt, Online, Apr. 2007, XP055079380, Retrieved from EBI accession No. UniProt:A3JBY1.
Database UniProt, Predicted: zinc finger protein 651 [Oryctolagus cuniculus], Online, Aug. 2012, XP002713103, Retrieved from EBI accession No. UniProt: M1FI28.
Delegrave et al., "Searching Sequence Space to Engineer Proteins: Exponential Ensemble Mutagenesis," Biotech. Res, 11: 1548-1552 (1993).
Ecker et al., "Chemical Synthesis and Expression of a Cassette Adapted Ubiquitin Gene," The Journal of Biological Chemistry, Mar. 15, 1987, vol. 262, No. 8: 3524-3527.
Grosjean et al., "Preferential codon usage in prokaryotic genes: the optimal codon-anticodon interaction energy and the selective codon usage in efficiently expressed genes," Gene 18:199-209 (1982).
Holtzapple and Schmidt-Dannert, "Marinobacter hydrocarbonoclasticus strain DSM8798 wax ester synthase (ws2)gene, complete cds" Genbank, Accession No. EF219377.(§§) Https://www.ncbi.nlm.nih.gov/nuccore/EF219377.
Holtzapple et al., "Biosynthesis of Isoprenoid Wax Ester in Marinobacter hydrocarbonoclasticus DSM 8798: Identification and Characterization of Isoprenoid Coenzyme A Synthetase and Wax Ester Synthases," J. Bacteriology 189(10): 3804-3812 (2007).
International Preliminary Report on Patentability on PCT/US2013/032564, dated Sep. 23, 2014, 18 pages.
International Search Report and Written Opinion on PCT/US2013/032564, dated Oct. 2, 2013, 25 pages.

(Continued)

*Primary Examiner* — Marsha Tsay
(74) *Attorney, Agent, or Firm* — Harness Dickey & Pierce, PLC

(57) ABSTRACT

The disclosure relates to enzyme variants with improved ester synthase properties for the production of fatty acid esters. Further contemplated are recombinant host cells that express such variants, cell cultures comprising the recombinant host cells and fatty acid ester compositions produced by such recombinant host cells.

1 Claim, 7 Drawing Sheets

Specification includes a Sequence Listing.

(56) References Cited

OTHER PUBLICATIONS

Kegler-Ebo et al., "Codon cassette mutagenesis: a general method to insert or replace individual codons by using universal mutagenic cassettes," Nucleic Acids Res., 1994, 22(9): 1593-1599.
Labrou, "Random Mutagenesis Methods for In Vitro Directed Enzyme evolution," Current Protein and Peptide Science, 2010: 91-100.
Leung et al. "A Journal of Methods in Cell and Molecular Biology," Technique 1:(1): 11-15 (1989).
Maniatis et al., "Regulation of Inducible and Tissue-Specific Gene Expression," Science 236: 1237-1245 (1987).
Needleman et al., "A General Method Applicable to the Search for Similarities in the Amino Acid Sequence of Two Proteins," J. Mol. Biol., vol. 48, pp. 443-453, 1970.
Non-Final Office Action U.S. Appl. No. 14/424,387, dated Aug. 22, 2016, 7 pages.
Notice of Allowance on U.S. Appl. No. 14/424,387, dated Sep. 19, 2017, 11 pages.
Office Action on AU 2013316124, dated Apr. 13, 2019, 3 pages.
Office Action on BR 112015005782.9, dated Aug. 14, 2019, 7 pages.
Office Action on CA 2885041, dated Dec. 7, 2018, 3 pages.
Office Action on CA 2885041, dated Nov. 22, 2018, 4 pages.
Office Action on CN 2013380058918.5, dated Aug. 31, 2017, 5 pages with translation.
Office Action on CN 201380058918.5, dated Mar. 13, 2018, 9 pages with translation.
Office Action on CN 201380058918.5, dated Oct. 25, 2016, 12 pages with translation.
Office Action on CO 15-067.845, dated Sep. 20, 2016, 8 pages.
Office Action on EP 13714142.0, dated Apr. 7, 2016, 5 pages.
Office Action on ID P00201502165, dated Apr. 18, 2018, 2 pages with translation.
Office Action ON IN 2323/DELNP/2015, dated May 23, 2019, 6 pages.
Office Action on JP 2015-531914, dated Oct. 26, 2017, 11 pages with translation.
Office Action on JP 2015-531914, dated Dec. 15, 2016, 15 pages with translation.
Office Action on JP 2018-168156, dated Aug. 6, 2019, 10 pages with translation.
Office Action on KR 10-2015-7009459, dated Feb. 26, 2019, 9 pages with translation.
Office Action on MX MX/a/2015/003305, dated Jul. 4, 2018, 3 pages.
Office Action on MY PI2015000505, dated Nov. 30, 2017, 4 pages.
Office Action on U.S. Appl. No. 14/424,387, dated Jan. 29, 2106, 12 pages.
Office Action on U.S. Appl. No. 14/424,387, dated May 4, 2017, 10 pages.
Reetz et al., "Iterative Saturation Mutagenesis Accelerates Laboratory Evolution of Enzyme Steroselectivity: Rigorous Comparison with Traditional Methods," J. Am. Chem. Soc., 2010, vol. 132, pp. 9144-9152.
Richards, "Cassette mutagenesis shows its strength," Nature, 1986, 323: 187.
Rosenberg, "Multiple Sequence Alignment Accuracy and Evolutionary Distance Estimation," BMC Bioinformatics 6: 278 (2005).
Sambrook et al., "Molecular Cloning: A Laboratory Manual," 1989, 2nd Ed., Cold Spring Harbor Laboratory Press, Cold Spring Harbor, NY.
Schmidt-Dannert and Holtzapple, Sequence 2 from U.S. Pat. No. 7,897,369 Genbank, Database accession NR. AED56603.1 (§) https://www.ncbi.nlm.nih.gov/protein/AED56603.1.
Stemmer, "DNA shuffling by random fragmentation and reassembly: In vitro recombination for molecular evolution," Proc. Natl. Acad. Sci. USA. 91: 10747-10751 (1994).
Tracewell et al., "Directed enzyme evolution: climbing fitness peaks one amino acid at a time," Curr. Opinion in Chemical Biol., 2009, vol. 13: 3-9.
Vezzi et al., "Life at Depth: Photobacterium Profundum Genome Sequence and Expression Analysis," Science (2005) 307: 1459-1461.
Wilson et al., "Increased Protein Expression Through Improved Ribosome-Binding Sites Obtained by Library Mutagenesis," Biotechniques, 1994, 17: 944-953.
Xu et al., "Cloning and characterization of an acyl-CoA-dependent diacyglycerol acyltransferase 1 (DGAT1) gene from Tropaeolum majus, and a study of the functional motifs of the DGAT protein using site-directed mutagenesis to modify enzyme activity and oil content" Plant Biotechnol. J., 2008, vol. 6: 799-818.
Yang et al., "Biosynthesis of Polylactic Acid and Its Copolymers Using Evolved Propionate CoA Transferase and PHA Synthase," Biotech. and Bioengineering, 2010, vol. 105, No. 1: 150-160.
Communication pursuant to Article 94(3) EPC in EP Patent Application No. 17187284.9 dated May 28, 2020 (4 pages).
Decision of Rejection on JP 2018-168156, dated Jun. 11, 2020 (12 pages) (with English translation).
Office Action in KR Patent Application No. 10-2020-7002289 dated May 13, 2020 (with English Translation) (9 pages).
Third Office Action on CN 201380058918.5, dated Jun. 18, 2020 (10 pages) (with English translation).

* cited by examiner

*"Futile cycle"*

| Cycles | % Mass Yield |
|---|---|
| 0 (single gene) | 37 |
| 1 (best 3 gene) | 36.1 |
| 10 | 30 |
| 20 | 25.6 |

SEQUENCE LISTING

```
<160> NUMBER OF SEQ ID NOS: 67

<210> SEQ ID NO 1
<211> LENGTH: 1422
<212> TYPE: DNA
<213> ORGANISM: Marinobacter hydrocarbonoclasticus

<400> SEQUENCE: 1

atgaaacgtc tcggaaccct ggacgcctcc tggctggcgg ttgaatctga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg gggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aaccccctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acggtacgcc cacaccagcg ccgtggtgca     540

aaaaccgaca aagaggccag cgtgcccgca gcggtttccc aggcaatgga cgccctgaag     600

ctccaggcag acatggcccc caggctgtgg caggccggca atcgcctggt gcattcggtt     660

cgacacccgg aagacggact gaccgcgccc ttcactggac cggtttcggt gctcaatcac     720

cgggttaccg cgcagcgacg ttttgccacc cagcattatc aactggaccg gctgaaaaac     780

ctggcccatg cttccggcgg ttccttgaac gacatcgttc tttacctgtg tggcaccgca     840

ttgcggcgct ttctggctga gcagaacaat ctgccagaca ccccgctgac ggctggtata     900

ccggtgaata tccggccggc agacgacgag ggtacgggca cccagatcag ttttatgatt     960

gcctcgctgg ccaccgacga agctgatccg ttgaaccgcc tgcaacagat caaaacctcg    1020

acccgacggg ccaaggagca cctgcagaaa cttccaaaaa gtgccctgac ccagtacacc    1080

atgctgctga tgtcacccta cattctgcaa ttgatgtcag gtctcggggg gaggatgcga    1140

ccagtcttca acgtgaccat ttccaacgtg cccggcccgg aaggcacgct gtattatgaa    1200

ggagcccggc ttgaggccat gtatccggta tcgctaatcg ctcacggcgg cgccctgaac    1260

atcacctgcc tgagctatgc cggatcgctg aatttcggtt ttaccggctg tcgggatacg    1320

ctgccgagca tgcagaaact ggcggtttat accggtgaag ctctggatga gctggaatcg    1380

ctgattctgc cacccaagaa gcgcgcccga acccgcaagt aa                       1422

<210> SEQ ID NO 2
```

<211> LENGTH: 473
<212> TYPE: PRT
<213> ORGANISM: Marinobacter hydrocarbonoclasticus

<400> SEQUENCE: 2

```
Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
```

```
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 3
<211> LENGTH: 1422
<212> TYPE: DNA
<213> ORGANISM: Marinobacter hydrocarbonoclasticus

<400> SEQUENCE: 3

```
atgaaacgtc tcggaaccct gaacgcctcc tggctggcgg ttgaatctga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg ggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aaccccctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acggtacgcc cacaccaacg ccgtggtgta     540

aaaaccgaca aagaggccag cgtgcccgca gcggtttccc aggcaatgga cgccctgaag     600

ctccaggcag acatggcccc caggctgtgg caggccggca atcgcctggt gcattcggtt     660

cgacacccgg aagacggact gaccgcgccc ttcactggac cggtttcggt gctcaatcac     720

cgggttaccg cgcagcgacg ttttgccacc cagcattatc aactggaccg gctgaaaaac     780

ctggcccatg cttccggcgg ttccttgaac gacatcgttc tttacctgtg tggcaccgca     840

ttgcggcgct ttctggctga gcagaacaat ctgccagaca ccccgctgac ggctggtata     900

ccggtgaata tccggccggc agacgacgag ggtacgggca cccagatcag ttttatgatt     960

gcctcgctgg ccaccgacga agctgatccg ttgaaccgcc tgcaacagat caaaacctcg    1020

acccgacggg ccaaggagca cctgcagaaa cttccaaaaa gtgccctgac ccagtacacc    1080

atgctgctga tgtcacccta cattctgcaa ttgatgtcag gtctcggggg gaggatgcga    1140

ccattcttca acgtgaccat ttccaacgtg cccggcccgg aaggcacgct gtattatgaa    1200

ggagcccggc ttgaggccat gtatccggta tcgctaatcg ctcacggcgg cgccctgaac    1260

atcacctgcc tgagctatgc cggatcgctg aatttcggtt ttaccggctg tcgggatacg    1320

ctgccgagca tgcagaaact ggcggtttat accggtgaag ctctggatga gctggaatcg    1380

ctgattctgc cacccaagaa gcgcgcccga acccgcaagt aa                       1422
```

<210> SEQ ID NO 4
<211> LENGTH: 473
<212> TYPE: PRT
<213> ORGANISM: Marinobacter hydrocarbonoclasticus

<400> SEQUENCE: 4

Met Lys Arg Leu Gly Thr Leu Asn Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Val Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

```
Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 5
<211> LENGTH: 1422
<212> TYPE: DNA
<213> ORGANISM: Marinobacter hydrocarbonoclasticus

<400> SEQUENCE: 5

```
atgaaacgtc tcggaaccct gaacgcctcc tggctggcgg ttgaatctga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg gggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacccccctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acggtacgcc cacaccaacg ccgtggtgta     540

aaaaccgaca aagaggccag cgtgcccgca gcggtttccc aggcaatgga cgccctgaag     600

ctccaggcag acatggcccc caggctgtgg caggccggca atcgcctggt gcattcggtt     660

cgacacccgg aagacggact gaccgcgccc ttcactggac cggtttcggt gctcaatcac     720

cgggttaccg cgcagcgacg ttttgccacc cagcattatc aactggaccg gctgaaaaac     780

ctggcccatg cttccggcgg ttccttgaac gacatcgttc tttacctgtg tggcaccgca     840

ttgcggcgct ttctggctga gcagaacaat ctgccagaca ccccgctgac ggctggtata     900

ccggtgaata tccggccggc agacgacgag ggtacgggca cccagatcag ttttatgatt     960

gcctcgctgg ccaccgacga agctgatccg ttgaaccgcc tgcaacagat caaaacctcg    1020

acccgacggg ccaaggagca cctgaggaaa cttccaaaaa gtgccctgac ccagtacacc    1080

atgctgctga tgtcacccta cattctgcaa ttgatgtcag gtctcggggg gaggatgcga    1140

ccattcttca acgtgaccat ttccaacgtg cccggcccgg aaggcacgct gtattatgaa    1200

ggagcccggc ttgaggccat gtatccggta tcgctaatcg ctcacggcgg cgccctgaac    1260

atcacctgcc tgagctatgc cggatcgctg aatttcggtt ttaccggctg tcgggatacg    1320

ctgccgagca tgcagaaact ggcggtttat accggtgaag ctctggatga gctggaatcg    1380

ctgattctgc cacccaagaa gcgcgcccga acccgcaagt aa                       1422
```

<210> SEQ ID NO 6
<211> LENGTH: 473
<212> TYPE: PRT
<213> ORGANISM: Marinobacter hydrocarbonoclasticus

<400> SEQUENCE: 6

```
Met Lys Arg Leu Gly Thr Leu Asn Ala Ser Trp Leu Ala Val Glu Ser
1               5                   10                  15
```

-continued

```
Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Val Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Arg Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430
```

```
Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470


<210> SEQ ID NO 7
<211> LENGTH: 1422
<212> TYPE: DNA
<213> ORGANISM: Marinobacter hydrocarbonoclasticus

<400> SEQUENCE: 7

atgaaacgtc tcggaaccct gaacgcctcc tggctggcgg ttgaatctga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg gggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aaccccctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acggtacgcc cacaccaacg ccgtggtgta     540

aaaaccgaca aagaggccag cgtgcccgca gcggtttccc aggcaatgga cgccctgaag     600

ctccaggcag acatggcccc caggctgtgg caggccggca atcgcctggt gcattcggtt     660

cgacacccgg aagacggact gaccgcgccc ttcactggac cggtttcggt gctcaatcac     720

cgggttaccg cgcagcgacg ttttgccacc cagcattatc aactggaccg gctgaaaaac     780

ctggcccatg cttccggcgg ttccttgaac gacatcgttc tttacctgtg tggcaccgca     840

ttgcggcgct ttctggctga gcagaacaat ctgccagaca ccccgctgac ggctggtata     900

ccggtgaata tccggccggc agacgacgag ggtacgggca cccagatcag ttttatgatt     960

gcctcgctgg ccaccgacga agctgatccg ttgaaccgcc tgcaacagat caaaacctcg    1020

acccgacggg ccaaggagca cctgcagaaa cttccaaaaa gtgccctgac ccagtacacc    1080

atgctgctga tgtcacccta cattctgcaa ttgatgtcag gtctcggggg gaggatgcga    1140

ccattcttca acgtgaccat ttccaacgtg cccggcccgg aaggcacgct gtattatgaa    1200

ggagcccggc ttgaggccat gtatccggta tcgctaatcg ctcacggcgg cgccctgaac    1260

atcacctgcc tgagctatgc cggatcgctg aatttcggtt ttaccggctg tcgggatacg    1320

ctgccgagca tgcagaaact ggcggtttat accggtgaag ctctggatga gctggaatcg    1380

ctgattctgc cacccaagaa gcgcgcccga acccgcaagt aa                        1422


<210> SEQ ID NO 8
<211> LENGTH: 473
<212> TYPE: PRT
<213> ORGANISM: Marinobacter hydrocarbonoclasticus

<400> SEQUENCE: 8

Met Lys Arg Leu Gly Thr Leu Asn Ala Ser Trp Leu Ala Val Glu Ser
1               5                   10                  15

Glu Asp Thr Pro Met His Val Gly Thr Leu Gln Ile Phe Ser Leu Pro
            20                  25                  30
```

-continued

```
Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Val Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
```

```
    450                 455                 460

Pro Lys Lys Arg Ala Arg Thr Arg Lys
465                 470


<210> SEQ ID NO 9
<211> LENGTH: 1422
<212> TYPE: DNA
<213> ORGANISM: Marinobacter hydrocarbonoclasticus

<400> SEQUENCE: 9

atgaaacgtc tcggaaccct gaacgcctcc tggctggcgg ttgaatctga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg gggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aaccccctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acggtacgcc cacaccaacg ccgtggtgta     540

aaaaccgaca aagaggccag cgtgcccgca gcggtttccc aggcaatgga cgccctgaag     600

ctccaggcag acatggcccc caggctgtgg caggccggca atcgcctggt gcattcggtt     660

cgacacccgg aagacggact gaccgcgccc ttcactggac cggtttcggt gctcaatcac     720

cgggttaccg cgcagcgacg ttttgccacc cagcattatc aactggaccg gctgaaaaac     780

ctggcccatg cttccggcgg ttccttgaac gacatcgtgc tttacctgtg tggcaccgca     840

ttgcggcgct ttctggctga gcagaacaat ctgccagaca ccccgctgac ggctggtata     900

ccggtgaata tccggccggc agacgacgag ggtacgggca cccagatcag ttttatgatt     960

gcctcgctgg ccaccgacga agctgatccg ttgaaccgcc tgcaacagat caaaacctcg    1020

acccgacggg ccaaggagca cctgaggaaa cttccaaaaa gtgccctgac ccagtacacc    1080

atgctgctga tgtcacccta cattctgcaa ttgatgtcag gtctcggggg gaggatgcga    1140

ccattcttca acgtgaccat ttccaacgtg cccggcccgg aaggcacgct gtattatgaa    1200

ggagcccggc ttgaggccat gtatccggta tcgctaatcg ctcacggcgg cgccctgaac    1260

atcacctgcc tgagctatgc cggatcgctg aatttcggtt ttaccggctg tcgggatacg    1320

ctgccgagca tgcagaaact ggcggtttat accggtgaag ctctggatga gctggaatcg    1380

ctgattctgc cacccaagaa gcgcgcccga acccgcaagt aa                       1422


<210> SEQ ID NO 10
<211> LENGTH: 473
<212> TYPE: PRT
<213> ORGANISM: Marinobacter hydrocarbonoclasticus

<400> SEQUENCE: 10

Met Lys Arg Leu Gly Thr Leu Asn Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
```

```
        50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Val Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Arg Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 11
<211> LENGTH: 1422
<212> TYPE: DNA
<213> ORGANISM: Marinobacter hydrocarbonoclasticus

<400> SEQUENCE: 11
atgaaacgtc tcggaaccct gaacgcctcc tggctggcgg ttgaatctga agacaccccg 60
atgcatgtgg gtacgcttca gattttctca ctgccggaag gcgcaccaga aaccttcctg 120
cgtgacatgg tcactcgaat gaaagaggcc ggcgatgtgg caccaccctg gggatacaaa 180
ctggcctggt ctggtttcct cgggcgcgtg atcgccccgg cctggaaagt cgataaggat 240
atcgatctgg attatcacgt ccgacactca gccctgcctc gccccggcgg ggagcgcgaa 300
ctgggtattc tggtatcccg actgcactct aaccccctgg atttttcccg ccctctttgg 360
gaatgccacg ttattgaagg cctggagaat aaccgttttg ccctttacac caaaatgcac 420
cactcgatga ttgacggcat cagcggcgtg cgactgatgc agagggtgct caccaccgat 480
cccgaacgct gcaatatgcc accgccctgg acggtacgcc cacaccaacg ccgtggtgta 540
aaaaccgaca aagaggccag caggcccgca gcggtttccc aggcaatgga cgccctgaag 600
ctccaggcag acatggcccc caggctgtgg caggccgcga atcgcctggt gcattcggtt 660
cgacacccgg aagacggact gaccgcgccc ttcactggac cggtttcggt gctcaatcac 720
cgggttaccg cgcagcgacg ttttgccacc cagcattatc aactggaccg gctgaaaaac 780
ctggcccatg cttccggcgg ttccttgaac gacatcgttc tttacctgtg tggcaccgca 840
ttgcggcgct ttctggctga gcagaacaat ctgccagaca ccccgctgac ggctggtata 900
ccggtgaata tccggccggc agacgacgag ggtacgggca cccagatcag ttttatgatt 960
gcctcgctgg ccaccgacga agctgatccg ttgaaccgcc tgcaacagat caaaacctcg 1020
acccgacggg ccaaggagca cctgcagaaa cttccaaaaa gtgccctgac cgtgtacacc 1080
atgctgctga tgtcacccta cattctgcaa ttgatgtcag gtctcggggg gaggatgcga 1140
ccattcttca acgtgaccat ttccaacgtg cccggcccgg aaggcacgct gtattatgaa 1200
ggagcccggc ttgaggccat gtatccggta tcgctaatcg ctcacggcgg cgccctgaac 1260
atcacctgcc tgagctatgc cggatcgctg aatttcggtt ttaccggctg tcgggatacg 1320
ctgccgagcg gccagaaact ggcggtttat accggtgaag ctctggatga gctggaatcg 1380
ctgattctgc cacccaagaa gcgcgcccga acccgcaagt aa 1422

<210> SEQ ID NO 12
<211> LENGTH: 473
<212> TYPE: PRT
<213> ORGANISM: Marinobacter hydrocarbonoclasticus

<400> SEQUENCE: 12

Met Lys Arg Leu Gly Thr Leu Asn Ala Ser Trp Leu Ala Val Glu Ser
1 5 10 15

Glu Asp Thr Pro Met His Val Gly Thr Leu Gln Ile Phe Ser Leu Pro
20 25 30

Glu Gly Ala Pro Glu Thr Phe Leu Arg Asp Met Val Thr Arg Met Lys
35 40 45

Glu Ala Gly Asp Val Ala Pro Pro Trp Gly Tyr Lys Leu Ala Trp Ser
50 55 60

Gly Phe Leu Gly Arg Val Ile Ala Pro Ala Trp Lys Val Asp Lys Asp
65 70 75 80

```
Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Val Lys Thr Asp Lys Glu Ala Ser Arg Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Ala Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Val Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Gly Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 13
<211> LENGTH: 1422

<212> TYPE: DNA
<213> ORGANISM: Marinobacter hydrocarbonoclasticus

<400> SEQUENCE: 13
atgaaacgtc tcggatccct ggacgcctcc tggctggcgg ttgaaggtga agacaccccg 60
atgcatgtgg gtacgcttca gattttctca ctgccggaag gcgcaccaga aaccttcctg 120
cgtgacatgg tcactcgaat gaaagaggcc ggcgatgtgg caccaccctg ggatacaaa 180 ctggcctggt ctggtttcct cgggcgcgtg atcgccccgg cctggaaagt cgataaggat 240
atcgatctgg attatcacgt ccggcactca gccctgcctc gccccggcgg ggagcgcgaa 300
ctgggtattc tggtatcccg actgcactct aacagtctgg atttttcccg ccctctttgg 360
gaatgccacg ttattgaagg cctggagaat aaccgttttg ccctttacac caaaatgcac 420
cactcgatga ttgacggcat cagcggcgtg cgactgatgc agagggtgct caccaccgat 480
cccgaacgct gcaatatgcc accgccctgg acgcgccgcc cacaccagcg ccgtggtgca 540
aaaaccgaca aagaggccag cgtgcgggca gcggtttccc aggcaatgga cgccctgaag 600
ctccaggcag acatggcccc caggctgtgg caggccggca atcgcctggt gcattcggtt 660
cgacacccgg aagacggact gaccgcgccc ttcactggac cggtttcggt gctcaatcac 720
cgggttaccg cgcagcgacg ttttgccacc cagcattatc aactggaccg gctgaaaaac 780
ctggcccatg cttccggcgg ttccttgaac gacatcgttc tttacctgtg tggcaccgca 840
ttgcggcgct ttctggctga gcagaacaat ctgccagaca ccccgctgac ggctggtata 900
ccggtgaata tccggccggc agacgacgag ggtacgggca cccagatcag ttggatgatt 960
gcctcgctgg ccaccgacga agctgatccg ttgaaccgcc tgcaacagat caaaacctcg 1020
acccgacggg ccaaggagca cctgcagaaa cttccaaaaa cggccctgac ccagtacacc 1080
atgctgctga tgtcacccta cattctgcaa ttgatgtcag gtctcggggg gaggatgcga 1140
ccagtcttca acgtgaccat ttccaacgtg cccggcccgg aaggcacgct gtattatgaa 1200
ggagcccggc ttgaggccat gtatccgttg tcgctaatcg ctcacggcgg cgccctgaac 1260
atcacctgcc tgagctatgc cggatcgctg aatttcggtt ttaccggctg tcgggatacg 1320
ctgccgggga tgcagaaact ggcggtttat accggtgaag ctctggatga gctggaatcg 1380
ctgattctgc cacccaagaa gcgcgcccga acccgcaagt aa 1422

<210> SEQ ID NO 14
<211> LENGTH: 473
<212> TYPE: PRT
<213> ORGANISM: Marinobacter hydrocarbonoclasticus

<400> SEQUENCE: 14

Met Lys Arg Leu Gly Ser Leu Asp Ala Ser Trp Leu Ala Val Glu Gly
1 5 10 15

Glu Asp Thr Pro Met His Val Gly Thr Leu Gln Ile Phe Ser Leu Pro
20 25 30

Glu Gly Ala Pro Glu Thr Phe Leu Arg Asp Met Val Thr Arg Met Lys
35 40 45

Glu Ala Gly Asp Val Ala Pro Pro Trp Gly Tyr Lys Leu Ala Trp Ser
50 55 60

Gly Phe Leu Gly Arg Val Ile Ala Pro Ala Trp Lys Val Asp Lys Asp
65 70 75 80

Ile Asp Leu Asp Tyr His Val Arg His Ser Ala Leu Pro Arg Pro Gly
85 90 95

-continued

```
Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 15
<211> LENGTH: 1422
<212> TYPE: DNA
<213> ORGANISM: Marinobacter hydrocarbonoclasticus

<400> SEQUENCE: 15

```
atgaaacgtc tcggatccct ggacgcctcc tggctggcgg ttgaaggtga agacaccccg     60
atgcatgtgg gtacgcttca gattttctca ctgccggaag gcgcaccaga aaccttcctg    120
cgtgacatgg tcactcgaat gaaagaggcc ggcgatgtgg caccaccctg ggatacaaa    180
ctggcctggt ctggtttcct cgggcgcgtg atcgccccgg cctggaaagt cgatttcgat    240
atcgatctgg attatcacgt ccggcactca gccctgcctc gccccggcgg ggagcgcgaa    300
ctgggtattc tggtatcccg actgcactct aacagtctgg atttttcccg ccctctttgg    360
gaatgccacg ttattgaagg cctggagaat aaccgttttg ccctttacac caaaatgcac    420
cactcgatga ttgacggcat cagcggcgtg cgactgatgc agagggtgct caccaccgat    480
cccgaacgct gcaatatgcc accgccctgg acgcgccgcc cacaccagcg ccgtggtgca    540
aaaaccgaca aagaggccag cgtgcgggca gcggttgtgc aggcaatgga cgccctgaag    600
ctccaggcag acatggcccc caggctgtgg caggccggca atcgcctggt gcattcggtt    660
cgacacccgg aagacggact gaccgcgccc ttcactggac cggtttcggt gctcaatcac    720
cgggttacca ggcagcgacg ttttgccacc cagcattatc aactggaccg gctgaaaaac    780
ctggcccatg cttccggcgg ttccttgaac gacatcgttc tttacctgtg tggcaccgca    840
ttgcggcgct ttctggctga gcagaacaat ctgccagaca ccccgctgac ggctggtata    900
ccggtgaata tccggccggc agacgacgag ggtacgggca cccagatcag ttggatgatt    960
gcctcgctgg ccaccgacga agctgatccg ttgaaccgcc tgcaacagat caaaacctcg   1020
acccgacggg ccaaggagca cctgcagcac cttccaaaaa cggccctgac ccagtacacc   1080
atgctgctga tgtcacccta cattctgcaa ttgatgtcag gtctcggggg gaggatgcga   1140
ccagtcttca acgtgaccat ttccaacgtg cccggcccgg aaggcacgct gtattatgaa   1200
ggagcccggc ttgaggccat gtatccgttg tcgctaatcg ctcacggcgg cgccctgaac   1260
atcacctgcc tgagctatgc cggatcgctg aatttcggtt ttaccggctg tcgggatacg   1320
ctgccgggga tgcagaaact ggcggtttat accggtgaag ctctggatga gctggaatcg   1380
ctgattctgc cacccaagaa gcgcgcccga acccgcaagt aa                      1422
```

<210> SEQ ID NO 16
<211> LENGTH: 473
<212> TYPE: PRT
<213> ORGANISM: Marinobacter hydrocarbonoclasticus

<400> SEQUENCE: 16

```
Met Lys Arg Leu Gly Ser Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Phe Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
```

```
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Val Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Arg Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln His Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470


<210> SEQ ID NO 17
<211> LENGTH: 1422
<212> TYPE: DNA
<213> ORGANISM: Marinobacter hydrocarbonoclasticus

<400> SEQUENCE: 17

atgaaacgtc tcggatccct ggacgcctcc tggctggcgg ttgaaggtga agacaccccg      60

atgcatgtgg gtacgcttca gattttctca ctgccggaag gcgcaccaga aaccttcctg     120
```

```
cgtgacatgg tcactcgaat gaaagaggcc ggcgatgtgg caccaccctg gggatacaaa    180

ctggcctggt ctggtttcct cgggcgcgtg atcgccccgg cctggaaact ggataaggat    240

atcgatctgg attatcacgt ccggcactca gccctgcctc gccccggcgg ggagcgcgaa    300

ctgggtattc tggtatcccg actgcactct aacagtctgg atttttcccg ccctctttgg    360

gaatgccacg ttattgaagg cctggagaat aaccgttttg ccctttacac caaaatgcac    420

cactcgatga ttgacggcat cagcggcgtg cgactgatgc agagggtgct caccaccgat    480

cccgaacgct gcaatatgcc accgccctgg acgcgccgcc cacaccagcg ccgtggtgca    540

aaaaccgaca aagaggccag cgtgcgggca gcggtttccc aggcaatgga cgccctgaag    600

ctccaggcag acatggcccc caggctgtgg caggccggca atcgcctggt gcattcggtt    660

cgacacccgg aagacggact gaccgcgccc ttcactggac cggtttcggt gctcaatcac    720

cgggttaccg cgcagcgacg ttttgccacc cagcattatc aactggaccg gctgaggaac    780

ctggcccatg cttccggcgg ttccttgaac gacatcgttc tttacctgtg tggcaccgca    840

ttgcggcgct ttctggctga gcagaacaat ctgccagaca ccccgctgac ggctggtata    900

ccggtgaata tccggccggc agacgacgag ggtacgggca cccagatcgg gtggatgatt    960

gcctcgctgg ccaccgacga agctgatccg ttgaaccgcc tgcaacagat caaaacctcg   1020

acccgacggg ccaaggagca cctgcagaaa cttccaaaaa cggccctgac ccagtacacc   1080

cgcctgctga tgtcacccta cattctgcaa ttgatgtcag gtctcggggg gaggatgcga   1140

ccagtcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                      1422
```

<210> SEQ ID NO 18
<211> LENGTH: 473
<212> TYPE: PRT
<213> ORGANISM: Marinobacter hydrocarbonoclasticus

<400> SEQUENCE: 18

```
Met Lys Arg Leu Gly Ser Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Leu Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140
```

```
Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Arg Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Gly Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Arg Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 19
<211> LENGTH: 1422
<212> TYPE: DNA
<213> ORGANISM: Marinobacter hydrocarbonoclasticus

<400> SEQUENCE: 19

```
atgaaacgtc tcggatccct ggacgcctcc tggctggcgg ttgaaggtga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg gggatacaaa     180

ctggcctggt ctggtttcct cgggcgcgtg atcgccccgg cctggaaagt cgataaggat     240
```

```
atcgatctgg attatcacgt ccggcactca gccctgcctc gccccggcgg ggagcgcgaa    300

ctgggtattc tggtatcccg actgcactct aacagtctgg atttttcccg ccctctttgg    360

gaatgccacg ttattgaagg cctggagaat aaccgttttg ccctttacac caaaatgcac    420

cactcgatga ttgacggcat cagcggcgtg cgactgatgc agagggtgct caccaccgat    480

cccgaacgct gcaatatgcc accgccctgg acgcgccgcc cacaccagcg ccgtggtgca    540

aaaaccgaca aagaggccag cgtgcgggca gcggtttccc aggcaatgga cgccctgaag    600

ctccaggcag acatggcccc caggctgtgg caggccggca atcgcctggt gcattcggtt    660

cgacacccgg aagacggact gaccgcgccc ttcactggac cggtttcggt gctcaatcac    720

cgggttaccg cgggccgacg ttttgccacc cagcattatc aactggaccg gctgaaaaac    780

ctggcccatg cttccggcgg tgggttgaac gacatcgttc tttacctgtg tggcaccgca    840

ttgcggcgct ttctggctga gcagaacaat ctgccagaca ccccgctgac ggctggtata    900

ccggtgaata tccggccggc agacgacgag gtcacgggca cccagatcag ttggatgatt    960

tgttcgctgg ccaccgacga agctgatccg ttgaaccgcc tgcaacagat caaaacctcg   1020

acccgacggg ccaaggagca cctgcagaaa cttccaaaaa cggccctgac ccagtacacc   1080

atgctgctga tgtcaccctg gattctgcaa ttgatgtcag gtctcggggg gaggatgcga   1140

ccagtcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                      1422
```

<210> SEQ ID NO 20
<211> LENGTH: 473
<212> TYPE: PRT
<213> ORGANISM: Marinobacter hydrocarbonoclasticus

<400> SEQUENCE: 20

```
Met Lys Arg Leu Gly Ser Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160
```

-continued

```
Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gly Arg Arg Phe Ala Thr Gln His Tyr Gln Leu Asp
                245                 250                 255

Arg Leu Lys Asn Leu Ala His Ala Ser Gly Gly Gly Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Val Thr Gly Thr Gln Ile Ser Trp Met Ile
305                 310                 315                 320

Cys Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Trp Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 21
<211> LENGTH: 1422
<212> TYPE: DNA
<213> ORGANISM: Marinobacter hydrocarbonoclasticus

<400> SEQUENCE: 21

```
atgaaacgtc tcggaaccct ggacgcctcc tggctggcgg ttgaaggtga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg ggatacaaa      180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360
```

```
gaatgccacg ttattgaagg cctggagaat aaccgttttg ccctttacac caaaatgcac    420

cactcgatga ttgacggcat cagcggcgtg cgactgatgc agaggggcct caccaccgat    480

cccgaacgct gcaatatgtc accgccctgg acgcgccgcc cacaccagcg ccgtggtgca    540

aaaaccgaca aagaggccag cgtgcgggca gcggtttccc aggcaatgga cgccctgaag    600

ctccaggcag acatggcccc caggctgtgg caggccggca atcgcctggt gcattcggtt    660

cgacacccgg aagacggact gaccgcgccc ttcactggac cggtttcggt gctcaatcac    720

cgggttaccg cgcagcgacg ttttgccacc cagcattatc aactggaccg gctgaaaaac    780

ctggcccatg cttccggcgg ttccttgaac gacatcgttc tttacctgtg tggcaccgca    840

ttgcggcgct ttctggctga gcagaacaat ctgccagaca ccccgctgac ggctggtata    900

ccggtgaata tccggccggc agacgacgag ggtacgggca cccagatcag ttggatgatt    960

gcctcgctgg ccaccgacga agctgatccg ttgaaccgcc tgcaacagat caaaacctcg   1020

acccgacggg ccaaggagca cctggcgaaa cttccaaaaa cggccctgac ccagtacacc   1080

atgctgctga tgtcacccta cattctgcaa ttgatgtcag gtctcggggg gaggatgcga   1140

ccattcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                      1422
```

<210> SEQ ID NO 22
<211> LENGTH: 473
<212> TYPE: PRT
<213> ORGANISM: Marinobacter hydrocarbonoclasticus

<400> SEQUENCE: 22

```
Met Lys Arg Leu Gly Thr Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Gly Leu Thr Thr Asp
145                 150                 155                 160

Pro Glu Arg Cys Asn Met Ser Pro Pro Trp Thr Arg Arg Pro His Gln
                165                 170                 175

Arg Arg Gly Ala Lys Thr Asp Lys Glu Ala Ser Val Arg Ala Ala Val
```

-continued

```
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Ala Lys Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 23
<211> LENGTH: 1422
<212> TYPE: DNA
<213> ORGANISM: Marinobacter hydrocarbonoclasticus

<400> SEQUENCE: 23

```
atgaaacgtc tcggaaccct ggacgcctcc tggctggcgg ttgaaggtga agacaccccg      60

atgcatgtgg gtacgcttca gattttctca ctgccggaag gcgcaccaga aaccttctcg     120

cgtgacatgg tcactcgaat gaaagaggcc ggcgatgtgg caccaccctg ggatacaaa      180

ctggcctggt ctggtttcct cgggcgcgtg atcgccccgg cctggaaagt cgcgaaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480
```

-continued

```
cccgaacgct gcaatatgcc accgccctgg acgcgccgcc cacaccagcg ccgtggtgca    540

aaaaccgaca aagaggccag cgtgcgggca gcggtttccc aggcaatgga cgccctgaag    600

ctccaggcag acatggcccc caggctgtgg caggccggca atcgcctggt gcattcggtt    660

cgacacccgg aagacggact gaccgcgccc ttcactggac cggtttcggt gctcaatcac    720

cgggttaccg cgcagcgacg ttttgccacc cagcattatc aactggaccg gctgaaaaac    780

ctggcccatg cttccggcgg ttccttgaac gacatcgttc tttacctgtg tggcaccgca    840

ttgcggcgct ttctggctga gcagaacaat ctgccagaca ccccgctgac ggctggtata    900

ccggtgaata tccggccggc agacgacgag ggtacgggca gtcagatcag ttggatgatt    960

gcctcgctgg ccaccgacga agctgatccg ttgaaccgcc tgcaacagat caaaacctcg   1020

acccgacggg ccaaggagca cctggcgaaa cttccaaaaa cggccctgac ccagtacacc   1080

atgctgctga tgtcacccta cattctgcaa ttgatgtcag gtctcggggg gaggatgcga   1140

ccattcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

gtgacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                      1422
```

<210> SEQ ID NO 24
<211> LENGTH: 473
<212> TYPE: PRT
<213> ORGANISM: Marinobacter hydrocarbonoclasticus

<400> SEQUENCE: 24

```
Met Lys Arg Leu Gly Thr Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Ser Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Ala Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Arg
        195                 200                 205
```

```
Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Ser Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Ala Lys Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Val Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 25
<211> LENGTH: 1422
<212> TYPE: DNA
<213> ORGANISM: Marinobacter hydrocarbonoclasticus

<400> SEQUENCE: 25

```
atgaaacgtc tcggatccct ggacgcctcc tggctggcgg ttgaaggtga agacaccccg      60

atgcatgtgg gttggcttca gattttctca ctgccggaag gcgcaccaga aaccttcctg     120

cgtgacatgg tcttccgaat gaaagaggcc ggcgatgtgg caccaccctg gggatacaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360

gaatgccacg ttattgaagg cctggagaat aaccgttttg ccctttacac caaaatgcac     420

cactcgatga ttgacggctt gagcggcgtg cgactgatgc agagggtgct caccaccgat     480

cccgaacgct gcaatatgcc accgccctgg acgcgccgcc cacaccagcg ccgtggtgca     540

aaaaccgaca aagaggccag cgtgcgggca gcggtttccc aggcaatgga cgccctgaag     600
```

ctccaggcag acatggcccc caggctgtgg caggccggca atcgcctggt gcattcggtt 660
cgacacccgg aagacggact gaccgcgccc ttcactggac cggtttcggt gctcaatcac 720
cgggttaccg cgcagcgacg ttttgccacc cagcattatc aactggaccg gctgaaaaac 780
ctggcccatg cttccggcgg ttccttgaac gacatcgttc tttacctgtg tggcaccgca 840
ttgcggcgct ttctggctga gcagaacaat ctgccagaca ccccgctgac ggctggtata 900
ccggtgaata tccggccggc aaacgacgag ggtacgggca cccagatcag ttggatgatt 960
gcctcgctgg ccaccgacga agctgatccg ttgaaccgcc tgcaacagat caaaacctcg 1020
acccgacggg ccaaggagca cctgcagaaa cttccaaaaa cggccctgac ccagtacacc 1080
atgctgctga tgtcacccta cattctgcaa ttgatgtcag gtctcggggg gaggatgcga 1140
ccagtcttca acgtgaccat ttccaacgtg cccggcccgg aaggcacgct gtattatgaa 1200
ggagcccggc ttgaggccat gtatccgttg tcgctaatcg ctcacggcgg cgccctgaac 1260
atcacctgcc tgagctatgc cggatcgctg aatttcggtt ttaccggctg tcgggatacg 1320
ctgccgggga tgcagaaact ggcggtttat accggtgaag ctctggatga gctggaatcg 1380
ctgattctgc cacccaagaa gcgcgcccga acccgcaagt aa 1422

<210> SEQ ID NO 26
<211> LENGTH: 473
<212> TYPE: PRT
<213> ORGANISM: Marinobacter hydrocarbonoclasticus

<400> SEQUENCE: 26

Met Lys Arg Leu Gly Ser Leu Asp Ala Ser Trp Leu Ala Val Glu Gly
1 5 10 15

Glu Asp Thr Pro Met His Val Gly Trp Leu Gln Ile Phe Ser Leu Pro
20 25 30

Glu Gly Ala Pro Glu Thr Phe Leu Arg Asp Met Val Phe Arg Met Lys
35 40 45

Glu Ala Gly Asp Val Ala Pro Pro Trp Gly Tyr Lys Leu Ala Trp Ser
50 55 60

Gly Phe Leu Gly Arg Val Ile Ala Pro Ala Trp Lys Val Asp Lys Asp
65 70 75 80

Ile Asp Leu Asp Tyr His Val Arg His Ser Ala Leu Pro Arg Pro Gly
85 90 95

Gly Glu Arg Glu Leu Gly Ile Leu Val Ser Arg Leu His Ser Asn Ser
100 105 110

Leu Asp Phe Ser Arg Pro Leu Trp Glu Cys His Val Ile Glu Gly Leu
115 120 125

Glu Asn Asn Arg Phe Ala Leu Tyr Thr Lys Met His His Ser Met Ile
130 135 140

Asp Gly Leu Ser Gly Val Arg Leu Met Gln Arg Val Leu Thr Thr Asp
145 150 155 160

Pro Glu Arg Cys Asn Met Pro Pro Pro Trp Thr Arg Arg Pro His Gln
165 170 175

Arg Arg Gly Ala Lys Thr Asp Lys Glu Ala Ser Val Arg Ala Ala Val
180 185 190

Ser Gln Ala Met Asp Ala Leu Lys Leu Gln Ala Asp Met Ala Pro Arg
195 200 205

Leu Trp Gln Ala Gly Asn Arg Leu Val His Ser Val Arg His Pro Glu
210 215 220

```
Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asn Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470


<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

atgaaacgtc tcggaaccct ggac                                            24


<210> SEQ ID NO 28
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

atgaaacgtc tcggaaccct ggacatgaaa cgtctcggaa ccctggacgc ctcctggctg     60

gcggttgaat ctgaagacac cccgatgcat gtgggtacgc ttcagatttt ctcactgccg    120

gaaggcgcac cagaaacctt cctgcgtgac atggtcactc gaatgaaaga ggccggcgat    180

gtggcaccac cctggggata caaactggcc tggtctggtt tcctcgggcg cgtgatcgcc    240
```

```
ccggcctgga aagtcgataa ggatatcgat ctggattatc acgtccggca ctcagccctg    300

cctcgccccg gcggggagcg cgaactgggt attctggtat cccgactgca ctctaacccc    360

ctggattttt cccgccctct ttgggaatgc cacgttattg aaggcctgga gaataaccgt    420

tttgcccttt acaccaaaat gcaccactcg atgattgacg gcatcagcgg cgtgcgactg    480

atgcagaggg tgctcaccac cgatcccgaa cgctgcaata tgccaccgcc ctggacggta    540

cgcccacacc agcgccgtgg tgcaaaaacc gacaaagagg ccagcgtgcc cgcagcggtt    600

tcccaggcaa tggacgccct gaagctccag gcagacatgg cccccaggct gtggcaggcc    660

ggcaatcgcc tggtgcattc ggttcgacac ccggaagacg gactgaccgc gcccttcact    720

ggaccggttt cggtgctcaa tcaccgggtt accgcgcagc gacgttttgc cacccagcat    780

tatcaactgg accggctgaa aaacctggcc catgcttccg gcggttcctt gaacgacatc    840

gttctttacc tgtgtggcac cgcattgcgg cgctttctgg ctgagcagaa caatctgcca    900

gacaccccgc tgacggctgg tataccggtg aatatccggc cggcagacga cgagggtacg    960

ggcacccaga tcagttttat gattgcctcg ctggccaccg acgaagctga tccgttgaac   1020

cgcctgcaac agatcaaaac ctcgacccga cgggccaagg agcacctgca gaaacttcca   1080

aaaagtgccc tgacccagta caccatgctg ctgatgtcac cctacattct gcaattgatg   1140

tcaggtctcg gggggaggat gcgaccagtc ttcaacgtga ccatttccaa cgtgcccggc   1200

ccggaaggca cgctgtatta tgaaggagcc cggcttgagg ccatgtatcc ggtatcgcta   1260

atcgctcacg gcggcgccct gaacatcacc tgcctgagct atgccggatc gctgaatttc   1320

ggttttaccg gctgtcggga tacgctgccg agcatgcaga aactggcggt ttataccggt   1380

gaagctctgg atgagctgga atcgctgatt ctgccaccca agaagcgcgc ccgaacccgc   1440

aagtaa                                                               1446
```

<210> SEQ ID NO 29
<211> LENGTH: 481
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 29

```
Met Lys Arg Leu Gly Thr Leu Asp Met Lys Arg Leu Gly Thr Leu Asp
1               5                   10                  15

Ala Ser Trp Leu Ala Val Glu Ser Glu Asp Thr Pro Met His Val Gly
            20                  25                  30

Thr Leu Gln Ile Phe Ser Leu Pro Glu Gly Ala Pro Glu Thr Phe Leu
        35                  40                  45

Arg Asp Met Val Thr Arg Met Lys Glu Ala Gly Asp Val Ala Pro Pro
    50                  55                  60

Trp Gly Tyr Lys Leu Ala Trp Ser Gly Phe Leu Gly Arg Val Ile Ala
65                  70                  75                  80

Pro Ala Trp Lys Val Asp Lys Asp Ile Asp Leu Asp Tyr His Val Arg
                85                  90                  95

His Ser Ala Leu Pro Arg Pro Gly Gly Glu Arg Glu Leu Gly Ile Leu
            100                 105                 110

Val Ser Arg Leu His Ser Asn Pro Leu Asp Phe Ser Arg Pro Leu Trp
        115                 120                 125

Glu Cys His Val Ile Glu Gly Leu Glu Asn Asn Arg Phe Ala Leu Tyr
```

```
    130                 135                 140

Thr Lys Met His His Ser Met Ile Asp Gly Ile Ser Gly Val Arg Leu
145                 150                 155                 160

Met Gln Arg Val Leu Thr Thr Asp Pro Glu Arg Cys Asn Met Pro Pro
                165                 170                 175

Pro Trp Thr Val Arg Pro His Gln Arg Arg Gly Ala Lys Thr Asp Lys
            180                 185                 190

Glu Ala Ser Val Pro Ala Ala Val Ser Gln Ala Met Asp Ala Leu Lys
        195                 200                 205

Leu Gln Ala Asp Met Ala Pro Arg Leu Trp Gln Ala Gly Asn Arg Leu
    210                 215                 220

Val His Ser Val Arg His Pro Glu Asp Gly Leu Thr Ala Pro Phe Thr
225                 230                 235                 240

Gly Pro Val Ser Val Leu Asn His Arg Val Thr Ala Gln Arg Arg Phe
                245                 250                 255

Ala Thr Gln His Tyr Gln Leu Asp Arg Leu Lys Asn Leu Ala His Ala
            260                 265                 270

Ser Gly Gly Ser Leu Asn Asp Ile Val Leu Tyr Leu Cys Gly Thr Ala
        275                 280                 285

Leu Arg Arg Phe Leu Ala Glu Gln Asn Asn Leu Pro Asp Thr Pro Leu
    290                 295                 300

Thr Ala Gly Ile Pro Val Asn Ile Arg Pro Ala Asp Asp Glu Gly Thr
305                 310                 315                 320

Gly Thr Gln Ile Ser Phe Met Ile Ala Ser Leu Ala Thr Asp Glu Ala
                325                 330                 335

Asp Pro Leu Asn Arg Leu Gln Gln Ile Lys Thr Ser Thr Arg Arg Ala
            340                 345                 350

Lys Glu His Leu Gln Lys Leu Pro Lys Ser Ala Leu Thr Gln Tyr Thr
        355                 360                 365

Met Leu Leu Met Ser Pro Tyr Ile Leu Gln Leu Met Ser Gly Leu Gly
    370                 375                 380

Gly Arg Met Arg Pro Val Phe Asn Val Thr Ile Ser Asn Val Pro Gly
385                 390                 395                 400

Pro Glu Gly Thr Leu Tyr Tyr Glu Gly Ala Arg Leu Glu Ala Met Tyr
                405                 410                 415

Pro Val Ser Leu Ile Ala His Gly Gly Ala Leu Asn Ile Thr Cys Leu
            420                 425                 430

Ser Tyr Ala Gly Ser Leu Asn Phe Gly Phe Thr Gly Cys Arg Asp Thr
        435                 440                 445

Leu Pro Ser Met Gln Lys Leu Ala Val Tyr Thr Gly Glu Ala Leu Asp
    450                 455                 460

Glu Leu Glu Ser Leu Ile Leu Pro Pro Lys Lys Arg Ala Arg Thr Arg
465                 470                 475                 480

Lys


<210> SEQ ID NO 30
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

atgggcaaca cccttctcgt cgtcggcgat tcactctccg caggctacca aatgcgtgca     60
```

```
gaacaaagct ggccggtatt gctgcaacct gccctgaaac agcagggtca tgagatcact    120

gtggttaatg caagcattgt gggtatgctg acgcgtcggg gtttggctcg tctgccaacc    180

ctgttacaac aacacaagcc ggcgtatgtt atcatcgaat tgggtgcggt cgatggcttg    240

cgcggttttc cggcgggcac gattcgtaat aacctgagcc agatgattac cgagattcag    300

aacgctgacg cgaagccgat gctggttcag atcaaactcc cgccgtggca cggtaaacgc    360

tacagcgaca tgttcagcag catttacccg cagctgtcta aggaactggc gacgccactg    420

ctgccgttct ttctggagca gatttatatg aagcaagaat ggatgatgaa tgacggtctg    480

catccgaaaa gcgatgcgca gccgtggatc gcagagtata tggccgagaa tatcgcgccg    540

tatttgtaa                                                            549


<210> SEQ ID NO 31
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Asn Thr Leu Leu Val Val Gly Asp Ser Leu Ser Ala Gly Tyr
1               5                   10                  15

Gln Met Arg Ala Glu Gln Ser Trp Pro Val Leu Leu Gln Pro Ala Leu
            20                  25                  30

Lys Gln Gln Gly His Glu Ile Thr Val Val Asn Ala Ser Ile Val Gly
        35                  40                  45

Met Leu Thr Arg Arg Gly Leu Ala Arg Leu Pro Thr Leu Leu Gln Gln
    50                  55                  60

His Lys Pro Ala Tyr Val Ile Ile Glu Leu Gly Ala Val Asp Gly Leu
65                  70                  75                  80

Arg Gly Phe Pro Ala Gly Thr Ile Arg Asn Asn Leu Ser Gln Met Ile
                85                  90                  95

Thr Glu Ile Gln Asn Ala Asp Ala Lys Pro Met Leu Val Gln Ile Lys
            100                 105                 110

Leu Pro Pro Trp His Gly Lys Arg Tyr Ser Asp Met Phe Ser Ser Ile
        115                 120                 125

Tyr Pro Gln Leu Ser Lys Glu Leu Ala Thr Pro Leu Leu Pro Phe Phe
    130                 135                 140

Leu Glu Gln Ile Tyr Met Lys Gln Glu Trp Met Met Asn Asp Gly Leu
145                 150                 155                 160

His Pro Lys Ser Asp Ala Gln Pro Trp Ile Ala Glu Tyr Met Ala Glu
                165                 170                 175

Asn Ile Ala Pro Tyr Leu
            180


<210> SEQ ID NO 32
<211> LENGTH: 1422
<212> TYPE: DNA
<213> ORGANISM: Marinobacter hydrocarbonoclasticus

<400> SEQUENCE: 32

atgaaacgtc tcggatccct ggacgcctcc tggctggcgg ttgaaggtga agacaccccg     60

atgcatgtgg gtacgcttca gattttctca ctgccggaag gcgcaccaga aaccttcctg    120

cgtgacatgg tcactcgaat gaaagaggcc ggcgatgtgg caccaccctg ggatacaaa     180
```

-continued

```
ctggcctggt ctggtttcct cgggcgcgtg atcgccccgg cctggaaagt cgatttcgat    240

atcgatctgg attatcacgt ccggcactca gccctgcctc gccccggcgg ggagcgcgaa    300

ctgggtattc tggtatcccg actgcactct aacagtctgg atttttcccg ccctctttgg    360

gaatgccacg ttattgaagg cctggagaat aaccgttttg ccctttacac caaaatgcac    420

cactcgatga ttgacggcat cagcggcgtg cgactgatgc agagggtgct caccaccgat    480

cccgaacgct gcaatatgcc accgccctgg acgcgccgcc cacaccagcg ccgtggtgca    540

aaaaccgaca aagaggccag cgtgcgggca gcggttgtgc aggcaatgga cgccctgaag    600

ctccaggcag acatggcccc cgcgctgtgg caggccggca atcgcctggt gcattcggtt    660

cgacacccgg aagacggact gaccgcgccc ttcactggac cggtttcggt gctcaatcac    720

cgggttacca ggcagcgccg ttttgcaacc caacactatc agctggagcg catcaagcag    780

gtggcgcagg cgagcaatgg ctccctgaat gacatcgtct tgtatctgtg cggcaccgca    840

ttgcgtcgct ttctggttga acaagacggt ttgccggata ccccactgac cgcaggcatc    900

ccggtgaata tccggccggc agacgacgag ggtacgggca cccagatcag ttggatgatt    960

gcctcgctgg ccaccgacga agctgatccg ttgaaccgcc tgcaacagat caaaacctcg   1020

acccgacggg ccaaggagca cctgaggaaa cttccaaaaa cggccctgac ccagtacacc   1080

atgctgctga tgtcacccta cattctgcaa ttgatgtcag gtctcggggg gaggatgcga   1140

ccattcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                      1422
```

```
<210> SEQ ID NO 33
<211> LENGTH: 473
<212> TYPE: PRT
<213> ORGANISM: Marinobacter hydrocarbonoclasticus

<400> SEQUENCE: 33

Met Lys Arg Leu Gly Ser Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Phe Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
```

-continued

```
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Val Gln Ala Met Asp Ala Leu Lys Leu Gln Ala Asp Met Ala Pro Ala
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Arg Gln Arg Arg Phe Ala Thr Gln His Tyr Gln Leu Glu
                245                 250                 255

Arg Ile Lys Gln Val Ala Gln Ala Ser Asn Gly Ser Leu Asn Asp Ile
            260                 265                 270

Val Leu Tyr Leu Cys Gly Thr Ala Leu Arg Arg Phe Leu Val Glu Gln
        275                 280                 285

Asp Gly Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Arg Lys Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470


<210> SEQ ID NO 34
<211> LENGTH: 1422
<212> TYPE: DNA
<213> ORGANISM: Marinobacter hydrocarbonoclasticus

<400> SEQUENCE: 34

atgaaacgtc tcggatccct ggacgcctcc tggctggcgg ttgaaggtga agacaccccg      60

atgcatgtgg gtacgcttca gattttctca ctgccggaag gcgcaccaga aaccttcctg     120

cgtgacatgg tcactcgaat gaaagaggcc ggcgatgtgg caccaccctg ggatacaaa      180

ctggcctggt ctggtttcct cgggcgcgtg atcgccccgg cctggaaagt cgatttcgat     240

atcgatctgg attatcacgt ccggcactca gccctgcctc gccccggcgg ggagcgcgaa     300
```

```
ctgggtattc tggtatcccg actgcactct aacagtctgg atttttcccg ccctctttgg    360

gaatgccacg ttattgaagg cctggagaat aaccgttttg ccctttacac caaaatgcac    420

cactcgatga ttgacggcat cagcggcgtg cgactgatgc agagggtgct caccaccgat    480

cccgaacgct gcaatatgcc accgccctgg acgcgccgcc cacaccagcg ccgtggtgca    540

aaaaccgaca aagaggccag cgtgcgggca gcggttgtgc aggcaatgga cgccctgaag    600

ctccaggcag acatggcccc cgcgctgtgg caggccggca atcgcctggt gcattcggtt    660

cgacacccgg aagacggact gaccgcgccc ttcactggac cggtttcggt gctcaatcac    720

cgggttacca ggcagcgccg ttttgcaacc caacactatc agctggagcg catcaagcag    780

gtggcgcagg cgagcaatgg ctccctgaat gacatcgtct tgtatctgtg cggcaccgca    840

ttgcgtcgct ttctggttga acaagacggt ttgccggata ccccactgac cgcaggcatc    900

ccggtgaata tccggccggc agacgacgag ggtacgggca cccagatcag ttggatgatt    960

gcctcgctgg ccaccgacga agctgatccg ttgaaccgcc tgcaacagat caaaacctcg   1020

acccgacggg ccaaggagca cctgcagcac cttccaaaaa cggccctgac ccagtacacc   1080

atgctgctga tgtcacccta cattctgcaa ttgatgtcag gtctcggggg gaggatgcga   1140

ccattcttca acgtgaccat ttccaacgtg cccggcccgg aaggcacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctgattctgc cacccaagaa gcgcgcccga acccgcaagt aa                       1422
```

<210> SEQ ID NO 35
<211> LENGTH: 473
<212> TYPE: PRT
<213> ORGANISM: Marinobacter hydrocarbonoclasticus

<400> SEQUENCE: 35

```
Met Lys Arg Leu Gly Ser Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Phe Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175
```

```
Arg Arg Gly Ala Lys Thr Asp Lys Glu Ala Ser Val Arg Ala Ala Val
            180                 185                 190

Val Gln Ala Met Asp Ala Leu Lys Leu Gln Ala Asp Met Ala Pro Ala
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Arg Gln Arg Arg Phe Ala Thr Gln His Tyr Gln Leu Glu
                245                 250                 255

Arg Ile Lys Gln Val Ala Gln Ala Ser Asn Gly Ser Leu Asn Asp Ile
            260                 265                 270

Val Leu Tyr Leu Cys Gly Thr Ala Leu Arg Arg Phe Leu Val Glu Gln
        275                 280                 285

Asp Gly Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Trp Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln His Leu Pro
            340                 345                 350

Lys Thr Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Phe Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Ile Leu Pro
    450                 455                 460

Pro Lys Lys Arg Ala Arg Thr Arg Lys
465                 470
```

<210> SEQ ID NO 36
<211> LENGTH: 1422
<212> TYPE: DNA
<213> ORGANISM: Marinobacter hydrocarbonoclasticus

<400> SEQUENCE: 36

```
atgaaacgtc tcggacccct ggacgcctcc tggctggcgg ttgaaggtga agacaccccg      60

atgcatgtgg gtacgcttca gattttctca ctgccggaag acgcaccaga aaccttcctg     120

cgtgacatgg tcaagcgaat gaaagaggcc ggcgatgtgg caccaccctg ggattaaaa      180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360

gaatgccacg ttattgaagg cctggagaat aaccgttttg ccctttacac caaaatgcac     420
```

```
cactcgatga ttgacggcat cagcggcgtg cgactgatgc agagggtgct caccaccgat    480
cccgaagagt gcaatatgcc accgccctgg acgcgccgcc cacaccagcg ccgtggtgca    540
aaaaccgaca aagaggccag cgtgcgggca gcggtttccc aggcaatgga cgccctgaag    600
ctccaggcag acatggcccc cgcgctgtgg caggccggca atcgcctggt gcattcggtt    660
cgacacccgg aagacggact gaccgcgccc ttcactggac cgtgctcggt gctcaatcac    720
cgggttaccg cgggccgacg ttttgccacc cagcattatc aactggagcg gctgaaaaac    780
ctggcccatg cttccggcgg tggttgaac gacatcgttc tttacctgtg tggcaccgca    840
ttgcggcgct ttctggctga gcagaacaat ctgccagaca ccccgctgac ggctggtata    900
ccggtgaata tccggccggc aaacgacgag gtcacgggca cccagatcag ttggatgatt    960
tgttcgctgg ccaccgacga agctgatccg ttgaaccgcc tgcaacagat caaaacctcg   1020
acccgacggg ccaaggagca cctgcagaaa cttccaaaaa cggccctgac ccagtacacc   1080
atgctgctga tgtcaccctg gattctgcaa ttgatgtcag gtctcggggg gaggatgcga   1140
ccagtcttca acgtgaccat ttccaacgtg cccggcccgg aagagacgct gtattatgaa   1200
ggagcccggc ttgaggccat gtatccgttg tcgctaatcg ctcacggcgg cgccctgaac   1260
atcacctgcc tgagctatgc cggatcgctg aatttcggtt ttaccggctg tcgggatacg   1320
ctgccgggga tgcagaaact ggcggtttat accggtgaag ctctggatga gctggaatcg   1380
ctggttctgc cacccaagaa gcgcgcccga acccgcaagt aa                      1422
```

<210> SEQ ID NO 37
<211> LENGTH: 473
<212> TYPE: PRT
<213> ORGANISM: Marinobacter hydrocarbonoclasticus

<400> SEQUENCE: 37

```
Met Lys Arg Leu Gly Pro Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Asp Ala Pro Glu Thr Phe Leu Arg Asp Met Val Lys Arg Met Lys
        35                  40                  45

Glu Ala Gly Asp Val Ala Pro Pro Trp Gly Leu Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Glu Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190
```

-continued

```
Ser Gln Ala Met Asp Ala Leu Lys Leu Gln Ala Asp Met Ala Pro Ala
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Cys Ser Val Leu Asn His
225                 230                 235                 240

Arg Val Thr Ala Gly Arg Arg Phe Ala Thr Gln His Tyr Gln Leu Glu
                245                 250                 255

Arg Leu Lys Asn Leu Ala His Ala Ser Gly Gly Gly Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asn Asp Glu Val Thr Gly Thr Gln Ile Ser Trp Met Ile
305                 310                 315                 320

Cys Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Trp Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Glu Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Val Leu Pro
    450                 455                 460

Pro Lys Lys Arg Ala Arg Thr Arg Lys
465                 470
```

<210> SEQ ID NO 38
<211> LENGTH: 1422
<212> TYPE: DNA
<213> ORGANISM: Marinobacter hydrocarbonoclasticus

<400> SEQUENCE: 38

```
atgaaacgtc tcggacccct ggacgcctcc tggctggcgg ttgaaggtga agacaccccg      60

atgcatgtgg gtacgcttca gattttctca ctgccggaag acgcaccaga aaccttcctg     120

cgtgacatgg tcaagcgaat gaaagaggcc ggcgatgtgg caccaccctg gggatgcaaa     180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct caccaccgat     480

cccgaacgct gcaatatgcc accgccctgg acgcgccgcc cacaccagcg ccgtggtgca     540
```

```
aaaaccgaca aagaggccag cgtgcgggca gcggtttccc aggcaatgga cgccctgaag    600

ctccaggcag acatggcccc cgcgctgtgg caggccggca atcgcctggt gcattcggtt    660

cgacacccgg aagacggact gaccgcgccc ttcactggac cgtgctcggt gctcaatcac    720

cgggttaccg cgggccgacg ttttgccacc cagcattatc aactggaccg gatcaaaaac    780

ctggcccatg cttccggcgg tggttgaac gacatcgttc tttacctgtg tggcaccgca    840

ttgcggcgct ttctggctga gcagaacaat ctgccagaca ccccgctgac ggctggtata    900

ccggtgaata tccggccggc aaacgacgag gtcacgggca cccagatcag ttggatgatt    960

tgttcgctgg ccaccgacga agctgatccg ttgaaccgcc tgcaacagat caaaacctcg   1020

acccgacggg ccaaggagca cctgcagaaa cttccaaaaa cggccctgac ccagtacacc   1080

atgctgctga tgtcaccctg gattctgcaa ttgatgtcag gtctcggggg gaggatgcga   1140

ccagtcttca acgtgaccat ttccaacgtg cccggcccgg aagagacgct gtattatgaa   1200

ggagcccggc ttgaggccat gtatccgttg tcgctaatca ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctggttctgc cacccaagaa gcgcgcccga acccgcaagt aa                      1422
```

<210> SEQ ID NO 39
<211> LENGTH: 473
<212> TYPE: PRT
<213> ORGANISM: Marinobacter hydrocarbonoclasticus

<400> SEQUENCE: 39

```
Met Lys Arg Leu Gly Pro Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Asp Ala Pro Glu Thr Phe Leu Arg Asp Met Val Lys Arg Met Lys
        35                  40                  45

Glu Ala Gly Asp Val Ala Pro Pro Trp Gly Cys Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Ala
        195                 200                 205

Leu Trp Gln Ala Gly Asn Arg Leu Val His Ser Val Arg His Pro Glu
```

```
    210                 215                 220

Asp Gly Leu Thr Ala Pro Phe Thr Gly Pro Cys Ser Val Leu Asn His
225                 230                 235                 240

Arg Val Thr Ala Gly Arg Arg Phe Ala Thr Gln His Tyr Gln Leu Asp
                245                 250                 255

Arg Ile Lys Asn Leu Ala His Ala Ser Gly Gly Gly Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asn Asp Glu Val Thr Gly Thr Gln Ile Ser Trp Met Ile
305                 310                 315                 320

Cys Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Trp Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Glu Thr Leu Tyr Tyr Glu
385                 390                 395                 400

Gly Ala Arg Leu Glu Ala Met Tyr Pro Leu Ser Leu Ile Thr His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Val Leu Pro
    450                 455                 460

Pro Lys Lys Arg Ala Arg Thr Arg Lys
465                 470
```

<210> SEQ ID NO 40
<211> LENGTH: 1422
<212> TYPE: DNA
<213> ORGANISM: Marinobacter hydrocarbonoclasticus

<400> SEQUENCE: 40

```
atgaaacgtc tcggacccct ggacgcctcc tggctggcgg ttgaaggtga agacaccccg      60

atgcatgtgg gtacgcttca gattttctca ctgccggaag gcgcaccaga aaccttcctg     120

cgtgacatgg tcgctcgaat gaaagaggcc ggcgatgtgg caccaccctg ggatacaaa      180

ctggcctggt ctggtttcct cgggcgcgtg atcgccccgg cctggaaagt cgataaggat     240

atcgatctgg attatcacgt ccggcactca gccctgcctc gccccggcgg ggagcgcgaa     300

ctgggtattc tggtatcccg actgcactct aacagtctgg atttttcccg ccctctttgg     360

gaatgccacg ttattgaagg cctggagaat aaccgttttg ccctttacac caaaatgcac     420

cactcgatga ttgacggcat cagcggcgtg cgactgatgc agagggtgct ctccaccgat     480

cccgaacgct gcgatatgcc accgccctgg tcgcgccgcc cacaccagcg ccgtggtgca     540

aaaaccgaca aagaggccag cgtgcgggca gcggtttccc aggcaatgga cgccctgaag     600

ctccaggcag acatggcccc cgcgctgtgg caggccggca atcgcctgat ccattcggtt     660
```

-continued

```
cgacacccgg aagacggact gaccgcgccc ttcactggac cgtgctcggt gctcaatcac    720

cgggttaccg cgggccgacg ttttgccacc cagcattatc aactggaccg gatcaaaaac    780

ctggcccatg cttccggcgg tggggttgaac gacatcgttc tttacctgtg tggcaccgca    840

ttgcggcgct ttctggctga gcagaacaat ctgccagaca ccccgctgac ggctggtata    900

ccggtgaata tccggccggc aaacgacgag gtcacgggca cccagatcag ttggatgatt    960

tgttcgctgg ccaccgacga agctgatccg ttgaaccgcc tgaaacagat caaaacctcg   1020

acccgacggg ccaaggagca cctgcagaaa cttccaaaaa cggccctgac ccagtacacc   1080

atgctgctga tgtcaccctg gattctgcaa ttgatgtcag gtctcggggg gaggatgcga   1140

ccagtcttca acgtgaccat ttccaacgtg cccggcccgg aagagacgct gtattatgaa   1200

ggagcccggc ttgaggccat gtatccgttg tcgctaatcg ctcacggcgg cgccctgaac   1260

atcacctgcc tgagctatgc cggatcgctg aatttcggtt ttaccggctg tcgggatacg   1320

ctgccgggga tgcagaaact ggcggtttat accggtgaag ctctggatga gctggaatcg   1380

ctggttctgc cacccaagaa gcgcgcccga acccgcaagt aa                      1422
```

<210> SEQ ID NO 41
<211> LENGTH: 473
<212> TYPE: PRT
<213> ORGANISM: Marinobacter hydrocarbonoclasticus

<400> SEQUENCE: 41

```
Met Lys Arg Leu Gly Pro Leu Asp Ala Ser Trp Leu Ala Val Glu Gly
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Ala Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Ser
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Ser Thr Asp
145                 150                 155                 160

Pro Glu Arg Cys Asp Met Pro Pro Pro Trp Ser Arg Arg Pro His Gln
                165                 170                 175

Arg Arg Gly Ala Lys Thr Asp Lys Glu Ala Ser Val Arg Ala Ala Val
            180                 185                 190

Ser Gln Ala Met Asp Ala Leu Lys Leu Gln Ala Asp Met Ala Pro Ala
        195                 200                 205

Leu Trp Gln Ala Gly Asn Arg Leu Ile His Ser Val Arg His Pro Glu
    210                 215                 220

Asp Gly Leu Thr Ala Pro Phe Thr Gly Pro Cys Ser Val Leu Asn His
225                 230                 235                 240
```

```
Arg Val Thr Ala Gly Arg Arg Phe Ala Thr Gln His Tyr Gln Leu Asp
                245                 250                 255

Arg Ile Lys Asn Leu Ala His Ala Ser Gly Gly Gly Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asn Asp Glu Val Thr Gly Thr Gln Ile Ser Trp Met Ile
305                 310                 315                 320

Cys Ser Leu Ala Thr Asp Glu Ala Asp Pro Leu Asn Arg Leu Lys Gln
                325                 330                 335

Ile Lys Thr Ser Thr Arg Arg Ala Lys Glu His Leu Gln Lys Leu Pro
            340                 345                 350

Lys Thr Ala Leu Thr Gln Tyr Thr Met Leu Leu Met Ser Pro Trp Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Glu Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Val Leu Pro
    450                 455                 460

Pro Lys Lys Arg Ala Arg Thr Arg Lys
465                 470
```

<210> SEQ ID NO 42
<211> LENGTH: 1422
<212> TYPE: DNA
<213> ORGANISM: Marinobacter hydrocarbonoclasticus

<400> SEQUENCE: 42

```
atgaaacgtc tcggacccct ggacgcctcc tggctggcgg ttgaaggtga agacaccccg     60

atgcatgtgg gtacgcttca gattttctca ctgccggaag gcgcaccaga aaccttcctg    120

cgtgacatgg tcactcgaat gaaagaggcc ggcgatgtgg caccaccctg gggattaaaa    180

ctggcctggt ctggtttcct cgggcgcgtg atcgccccgg cctggaaagt cgataaggat    240

atcgatctgg attatcacgt ccggcactca gccctgcctc gccccggcgg ggagcgcgaa    300

ctgggtattc tggtatcccg actgcactct aacagtctgg atttttcccg ccctctttgg    360

gaatgccacg ttattgaagg cctggagaat aaccgttttg ccctttacac caaaatgcac    420

cactcgatga ttgacggcat cagcggcgtg cgactgatgc agagggtgct caccaccgat    480

cccgaagagt gcaatatgcc accgccctgg tcgcgccgcc cacaccagcg ccgtggttca    540

aaaaccgaca aagaggccag cgtgcgggca gcggtttccc aggcaatgga cgccctgaag    600

ctccaggcag acatggcccc cgcgctgtgg caggccggca atcgcctggt gcattcggtt    660

cgacacccgg aagacggact gaccgcgccc ttcactggac cgtgctcggt gctcaatcac    720

cgggttaccg cgggccgacg ttttgccacc cagcattatc aactggaccg gatcaaaaac    780
```

ctggcccatg cttccggcgg tgggttgaac gacatcgttc tttacctgtg tggcaccgca 840
ttgcggcgct ttctggctga gcagaacaat ctgccagaca ccccgctgac ggctggtata 900
ccggtgaata tccggccggc aaacgacgag gtcacgggca cccagatcag ttggatgatt 960
tgttcgctgg ccaccgacga agctgatccg ttgaaccgcc tgcaacagat caaaacctcg 1020
acccgacggg ccaaggagca cctgcagaaa cttccaaaaa aggccctgac ccagtacacc 1080
atgctgctga tgtcaccctg gattctgcaa ttgatgtcag gtctcggggg gaggatgcga 1140
ccagtcttca acgtgaccat ttccaacgtg cccggcccgg aagagacgct gtattatgaa 1200
ggagcccggc ttgaggccat gtatccgttg tcgctaatcg ctcacggcgg cgccctgaac 1260
atcacctgcc tgagctatgc cggatcgctg aatttcggtt ttaccggctg tcgggatacg 1320
ctgccgggga tgcagaaact ggcggtttat accggtgaag ctctggatga gctggaatcg 1380
ctggttctgc cacccaagaa gcgcgcccga acccgcaagt aa 1422

<210> SEQ ID NO 43
<211> LENGTH: 473
<212> TYPE: PRT
<213> ORGANISM: Marinobacter hydrocarbonoclasticus

<400> SEQUENCE: 43

Met Lys Arg Leu Gly Pro Leu Asp Ala Ser Trp Leu Ala Val Glu Gly
1 5 10 15

Glu Asp Thr Pro Met His Val Gly Thr Leu Gln Ile Phe Ser Leu Pro
20 25 30

Glu Gly Ala Pro Glu Thr Phe Leu Arg Asp Met Val Thr Arg Met Lys
35 40 45

Glu Ala Gly Asp Val Ala Pro Pro Trp Gly Leu Lys Leu Ala Trp Ser
50 55 60

Gly Phe Leu Gly Arg Val Ile Ala Pro Ala Trp Lys Val Asp Lys Asp
65 70 75 80

Ile Asp Leu Asp Tyr His Val Arg His Ser Ala Leu Pro Arg Pro Gly
85 90 95

Gly Glu Arg Glu Leu Gly Ile Leu Val Ser Arg Leu His Ser Asn Ser
100 105 110

Leu Asp Phe Ser Arg Pro Leu Trp Glu Cys His Val Ile Glu Gly Leu
115 120 125

Glu Asn Asn Arg Phe Ala Leu Tyr Thr Lys Met His His Ser Met Ile
130 135 140

Asp Gly Ile Ser Gly Val Arg Leu Met Gln Arg Val Leu Thr Thr Asp
145 150 155 160

Pro Glu Glu Cys Asn Met Pro Pro Pro Trp Ser Arg Arg Pro His Gln
165 170 175

Arg Arg Gly Ser Lys Thr Asp Lys Glu Ala Ser Val Arg Ala Ala Val
180 185 190

Ser Gln Ala Met Asp Ala Leu Lys Leu Gln Ala Asp Met Ala Pro Ala
195 200 205

Leu Trp Gln Ala Gly Asn Arg Leu Val His Ser Val Arg His Pro Glu
210 215 220

Asp Gly Leu Thr Ala Pro Phe Thr Gly Pro Cys Ser Val Leu Asn His
225 230 235 240

Arg Val Thr Ala Gly Arg Arg Phe Ala Thr Gln His Tyr Gln Leu Asp
245 250 255

-continued

```
Arg Ile Lys Asn Leu Ala His Ala Ser Gly Gly Gly Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asn Asp Glu Val Thr Gly Thr Gln Ile Ser Trp Met Ile
305                 310                 315                 320

Cys Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Lys Ala Leu Thr Gln Tyr Thr Met Leu Leu Met Ser Pro Trp Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Glu Thr Leu Tyr Tyr Glu
385                 390                 395                 400

Gly Ala Arg Leu Glu Ala Met Tyr Pro Leu Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Gly Met Gln Lys Leu Ala
        435                 440                 445

Val Tyr Thr Gly Glu Ala Leu Asp Glu Leu Glu Ser Leu Val Leu Pro
    450                 455                 460

Pro Lys Lys Arg Ala Arg Thr Arg Lys
465                 470
```

<210> SEQ ID NO 44
<211> LENGTH: 1470
<212> TYPE: DNA
<213> ORGANISM: Marinobacter adhaerens

<400> SEQUENCE: 44

```
atgaaacgcc tgggaacgct ggatgcctct tggctggccg tagaatctga agacaccccc     60

atgcatgtgg gcaacctgca gatcttttcg ctaccggagg gcgcccctga aaccttcctc    120

cgggacatgg tgacccgcat gaaggaaacc ggcgatgtcg cgcccccctg gggtttaaag    180

cttgcctggt ccggactgtt gggtcgggta ctggcgccgg gctggaaagt cgacaagaaa    240

atcgatctgg attaccacgt gcgtcactcg gcactgccgc gccccggcgg tgaacgggaa    300

ctgggcatat tggtatcgcg cctgcactcc aaccccctgg actttgcccg cccactctgg    360

gaatgccacg ttatcgaggg cctcgagaat aaccgttttg cgctctacac caagatgcat    420

cattccatga ttgatggcat cagtggtgta cgcctgatgc aacgggtact gacaaccgat    480

cccgacaaac gggacatgcc gccaccctgg tcggttcggc cggagcgccg tcgcggcagc    540

aaatccgatt ccgaggccag cgtgcccggc gcggtctcac aggccatgga ggcactgaaa    600

ctgcaagcgg atatggcgcc acgtctgttg caagcgggca acaggttggt gcattcggtc    660

cgtcaccccg aggatggtct cacggcaccg tttaccgggc ccgtgtccaa gatcaatcac    720

cgggttaccg gccagcgccg gtttgccacc cagcattacc agctcgacag gatcaaggag    780

cttgcccacg tttccggcgc ttccctcaac gatatcgttc tgtacctgtg cggaactgcc    840

ctcaggcgtt ttctgctgga acagaatgaa ctgccggacg ctcccctcac cgccggcata    900
```

-continued

```
ccggttaaca tccggccgtc cgatgacgaa gggacaggca cccagatcag tttcatgatc    960

tcttcgcttg cgaccgacga agccgatccg ctgacccgcc tgcaaaacat caaggcgtca   1020

acgcgaaggg ccaaagagca tttgcagaag ctgcccaaaa gcgcgctcac ccagtacacc   1080

atgctcctga tgtcgcctta tattctgcag ctgatgtccg gccttggcgg tcgcatgcgg   1140

ccggtattta acgtcacgat ttccaatgtg ccggggcccc agagaacgct ctactacgag   1200

ggcgcgaaac tggaagccat gtaccctgtc tcgctgatta ctcacggtgg cgctttgaac   1260

atcacctgcc tgagctatga cggttcactg aacttcggct atacgggctg cagggatacc   1320

ctgccgagca tgcagagact tgcggtttac acgggtgagg cactggacga actggaaagc   1380

ctgattcttc cgccaaaggc caaaccgaaa gctgcggcca agcccagtgc gccgcgcaaa   1440

cagccgacga aaaagagtaa agcggactga                                    1470


<210> SEQ ID NO 45
<211> LENGTH: 489
<212> TYPE: PRT
<213> ORGANISM: Marinobacter adhaerens

<400> SEQUENCE: 45

Met Lys Arg Leu Gly Thr Leu Asp Ala Ser Trp Leu Ala Val Glu Ser
1               5                   10                  15

Glu Asp Thr Pro Met His Val Gly Asn Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Thr Gly Asp Val Ala Pro Pro Trp Gly Leu Lys Leu Ala Trp Ser
    50                  55                  60

Gly Leu Leu Gly Arg Val Leu Ala Pro Gly Trp Lys Val Asp Lys Lys
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ala Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Asp Lys Arg Asp Met Pro Pro Pro Trp Ser Val Arg Pro Glu Arg
                165                 170                 175

Arg Arg Gly Ser Lys Ser Asp Ser Glu Ala Ser Val Pro Gly Ala Val
            180                 185                 190

Ser Gln Ala Met Glu Ala Leu Lys Leu Gln Ala Asp Met Ala Pro Arg
        195                 200                 205

Leu Leu Gln Ala Gly Asn Arg Leu Val His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln His Tyr Gln Leu Asp
                245                 250                 255

Arg Ile Lys Glu Leu Ala His Val Ser Gly Ala Ser Leu Asn Asp Ile
            260                 265                 270
```

Val Leu Tyr Leu Cys Gly Thr Ala Leu Arg Arg Phe Leu Leu Glu Gln
275 280 285

Asn Glu Leu Pro Asp Ala Pro Leu Thr Ala Gly Ile Pro Val Asn Ile
290 295 300

Arg Pro Ser Asp Asp Glu Gly Thr Gly Thr Gln Ile Ser Phe Met Ile
305 310 315 320

Ser Ser Leu Ala Thr Asp Glu Ala Asp Pro Leu Thr Arg Leu Gln Asn
325 330 335

Ile Lys Ala Ser Thr Arg Arg Ala Lys Glu His Leu Gln Lys Leu Pro
340 345 350

Lys Ser Ala Leu Thr Gln Tyr Thr Met Leu Leu Met Ser Pro Tyr Ile
355 360 365

Leu Gln Leu Met Ser Gly Leu Gly Gly Arg Met Arg Pro Val Phe Asn
370 375 380

Val Thr Ile Ser Asn Val Pro Gly Pro Gln Arg Thr Leu Tyr Tyr Glu
385 390 395 400

Gly Ala Lys Leu Glu Ala Met Tyr Pro Val Ser Leu Ile Thr His Gly
405 410 415

Gly Ala Leu Asn Ile Thr Cys Leu Ser Tyr Asp Gly Ser Leu Asn Phe
420 425 430

Gly Tyr Thr Gly Cys Arg Asp Thr Leu Pro Ser Met Gln Arg Leu Ala
435 440 445

Val Tyr Thr Gly Glu Ala Leu Asp Glu Leu Glu Ser Leu Ile Leu Pro
450 455 460

Pro Lys Ala Lys Pro Lys Ala Ala Ala Lys Pro Ser Ala Pro Arg Lys
465 470 475 480

Gln Pro Thr Lys Lys Ser Lys Ala Asp
485

<210> SEQ ID NO 46
<211> LENGTH: 1458
<212> TYPE: DNA
<213> ORGANISM: Marinobacter algicola

<400> SEQUENCE: 46
atgaaacgcc tgggcacact ggacgcttcc tggttggcgg tggaatcgga agacaccccg 60
atgcacgtcg gcaacctgca gattttttca ctaccggaag atgctccgga gacgtttcta 120
agagacatgc tcgcccgcat gaaagccgat gccgatgtag cgccgccctg gtgctacaag 180
ctcgcctttt cggggttcct gggccgcctg gtcgccccgt cctggaaggt cgacaagaag 240
ctggatctcg actaccacgt tcgacactcg gcgttgccgc gccccggcag tgaacgggaa 300
cttggcatcc tggtatccag gctgcattcc aacccgctgg atttttcccg cccgctttgg 360
gaatgccaca ttatcgaggg cctggagaac aaccgttttg ccctctacac caagatgcat 420
cattccatga ttgatggcat aagcggtgtt cggctgatgc agcgggtgct cagcgaggac 480
cccggtgaga ttaatatgct gccgccatgg tcggtacgcc cggagcggac acggggcagc 540
aagacagatt ccgaagccag catttcagcc gccctgtccc aggccatgga agccctgagg 600
attcaggccg acatggcgcc gaggctctgg aatgcgatga accgcctgat ccagtccgca 660
cggcacccgg aagaggggct gaccgcgccc tttgccggcc cggtttccgc cctcaatcac 720
cgggtcaccg gtcagcggcg gtttgccacc cagcactacc agctcgaacg gatcaaacag 780
gtcgcccagg cgtccaacgg ctccctgaac gacattgtgc tctacctctg tggcactgcc 840

-continued

```
ctgcgccgct ttcttgttga acaggatggt ttgccggata cgccactcac cgccggaatt    900

ccggtgaata tccgcccctc cgatgaccag ggcacgggca cccagatcag cttcatgatt    960

gcctcactgg cgaccgacga agccgatccc ctcaagcggc tgaagagcat caaacactct   1020

acccgcaggg ccaaacaaca ccttcagaaa ctgccgcgta aagccctgac ccaatacacc   1080

atgctgctga tgtcgcccta catcctgcag ttgatgtcag gcctgggcgg gcgaatgcgc   1140

ccggtgttca acgtgaccat ctccaacgtg ccagggccag ggaaaccct ttactatgaa     1200

ggagcacgac tggaggcgat gtacccggtt tcgcttattg cccacggcgg tgcgctcaac   1260

attacttgcc tgagctacgc cggctcgctc aacttcggtt tcacgggctg ccgcgatacg   1320

ttgcccagta tgcagaagct ggcggtctac accggtgagg ctttggatga actggaaagc   1380

ctggtttcgc caccaccaaa tcagaccaaa accaacgctc gaaaggcgcc tcgcaaaaag   1440

actgcggaaa agagctaa                                                 1458
```

<210> SEQ ID NO 47
<211> LENGTH: 485
<212> TYPE: PRT
<213> ORGANISM: Marinobacter algicola

<400> SEQUENCE: 47

```
Met Lys Arg Leu Gly Thr Leu Asp Ala Ser Trp Leu Ala Val Glu Ser
1               5                   10                  15

Glu Asp Thr Pro Met His Val Gly Asn Leu Gln Ile Phe Ser Leu Pro
            20                  25                  30

Glu Asp Ala Pro Glu Thr Phe Leu Arg Asp Met Leu Ala Arg Met Lys
        35                  40                  45

Ala Asp Ala Asp Val Ala Pro Pro Trp Cys Tyr Lys Leu Ala Phe Ser
    50                  55                  60

Gly Phe Leu Gly Arg Leu Val Ala Pro Ser Trp Lys Val Asp Lys Lys
65                  70                  75                  80

Leu Asp Leu Asp Tyr His Val Arg His Ser Ala Leu Pro Arg Pro Gly
                85                  90                  95

Ser Glu Arg Glu Leu Gly Ile Leu Val Ser Arg Leu His Ser Asn Pro
            100                 105                 110

Leu Asp Phe Ser Arg Pro Leu Trp Glu Cys His Ile Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Ser Glu Asp
145                 150                 155                 160

Pro Gly Glu Ile Asn Met Leu Pro Pro Trp Ser Val Arg Pro Glu Arg
                165                 170                 175

Thr Arg Gly Ser Lys Thr Asp Ser Glu Ala Ser Ile Ser Ala Ala Leu
            180                 185                 190

Ser Gln Ala Met Glu Ala Leu Arg Ile Gln Ala Asp Met Ala Pro Arg
        195                 200                 205

Leu Trp Asn Ala Met Asn Arg Leu Ile Gln Ser Ala Arg His Pro Glu
    210                 215                 220

Glu Gly Leu Thr Ala Pro Phe Ala Gly Pro Val Ser Ala Leu Asn His
225                 230                 235                 240

Arg Val Thr Gly Gln Arg Arg Phe Ala Thr Gln His Tyr Gln Leu Glu
                245                 250                 255

Arg Ile Lys Gln Val Ala Gln Ala Ser Asn Gly Ser Leu Asn Asp Ile
```

```
            260                 265                 270

Val Leu Tyr Leu Cys Gly Thr Ala Leu Arg Arg Phe Leu Val Glu Gln
        275                 280                 285

Asp Gly Leu Pro Asp Thr Pro Leu Thr Ala Gly Ile Pro Val Asn Ile
    290                 295                 300

Arg Pro Ser Asp Asp Gln Gly Thr Gly Thr Gln Ile Ser Phe Met Ile
305                 310                 315                 320

Ala Ser Leu Ala Thr Asp Glu Ala Asp Pro Leu Lys Arg Leu Lys Ser
                325                 330                 335

Ile Lys His Ser Thr Arg Arg Ala Lys Gln His Leu Gln Lys Leu Pro
            340                 345                 350

Arg Lys Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Gly Glu Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Val Ser Pro
    450                 455                 460

Pro Pro Asn Gln Thr Lys Thr Asn Ala Arg Lys Ala Pro Arg Lys Lys
465                 470                 475                 480

Thr Ala Glu Lys Ser
                485
```

<210> SEQ ID NO 48
<211> LENGTH: 1470
<212> TYPE: DNA
<213> ORGANISM: Marinobacter sp.

<400> SEQUENCE: 48

```
atgaaacgcc tggcaacatt ggacgcgtct tggctagcgg tcgagtctga cgatacaccc     60

atgcacgtgg gcaacttgca gattttcagc ctgcccgaca acgccccatc tacattcgcg    120

ggcgacttgg tcaaaagcat gaagcaagcc ggtaatgttg agcttccctg gggctgcaag    180

ctggtatggc caggctttct gggccgcgtt ctggcgccca cctggaagca cgacaagcat    240

attgatctgg attatcacgt gcgccactcg gccctaccaa aacccggtgg tgaacgcgaa    300

ctgggggaac tggtatcgcg cctgcactcc aacccgctgg atctgtcgcg gccgctgtgg    360

gagtgccaca tgatcgaagg gctggaacac aaccgttttg ccctgtacac gaagatgcat    420

cactgcatga ttgatggcat cagtggtgta cgcctgatgc aaagggtgct gagcaaatcc    480

cccgacgagc gcgacatgct gccaccctgg tcagtacgcc cggaaagcac gcgcggcaaa    540

aagaccgaca gcgaggccag cgtgccgggt gctatatccc aagctatgga agctctcaaa    600

ctgcagttgg gcttggcacc acggctgtgg caagccagca atcgcctgat tcactcggta    660

cgccatccgg aagacggtct gaccgcgccc ttcaccggcc cggtttccaa gatcaatcat    720

cgggttactg gccagcgccg cttcgccacc cagcagtatc agttagaaga tatgaaagcc    780

atggcccgcg cctcgggcag ctcgatgaac gacattgtgc tgtatttgtg cggtactgcg    840
```

```
ttgcggcgtt ttctgctgga acaggacgat ttgcctgaaa tatcattaac agcaggcata    900

ccggtcaaca ttcgcccggc ggatgacgaa ggcacaggaa cccagatcag cttcatgatt    960

gccgccctgg ccaccaacca acctgatccg ctaacgcgcc tgaaatgcat caaggaatct   1020

tcgtgcaaag ccaaagagca cttgcaaaaa ttgcccaaga aagcgttgac ccaatacacc   1080

atgatgctga tgtcgcccta catattgcag ctgatgtctg gcttgggcgg gcgcatgcga   1140

ccggtattta acgtaaccat ctccaacgtt ccggggccca ccgaagatct ttattacgaa   1200

ggcgccaaac tcgaagccat gtatccggtg tcgctgatca cccacggcgg agcgttgaac   1260

attacttgcc tgagctatgc cggatcattg aactttggtt tcactggttg ccgcgacacc   1320

ttacccagca tgcagaagct ggccgtgtat accggggaag cattggaaga actcagaacc   1380

ctgctgttac cgccaaagaa aaaacccagc ccacgcaaac ctagaacggc cgcgaaaaag   1440

aagcccgcgg tgaacagcaa cgctagctga                                    1470
```

<210> SEQ ID NO 49
<211> LENGTH: 489
<212> TYPE: PRT
<213> ORGANISM: Marinobacter sp.

<400> SEQUENCE: 49

```
Met Lys Arg Leu Ala Thr Leu Asp Ala Ser Trp Leu Ala Val Glu Ser
1               5                   10                  15

Asp Asp Thr Pro Met His Val Gly Asn Leu Gln Ile Phe Ser Leu Pro
            20                  25                  30

Asp Asn Ala Pro Ser Thr Phe Ala Gly Asp Leu Val Lys Ser Met Lys
        35                  40                  45

Gln Ala Gly Asn Val Glu Leu Pro Trp Gly Cys Lys Leu Val Trp Pro
    50                  55                  60

Gly Phe Leu Gly Arg Val Leu Ala Pro Thr Trp Lys His Asp Lys His
65                  70                  75                  80

Ile Asp Leu Asp Tyr His Val Arg His Ser Ala Leu Pro Lys Pro Gly
                85                  90                  95

Gly Glu Arg Glu Leu Gly Glu Leu Val Ser Arg Leu His Ser Asn Pro
            100                 105                 110

Leu Asp Leu Ser Arg Pro Leu Trp Glu Cys His Met Ile Glu Gly Leu
        115                 120                 125

Glu His Asn Arg Phe Ala Leu Tyr Thr Lys Met His His Cys Met Ile
    130                 135                 140

Asp Gly Ile Ser Gly Val Arg Leu Met Gln Arg Val Leu Ser Lys Ser
145                 150                 155                 160

Pro Asp Glu Arg Asp Met Leu Pro Pro Trp Ser Val Arg Pro Glu Ser
                165                 170                 175

Thr Arg Gly Lys Lys Thr Asp Ser Glu Ala Ser Val Pro Gly Ala Ile
            180                 185                 190

Ser Gln Ala Met Glu Ala Leu Lys Leu Gln Leu Gly Leu Ala Pro Arg
        195                 200                 205

Leu Trp Gln Ala Ser Asn Arg Leu Ile His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln Gln Tyr Gln Leu Glu
                245                 250                 255
```

```
Asp Met Lys Ala Met Ala Arg Ala Ser Gly Ser Ser Met Asn Asp Ile
            260                 265                 270

Val Leu Tyr Leu Cys Gly Thr Ala Leu Arg Arg Phe Leu Leu Glu Gln
        275                 280                 285

Asp Asp Leu Pro Glu Ile Ser Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ala Leu Ala Thr Asn Gln Pro Asp Pro Leu Thr Arg Leu Lys Cys
                325                 330                 335

Ile Lys Glu Ser Ser Cys Lys Ala Lys Glu His Leu Gln Lys Leu Pro
            340                 345                 350

Lys Lys Ala Leu Thr Gln Tyr Thr Met Met Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Thr Glu Asp Leu Tyr Tyr Glu
385                 390                 395                 400

Gly Ala Lys Leu Glu Ala Met Tyr Pro Val Ser Leu Ile Thr His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Glu Glu Leu Arg Thr Leu Leu Leu Pro
    450                 455                 460

Pro Lys Lys Lys Pro Ser Pro Arg Lys Pro Arg Thr Ala Ala Lys Lys
465                 470                 475                 480

Lys Pro Ala Val Asn Ser Asn Ala Ser
                485
```

<210> SEQ ID NO 50
<211> LENGTH: 549
<212> TYPE: DNA
<213> ORGANISM: Photobacterium profundum

<400> SEQUENCE: 50

```
atgggtaaca cattactggt tgttggtgat agcttgagcg cgggctatca aatgcgtgca      60

gaacaaagct ggccggtgtt actgcaaccc gcattaaagc aacaaggtca cgaaatcacc     120

gttgtaaatg ccagtatttc aggtgataca acaggaaacg gcttggctcg cttgcctaca     180

ttactacaac aacataaacc agcttacgtc atcatagaac tcggggcgaa tgatggctta     240

cgtggtttcc ctcaaggtac tattcgtaac aatctcagcc aaatgatcac tgaaattcaa     300

aatgctgatg ccaagccaat gctcgtgcag atcaaagtgc cgcccaatta cggcaaacgc     360

tacagtgata tgttcagttc tatttaccct caactcagta aagagttagc cacaccattg     420

ttacctttct ttttagagca gatcatttta aaacaagaat ggatgatgaa tgacggttta     480

catcctaaat ctgatgctca gccgtggatt gccgaatata tggctgagaa tatcgcgcct     540

tatttataa                                                             549
```

<210> SEQ ID NO 51
<211> LENGTH: 182
<212> TYPE: PRT
<213> ORGANISM: Photobacterium profundum

<400> SEQUENCE: 51

Met Gly Asn Thr Leu Leu Val Val Gly Asp Ser Leu Ser Ala Gly Tyr
1               5                   10                  15

Gln Met Arg Ala Glu Gln Ser Trp Pro Val Leu Leu Gln Pro Ala Leu
            20                  25                  30

Lys Gln Gln Gly His Glu Ile Thr Val Val Asn Ala Ser Ile Ser Gly
        35                  40                  45

Asp Thr Thr Gly Asn Gly Leu Ala Arg Leu Pro Thr Leu Leu Gln Gln
    50                  55                  60

His Lys Pro Ala Tyr Val Ile Ile Glu Leu Gly Ala Asn Asp Gly Leu
65                  70                  75                  80

Arg Gly Phe Pro Gln Gly Thr Ile Arg Asn Asn Leu Ser Gln Met Ile
                85                  90                  95

Thr Glu Ile Gln Asn Ala Asp Ala Lys Pro Met Leu Val Gln Ile Lys
            100                 105                 110

Val Pro Pro Asn Tyr Gly Lys Arg Tyr Ser Asp Met Phe Ser Ser Ile
        115                 120                 125

Tyr Pro Gln Leu Ser Lys Glu Leu Ala Thr Pro Leu Leu Pro Phe Phe
    130                 135                 140

Leu Glu Gln Ile Ile Leu Lys Gln Glu Trp Met Met Asn Asp Gly Leu
145                 150                 155                 160

His Pro Lys Ser Asp Ala Gln Pro Trp Ile Ala Glu Tyr Met Ala Glu
                165                 170                 175

Asn Ile Ala Pro Tyr Leu
            180

<210> SEQ ID NO 52
<211> LENGTH: 549
<212> TYPE: DNA
<213> ORGANISM: Photobacterium profundum

<400> SEQUENCE: 52
atgggtaaca cattactggt tgttggtgat agcttgagcg cgggctatca aatgcgtgca 60
gaacaaagct ggccggtgtt actgcaaccc gcattaaagc aacaaggtca cgaaatcacc 120
gttgtaaatg ccagtattgt cggtgacaca acaggaaacg gcttggctcg cttgcctacg 180
ttactacaac aacataaacc agcttacgtc atcatagaac tcggggcgaa tgatggcctg 240
cgtggtttcc cgcaaggtac tattcgtaac aatctgagcc aaatgatcac tgaaattcaa 300
aatgctgatg ccaagccaat gctcgtgcaa atcaaagtgc cgcccaatca cggcaaacgc 360
tacagtgata tgttcagttc tatttaccct caactcagta aagagttagc cacaccattg 420
ttacctttct ttttagagca gatcatttta aaacaagaat ggatgatgaa tgacggttta 480
catcctaaat ccgatgctca gccgtggatt gccgaatata tggctgagaa tatcgcgcct 540
tatttataa 549

<210> SEQ ID NO 53
<211> LENGTH: 182
<212> TYPE: PRT
<213> ORGANISM: Photobacterium profundum

<400> SEQUENCE: 53

Met Gly Asn Thr Leu Leu Val Val Gly Asp Ser Leu Ser Ala Gly Tyr
1               5                   10                  15

Gln Met Arg Ala Glu Gln Ser Trp Pro Val Leu Leu Gln Pro Ala Leu
            20                  25                  30

Lys Gln Gln Gly His Glu Ile Thr Val Val Asn Ala Ser Ile Val Gly
35 40 45

Asp Thr Thr Gly Asn Gly Leu Ala Arg Leu Pro Thr Leu Leu Gln Gln
50 55 60

His Lys Pro Ala Tyr Val Ile Ile Glu Leu Gly Ala Asn Asp Gly Leu
65 70 75 80

Arg Gly Phe Pro Gln Gly Thr Ile Arg Asn Asn Leu Ser Gln Met Ile
85 90 95

Thr Glu Ile Gln Asn Ala Asp Ala Lys Pro Met Leu Val Gln Ile Lys
100 105 110

Val Pro Pro Asn His Gly Lys Arg Tyr Ser Asp Met Phe Ser Ser Ile
115 120 125

Tyr Pro Gln Leu Ser Lys Glu Leu Ala Thr Pro Leu Leu Pro Phe Phe
130 135 140

Leu Glu Gln Ile Ile Leu Lys Gln Glu Trp Met Met Asn Asp Gly Leu
145 150 155 160

His Pro Lys Ser Asp Ala Gln Pro Trp Ile Ala Glu Tyr Met Ala Glu
165 170 175

Asn Ile Ala Pro Tyr Leu
180

<210> SEQ ID NO 54
<211> LENGTH: 549
<212> TYPE: DNA
<213> ORGANISM: Photobacterium profundum

<400> SEQUENCE: 54
atgggtaaca cattactggt tgttggtgat agcttgagcg cgggctatca aatgcgtgca 60
gaacaaagct ggccggtgtt actgcaaccc gcattaaagc aacaaggtca cgaaatcacc 120
gttgtaaatg ccagtattgt cggtatgaca acaagaaacg gcttggctcg cttgcctacg 180
ttactacaac aacataaacc agcttacgtc atcatagaac tcggggcggt ggatggcctg 240
cgtggtttcc cgcaaggtac tattcgtaac aatctgagcc aaatgatcac tgaaattcaa 300
aatgctgatg ccaagccaat gctcgtgcaa atcaaagtgc cgcccaatca cggcaaacgc 360
tacagtgata tgttcagttc tatttaccct caactcagta aagagttagc cacaccattg 420
ttacctttct ttttagagca gatcatttta aaacaagaat ggatgatgaa tgacggttta 480
catcctaaat ccgatgctca gccgtggatt gccgaatata tggctgagaa tatcgcgcct 540
tatttataa 549

<210> SEQ ID NO 55
<211> LENGTH: 182
<212> TYPE: PRT
<213> ORGANISM: Photobacterium profundum

<400> SEQUENCE: 55

Met Gly Asn Thr Leu Leu Val Val Gly Asp Ser Leu Ser Ala Gly Tyr
1 5 10 15

Gln Met Arg Ala Glu Gln Ser Trp Pro Val Leu Leu Gln Pro Ala Leu
20 25 30

Lys Gln Gln Gly His Glu Ile Thr Val Val Asn Ala Ser Ile Val Gly
35 40 45

Met Thr Thr Arg Asn Gly Leu Ala Arg Leu Pro Thr Leu Leu Gln Gln
50 55 60

```
His Lys Pro Ala Tyr Val Ile Ile Glu Leu Gly Ala Val Asp Gly Leu
65                  70                  75                  80

Arg Gly Phe Pro Gln Gly Thr Ile Arg Asn Asn Leu Ser Gln Met Ile
                85                  90                  95

Thr Glu Ile Gln Asn Ala Asp Ala Lys Pro Met Leu Val Gln Ile Lys
            100                 105                 110

Val Pro Pro Asn His Gly Lys Arg Tyr Ser Asp Met Phe Ser Ser Ile
        115                 120                 125

Tyr Pro Gln Leu Ser Lys Glu Leu Ala Thr Pro Leu Leu Pro Phe Phe
    130                 135                 140

Leu Glu Gln Ile Ile Leu Lys Gln Glu Trp Met Met Asn Asp Gly Leu
145                 150                 155                 160

His Pro Lys Ser Asp Ala Gln Pro Trp Ile Ala Glu Tyr Met Ala Glu
                165                 170                 175

Asn Ile Ala Pro Tyr Leu
            180


<210> SEQ ID NO 56
<211> LENGTH: 549
<212> TYPE: DNA
<213> ORGANISM: Photobacterium profundum

<400> SEQUENCE: 56

atgggcaaca cccttctcgt cgtcggcgat tcactctccg caggctacca aatgcgtgca      60

gaacaaagct ggccggtatt gctgcaacct gccctgaaac agcagggtca tgagatcact     120

gtggttaatg caagcattgt gggtatgacc acgcgtaacg gtttggctcg tctgccaacc     180

ctgttacaac aacacaagcc ggcgtatgtt atcatcgaat tgggtgcggt cgatggcttg     240

cgcggttttc cgcaaggcac gattcgtaat aacctgagcc agatgattac cgagattcag     300

aacgctgacg cgaagccgat gctggttcag atcaaagtgc cgccgaacca cggtaaacgc     360

tacagcgaca tgttcagcag catttacccg cagctgtcta aggaactggc gacgccactg     420

ctgccgttct ttctggagca gattatcctg aagcaagaat ggatgatgaa tgacggtctg     480

catccgaaaa gcgatgcgca gccgtggatc gcagagtata tggccgagaa tatcgcgccg     540

tatttgtaa                                                             549


<210> SEQ ID NO 57
<211> LENGTH: 549
<212> TYPE: DNA
<213> ORGANISM: Photobacterium profundum

<400> SEQUENCE: 57

atgggtaaca cattactggt tgttggtgat agcttgagcg cgggctatca aatgcgtgca      60

gaacaaagct ggccggtgtt actgcaaccc gcattaaagc aacaaggtca cgaaatcacc     120

gttgtaaatg ccagtattgt cggtatgctg acaagaaacg gcttggctcg cttgcctacg     180

ttactacaac aacataaacc agcttacgtc atcatagaac tcggggcggt ggatggcctg     240

cgtggtttcc cgcaaggtac tattcgtaac aatctgagcc aaatgatcac tgaaattcaa     300

aatgctgatg ccaagccaat gctcgtgcaa atcaaagtgc cgcccaatca cggcaaacgc     360

tacagtgata tgttcagttc tatttaccct caactcagta aagagttagc cacaccattg     420

ttacctttct ttttagagca gatctattta aaacaagaat ggatgatgaa tgacggttta     480

catcctaaat ccgatgctca gccgtggatt gccgaatata tggctgagaa tatcgcgcct     540

tatttataa                                                             549
```

<210> SEQ ID NO 58
<211> LENGTH: 182
<212> TYPE: PRT
<213> ORGANISM: Photobacterium profundum

<400> SEQUENCE: 58

```
Met Gly Asn Thr Leu Leu Val Val Gly Asp Ser Leu Ser Ala Gly Tyr
1               5                   10                  15

Gln Met Arg Ala Glu Gln Ser Trp Pro Val Leu Leu Gln Pro Ala Leu
            20                  25                  30

Lys Gln Gln Gly His Glu Ile Thr Val Val Asn Ala Ser Ile Val Gly
        35                  40                  45

Met Leu Thr Arg Asn Gly Leu Ala Arg Leu Pro Thr Leu Leu Gln Gln
    50                  55                  60

His Lys Pro Ala Tyr Val Ile Ile Glu Leu Gly Ala Val Asp Gly Leu
65                  70                  75                  80

Arg Gly Phe Pro Gln Gly Thr Ile Arg Asn Asn Leu Ser Gln Met Ile
                85                  90                  95

Thr Glu Ile Gln Asn Ala Asp Ala Lys Pro Met Leu Val Gln Ile Lys
            100                 105                 110

Val Pro Pro Asn His Gly Lys Arg Tyr Ser Asp Met Phe Ser Ser Ile
        115                 120                 125

Tyr Pro Gln Leu Ser Lys Glu Leu Ala Thr Pro Leu Leu Pro Phe Phe
    130                 135                 140

Leu Glu Gln Ile Tyr Leu Lys Gln Glu Trp Met Met Asn Asp Gly Leu
145                 150                 155                 160

His Pro Lys Ser Asp Ala Gln Pro Trp Ile Ala Glu Tyr Met Ala Glu
                165                 170                 175

Asn Ile Ala Pro Tyr Leu
            180
```

<210> SEQ ID NO 59
<211> LENGTH: 549
<212> TYPE: DNA
<213> ORGANISM: Photobacterium profundum

<400> SEQUENCE: 59

```
atgggcaaca cccttctcgt cgtcggcgat tcactctccg caggctacca aatgcgtgca     60

gaacaaagct ggccggtatt gctgcaacct gccctgaaac agcagggtca tgagatcact    120

gtggttaatg caagcattgt gggtatgctg acgcgtaacg gtttggctcg tctgccaacc    180

ctgttacaac aacacaagcc ggcgtatgtt atcatcgaat tgggtgcggt cgatggcttg    240

cgcggttttc cgcaaggcac gattcgtaat aacctgagcc agatgattac cgagattcag    300

aacgctgacg cgaagccgat gctggttcag atcaaagtgc cgccgaacca cggtaaacgc    360

tacagcgaca tgttcagcag catttacccg cagctgtcta aggaactggc gacgccactg    420

ctgccgttct ttctggagca gatttatctg aagcaagaat ggatgatgaa tgacggtctg    480

catccgaaaa gcgatgcgca gccgtggatc gcagagtata tggccgagaa tatcgcgccg    540

tatttgtaa                                                            549
```

<210> SEQ ID NO 60
<211> LENGTH: 549
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 60
atgggcaaca cccttctcgt cgtcggcgat tcactctccg caggctacca aatgcgtgca 60
gaacaaagct ggccggtatt gctgcaacct gccctgaaac agcagggtca tgagatcact 120
gtggttaatg caagcattgt gggtatgctg acgcgtaacg gtttggctcg tctgccaacc 180
ctgttacaac aacacaagcc ggcgtatgtt atcatcgaat tgggtgcggt cgatggcttg 240
cgcggttttc cgcaaggcac gattcgtaat aacctgagcc agatgattac cgagattcag 300
aacgctgacg cgaagccgat gctggttcag atcaaagtgc cgccgtttca cggtaaacgc 360
tacagcgaca tgttcagcag catttacccg cagctgtcta aggaactggc gacgccactg 420
ctgccgttct ttctggagca gatttatctg aagcaagaat ggatgatgaa tgacggtctg 480
catccgaaaa gcgatgcgca gccgtggatc gcagagtata tggccgagaa tatcgcgccg 540
tatttgtaa 549

<210> SEQ ID NO 61
<211> LENGTH: 182
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Met Gly Asn Thr Leu Leu Val Val Gly Asp Ser Leu Ser Ala Gly Tyr
1 5 10 15

Gln Met Arg Ala Glu Gln Ser Trp Pro Val Leu Leu Gln Pro Ala Leu
20 25 30

Lys Gln Gln Gly His Glu Ile Thr Val Val Asn Ala Ser Ile Val Gly
35 40 45

Met Leu Thr Arg Asn Gly Leu Ala Arg Leu Pro Thr Leu Leu Gln Gln
50 55 60

His Lys Pro Ala Tyr Val Ile Ile Glu Leu Gly Ala Val Asp Gly Leu
65 70 75 80

Arg Gly Phe Pro Gln Gly Thr Ile Arg Asn Asn Leu Ser Gln Met Ile
85 90 95

Thr Glu Ile Gln Asn Ala Asp Ala Lys Pro Met Leu Val Gln Ile Lys
100 105 110

Val Pro Pro Phe His Gly Lys Arg Tyr Ser Asp Met Phe Ser Ser Ile
115 120 125

Tyr Pro Gln Leu Ser Lys Glu Leu Ala Thr Pro Leu Leu Pro Phe Phe
130 135 140

Leu Glu Gln Ile Tyr Leu Lys Gln Glu Trp Met Met Asn Asp Gly Leu
145 150 155 160

His Pro Lys Ser Asp Ala Gln Pro Trp Ile Ala Glu Tyr Met Ala Glu
165 170 175

Asn Ile Ala Pro Tyr Leu
180

<210> SEQ ID NO 62
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
atgggcaaca cccttctcgt cgtcggcgat tcactctccg caggctacca aatgcgtgca 60
gaacaaagct ggccggtatt gctgcaacct gccctgaaac gccggggtca tgagatcact 120
gtggttaatg caagcattgt gggtatgctg acgcgtcggg gtttggctcg tctgccaacc 180
ctgttacaac aacacaagcc ggcgtatgtt atcatcgaat tgggtgcggt cgatggcttg 240
cgcggttttc cgcaaggcac gattcgtaat aacctgagcc agatgattac cgagattcag 300
aacgctgacg cgaagccgat gctggttcag atcaaactcc cgccgtggca cggtaaacgc 360
tacagcgaca tgttcagcag catttacccg cagctgtcta aggaactggc gacgccactg 420
ctgccgttct ttctggagca gatttatctg aagcaagaat ggatgatgaa tgacggtctg 480
catccgaaaa gcgatgcgca gccgtggatc gcagagtata tggccgagaa tatcgcgccg 540
tatttgtaa 549

<210> SEQ ID NO 63
<211> LENGTH: 182
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Met Gly Asn Thr Leu Leu Val Val Gly Asp Ser Leu Ser Ala Gly Tyr
1 5 10 15

Gln Met Arg Ala Glu Gln Ser Trp Pro Val Leu Leu Gln Pro Ala Leu
20 25 30

Lys Arg Arg Gly His Glu Ile Thr Val Val Asn Ala Ser Ile Val Gly
35 40 45

Met Leu Thr Arg Arg Gly Leu Ala Arg Leu Pro Thr Leu Leu Gln Gln
50 55 60

His Lys Pro Ala Tyr Val Ile Ile Glu Leu Gly Ala Val Asp Gly Leu
65 70 75 80

Arg Gly Phe Pro Gln Gly Thr Ile Arg Asn Asn Leu Ser Gln Met Ile
85 90 95

Thr Glu Ile Gln Asn Ala Asp Ala Lys Pro Met Leu Val Gln Ile Lys
100 105 110

Leu Pro Pro Trp His Gly Lys Arg Tyr Ser Asp Met Phe Ser Ser Ile
115 120 125

Tyr Pro Gln Leu Ser Lys Glu Leu Ala Thr Pro Leu Leu Pro Phe Phe
130 135 140

Leu Glu Gln Ile Tyr Leu Lys Gln Glu Trp Met Met Asn Asp Gly Leu
145 150 155 160

His Pro Lys Ser Asp Ala Gln Pro Trp Ile Ala Glu Tyr Met Ala Glu
165 170 175

Asn Ile Ala Pro Tyr Leu
180

<210> SEQ ID NO 64
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
atgggcaaca cccttctcgt cgtcggcgat tcactctccg caggctacca aatgcgtgca     60

gaacaaagct ggccggtatt gctgcaacct gccctgaaac gccagggtca tgagatcact    120

gtggttaatg caagcattgt gggtatgctg acgcgtaagg gtttggctcg tctgccaacc    180

ctgttacaac aacacaagcc ggcgtatgtt atcatcgaat tgggtgcggt cgatggcttg    240

cgcggttttc cgcaaggcac gattcgtaat aacctgagcc agatgattac cgagattcag    300

aacgctgacg cgaagccgat gctggttcag atcaaactcc cgccgtggca cggtaaacgc    360

tacagcgaca tgttcagcag catttacccg cagctgtcta aggaactggc gacgccactg    420

ctgccgttct ttctggagca gatttatatg aagcaagaat ggatgatgaa tgacggtctg    480

catccgaaaa gcgatgcgca gccgtggatc gcagagtata tggccgagaa tatcgcgccg    540

tatttgtaa                                                            549
```

<210> SEQ ID NO 65
<211> LENGTH: 182
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Met Gly Asn Thr Leu Leu Val Val Gly Asp Ser Leu Ser Ala Gly Tyr
1               5                   10                  15

Gln Met Arg Ala Glu Gln Ser Trp Pro Val Leu Leu Gln Pro Ala Leu
            20                  25                  30

Lys Arg Gln Gly His Glu Ile Thr Val Val Asn Ala Ser Ile Val Gly
        35                  40                  45

Met Leu Thr Arg Lys Gly Leu Ala Arg Leu Pro Thr Leu Leu Gln Gln
    50                  55                  60

His Lys Pro Ala Tyr Val Ile Ile Glu Leu Gly Ala Val Asp Gly Leu
65                  70                  75                  80

Arg Gly Phe Pro Gln Gly Thr Ile Arg Asn Asn Leu Ser Gln Met Ile
                85                  90                  95

Thr Glu Ile Gln Asn Ala Asp Ala Lys Pro Met Leu Val Gln Ile Lys
            100                 105                 110

Leu Pro Pro Trp His Gly Lys Arg Tyr Ser Asp Met Phe Ser Ser Ile
        115                 120                 125

Tyr Pro Gln Leu Ser Lys Glu Leu Ala Thr Pro Leu Leu Pro Phe Phe
    130                 135                 140

Leu Glu Gln Ile Tyr Met Lys Gln Glu Trp Met Met Asn Asp Gly Leu
145                 150                 155                 160

His Pro Lys Ser Asp Ala Gln Pro Trp Ile Ala Glu Tyr Met Ala Glu
                165                 170                 175

Asn Ile Ala Pro Tyr Leu
            180
```

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:

<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (4)..(4)
<223> OTHER INFORMATION: Val, Ile or Leu
<220> FEATURE:
<221> NAME/KEY: MOD_RES
<222> LOCATION: (7)..(7)
<223> OTHER INFORMATION: Ala or Gly

<400> SEQUENCE: 66

```
Leu Gly Xaa Xaa Asp Ala Xaa Leu Arg Gly
1               5                   10
```

<210> SEQ ID NO 67
<211> LENGTH: 472
<212> TYPE: PRT
<213> ORGANISM: Marinobacter hydrocarbonoclasticus

<400> SEQUENCE: 67

```
Lys Arg Leu Gly Thr Leu Asp Ala Ser Trp Leu Ala Val Glu Ser Glu
1               5                   10                  15

Asp Thr Pro Met His Val Gly Thr Leu Gln Ile Phe Ser Leu Pro Glu
            20                  25                  30

Gly Ala Pro Glu Thr Phe Leu Arg Asp Met Val Thr Arg Met Lys Glu
        35                  40                  45

Ala Gly Asp Val Ala Pro Pro Trp Gly Tyr Lys Leu Ala Trp Ser Gly
    50                  55                  60

Phe Leu Gly Arg Val Ile Ala Pro Ala Trp Lys Val Asp Lys Asp Ile
65                  70                  75                  80

Asp Leu Asp Tyr His Val Arg His Ser Ala Leu Pro Arg Pro Gly Gly
                85                  90                  95

Glu Arg Glu Leu Gly Ile Leu Val Ser Arg Leu His Ser Asn Pro Leu
            100                 105                 110

Asp Phe Ser Arg Pro Leu Trp Glu Cys His Val Ile Glu Gly Leu Glu
        115                 120                 125

Asn Asn Arg Phe Ala Leu Tyr Thr Lys Met His His Ser Met Ile Asp
    130                 135                 140

Gly Ile Ser Gly Val Arg Leu Met Gln Arg Val Leu Thr Thr Asp Pro
145                 150                 155                 160

Glu Arg Cys Asn Met Pro Pro Pro Trp Thr Val Arg Pro His Gln Arg
                165                 170                 175

Arg Gly Ala Lys Thr Asp Lys Glu Ala Ser Val Pro Ala Ala Val Ser
            180                 185                 190

Gln Ala Met Asp Ala Leu Lys Leu Gln Ala Asp Met Ala Pro Arg Leu
        195                 200                 205

Trp Gln Ala Gly Asn Arg Leu Val His Ser Val Arg His Pro Glu Asp
    210                 215                 220

Gly Leu Thr Ala Pro Phe Thr Gly Pro Val Ser Val Leu Asn His Arg
225                 230                 235                 240

Val Thr Ala Gln Arg Arg Phe Ala Thr Gln His Tyr Gln Leu Asp Arg
                245                 250                 255

Leu Lys Asn Leu Ala His Ala Ser Gly Gly Ser Leu Asn Asp Ile Val
            260                 265                 270

Leu Tyr Leu Cys Gly Thr Ala Leu Arg Arg Phe Leu Ala Glu Gln Asn
        275                 280                 285
```

-continued

```
Asn Leu Pro Asp Thr Pro Leu Thr Ala Gly Ile Pro Val Asn Ile Arg
    290                 295                 300

Pro Ala Asp Asp Glu Gly Thr Gly Thr Gln Ile Ser Phe Met Ile Ala
305                 310                 315                 320

Ser Leu Ala Thr Asp Glu Ala Asp Pro Leu Asn Arg Leu Gln Gln Ile
                325                 330                 335

Lys Thr Ser Thr Arg Arg Ala Lys Glu His Leu Gln Lys Leu Pro Lys
            340                 345                 350

Ser Ala Leu Thr Gln Tyr Thr Met Leu Leu Met Ser Pro Tyr Ile Leu
        355                 360                 365

Gln Leu Met Ser Gly Leu Gly Gly Arg Met Arg Pro Val Phe Asn Val
    370                 375                 380

Thr Ile Ser Asn Val Pro Gly Pro Glu Gly Thr Leu Tyr Tyr Glu Gly
385                 390                 395                 400

Ala Arg Leu Glu Ala Met Tyr Pro Val Ser Leu Ile Ala His Gly Gly
                405                 410                 415

Ala Leu Asn Ile Thr Cys Leu Ser Tyr Ala Gly Ser Leu Asn Phe Gly
            420                 425                 430

Phe Thr Gly Cys Arg Asp Thr Leu Pro Ser Met Gln Lys Leu Ala Val
        435                 440                 445

Tyr Thr Gly Glu Ala Leu Asp Glu Leu Glu Ser Leu Ile Leu Pro Pro
    450                 455                 460

Lys Lys Arg Ala Arg Thr Arg Lys
465                 470
```

ENZYME VARIANTS WITH IMPROVED ESTER SYNTHASE PROPERTIES

CROSS-REFERENCE TO RELATED APPLICATIONS

This application is a continuation of U.S. application Ser. No. 14/424,387, filed Feb. 26, 2015, which is the 371 National Stage of PCT/US2013/032564, filed Mar. 15, 2013 which claims the benefit of U.S. Provisional Application No. 61/708,424, filed Oct. 1, 2012, and U.S. Provisional Application No. 61/701,191, filed Sep. 14, 2012, the entire disclosures of which are hereby incorporated by reference.

SEQUENCE LISTING

The instant application contains a Sequence Listing which has been submitted in ASCII format via EFS-Web and is hereby incorporated by reference in its entirety. The ASCII copy, created on Mar. 12, 2013, is named LS00043-44PCT-_SL.txt and is 164,228 bytes in size.

FIELD

The disclosure relates to enzyme variants with improved ester synthase properties for the production of fatty esters.

BACKGROUND

Petroleum is a limited, natural resource found in the earth in liquid, gaseous, or solid forms. However, petroleum products are developed at considerable costs, both financial and environmental. In its natural form, crude petroleum extracted from the Earth has few commercial uses. It is a mixture of hydrocarbons, e.g., paraffins (or alkanes), olefins (or alkenes), alkynes, naphthenes (or cylcoalkanes), aliphatic compounds, aromatic compounds, etc. of varying length and complexity. In addition, crude petroleum contains other organic compounds (e.g., organic compounds containing nitrogen, oxygen, sulfur, etc.) and impurities (e.g., sulfur, salt, acid, metals, etc.). Due to its high energy density and its easy transportability, most petroleum is refined into fuels, such as transportation fuels (e.g., gasoline, diesel, aviation fuel, etc.), heating oil, liquefied petroleum gas, etc.

Petrochemicals can be used to make specialty chemicals, such as plastics, resins, fibers, elastomers, pharmaceuticals, lubricants, or gels. Examples of specialty chemicals which can be produced from petrochemical raw materials include fatty acids, hydrocarbons (e.g., long chain hydrocarbons, branched chain hydrocarbons, saturated hydrocarbons, unsaturated hydrocarbons, etc.), fatty alcohols, fatty esters, fatty aldehydes, ketones, lubricants, etc. Specialty chemicals have many commercial uses. Fatty acids are used commercially as surfactants. Surfactants can be found in detergents and soaps. Fatty acids can also be used as additives in fuels, lubricating oils, paints, lacquers, candles, shortenings, cosmetics, and emulsifiers. In addition, fatty acids are used as accelerator activators in rubber products. Fatty acids can also be used as a feedstock to produce methyl esters, amides, amines, acid chlorides, anhydrides, ketene dimers, and peroxy acids and esters.

Esters have many commercial uses. For example, biodiesel, an alternative fuel, is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

There is a need for alternative routes to create both fuels and products currently derived from petroleum. As such, microbial systems offer the potential for the biological production of numerous types of biofuels and chemicals. Renewable fuels and chemicals can be derived from genetically engineered organisms (such as bacteria, yeast and algae). Naturally occurring biosynthetic pathways can be genetically altered to enable engineered organisms to synthesize renewable fuel and chemical products. In addition, microbes can be tailored, or metabolically engineered, to utilize various carbon sources as feedstock for the production of fuel and chemical products. For example, FAME (fatty acid methyl ester) can be produced by adding methanol to a culture of a recombinant host cell expressing a wax ester synthase, for example, a wax ester synthase derived from *Marinobacter hydrocarbonoclasticus* ("*M. hydrocarbonoclasticus*"). However, the expression of the wild type wax ester synthase from *M. hydrocarbonoclasticus* does not produce significant amounts of FAME, thus development of an improved wax ester synthase is highly desirable. In addition, the wild-type wax ester synthase from *M. hydrocarbonoclasticus* produces significant amounts of beta hydroxy ("β-OH") esters, which are not typically found in fuel or chemicals derived from plant sources. See, e.g., Patent Cooperation Treaty Application No. PCT/US12/31682, which is incorporated by reference herein. Thus, it would be desirable to engineer an ester synthase to produce higher yields of fatty ester; and an ester synthase that produces higher yields of fatty ester without producing significant amounts of β-OH ester, when expressed in a recombinant host cell. Finally, it would be desirable to engineer other enzymes that have ester synthase activity to further improve the yield of fatty ester production.

Notwithstanding the advances in the field, there remains a need for improvements in genetically modified enzymes, recombinant host cells, methods and systems in order to achieve robust and cost-effective production of fuels and chemicals of interest by fermentation of recombinant host cells. The present disclosure addresses this need by providing a number of ester synthase enzyme variants that increase the yield of fatty esters. Some of the ester synthase enzyme variants of the disclosure also alter (i.e., increase or reduce) the β-OH ester content of the fatty ester composition produced by fermentation of recombinant host cells that express the ester synthase enzyme variants. The present disclosure further addresses this need by providing a number of thioesterase variants that have been engineered to have greater ester synthase activity, thereby further enhancing fatty ester production.

SUMMARY

One aspect of the disclosure provides a variant ester synthase polypeptide having SEQ ID NO: 2, wherein the variant ester synthase polypeptide is genetically engineered to have at least one mutation at an amino acid position including, but not limited to, amino acids 4, 5, 7, 15, 24, 30, 33, 39, 40, 41, 43, 44, 58, 73, 76, 77, 78, 80, 98, 99, 101, 102, 111, 122, 131, 146, 147, 149, 150, 155, 157, 162, 164, 166, 170, 171, 172, 173, 177, 179, 182, 184, 185, 186, 187, 188, 190, 192, 193, 195, 197, 201, 202, 203, 206, 207, 212, 216, 219, 234, 239, 242, 243, 244, 246, 255, 257, 258, 259, 260, 262, 263, 264, 265, 266, 267, 285, 288, 289, 293, 294, 301, 302, 303, 304, 306, 307, 309, 310, 311, 313, 314, 315, 316, 317, 319, 320, 323, 328, 334, 348, 349, 351, 352, 353, 356, 357, 360, 366, 375, 381, 393, 394, 395, 409, 411, 413, 420, 424, 442, 443, 447, 454, 455, 457, 458, 461, 466, 468, and 472, wherein the variant ester synthase polypeptide has improved fatty acid methyl ester activity compared to a corresponding wild type polypeptide. In a related aspect, the variant polypeptide is a *Marinobacter hydrocarbonoclasticus* (WS377) ester synthase polypeptide. In another related aspect, the expression of the variant ester synthase polypeptide in a recombinant host cell results in a higher titer of fatty ester compositions compared to a recombinant host cell expressing the corresponding wild type polypeptide. The titer is at least about 5 percent or greater. The fatty ester compositions include, but are not limited to, fatty acid methyl esters (FAME), fatty acid ethyl esters (FAEE), fatty acid propyl esters, fatty acid isopropyl esters, fatty acid butyl esters, monoglycerides, fatty acid isobutyl esters, fatty acid 2-butyl esters, and fatty acid tert-butyl esters. The variant ester synthase has improved ester synthase activity, particularly improved fatty acid methyl ester activity that results in improved properties including, but not limited to, increased beta hydroxy esters, decreased beta hydroxyl esters, increased chain lengths of fatty acid esters, and decreased chain lengths of fatty acid esters.

Another aspect of the disclosure provides a variant ester synthase polypeptide having SEQ ID NO: 2, wherein the variant ester synthase polypeptide is genetically engineered to have at least one mutation at an amino acid position including, but not limited to, amino acids 7, 24, 30, 41, 99, 111, 122, 146, 147, 149, 150, 171, 172, 173, 179, 187, 192, 212, 234, 239, 244, 246, 258, 264, 266, 267, 285, 301, 302, 303, 304, 306, 307, 309, 310, 311, 313, 314, 315, 316, 320, 348, 349, 352, 356, 357, 360, 375, 381, 393, 409, 411, 424, 443, 455, 457, 458, 461 and 472. The expression of the variant ester synthase polypeptide in a recombinant host cell may result in the production of an altered percentage of beta hydroxy esters as compared to a recombinant host cell expressing the corresponding wild type ester synthase polypeptide, wherein the altered percentage of beta hydroxy esters is an increased or decreased percentage of beta hydroxy esters.

Another aspect of the disclosure provides a variant ester synthase polypeptide having SEQ ID NO: 2, wherein the variant ester synthase polypeptide is genetically engineered to have at least one mutation at an amino acid position including, but not limited to, amino acids 5, 7, 15, 24, 33, 44, 58, 73, 78, 101, 111, 162, 171, 179, 184, 187, 188, 192, 201, 207, 212, 234, 243, 244, 255, 257, 267, 307, 310, 317, 320, 348, 349, 353, 357, 366, 381, 394, 409, 411, 413, 442, 443, and 461.

Another aspect of the disclosure provides a variant ester synthase polypeptide having SEQ ID NO: 2, wherein the variant ester synthase polypeptide is genetically engineered to have at least one mutation at an amino acid position including, but not limited to, amino acids G4R, T5P, T5S, D7N, S15G, T24M, T24W, L30H, G33D, G33S, L39A, L39M, L39S, R40S, D41A, D41G, D41H, D41Y, V43K, V43S, T44A, T44F, T44K, Y58C, Y58L, A73Q, V76L, D77A, K78F, K78W, I80V, R98D, E99Q, G101L, I102R, P111D, P111G, P111S, H122S, R131M, I146K, I146L, I146R, S147A, V149L, R150P, V155G, T157S, R162E, N164D, N164R, P166S, T170R, T170S, V171E, V171F, V171H, V171R, V171W, R172S, R172W, P173W, R177V, A179S, A179V, D182G, E184F, E184G, E184L, E184R, E184S, A185L, A185M, S186T, V187G, V187R, P188R, A190P, A190R, A190W, S192A, S192L, S192V, Q193R, Q193S, M195G, A197T, A197V, Q201A, Q201V, Q201W, A202L, D203R, P206F, R207A, G212A, G212L, V216I, V219L, V234C, H239G, T242K, T242R, A243R, Q244G, R246A, R246G, R246L, R246Q, R246V, R246W, D255E, L257I, K258R, N259E, N259Q, L260V, H262Q, A263V, S264D, S264V, S264W, G265N, G266A, G266S, S267G, A285L, A285R, A285V, N288D, N289E, N289G, T293A, P294G, V301A, N302G, I303G, I303R, I303W, R304W, A306G, D307F, D307G, D307L, D307N, D307R, D307V, E309A, E309G, E309S, G310H, G310R, G310V, T311S, T313S, Q314G, I315F, S316G, F317W, I319G, A320C, A323G, D328F, Q334K, Q334S, Q348A, Q348R, K349A, K349C, K349H, K349Q, P351G, K352I, K352N, S353K, S353T, T356G, T356W, Q357V, M360Q, M360R, M360S, M360W, Y366G, Y366W, G375A, G375V, G375S, V381F, E393G, E393R, E393W, G394E, T395E, V409L, L411A, A413T, I420V, S424G, S424Q, S442E, S442G, M443G, A447C, A447I, A447L, L454V, D455E, L457Y, E458W, I461G, I461L, I461V, K466N, A468G, K472T and K472. In a particular aspect of the disclosure the variant ester synthase polypeptide includes mutations D7N, A179V and V381F; D7N, A179V, Q348R and V381F; D7N, A179V, V187R, G212A, Q357V, V381F and M443G; T5S, S15G, P111S, V171R, P188R, F317W, S353T, V409L and S442G; T5S, S15G, K78F, P111S, V171R, P188R, S192V, A243R, F317W, K349H, S353T, V409L and S442G; T5S, S15G, V76L, P111S, V171R, P188R, K258R, S316G, F317W, S353T, M360R, V409L and S442G; T5S, S15G, P111S, V171R, P188R, Q244G, S267G, G310V, F317W, A320C, S353T, Y366W, V409L and S442G; S15G, P111S, V155G, P166S, V171R, P188R, F317W, Q348A, S353T, V381F, V409L and S442G; S15G, L39S, D77A, P111S, V171R, P188R, T313S, F317W, Q348A, S353T, V381F, V409L, I420V and S442G; T5S, S15G, T24W, T44F, P111S, I146L, V171R, P188R, D307N, F317W, S353T, V409L and S442G; T5S, S15G, K78F, P111S, V171R, P188R, S192V, R207A, A243R, D255E, L257I, N259Q, L260V, H262Q, G265N, A285V, N288D, N289G, F317W, Q348R, S353T, V381F, V409L and S442G; T5S, S15G, K78F, P111S, V171R, P188R, S192V, R207A, A243R, D255E, L257I, N259Q, L260V, H262Q, G265N, A285V, N288D, N289G, F317W, H349K, S353T, V381F, V409L and S442G; T5P, S15G, G33D, T44K, Y58L, P111S, R162E, V171R, P188R, R207A, V234C, Q244G, D255E, S267G, D307N, G310V, F317W, A320C, S353T, Y366W, G394E, V409L, S442G and I461V; T5P, S15G, G33D, T44K, Y58C, P111S, V171R, P188R, R207A, V234C, Q244G, L257I, S267G, D307N, G310V, F317W, A320C, S353T, Y366W, G394E, V409L, A413T, S442G and I461V; T5P, S15G, T44A, P111S, T157S, N164D, T170S, V171R, P188R, R207A, V216I, V234C, Q244G, L257I, S267G, D307N, G310V, F317W, A320C, Q334K, S353T, Y366W, G394E, V409L, S442G and I461V; or mutations T5P, S15G, Y58L, P111S, R162E, T170S, V171R, A179S, P188R, R207A, V234C, Q244G, L257I, S267G, D307N, G310V, F317W, A320C, S353K, Y366W, G394E, V409L, S442G and I461V.

Another aspect of the disclosure provides a recombinant host cell genetically engineered to express a variant ester synthase polypeptide. In a related aspect, the disclosure provides a cultured recombinant host cell having a polynucleotide sequence encoding a variant ester synthase polypeptide, wherein the recombinant host cell when expressing the variant ester synthase polypeptide produces a fatty acid ester composition with higher titer, higher yield and/or higher productivity of fatty acid esters compared to a host cell expressing the corresponding wild type polypeptide, when cultured in medium containing a carbon source under conditions effective to express the variant ester synthase polypeptide. The titer is at least about 5 percent or greater. In a related aspect, the recombinant host cell when expressing the variant ester synthase polypeptide produces a fatty ester composition with an altered percentage of beta hydroxy esters as compared to a host cell that expresses the wild type ester synthase polypeptide. Herein, the altered percentage of beta hydroxy esters is an increased or decreased percentage of beta hydroxy esters.

Still another aspect of the invention provides a cell culture including the recombinant host cell and a fatty ester composition. The fatty ester composition may include one or more of a C6, C8, C10, C12, C13, C14, C15, C16, C17 or C18 fatty ester. In addition, the fatty ester composition may include unsaturated fatty esters and/or saturated fatty esters and/or branched chain fatty esters. The fatty ester composition may further include a fatty ester having a double bond at position 7 in the carbon chain between C7 and C8 from the reduced end of the fatty ester.

The disclosure further contemplates a variant *Marinobacter hydrocarbonoclasticus* (WS377) ester synthase polypeptide having SEQ ID NO: 2, wherein the variant WS377 polypeptide has improved fatty acid methyl ester activity compared to the wild type WS377 polypeptide, and wherein the variant WS377 has at least one mutation at an amino acid position including, but not limited to, amino acids 4, 5, 7, 15, 24, 30, 33, 39, 40, 41, 43, 44, 58, 73, 76, 77, 78, 80, 98, 99, 101, 102, 111, 122, 131, 146, 147, 149, 150, 155, 157, 162, 164, 166, 170, 171, 172, 173, 177, 179, 182, 184, 185, 186, 187, 188, 190, 192, 193, 195, 197, 201, 202, 203, 206, 207, 212, 216, 219, 234, 239, 242, 243, 244, 246, 255, 257, 258, 259, 260, 262, 263, 264, 265, 266, 267, 285, 288, 289, 293, 294, 301, 302, 303, 304, 306, 307, 309, 310, 311, 313, 314, 315, 316, 317, 319, 320, 323, 328, 334, 348, 349, 351, 352, 353, 356, 357, 360, 366, 375, 381, 393, 394, 395, 409, 411, 413, 420, 424, 442, 443, 447, 454, 455, 457, 458, 461, 466, 468, and 472.

Another aspect of the disclosure provides a variant thioesterase polypeptide comprising an amino acid sequence having at least about 90% sequence identity to SEQ ID NO: 51, wherein the variant ester synthase polypeptide is genetically engineered to have at least one mutation at an amino acid position including, but not limited to, amino acids 32, 33, 34, 38, 45, 46, 48, 49, 51, 52, 76, 81, 82, 84, 88, 112, 115, 116, 118, 119, 148, 149, 156, 159 and 164, wherein the variant thioesterase polypeptide has greater ester synthase activity compared to the corresponding wild type polypeptide. In a related aspect of the disclosure, the variant polypeptide is a *Photobacterium profundum* (Ppro) thioesterase polypeptide. The expression of the variant thioesterase polypeptide in a recombinant host cell results in a higher titer of fatty ester compositions compared to a recombinant host cell expressing the corresponding wild type polypeptide, wherein said titer is at least about 5 percent or greater.

Another aspect of the disclosure provides a variant thioesterase polypeptide having at least one mutation including, but not limited to, amino acids K32M, Q33A, Q33R, Q34R, I38Y, I45R, S46K, S46V, S46W, D48E, D48F, D48L, D48M, T49D, T49L, T49V, T49W, G51R, N52C, N52F, N52K, N52L, N52R, N76I, N76L, N76V, G81C, F82G, F82I, F82R, Q84A, Q84L, Q84V, R88H, V112L, N115F, N115W, N115Y, Y116H, Y116N, Y116P, Y116R, Y116S, Y116T, K118Q, R119C, I148Y, L149F, L149M, L149T, N156K, N156R, N156Y, L159K, L159M and D164T. A related aspect of the disclosure provides a variant thioesterase polypeptide having mutations S46V and Y116H; S46V, D48M, G51R, N76V and Y116H; S46V, D48M, T49L, G51R, N76V, Y116H and I148Y; S46V, D48M, T49L, G51R, N76V, N115F, Y116H and I148Y; Q33R, Q34R, S46V, D48M, T49L, G51R, N52R, N76V, V112L, N115W, Y116H and I148Y; Q33R, S46V, D48M, T49L, G51R, N52K, N76V, V112L, N115W, Y116H, I148Y and L149M; or mutations S46V, D48M, T49L, G51R, N52R, N76V, Q84A, V112L, N115W, Y116H, I148Y and L149M.

The disclosure further encompasses a recombinant host cell genetically engineered to express a variant thioesterase polypeptide that has ester synthase activity. A cultured recombinant host cell including a polynucleotide sequence encoding a variant thioesterase polypeptide is further contemplated by the disclosure. The recombinant host cell, when expressing the variant thioesterase polypeptide, produces a fatty acid ester composition with higher titer, higher yield and/or higher productivity of fatty acid esters compared to a host cell expressing the corresponding wild type thioesterase polypeptide, when cultured in medium containing a carbon source under conditions effective to express the variant thioesterase polypeptide. The titer is at least about 5 percent or greater. The cell culture further includes the recombinant host cell and a fatty ester composition. The fatty ester composition may include one or more of a C6, C8, C10, C12, C13, C14, C15, C16, C17 or C18 fatty ester. In addition, the fatty ester composition may include unsaturated fatty esters and/or saturated fatty esters and/or branched chain fatty esters. The fatty ester composition may further include a fatty ester having a double bond at position 7 in the carbon chain between C7 and C8 from the reduced end of the fatty ester.

Another aspect of the disclosure provides a variant thioesterase polypeptide with ester synthase activity, wherein the variant thioesterase polypeptide includes amino acids 73-81 of SEQ ID NO: 51 as follows LG[AG][VIL]D[AG]LRG.

Yet, another aspect of the disclosure provides a variant *Photobacterium profundum* (Ppro) thioesterase polypeptide having at least about 90% sequence identity to a corresponding wild type Ppro polypeptide sequence having SEQ ID NO: 51, wherein the variant Ppro polypeptide has greater ester synthase activity compared to the wild type Ppro polypeptide, and where the variant Ppro polypeptide has at least one mutation including, but not limited to, amino acids 32, 33, 34, 38, 45, 46, 48, 49, 51, 52, 76, 81, 82, 84, 88, 112, 115, 116, 118, 119, 148, 149, 156, 159 and 164.

The disclosure still encompasses a recombinant host cell including (a) a polynucleotide encoding a variant polypeptide with increased ester synthase activity, (b) an activated fatty acid, and (c) an alcohol, wherein the recombinant host cell produces a fatty ester composition under conditions effective to express an ester synthase activity of the variant polypeptide. The activated fatty acid is an Acyl-ACP or an Acyl-CoA. The recombinant host cells may further utilize a carbon source. The fatty ester composition is produced at a titer of least about 5 percent or higher.

Another aspect of the disclosure provides a polynucleotide encoding a variant ester synthase polypeptide, wherein the polynucleotide has at least about 85% sequence identity to SEQ ID NO: 1, wherein the polynucleotide further includes SEQ ID NO: 27 prior to ATG start.

Yet, another aspect of the disclosure provides a variant ester synthase polypeptide having an amino acid sequence that has at least about 95% sequence identity to SEQ ID NO: 29; or 95% sequence identity to SEQ ID NO: 33; or 95% sequence identity to SEQ ID NO: 35; or 95% sequence identity to SEQ ID NO: 37; or 95% sequence identity to SEQ ID NO: 39; or 95% sequence identity to SEQ ID NO: 41; or 95% sequence identity to SEQ ID NO: 43. Herein, the expression of the variant ester synthase polypeptide in a recombinant host cell results in a production of a higher titer, higher yield, or increased productivity of fatty acid esters as compared to a recombinant host cell expressing a wild type *Marinobacter hydrocarbonoclasticus* (WS377) ester synthase polypeptide. The titer is at least about 5% or higher.

BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

DETAILED DESCRIPTION

General Overview

The disclosure relates to variant enzymes with improved ester synthase properties for the production of fatty esters. Herein, the disclosure relates to enzymes such as variant ester synthase enzymes having improved ester synthase properties and variant thioesterase enzymes designed to have ester synthase activity. Both types of enzymes are engineered to improve the production of fatty esters when used alone or in combination with other proteins. In order to illustrate this, the applicants have engineered an ester synthase from *Marinobacter hydrocarbonoclasticus* and a thioesterase from *Photobacterium profundum* to produce fatty esters in vivo without the need to overexpress a fatty acyl-CoA synthetase or a different thioesterase. So far, it has been thought that in order to produce higher yields of fatty esters, at least an acyl-CoA synthetase or a thioesterase enzyme has to be simultaneously overexpressed with an ester synthase because any fatty ester production requires the co-expression of thioesterase, acyl-CoA synthetase, and ester synthase. Moreover, native *Marinobacter* ester synthases, and native thioesterases in general are not known to utilize short chain alcohols. However, the applicants have engineered variant enzymes with ester synthase activity such that the enzymes can utilize short chain alcohols, including methanol and ethanol, allowing the enzymes to produce fatty esters. For example, the variant ester synthase and variant thioesterase with ester synthase activity can produce fatty acid methyl ester(s) (FAME) and/or fatty acid ethyl ester(s) (FAEE) at high quantities. As such, the applicants have engineered variant enzymes that each lead to a higher production of esters in vivo.

Figure 3:
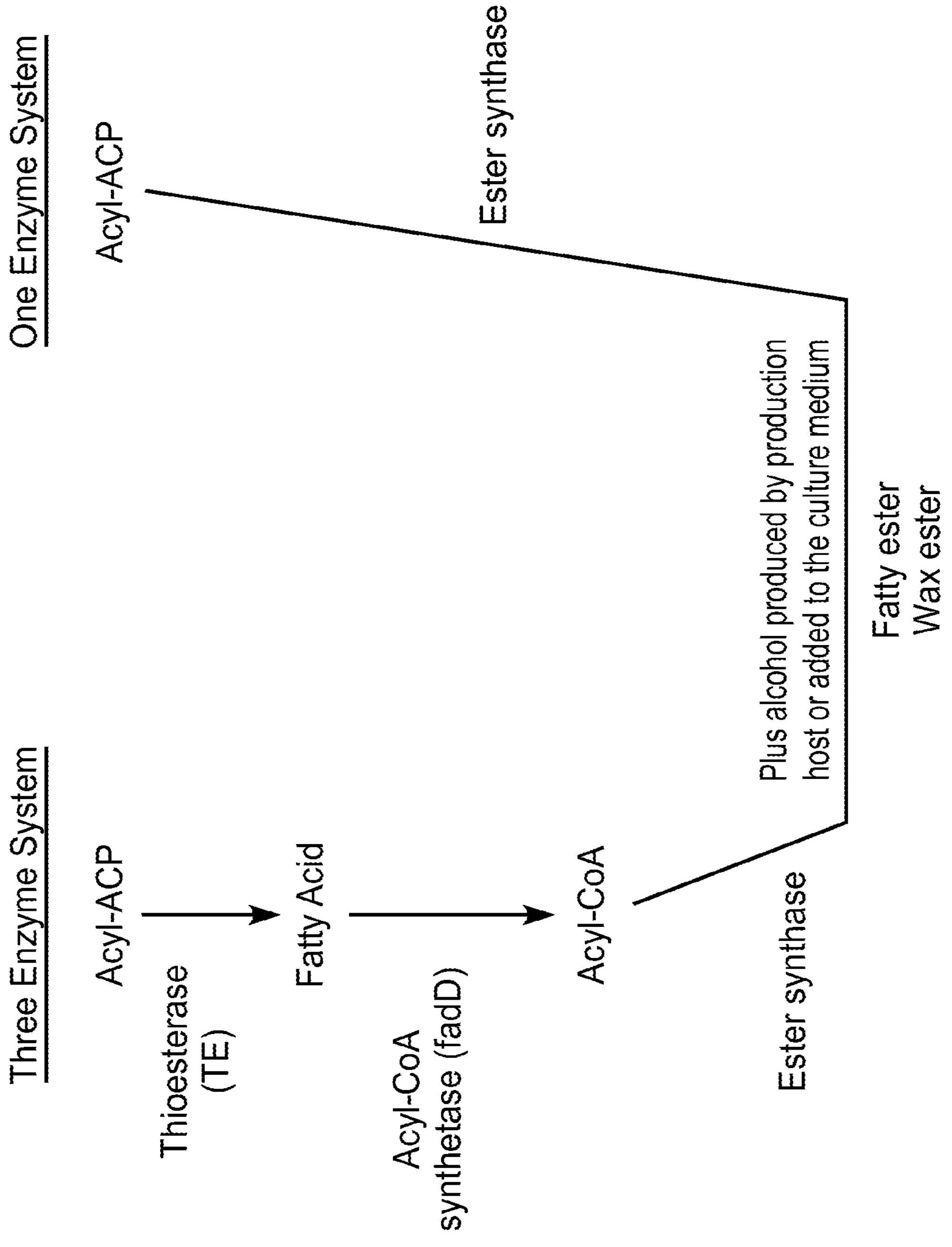
FIG. 3 is a schematic depiction of two exemplary biosynthetic pathways for production of fatty esters starting with acyl-ACP, where the production of fatty esters is accomplished by a one enzyme system or a three enzyme system.

Herein, the applicants employ a convenient one-gene-system (see FIG. 3) for the production of fatty esters. A one-gene-system typically employs a gene that encodes a variant enzyme with improved ester synthase activity in combination with an activated fatty acid, such as an Acyl-ACP or Acyl-CoA, (i.e., as a substrate) and alcohol to produce fatty esters in a recombinant host cell. There are certain advantages of using a one-gene-system (i.e., rather than a multi-gene-system) for the production of fatty esters. For example, one such advantage is the simplicity of the system itself which allows it to be faster implemented and more readily monitored. Another advantage is that a one-gene-system is more energy efficient for the cell because it likely bypasses or avoids the so-called futile cycle (i.e., a substrate futile cycle, wherein two metabolic pathways run simultaneously in opposite directions and have no overall effect), thereby increasing the yield of ester production in vivo.

More specifically, fatty acid ester production in *Escherichia coli* typically relies on the co-expression of a thioesterase ('tesA), an acyl-CoA synthetase (fadD) and a wax or ester synthase. In order to maximize ester production the three genes are carefully balanced in order to minimize production of free fatty acids ("FFA"). The thioesterase can act on both acyl-ACP (product of fatty acid biosynthesis) and acyl-CoA (product of acyl-CoA synthetase) generating free fatty acids (substrate of acyl-CoA synthetase). The present disclosure is directed to a modified ester synthase which has improved properties relative to the wild type enzyme, cloned from *Marinobacter hydrocarbonoclasticus* DSM 8798 GenBank: EF219377 (referred to herein as "'377"). The modified '377 has been shown to act on both acyl-ACP and acyl-CoA to generate fatty acid esters such as fatty acid methyl ester ("FAME").

In addition, the percentage of FAME of the total acyl species (FAME+FFA) generated varies depending on the thioesterase being used. The 'tesA of *Photobacterium profundum* ("*P. profundum*" or "Ppro") naturally produces a small percentage of FAME. The *Photobacterium profundum* 'tesA was engineered to produce a higher percentage of FAME. Thus, the present disclosure is further directed to a modified thioesterase ('tesA) from *Photobacterium profundum* (referred to herein as "Ppro") that was genetically engineered to produce a higher percentage of FAME without the need to overexpress any other gene in a host cell such as *E. coli*. While not wanting to be bound by theory, an ester synthase that acts directly on acyl-ACP (a product of fatty acid biosynthesis) could eliminate the futile cycle that theoretically exists in the current biodiesel pathway, thus reserving resources from the cell, which could be directed towards fatty acid biosynthesis, which should also improve the production.

Definitions

As used in this specification and the appended claims, the singular forms “a,” “an” and “the” include plural referents unless the context clearly dictates otherwise. Thus, for example, reference to “a recombinant host cell” includes two or more such recombinant host cells, reference to “a fatty ester” includes one or more fatty esters, or mixtures of esters, reference to “a nucleic acid coding sequence” includes one or more nucleic acid coding sequences, reference to “an enzyme” includes one or more enzymes, and the like.

Sequence Accession numbers throughout this description were obtained from databases provided by the NCBI (National Center for Biotechnology Information) maintained by the National Institutes of Health, U.S.A. (which are identified herein as “NCBI Accession Numbers” or alternatively as “GenBank Accession Numbers”), and from the UniProt Knowledgebase (UniProtKB) and Swiss-Prot databases provided by the Swiss Institute of Bioinformatics (which are identified herein as “UniProtKB Accession Numbers”).

EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed.

As used herein, the term “nucleotide” refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

The term “polynucleotide” refers to a polymer of ribonucleotides (RNA) or deoxyribonucleotides (DNA), which can be single-stranded or double-stranded and which can contain non-natural or altered nucleotides. The terms “polynucleotide,” “nucleic acid sequence,” and “nucleotide sequence” are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms “polypeptide” and “protein” are used interchangeably to refer to a polymer of amino acid residues. The term “recombinant polypeptide” refers to a polypeptide that is produced by recombinant techniques, wherein generally DNA or RNA encoding the expressed protein is inserted into a suitable expression vector that is in turn used to transform a host cell to produce the polypeptide.

As used herein, the terms “homolog,” and “homologous” refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence “homology” and sequence “identity” are used interchangeably.

One of ordinary skill in the art is well aware of methods to determine homology between two or more sequences. Briefly, calculations of “homology” between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 85%, at least about 90%, at least about 95%, at least about 98%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al., J. Mol. Biol., 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, J. Mol. Biol., 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg, BMC Bioinformatics, 6: 278 (2005); Altschul, et al., FEBS J., 272(20): 5101-5109 (2005)).

The term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and non-aqueous methods are described in that reference and either method can be used. Specific hybridization conditions referred to herein are as follows: 1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions—6×SSC at about 45° C., followed by one or more washes in 0.2×SSC, 0.1% SDS at 60° C.; 3) high stringency hybridization conditions—6×SSC at about 45° C., followed by one or more washes in 0.2×SSC, 0.1% SDS at 65° C.; and 4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the parental microbial cell (also termed "host cell") from which the recombinant cell is engineered (or "derived"). An "exogenous" polypeptide refers to a polypeptide which is not encoded by the genome of the parental microbial cell. A variant (i.e., mutant) polypeptide is an example of an exogenous polypeptide.

The term "heterologous" as used herein typically refers to a nucleotide, polypeptide or protein sequence, not naturally present in a given organism. For example, a polynucleotide sequence endogenous to a plant can be introduced into a host cell by recombinant methods, and the plant polynucleotide is then heterologous to that recombinant host cell. The term "heterologous" may also be used with reference to a nucleotide, polypeptide, or protein sequence which is present in a recombinant host cell in a non-native state. For example, a "heterologous" nucleotide, polypeptide or protein sequence may be modified relative to the wild type sequence naturally present in the corresponding wild type host cell, e.g., a modification in the level of expression or in the sequence of a nucleotide, polypeptide or protein.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

A "mutation", as used herein, refers to a permanent change in a nucleic acid position of a gene or in an amino acid position of a polypeptide or protein. Mutations include substitutions, additions, insertions, and deletions. For example, a mutation in an amino acid position can be a substitution of one type of amino acid with another type of amino acid (e.g., a serine (S) may be substituted with an alanine (A); a lysine (L) may be substituted with an T (Threonine); etc.). As such, a polypeptide or a protein can have one or more mutations wherein one amino acid is substituted with another amino acid. For example, an ester synthase polypeptide or protein can have one or more mutations in its amino acid sequence.

An "ester synthase variant" is an ester synthase polypeptide or protein that has one or more mutations in its amino acid sequence. In one example, the amino acid sequence ranges from 0 (i.e., the initial methionine (M) based on the ATG start site) to 473. Such an ester synthase variant can have one or more mutation in the amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, and/or 473. Notably, amino acid positions 139 and 140 are part of a conserved motif, and thus, are important for the activity of the enzyme. In one embodiment, the mutations include G4R, T5P, T5S, D7N, S15G, T24M, T24N, T24W, Q26T, L30H, G33D, G33N, G33S, L39A, L39M, L39S, R40S, D41A, D41G, D41H, D41Y, V43K, V43S, T44A, T44F, T44K, E48A, E48Q, A49D, A49T, Y58C, Y58L, I70L, I70V, A73G, A73Q, A73S, A73T, V76L, D77A, K78F, K78W, D79H, D79K, I80V, R98D, E99Q, G101L, I102R, P111D, P111G, P111S, H122S, V123I, V123M, R131M, I146K, I146L, I146R, S147A, V149L, R150P, V155G, T157S, T158E, T158K, R162E, R162K, C163I, C163R, N164D, N164R, P166L, P166S, T170R, T170S, V171E, V171F, V171H, V171R, V171W, R172S, R172W, P173W, H174E, Q175R, Q175S, R176T, R177V, A179K, A179S, A179V, D182G, K183S, E184F, E184G, E184L, E184R, E184S, A185L, A185M, S186T, V187G, V187R, P188R, A189G, A190P, A190R, A190W, V191I, V191L, S192A, S192L, S192V, Q193R, Q193S, M195G, D196E, A197T, A197V, Q201A, Q201V, Q201W, A202L, D203R, P206F, R207A, G212A, G212L, G212M, G212S, V216I, V219L, V234C, V236A, V236K, L237I, H239G, T242K, T242R, A243G, A243R, Q244G, R246A, R246G, R246L, R246Q, R246V, R246W, D255E, L257I, L257M, K258R, N259A, N259E, N259Q, L260M, L260V, H262Q, H262R, A263V, S264D, S264V, S264W, G265N, G266A, G266S, S267G, A285L, A285R, A285V, N288D, N289E, N289G, T293A, T293I, P294G, V301A, N302G, I303G, I303R, I303W, R304W, A306G, A306S, D307F, D307G, D307L, D307N, D307R, D307V, E309A, E309G, E309S, G310H, G310R, G310V, T311S, T313S, Q314G, I315F, S316G, F317W, I319G, A320C, A323G, D328F, N331I, N331K, N331T, Q334K, Q334S, Q335C, Q335N, Q335S, T338A, T338E, T338H, Q348A, Q348R, K349A, K349C, K349H, K349Q, P351G, K352I, K352N, S353K, S353T, T356G, T356W, Q357V, M360R, M360Q, M360S, M360W, Y366G, Y366W, G375A, G375V, G375S, V381F, E393G, E393R, E393W, G394E, G394R, T395E, R402K, V409L, L411A, A413T, I420V, S424G, S424Q, S442E, S442G, M443G, A447C, A447I, A447L, L454V, D455E, L457Y, E458W, I461G, I461L, I461V, K466N, A468G, K472T and K472.

The terms "thioesterase variant with ester synthase activity" or "thioesterase variant" are used interchangeably herein and refer to a thioesterase polypeptide or protein that has ester synthase activity and has one or more mutations in its amino acid sequence. In one example, the amino acid sequence ranges from 0 (i.e., the initial methionine (M) based on the ATG start site) to 182. Such a thioesterase variant can have one or more mutation(s) in the amino acid position 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 162, 163, 164, 165, 166, 167, 168, 169, 170, 171, 172, 173, 174, 175, 176, 177, 178, 179, 180, 181 and/or 182. However, amino acid positions 10, 157 and 160 are part of the catalytic triad, and thus, are important for the activity of the enzyme. In one embodiment, the mutations include R18C, K32M, Q33A, Q33R, Q34R, E37D, I38Y, I45R, I45T, S46K, S46V, S46W, D48E, D48F, D48L, D48M, T49D, T49L, T49V, T49W, G51R, N52C, N52F, N52K, N52L, N52R, K65M, N76I, N76L, N76V, G81C, F82G, F82I, F82R, Q84A, Q84L, Q84V, R88H, D102V, V112L, N115F, N115W, N115Y, Y116H, Y116N, Y116P, Y116R, Y116S, Y116T, K118Q, R119C, I148Y, L149F, L149M, L149T, N156K, N156R, N156Y, L159K, L159M and D164T.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science,* 236: 1237-1245 (1987)). Exemplary expression control sequences are described in, for example, Goeddel, Gene Expression Technology: Methods in Enzymology, Vol. 185, Academic Press, San Diego, Calif. (1990). In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further includes a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

As used herein, a recombinant or engineered "host cell" is a host cell, e.g., a microorganism used to produce one or more of fatty acid derivatives include, for example, acyl- CoA, fatty acids, fatty aldehydes, short and long chain alcohols, hydrocarbons, fatty alcohols, fatty esters (e.g., waxes, fatty acid esters, fatty esters, and/or fatty fatty esters), terminal olefins, internal olefins, and ketones. In some embodiments, the recombinant host cell comprises one or more polynucleotides, each polynucleotide encoding a polypeptide having fatty acid biosynthetic enzyme activity, wherein the recombinant host cell produces a fatty ester composition when cultured in the presence of a carbon source under conditions effective to express the polynucleotides.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid derivative" means a "fatty acid" or a "fatty acid derivative", which may be referred to as a "fatty acid or derivative thereof". The term "fatty acid" means a carboxylic acid having the formula RCOOH. R represents an aliphatic group, preferably an alkyl group. R can comprise between about 4 and about 22 carbon atoms. Fatty acids can have a branched chain or straight chain and may be saturated, monounsaturated, or polyunsaturated. A "fatty acid derivative" is a product made in part from the fatty acid biosynthetic pathway of the production host organism. "Fatty acid derivatives" include products made in part from acyl-ACP or acyl-ACP derivatives. Exemplary fatty acid derivatives include, acyl-CoA, fatty acids, fatty aldehydes, short and long chain alcohols, fatty alcohols, hydrocarbons, esters (e.g., waxes, fatty acid esters, fatty esters), terminal olefins, internal olefins, and ketones.

A "fatty acid derivative composition" as referred to herein is produced by a recombinant host cell and typically includes a mixture of fatty acid derivatives. In some cases, the mixture includes more than one type of fatty acid derivative product (e.g., fatty acids, fatty esters, fatty alcohols, fatty aldehydes, fatty ketones, hydrocarbons, etc.). In other cases, a fatty acid derivative composition may include, for example, a mixture of fatty esters (or another fatty acid derivative) with different chain lengths, saturation and/or branching characteristics. In still other cases, the fatty acid derivative composition may comprise both a mixture of more than one type of fatty acid derivative product and fatty acid derivatives with different chain lengths, saturation and/or branching characteristics. In still other cases, a fatty acid derivative composition may include, for example, a mixture of fatty esters and beta hydroxy esters.

As used herein, the term "fatty acid biosynthetic pathway" means a biosynthetic pathway that produces fatty acid derivatives. The fatty acid biosynthetic pathway may include additional enzymes to produce fatty acids derivatives having desired characteristics.

As used herein, "fatty ester" means an ester having the formula RCOOR'. A fatty ester as referred to herein can be any ester made from a fatty acid, for example a fatty acid ester. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty ester composition comprises one or more of a C6, C7, C8, C9, C10, C11, C12, C13, C14, C15, C16, C17, C18, C19, C20, C21, C22, C23, C24, C25, and a C26 fatty ester. In other embodiments, the fatty ester composition includes one or more of a C6, C7, C8, C9, C10, C11, C12, C13, C14, C15, C16, C17, and a C18 fatty ester. In still other embodiments, the fatty ester composition includes C12, C14, C16 and C18 fatty esters; C12, C14 and C16 fatty esters; C14, C16 and C18 fatty esters; or C12 and C14 fatty esters.

The R group of a fatty acid derivative, for example a fatty ester, can be a straight chain or a branched chain. Branched chains may have more than one point of branching and may include cyclic branches. In some embodiments, the branched fatty acid, branched fatty aldehyde, or branched fatty ester is a C6, C7, C8, C9, C10, C11, C12, C13, C14, C15, C16, C17, C18, C19, C20, C21, C22, C23, C24, C25, or a C26 branched fatty acid, branched fatty aldehyde, or branched fatty ester. In particular embodiments, the branched fatty acid, branched fatty aldehyde, or branched fatty ester is a C6, C7, C8, C9, C10, C11, C12, C13, C14, C15, C16, C17, or C18 branched fatty acid, or branched fatty ester. A fatty ester of the present disclosure may be referred to as containing an A side and a B side. As used herein, an "A side" of an ester refers to the carbon chain attached to the carboxylate oxygen of the ester. As used herein, a "B side" of an ester refers to the carbon chain comprising the parent carboxylate of the ester. When the fatty ester is derived from the fatty acid biosynthetic pathway, the A side is typically contributed by an alcohol, and the B side is contributed by a fatty acid.

Any alcohol can be used to form the A side of the fatty esters. For example, the alcohol can be derived from the fatty acid biosynthetic pathway, such as those describe herein. Alternatively, the alcohol can be produced through non-fatty acid biosynthetic pathways. Moreover, the alcohol can be provided exogenously. For example, the alcohol can be supplied in the fermentation broth in cases where the fatty ester is produced by an organism. Alternatively, a carboxylic acid, such as a fatty acid or acetic acid, can be supplied exogenously in instances where the fatty ester is produced by an organism that can also produce alcohol.

The carbon chains comprising the A side or B side of the ester can be of any length. In one embodiment, the A side of the ester is at least about 1, 2, 3, 4, 5, 6, 7, 8, 10, 12, 14, 16, or 18 carbons in length. When the fatty ester is a fatty acid methyl ester, the A side of the ester is 1 carbon in length. When the fatty ester is a fatty acid ethyl ester, the A side of the ester is 2 carbons in length. The B side of the ester can be at least about 4, 6, 8, 10, 12, 14, 16, 18, 20, 22, 24, or 26 carbons in length. The A side and/or the B side can be straight or branched chain. The branched chains can have one or more points of branching. In addition, the branched chains can include cyclic branches. Furthermore, the A side and/or B side can be saturated or unsaturated. If unsaturated, the A side and/or B side can have one or more points of unsaturation. In addition, the alcohol group of a fatty ester produced in accordance with the present disclosure need not be in the primary (C1) position. In one embodiment, the fatty ester is produced biosynthetically. In this embodiment, first the fatty acid is "activated." Non-limiting examples of "activated" fatty acids are acyl-CoA, acyl ACP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase.

In certain embodiments, the branched fatty acid derivative is an iso-fatty acid derivative, for example an iso-fatty ester, or an anteiso-fatty acid derivative, e.g., an anteiso-fatty ester. In exemplary embodiments, the branched fatty acid derivative is selected from iso-C7:0, iso-C8:0, iso-C9:0, iso-C10:0, iso-C11:0, iso-C12:0, iso-C13:0, iso-C14:0, iso-C15:0, iso-C16:0, iso-C17:0, iso-C18:0, iso-C19:0, anteiso-C7:0, anteiso-C8:0, anteiso-C9:0, anteiso-C10:0, anteiso-C11:0, anteiso-C12:0, anteiso-C13:0, anteiso-C14:0, anteiso-C15:0, anteiso-C16:0, anteiso-C17:0, anteiso-C18:0, and an anteiso-C19:0 branched fatty ester.

The R group of a branched or unbranched fatty acid derivative can be saturated or unsaturated. If unsaturated, the R group can have one or more than one point of unsaturation. In some embodiments, the unsaturated fatty acid derivative is a monounsaturated fatty acid derivative. In certain embodiments, the unsaturated fatty acid derivative is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid derivative. In certain embodiments, the unsaturated fatty acid derivative, is a C10:1, C12:1, C14:1, C16:1, or C18:1 unsaturated fatty acid derivative. In other embodiments, the unsaturated fatty acid derivative is unsaturated at the omega-7 position. In certain embodiments, the unsaturated fatty acid derivative comprises a cis double bond.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., Difco™ media and BBL™ media. In one non-limiting example, the aqueous nutrient medium is a "rich medium" including complex sources of nitrogen, salts, and carbon, such as YP medium, comprising 10 g/L of peptone and 10 g/L yeast extract of such a medium.

As used herein, the term "under conditions effective to express said heterologous nucleotide sequence(s)" means any conditions that allow a host cell to produce a desired fatty acid derivative. Suitable conditions include, for example, fermentation conditions.

As used herein, "modified" or an "altered level of" activity of a protein, for example an enzyme, in a recombinant host cell refers to a difference in one or more characteristics in the activity determined relative to the parent or native host cell. Typically, differences in activity are determined between a recombinant host cell, having modified activity, and the corresponding wild-type host cell (e.g., comparison of a culture of a recombinant host cell relative to the corresponding wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein, e.g., WS377 ("'377"), Ppro. In certain instances, the coding sequences for the polypeptides described herein are codon optimized for expression in a particular host cell. For example, for expression in *E. coli*, one or more codons can be optimized as described in, e.g., Grosjean et al., Gene 18:199-209 (1982).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons). As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence. The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions. As used herein, the term "express" with respect to a polynucleotide is to cause it to function. A polynucleotide which encodes a polypeptide (or protein) will, when expressed, be transcribed and translated to produce that polypeptide (or protein). As used herein, the term "overexpress" means to express or cause to be expressed a polynucleotide or polypeptide in a cell at a greater concentration than is normally expressed in a corresponding wild-type cell under the same conditions.

As used herein, the term "titer" refers to the quantity of fatty acid derivative produced per unit volume of host cell culture. In any aspect of the compositions and methods described herein, a fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative is produced at a titer of more than 100 g/L, more than 200 g/L, or more than 300 g/L. One preferred titer of fatty acid derivative produced by a recombinant host cell according to the methods of the disclosure is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives produced by a given recombinant host cell culture. For example, the expression of a variant polypeptide with ester synthase activity in a recombinant host cell such as *E. coli* results in the production of a higher titer as compared to a recombinant host cell expressing the corresponding wild type polypeptide. In one embodiment, the higher titer ranges from at least about 5 g/L to about 200 g/L.

As used herein, the "yield of fatty acid derivative produced by a host cell" refers to the efficiency by which an input carbon source is converted to product (i.e., a fatty ester) in a host cell. Host cells engineered to produce fatty acid derivatives according to the methods of the disclosure have a yield of at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives is produced at a yield of more than about 30%, about 40%, about 50%, about 60%, about 70%, about 80%, about 90% or more. Alternatively, or in addition, the yield is about 30% or less, about 27% or less, about 25% or less, or about 22% or less. Thus, the yield can be bounded by any two of the above endpoints. For example, the yield of a fatty acid derivative or derivatives produced by the recombinant host cell according to the methods of the disclosure can be about 5% to about 15%, about 10% to about 25%, about 10% to about 22%, about 15% to about 27%, about 18% to about 22%, about 20% to about 28%, or about 20% to about 30%. The yield may refer to a particular fatty acid derivative or a combination of fatty acid derivatives produced by a given recombinant host cell culture. For example, the expression of a variant polypeptide with ester synthase activity in a recombinant host cell such as *E. coli* results in the production of a higher yield of fatty acid esters as compared to a recombinant host cell expressing the corresponding wild type polypeptide. In one embodiment, the higher yield ranges from about 10% to about 100% of theoretical yield.

As used herein, the term "productivity" refers to the quantity of a fatty acid derivative or derivatives produced per unit volume of host cell culture per unit time. In any aspect of the compositions and methods described herein, the productivity of a fatty acid derivative or derivatives produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hr (dependent upon cell mass). For example, the productivity of a fatty acid derivative or derivatives produced by a recombinant host cell according to the methods of the may be from 500 mg/L/hour to 2500 mg/L/hour, or from 700 mg/L/hour to 2000 mg/L/hour. The productivity may refer to a particular fatty acid derivative or a combination of fatty acid derivatives produced by a given recombinant host cell culture. For example, the expression of a variant polypeptide with ester synthase activity in a recombinant host cell such as *E. coli* results in the production of an increased productivity of fatty acid esters as compared to a recombinant host cell expressing the corresponding wild type polypeptide. In one embodiment, the higher productivity ranges from about 0.3 g/L/h to about 3 g/L/h.

As used herein, the term "total fatty species" and "total fatty acid product" may be used interchangeably herein with reference to the amount of fatty esters and fatty acids, as evaluated by GC-FID. The same terms may be used to mean fatty alcohols, fatty aldehydes and free fatty acids when referring to a fatty alcohol analysis.

As used herein, the term "glucose utilization rate" means the amount of glucose used by the culture per unit time, reported as grams/liter/hour (g/L/hr).

As used herein, the term "greater ester synthase activity as compared to the wild type polypeptide" is used with reference to an ester synthase or thioesterase with ester synthase activity with a higher titer, higher yield and/or higher productivity than the corresponding wild type enzyme. In one preferred embodiment, the titer, yield or productivity is at least twice that of the wild type polypeptide. In other preferred embodiments, the titer, yield or productivity is at least 3 times, 4 times, 5 times, 6 times, 7 times, 8 times, 9 times or 10 times that of the wild type polypeptide. In one particular embodiment, the titer is at least about 5% or greater. In some cases, "greater ester synthase activity as compared to the wild type polypeptide", also means that in addition to the higher titer, yield and/or productivity than the corresponding wild type ester synthase enzyme, the ester synthase produces a low or lower percentage (e.g., 1-5%) of beta hydroxy esters (see Examples, infra). In other cases, "greater ester synthase activity as compared to the wild type polypeptide", also means that in addition to the higher titer, yield and/or productivity than the corresponding wild type ester synthase enzyme, the ester synthase produces a higher percentage of beta hydroxy esters (see Examples, infra).

The term "improved fatty acid methyl ester activity" means that the variant polypeptide or enzyme can produce fatty acid methyl esters, fatty acid ethyl esters, fatty acid propyl esters, fatty acid isopropyl esters, fatty acid butyl esters, monoglycerides, fatty acid isobutyl esters, fatty acid 2-butyl esters, and fatty acid tert-butyl esters, and the like. A variant polypeptide or enzyme with improved fatty acid methyl ester activity has improved properties including, but not limited to, increased beta hydroxy esters, decreased beta hydroxyl esters, increased chain lengths of fatty acid esters, and decreased chain lengths of fatty acid esters. A variant ester synthase polypeptide with improved fatty acid methyl ester activity produces a titer that is at least about 5% or greater when the variant polypeptide is expressed in a recombinant microorganism.

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose. In other preferred embodiments the carbon source is sucrose. In other embodiments the carbon source is glycerol.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a composition comprising fatty esters. Fatty esters find utility in a number of products including, but not limited to, surfactants, polymers, films, textiles, dyes, pharmaceuticals, fragrances and flavoring agents, lacquers, paints, varnishes, softening agents in resins and plastics, plasticizers, flame retardants, and additives in gasoline and oil.

An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" also can refer to sources of carbon, such as carbohydrates (e.g., monosaccharides, disaccharides, or polysaccharides).

As used herein, the term "isolated," with respect to products (such as fatty acids and derivatives thereof) refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives in a sample. For example, when a fatty acid derivative is produced in a recombinant host cell, the fatty acid derivative can be purified by the removal of host cell proteins. After purification, the percentage of fatty acid derivative in the sample is increased. The terms "purify," "purified," and "purification" are relative terms which do not require absolute purity. Thus, for example, when a fatty acid derivative is produced in recombinant host cells, a purified fatty acid derivative is a fatty acid derivative that is substantially separated from other cellular components (e.g., nucleic acids, polypeptides, lipids, carbohydrates, or other hydrocarbons). As used herein, the term "attenuate" means to weaken, reduce, or diminish. For example, a polypeptide can be attenuated by modifying the polypeptide to reduce its activity (e.g., by modifying a nucleotide sequence that encodes the polypeptide).

Ester Synthase Variants

The present disclosure relates to, among other things, variant ester synthase enzymes, polypeptide sequences of such variants and functional fragments thereof with improved properties; polynucleotides encoding variant ester synthase polypeptide sequences; recombinant microorganisms including a nucleic acid encoding an improved ester synthase polypeptide; microorganisms capable of expressing the improved ester synthase polypeptide; cultures of such microorganisms; processes for producing fatty acid esters; fatty acid ester compositions and other compositions derived therefrom using the improved ester synthase polypeptides; and the resultant compositions.

Particularly, ester synthase polypeptides with improved properties and microorganisms expressing these polypeptides are provided herein. Wild-type ester synthase polypeptides from *Marinobacter hydrocarbonoclasticus* strain DSM8798, have been described in Holtzapple et al. (see *J Bacteriol.* (2007) 189(10):3804-3812) and U.S. Pat. No. 7,897,369. SEQ ID NO: 2 is the amino acid sequence of the wild-type ester synthase, i.e., ES9/DSM8798 from *Marinobacter hydrocarbonoclasticus* (*M. hydrocarbonoclasticus*; GenBankAccession No. ABO21021), which was used as a template to generate the improved ester synthase enzymes in order to illustrate the disclosure (see Examples, infra). A preferred ester synthase variant has at least about 90% sequence identity to the amino acid sequence of the wild type *M. hydrocarbonoclasticus* ester synthase enzyme (referred to herein as "WS377" or "'377") of SEQ ID NO: 2. Furthermore, SEQ ID NO: 1 is the polynucleotide sequence encoding SEQ ID NO: 2. With respect to the ester synthase polypeptide sequences described herein "M" (ATG) is considered to be amino acid "0". The first amino acid after the ATG is designated amino acid "1".

In one aspect, the disclosure provides improved ester synthase polypeptides with enhanced ester synthase activity and nucleotide sequences that encode them. In another aspect, it can be seen that substitutions introduced at numerous different amino acid positions (also referred to herein as "residues") within the wild-type '377 polypeptide of SEQ ID NO: 2 yield improved '377 polypeptides, capable of catalyzing increased production of fatty esters relative to wild-type '377. Depending upon the position mutated, single amino acid changes at specified positions give rise to increases or decreases in fatty ester production. Single amino acid changes at specified positions may also give rise to increases or decreases in beta hydroxy (β-OH) ester production. In one embodiment, a single amino acid change results in an increase in fatty ester production and a decrease in β-OH ester production. In another embodiment, a single amino acid change results in an increase in fatty ester production and no change in β-OH ester production. In still another embodiment, a single amino acid change results in an increase in fatty ester production and an increase in β-OH ester production. A single amino acid change may also result in a decrease in fatty ester production and an increase, decrease or no change in β-OH ester production. In other embodiments, single or multiple amino acid changes result in an increase in fatty ester production. In still other embodiments, single or multiple amino acid changes result in an increase or decrease in β-OH production.

Thus, combinations of two or more amino acid changes at specified positions may give rise to increases or decreases in fatty ester and/or free fatty acid production. The effect of each individual amino acid change on fatty ester and free fatty acid production may or may not be additive to the effect of other individual amino acid changes on fatty ester and free fatty acid production. In some preferred embodiments, a combination of two or more amino acid changes at specified positions results in an increase in fatty ester production and a decrease in free fatty acid production. Accordingly, multiple amino acid changes at specified positions give rise to increases or decreases in fatty ester production. As such, multiple amino acid changes at specified positions may also give rise to decreases in β-OH ester production. In some embodiments, multiple amino acid changes result in an increase in fatty ester production and a decrease in β-OH ester production. In other embodiments, multiple amino acid changes result in an increase in fatty ester production and no change in β-OH ester production. In still other embodiments, multiple amino acid changes result in an increase in fatty ester production and an increase in β-OH ester production. Multiple amino acid changes may also result in a decrease in fatty ester production and an increase, decrease or no change in β-OH ester production.

A full saturation library was prepared using WS377 ester synthase as a template, as described in Example 1 (infra). Over 200 beneficial mutations were identified based on increased titer of fatty ester and/or a decrease in the percentage of beta hydroxy ester produced. A combination library was prepared based on "hits" from the saturation library, as detailed in Examples 2 and 5. In one aspect, the disclosure relates to improved ester synthase polypeptides with at least about 70% sequence identity to SEQ ID NO: 2. In some embodiments, an improved ester synthase polypeptide shows at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the wild-type '377 sequence of SEQ ID NO: 2 and also includes one or more substitutions which results in useful characteristics and/or properties as described herein. In one aspect of the disclosure, the improved ester synthase polypeptide has about 100% sequence identity to SEQ ID NO: 4. In another aspect of the disclosure, the improved ester synthase polypeptide has about 100% sequence identity to any one of the following SEQ ID NOS, including, but not limited to, SEQ ID NO: 6, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 29, SEQ ID NO: 33, SEQ ID NO: 35, SEQ ID NO: 37, SEQ ID NO: 39, SEQ ID NO: 41 and SEQ ID NO: 43.

In a related aspect, an improved ester synthase polypeptide is encoded by a nucleotide sequence having 100% sequence identity to SEQ ID NO: 3 or SEQ ID NO: 7. In another related aspect, an improved ester synthase polypeptide is encoded by a nucleotide sequence having about 100% sequence identity to any one of the following SEQ ID NOS including, but not limited to, SEQ ID NO: 5, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 28, SEQ ID NO: 32, SEQ ID NO: 34, SEQ ID NO: 36, SEQ ID NO: 38, SEQ ID NO: 40 and SEQ ID NO: 42.

In another aspect, the disclosure relates to improved ester synthase polypeptides with at least about 70% sequence identity to SEQ ID NO: 4. In some embodiments, an improved ester synthase polypeptide has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the ester synthase sequence of SEQ ID NO: 4 and also includes one or more substitutions which results in improved characteristics and/or properties as described herein. In another aspect, the disclosure relates to improved ester synthase polypeptides with at least about 70% sequence identity to any one of the following SEQ ID NOS including, but not limited to, SEQ ID NO: 6, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 29, SEQ ID NO: 33, SEQ ID NO: 35, SEQ ID NO: 37, SEQ ID NO: 39, SEQ ID NO: 41 and SEQ ID NO: 43. In some embodiments, an improved ester synthase polypeptide has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to the ester synthase sequence of any one of the following SEQ ID NOS including, but not limited to, SEQ ID NO: 6, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 29, SEQ ID NO: 33, SEQ ID NO: 35, SEQ ID NO: 37, SEQ ID NO: 39, SEQ ID NO: 41 and SEQ ID NO: 43, and also includes one or more substitutions which results in improved characteristics and/or properties as described herein.

In another aspect, the disclosure relates to improved ester synthase polypeptides that comprise an amino acid sequence encoded by a nucleic acid sequence that has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the ester synthase sequence of SEQ ID NO: 5. In some embodiments the nucleic acid sequence encodes an ester synthase variant with one or more substitutions which results in improved characteristics and/or properties as described herein. In other embodiments, the improved or variant ester synthase nucleic acid sequence is derived from a species other than *Marinobacter hydrocarbonoclasticus*. In another aspect, the disclosure relates to improved ester synthase polypeptides that comprise an amino acid sequence encoded by a nucleic acid sequence that has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the ester synthase sequence of any one of the following SEQ ID NOS including, but not limited to, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 28, SEQ ID NO: 32, SEQ ID NO: 34, SEQ ID NO: 36, SEQ ID NO: 38, SEQ ID NO: 40 and SEQ ID NO: 42. In some embodiments the nucleic acid sequence encodes an ester synthase variant with one or more substitutions which results in improved characteristics and/or properties as described herein. In other embodiments, the improved or variant ester synthase nucleic acid sequence is derived from a species other than *Marinobacter hydrocarbonoclasticus*.

In another aspect, the disclosure relates to ester synthase polypeptides that comprise an amino acid sequence encoded by a nucleic acid that hybridizes under stringent conditions over substantially the entire length of a nucleic acid corresponding to any one of the following SEQ ID NOS including, but not limited to, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 28, SEQ ID NO: 32, SEQ ID NO: 34, SEQ ID NO: 36, SEQ ID NO: 38, SEQ ID NO: 40 and SEQ ID NO: 42. In some embodiments the nucleic acid sequence encodes an improved or variant ester synthase nucleic acid sequence derived from a species other than *Marinobacter hydrocarbonoclasticus*. In a related aspect, the disclosure provides ester synthase encoded by a nucleotide sequence having at least about 70% (e.g., at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to SEQ ID NO: 1 and comprises one or more of the substitutions disclosed herein.

Improved Properties of Ester Synthase Variants

Figure 1:
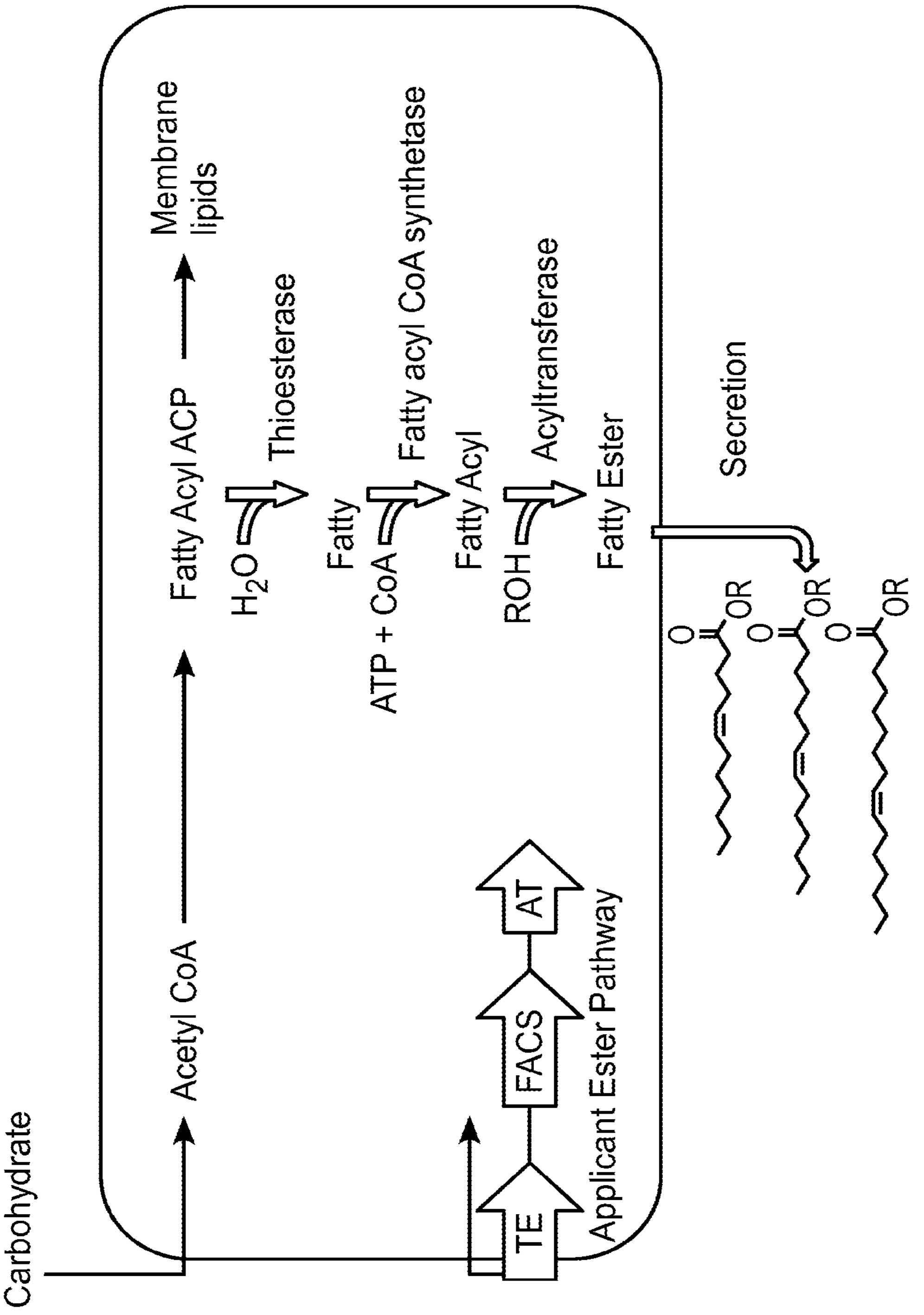
FIG. 1 is a schematic depiction of an exemplary three gene biosynthetic pathway that may be incorporated into a recombinant host cells for production of fatty acid esters of various chain lengths. The abbreviations used include TE for thioesterase, FACS for fatty acyl CoA synthetase, and AT for acyltransferase.
Figure 2:
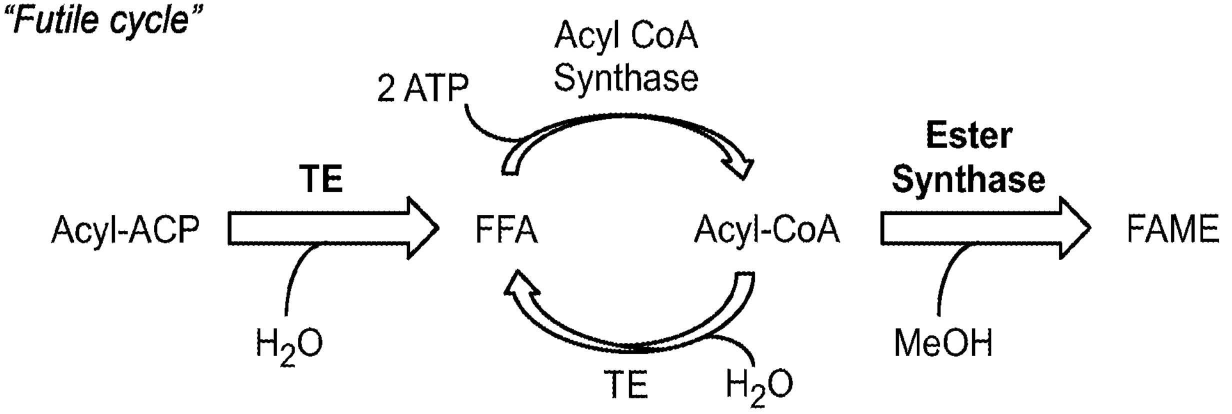
FIG. 2 is a schematic depiction of a proposed futile cycle catalyzed by thioesterase.

The wild type ester synthase from *Marinobacter hydrocarbonoclasticus* DSM 8798 ("'377") was engineered to produce a high percentage of fatty ester without the need to overexpress any other gene using expression in *E. coli* as an illustrative model. In addition, when expressed in a recombinant host cell such as *E. coli*, variants of the wild type ester synthase enzyme that result in a higher titer, yield or productivity also produce greater than about 20%, 25%, 30%, 35%, 40%, 45%, 50% or more β-OH esters. In one aspect, the present disclosure provides an improved variant of an ester synthase that has a higher titer, yield or productivity than the wild type ester synthase, and also produces a lower percentage of β-OH esters than the wild type enzyme. In a preferred embodiment, the variant ester synthase enzymes of the disclosure produce less than about 20%, 18%, 16%, 14%, 12%, 10%, 9%, 8%, 7%, 6%, 5%, 4%, 3%, 2% or less than 1% β-OH esters. As such, the ester synthase variants of the disclosure exhibit improved characteristics and/or properties as described herein, for example, an increase in titer, yield and/or productivity of fatty acid esters; and/or a decrease in titer, yield or productivity of beta hydroxyl esters. Thus, the engineering of an ester synthase to have a higher titer, yield and/or productivity essentially prevents *E. coli* from using resources in a futile cycle (see FIG. 2), while allowing for a high level production of fatty acid esters, e.g., for use as biodiesel or in the manufacture of surfactants.

*Photobacterium profundum* Variants

The present disclosure relates to, among other things, variant thioesterase enzymes with increased ester synthase activity; polypeptide sequences of such variants and functional fragments thereof with improved properties; polynucleotides encoding variant thioesterase polypeptide sequences with increased ester synthase activity; recombinant microorganisms comprising a nucleic acid encoding an improved thioesterase polypeptide with increased ester synthase activity; microorganisms capable of expressing the improved thioesterase polypeptide sequences with increased ester synthase activity; cultures of such microorganisms; processes for producing fatty acid esters; fatty acid ester compositions and other compositions derived therefrom using the improved thioesterase polypeptide sequences with increased ester synthase activity; and the resultant compositions.

Particularly, thioesterase polypeptides with improved properties such as an increased ester synthase activity and microorganisms expressing these polypeptides are provided herein. Wild-type *Photobacterium profundum* (Ppro) polypeptides have been described in Vezzi et al. (see *Science* (2005) 307:1459-1461). SEQ ID NO: 51 is the wild-type amino acid sequence for thioesterase from *Photobacterium profundum*. SEQ ID NO: 50 is the polynucleotide sequence encoding SEQ ID NO: 51. The leader sequence that targets the thioesterase into the periplasm was removed from SEQ ID NO: 50. Improved thioesterase polypeptides, for example, variant Ppro polypeptides, have enhanced ester synthase activity. With respect to the Ppro polypeptide sequences described herein "M" (ATG) is considered to be amino acid "0". The first amino acid after the ATG is designated amino acid "1".

In one aspect, the disclosure provides improved Ppro polypeptides with enhanced ester synthase activity and nucleotide sequences that encode them. Improved Ppro polypeptides are examples of variant thioesterase polypeptides with increased or enhanced ester synthase activity. In another aspect, it can be seen that substitutions introduced at numerous different amino acid positions (also referred to herein as "residue" positions) within the wild-type Ppro of SEQ ID NO: 51 yield improved Ppro polypeptides capable of catalyzing increased production of fatty esters relative to wild-type Ppro. Depending upon the position mutated, single amino acid changes at specified positions gives rise to increases or decreases in fatty ester production. Single amino acid changes at specified positions may also give rise to increases or decreases in free fatty acid production. In some preferred embodiments, a single amino acid change results in an increase in fatty ester production and a decrease in free fatty acid production. In other embodiments, a single amino acid change results in an increase in fatty ester production and no change in free fatty acid production. In still other embodiments, a single amino acid change results in an increase in fatty ester production and an increase in free fatty acid production. A single amino acid change may also result in a decrease in fatty ester production and an increase, decrease or no change in free fatty acid production. Combinations of two or more amino acid changes at specified positions may also give rise to increases or decreases in fatty ester and/or free fatty acid production. The effect of each individual amino acid change on fatty ester and free fatty acid production may or may not be additive to the effect of other individual amino acid changes on fatty ester and free fatty acid production. In some preferred embodiments, a combination of two or more amino acid changes at specified positions results in an increase in fatty ester production and a decrease in free fatty acid production.

In one aspect, the disclosure relates to Ppro polypeptides that have at least about 70% sequence identity with SEQ ID NO: 51. In some embodiments, a Ppro polypeptide shows at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the wild-type Ppro sequence of SEQ ID NO: 51 and also includes one or more substitutions which results in improved characteristics and/or properties as described herein. In a related aspect the Ppro polypeptide has a 100% sequence identity with SEQ ID NO: 51. In other related aspects the Ppro polypeptides have 100% sequence identity with SEQ ID NO: 53, SEQ ID NO: 55, SEQ ID NO: 58, SEQ ID NO: 61, SEQ ID NO: 63, SEQ ID NO: 65, or SEQ ID NO: 31.

In one aspect, the disclosure relates to Ppro polypeptides that have at least about 70% sequence identity with SEQ ID NO: 61. In some embodiments, a Ppro polypeptide has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the wild-type Ppro sequence of SEQ ID NO: 61 and also includes one or more substitutions which results in improved characteristics and/or properties as described herein.

In another aspect the disclosure relates to Ppro polypeptides that have at least about 70% sequence identity with SEQ ID NO: 31. In some embodiments, a Ppro polypeptide has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the wild-type Ppro sequence of SEQ ID NO: 31 and also includes one or more substitutions which results in improved characteristics and/or properties as described herein.

In another aspect, the disclosure relates to Ppro polypeptides that comprise an amino acid sequence encoded by a nucleic acid sequence that has at least about 75% (e.g., at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or and at least 99%) sequence identity to the wild-type Ppro sequence of SEQ ID NO: 50, SEQ ID NO: 52, SEQ ID NO: 54, SEQ ID NO: 56, SEQ ID NO: 57, SEQ ID NO: 59, SEQ ID NO: 60, SEQ ID NO: 62, SEQ ID NO: 64 or SEQ ID NO: 30. In some embodiments the nucleic acid sequence encodes a Ppro variant with one or more substitutions which results in improved characteristics and/or properties as described herein. In other embodiments, the Ppro nucleic acid sequence is derived from a species other than *Photobacterium profundum.*

In another aspect, the disclosure relates to Ppro polypeptides that comprise an amino acid sequence encoded by a nucleic acid that hybridizes under stringent conditions over substantially the entire length of a nucleic acid corresponding to SEQ ID NO: 50, SEQ ID NO: 52, SEQ ID NO: 54, SEQ ID NO: 56, SEQ ID NO: 57, SEQ ID NO: 59, SEQ ID NO: 60, SEQ ID NO: 62, SEQ ID NO: 64 or SEQ ID NO: 30. In some embodiments the nucleic acid sequence encodes a Ppro variant derived from a species other than *Photobacterium profundum*. In a related aspect, the disclosure provides Ppro encoded by a nucleotide sequence having at least about 70% (e.g., at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%) sequence identity to SEQ ID NO: 50 and comprises substitutions disclosed herein (see, e.g., Table 13).

Improved Properties of Ppro Variants

In order to illustrate the disclosure, the 'tesA from *P. profundum* was engineered to produce a higher percentage of FAME without the need to overexpress any other gene in *E. coli.* An ester synthase that acts directly on acyl-ACP (product of fatty acid biosynthesis) could be directed towards increased ester production, as well as allow direct pull of the pathway from the fatty acid biosynthesis, which should also improve the production. In addition, one of the libraries was tested for production of FAEE, and it was observed that engineered 'tesA from *P. profundum* for FAME, also produced higher levels of FAEE than the wild type strain. These Ppro variants exhibit improved characteristics and/or properties as described herein, for example an increase in titer, yield and/or productivity of fatty acid esters; and/or a decrease in titer, yield and/or productivity of free fatty acids. As an example, the tesA of *P. profundum* (Ppro) was engineered to have ester synthase activity. In other words, the tesA of Ppro was engineered to act as an ester synthase. When screened in plates, the wild type tesA Ppro gene produced about 15-18% FAME of the total acyl products (FAME+free fatty acids ("FFA")). Mutants were identified that resulted in an increase of FAME production of 42-44% when tested on plates. When these same mutants were tested in shake flasks, they produced 62-65% FAME when compared to the wild type tesA Ppro which only produced 30% FAME (see Example 7, infra).

Methods of Making Ester Synthase or Ppro Variants

In practicing the methods of the present disclosure, mutagenesis is used to prepare groups of recombinant host cells for screening. Typically, the recombinant host cells comprise one or more polynucleotide sequences that include an open reading frame for an ester synthase or Ppro polypeptide, such as a variant of ester synthase or a variant of thioesterase (e.g., Ppro) together with operably-linked regulatory sequences. Numerous examples of variant ester synthase polypeptides and variant thioesterase polypeptides useful in the practice of the methods of the present disclosure are described herein. Examples of regulatory sequences useful in the practice of the methods of the present disclosure are also described herein. Mutagenesis of such polynucleotide sequences can be performed using genetic engineering techniques, such as site directed mutagenesis, random chemical mutagenesis, exonuclease III deletion procedures, or standard cloning techniques. Alternatively, mutations in polynucleotide sequences can be created using chemical synthesis or modification procedures.

Mutagenesis methods are well known in the art and include, for example, the following. In error prone PCR (see, e.g., Leung et al., Technique 1:11-15, 1989; and Caldwell et al., PCR Methods Applic. 2:28-33, 1992), PCR is performed under conditions where the copying fidelity of the DNA polymerase is low, such that a high rate of point mutations is obtained along the entire length of the PCR product. Briefly, in such procedures, polynucleotides to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min., 45° C. for 1 min., and 72° C. for 1 min. It will be appreciated that these parameters can be varied as appropriate. The mutagenized polynucleotides are then cloned into an appropriate vector and the activities of the affected polypeptides encoded by the mutagenized polynucleotides are evaluated. Mutagenesis can also be performed using oligonucleotide directed mutagenesis (see, e.g., Reidhaar-Olson et al., *Science* 241:53-57, 1988) to generate site-specific mutations in any cloned DNA of interest. Briefly, in such procedures a plurality of double stranded oligonucleotides bearing one or more mutations to be introduced into the cloned DNA are synthesized and assembled into the cloned DNA to be mutagenized. Clones containing the mutagenized DNA are recovered, and the activities of affected polypeptides are assessed. Another mutagenesis method for generating polynucleotide sequence variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another mutagenesis method of generating polynucleotide sequence variants is sexual PCR mutagenesis (Stemmer, PNAS, USA 91:10747-10751, 1994). In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction.

Ester synthase (e.g., '377) or thioesterase (e.g., Ppro) sequence variants can also be created by in vivo mutagenesis. In some embodiments, random mutations in a nucleic acid sequence are generated by propagating the polynucleotide sequence in a bacterial strain, such as an *E. coli* strain, which carries mutations in one or more of the DNA repair pathways. Such "mutator" strains have a higher random mutation rate than that of a wild-type strain. Propagating a DNA sequence in one of these strains will eventually generate random mutations within the DNA. Mutator strains suitable for use for in vivo mutagenesis are described in, for example, PCT International Publication No. WO 91/16427.

Ester synthase (e.g., '377) or thioesterase (e.g., Ppro) sequence variants can also be generated using cassette mutagenesis. In cassette mutagenesis, a small region of a double stranded DNA molecule is replaced with a synthetic oligonucleotide "cassette" that differs from the starting polynucleotide sequence. The oligonucleotide often contains completely and/or partially randomized versions of the starting polynucleotide sequence. There are many applications of cassette mutagenesis; for example, preparing mutant proteins by cassette mutagenesis (see, e.g., Richards, J. H., Nature 323, 187 (1986); Ecker, D. J., et al., J. Biol. Chem. 262:3524-3527 (1987)); codon cassette mutagenesis to insert or replace individual codons (see, e.g., Kegler-Ebo, D. M., et al., Nucleic Acids Res. 22(9): 1593-1599 (1994)); preparing variant polynucleotide sequences by randomization of non-coding polynucleotide sequences comprising regulatory sequences (e.g., ribosome binding sites, see, e.g., Barrick, D., et al., Nucleic Acids Res. 22(7): 1287-1295 (1994); Wilson, B. S., et al., Biotechniques 17:944-953 (1994)).

Recursive ensemble mutagenesis (see, e.g., Arkin et al., PNAS, USA 89:7811-7815, 1992) can also be used to generate polynucleotide sequence variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Exponential ensemble mutagenesis (see, e.g., Delegrave et al., Biotech. Res. 11:1548-1552, 1993) can also be used to generate polynucleotide sequence variants. Exponential ensemble mutagenesis is a process for generating combinatorial libraries with a high percentage of unique and functional mutants, wherein small groups of residues are randomized in parallel to identify, at each altered position, amino acids which lead to functional proteins. Random and site-directed mutagenesis can also be used (see, e.g., Arnold, Curr. Opin. Biotech. 4:450-455, 1993).

Further, standard methods of in vivo mutagenesis can be used. For example, host cells, comprising one or more polynucleotide sequences that include an open reading frame for an ester synthase (e.g., '377) or thioesterase (e.g., Ppro) polypeptide, as well as operably-linked regulatory sequences, can be subject to mutagenesis via exposure to radiation (e.g., UV light or X-rays) or exposure to chemicals (e.g., ethylating agents, alkylating agents, or nucleic acid analogs). In some host cell types, for example, bacteria, yeast, and plants, transposable elements can also be used for in vivo mutagenesis.

The mutagenesis of one or more polynucleotide sequences that encode an ester synthase variant such as a '377 variant generally results in expression of an ester synthase polypeptide product that demonstrates a modified and improved biological function. Similarly, the mutagenesis of one or more polynucleotide sequences that encode a Ppro variant generally results in expression of a Ppro polypeptide product that demonstrates a modified and improved biological function such as enhanced ester synthase activity. For example, when preparing a group of recombinant microorganisms by mutagenesis of one or more polynucleotide sequences including the open reading frame encoding a '377 polypeptide and operably-linked regulatory sequences, the protein expressed from the resulting mutagenized polynucleotide sequences may maintain the '377 ester synthase biological function, however, an improved yield of fatty esters, a decreased yield of beta hydroxy esters and/or an improved compositions comprising a modified mixture of fatty ester products (in terms of chain length, saturation, and the like) is observed upon culture of the recombinant microorganism under conditions effective to express the mutant '377 polynucleotide. Similarly, when preparing a group of recombinant microorganisms by mutagenesis of one or more polynucleotide sequences including the open reading frame encoding a Ppro polypeptide and operably-linked regulatory sequences, the protein expressed from the resulting mutagenized polynucleotide sequences may maintain the Ppro thioesterase biological function but an ester synthase activity is observed in the recombinant microorganism. Because of the ester synthase activity, an improved yield of fatty esters, an improved compositions comprising a modified mixture of fatty ester products (in terms of chain length, saturation, and the like) is observed upon culture of the recombinant microorganism under conditions effective to express the mutant Ppro polynucleotide. In another embodiment, the mutagenesis of one or more Ppro polynucleotide sequences generally results in expression of a Ppro polypeptide product that may retain the same biological function as the wild type or parent Ppro polypeptide even though the mutant Ppro polypeptide demonstrates a modified biological function. For example, when preparing a group of recombinant microorganisms by mutagenesis of one or more polynucleotide sequences including the open reading frame encoding a Ppro polypeptide and operably-linked regulatory sequences, the protein expressed from the resulting mutagenized polynucleotide sequences may maintain the Ppro thioesterase biological function but a ester synthase activity is observed in the recombinant microorganism.

Hot Spots

The disclosure is also based, at least in part, on the identification of certain structurally conserved "hot spots" among variant ester synthase polypeptides such as '377 polypeptides. Hot spots are regions where a high number of mutations were observed that lead to a higher titer of fatty ester product and/or a lower production of beta hydroxy esters in '377 polypeptides. Notably, such regions are seen in variant ester synthase polypeptides that exhibit a greater ester synthase activity as compared to the wild type polypeptide that lacks those hot spots. Hot spots include amino acid regions 39-44; 76-80; 98-102; 146-150; 170-207, in particular 182-207 (e.g., showing the highest number of mutations); 242-246; 300-320; 348-357; and 454-458.

Motifs

The disclosure is also based, at least in part, on the identification of certain structurally conserved motifs among thioesterase polypeptides with enhanced ester synthase activity, wherein a thioesterase polypeptide, such as Ppro, that comprises one of these motifs has greater ester synthase activity as compared to the wild type thioesterase polypeptide which lacks the motif. Accordingly, the disclosure features variant thioesterase polypeptides, such as Ppro, that comprise a motif at amino acid region 73-81 of SEQ ID NO: 51, with the substitutions indicated below.

```
                                        (SEQ ID NO: 66)
Leu-Gly-[Ala or Gly]-[Val or Ile or Leu]-Asp-
[Ala or Gly]-Leu-Arg-Gly

LG[AG][VIL]D[AG]LRG
```

The potential substitutions include alanine (A) or glycine (G) at amino acid position 75; valine (V), isoleucine (I) or leucine (L) at amino acid position 76; and alanine (A) or glycine (G) at amino acid position 78.

Recombinant Host Cells and Recombinant Host Cell Cultures

The recombinant host cells of the disclosure comprise one or more polynucleotide sequences that comprise an open reading frame encoding a polypeptide having ester synthase activity, e.g., any polypeptide which catalyzes the conversion of an acyl-thioester to a fatty ester, together with operably-linked regulatory sequences that facilitate expression of the polypeptide having ester synthase activity in a recombinant host cell. In one preferred embodiment, the polypeptide having improved ester synthase activity is a variant or mutant of '377. In another preferred embodiment, the polypeptide having improved ester synthase activity is a variant or mutant of Ppro. In a recombinant host cell of the disclosure, the open reading frame coding sequences and/or the regulatory sequences may be modified relative to the corresponding wild-type coding sequence of the '377 or Ppro polypeptide. A fatty ester composition is produced by culturing a recombinant host cell in the presence of a carbon source under conditions effective to express the variant ester synthase polypeptide (e.g., '377) or the variant thioesterase polypeptide with ester synthase activity (e.g., Ppro). Expression of mutant or variant '377 polypeptides results in production of fatty ester compositions with increased yields of fatty esters and decreased yields of beta hydroxyl esters. Expression of mutant or variant Ppro polypeptides results in production of fatty ester compositions with increased yields of fatty esters.

In order to illustrate the disclosure, the applicants have constructed host strains that express variant ester synthase polypeptide sequences (see Examples, infra). Examples of variant ester synthase polypeptide sequences that when expressed in a recombinant host cell result in a higher titer of fatty esters include but are not limited to, sequences expressed in host strains 9B12 (SEQ ID NO: 4), pKEV022 (SEQ ID NO: 10), KASH008 (SEQ ID NO: 16), KASH280 (SEQ ID NO: 33) and KASH281 (SEQ ID NO: 35). Examples of variant ester synthase polypeptide sequences that when expressed in a recombinant host cell result in a higher titer of fatty esters and a decrease in β-OH ester production include polypeptide sequences expressed in host strains pKEV28 (SEQ ID NO: 12), and KASH008 (SEQ ID NO: 16), KASH285 (SEQ ID NO: 37), KASH286 (SEQ ID NO: 39), KASH288 (SEQ ID NO: 41) and KASH289 (SEQ ID NO: 43).

Examples of variant Ppro polypeptide sequences that when expressed in a recombinant host cell result in a higher titer of fatty esters include but are not limited to, sequences expressed in host strains PROF1 (SEQ ID NO: 53), PROF2 (SEQ ID NO: 55), P1B9 (SEQ ID NO: 58), N115F (SEQ ID NO: 61), Vc7P4H5 (SEQ ID NO: 63), Vc7P5H9 (SEQ ID NO: 65) and Vc7P6F9 (SEQ ID NO: 31).

The recombinant host cell may produce a fatty ester, such as a fatty acid methyl ester (FAME), a fatty acid ethyl ester (FAEE), a wax ester, or the like. The fatty acid esters are typically recovered from the culture medium. The fatty acid ester composition produced by a recombinant host cell can be analyzed using methods known in the art, for example, GC-FID, in order to determine the distribution of particular fatty acid esters as well as chain lengths and degree of saturation of the components of the fatty ester composition.

Methods of Making Recombinant Host Cells and Cultures

Various methods well known in the art can be used to genetically engineer host cells to produce fatty esters and/or fatty ester compositions. The methods can include the use of vectors, preferably expression vectors, comprising a nucleic acid encoding a mutant or variant '377 ester synthase or Ppro thioesterase with ester synthase activity, as described herein. Those skilled in the art will appreciate a variety of viral and non-viral vectors can be used in the methods described herein.

In some embodiments of the present disclosure, a "higher" titer of fatty esters in a particular composition is a higher titer of a particular type of fatty acid ester or a combination of fatty acid esters produced by a recombinant host cell culture relative to the titer of the same fatty acid ester or combination of fatty acid esters produced by a control culture of a corresponding wild-type host cell. In some embodiments, a mutant or variant '377 ester synthase polynucleotide (or gene) sequence or a mutant or variant Ppro polynucleotide (or gene) sequence is provided to the host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. The one or more polynucleotide sequences, comprising open reading frames encoding proteins and operably-linked regulatory sequences can be integrated into a chromosome of the recombinant host cells, incorporated in one or more plasmid expression system resident in the recombinant host cells, or both.

The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, *E. coli*, is most often carried out with vectors containing constitutive or inducible promoters directing the expression of either fusion or non-fusion polypeptides. Suitable expression systems for both prokaryotic and eukaryotic cells are well known in the art; see, e.g., Sambrook et al., "Molecular Cloning: A Laboratory Manual," second edition, Cold Spring Harbor Laboratory, (1989). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Examples of host cells that are microorganisms, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*. In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In still other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an Actinomycetes cell. In some embodiments, the host cell is a *Saccharomyces cerevisiae* cell.

In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity.

In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis.*

Culture and Fermentation of Genetically Engineered Host Cells

As used herein, the term "fermentation" broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, the term "conditions permissive for the production" means any conditions that allow a host cell to produce a desired product, such as a fatty acid ester composition. Similarly, the term "conditions in which the polynucleotide sequence of a vector is expressed" means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 μL, 200 μL, 300 μL, 400 μL, 500 μL, 1 mL, 5 mL, 10 mL, 15 mL, 25 mL, 50 mL, 75 mL, 100 mL, 500 mL, 1 L, 2 L, 5 L, or 10 L; fermented; and induced to express a desired polynucleotide sequence, such as a polynucleotide sequence encoding a polypeptide having ester synthase activity. For large scale production, the engineered host cells can be grown in cultures having a volume batches of about 10 L, 100 L, 1000 L, 10,000 L, 100,000 L, 1,000,000 L or larger; fermented; and induced to express a desired polynucleotide sequence. The fatty ester compositions described herein are found in the extracellular environment of the recombinant host cell culture and can be readily isolated from the culture medium. A fatty acid derivative may be secreted by the recombinant host cell, transported into the extracellular environment or passively transferred into the extracellular environment of the recombinant host cell culture. The fatty ester composition may be isolated from a recombinant host cell culture using routine methods known in the art.

Screening Genetically Engineered Host Cells

In one embodiment of the present disclosure, the activity of a mutant or variant '377 ester synthase polypeptide is determined by culturing recombinant host cells (comprising one or more mutagenized ester synthase such as '377 polynucleotide sequences), followed by screening to identify characteristics of fatty acid ester compositions produced by the recombinant host cells; for example, titer, yield and productivity of fatty acid esters; and percent beta hydroxy esters. In another embodiment, the activity of a mutant or variant Ppro polypeptide is determined by culturing recombinant host cells (comprising one or more mutagenized thioesterase such as Ppro polynucleotide sequences), followed by screening to identify characteristics of fatty acid ester compositions produced by the recombinant host cells; for example: titer, yield and productivity of fatty acid esters; and free fatty acids. Mutant or variant '377 ester synthase polypeptides or mutant or variant Ppro polypeptides and fragments thereof can be assayed for ester synthase activity using routine methods. For example, a mutant or variant '377 ester synthase polypeptide or Ppro polypeptide or fragment thereof is contacted with a substrate (e.g., an acyl-CoA, an acyl-ACP, a free fatty acid, or an alcohol) under conditions that allow the polypeptide to function. A decrease in the level of the substrate or an increase in the level of a fatty ester or a fatty ester composition can be measured to determine the ester synthase activity.

Products Derived from Recombinant Host Cells

As used herein, "fraction of modem carbon" or fM has the same meaning as defined by National Institute of Standards and Technology (NIST) Standard Reference Materials (SRMs 4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), fM is approximately 1.1.

Bioproducts (e.g., the fatty ester compositions produced in accordance with the present disclosure) comprising biologically produced organic compounds, and in particular, the fatty ester compositions produced using the fatty acid biosynthetic pathway herein, have been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al., Radiocarbon 19:355 (1977)). Coal and petroleum fall generally in this latter range.

$$\delta^{13}C\ (‰)=[(^{13}C/^{12}C)\ \text{sample}-(^{13}C/^{12}C)\ \text{standard}]/(^{13}C/^{12}C)\ \text{standard}\times1000$$

A series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include fatty ester compositions and products produced by any of the methods described herein. Specifically, fatty ester composition or product can have a $\delta^{13}C$ of about −28 or greater, about −27 or greater, −20 or greater, −18 or greater, −15 or greater, −13 or greater, −10 or greater, or −8 or greater. For example, the fatty ester composition or product can have a $\delta^{13}C$ of about −30 to about −15, about −27 to about −19, about −25 to about −21, about −15 to about −5, about −13 to about −7, or about −13 to about −10. In other instances, the fatty ester composition or product t can have a $\delta^{13}C$ of about −10, −11, −12, or −12.3. Fatty ester compositions and products produced in accordance with the disclosure herein can also be distinguished from petroleum based organic compounds by comparing the amount of $^{14}C$ in each compound. Because $^{14}C$ has a nuclear half-life of 5730 years, petroleum based fuels containing "older" carbon can be distinguished from fatty ester compositions and bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" (fM). The fatty ester compositions and products described herein include bioproducts that can have an fM $^{14}C$ of at least about 1. For example, the bioproduct of the disclosure can have an fM $^{14}C$ of at least about 1.01, an fM $^{14}C$ of about 1 to about 1.5, an fM $^{14}C$ of about 1.04 to about 1.18, or an fM $^{14}C$ of about 1.111 to about 1.124.

Another measurement of $^{14}C$ is known as the percent of modern carbon (pMC). For an archaeologist or geologist using $^{14}C$ dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty esters as described herein can have a pMC of at least about 50, 60, 70, 75, 80, 85, 90, 95, 96, 97, 98, 99, or 100. In other instances, a fatty ester composition described herein can have a pMC of between about 50 and about 100; about 60 and about 100; about 70 and about 100; about 80 and about 100; about 85 and about 100; about 87 and about 98; or about 90 and about 95. In yet other instances, a fatty ester composition described herein can have a pMC of about 90, 91, 92, 93, 94, or 94.2.

Fatty Ester Compositions

Examples of fatty esters include fatty acid esters, such as those derived from short-chain alcohols, including FAEE and FAME, and those derived from longer chain fatty alcohols. The fatty esters and/or fatty ester compositions that are produced can be used, individually or in suitable combinations, as a biofuel (e.g., a biodiesel), an industrial chemical, or a component of, or feedstock for, a biofuel or an industrial chemical. In some aspects, the disclosure pertains to a method of producing a fatty ester composition comprising one or more fatty acid esters, including, for example, FAEE, FAME and/or other fatty acid ester derivatives of longer chain alcohols. In related aspects, the method comprises a genetically engineered production host suitable for making fatty esters and fatty ester compositions including, but not limited to, FAME, FAEE, fatty acid propyl esters, fatty acid isopropyl esters, fatty acid butyl esters, monoglycerides, fatty acid isobutyl esters, fatty acid 2-butyl esters, and fatty acid tert-butyl esters, and the like.

Accordingly, in one aspect, the disclosure features a method of making a fatty ester composition that may comprise a decreased percentage of beta hydroxy esters and free fatty acids relative to a fatty ester compositions produced by a wild type ester synthase enzyme, such as '377. The variant '377 polypeptide or enzyme with improved fatty acid methyl ester activity has improved properties including, but not limited to, increased beta hydroxy esters, decreased beta hydroxyl esters, increased chain lengths of fatty acid esters, and decreased chain lengths of fatty acid esters. The method includes expressing in a host cell a gene encoding a polypeptide having ester synthase activity. In another aspect, the disclosure features a method of making a fatty ester composition that may or may not comprise free fatty acids, wherein the method includes expressing in a host cell a gene encoding a Ppro polypeptide having ester synthase activity. In some embodiments, the gene encoding the ester synthase polypeptide or thioesterase polypeptide with ester synthase activity is selected from the enzymes classified as EC 2.3.1.75 or EC 3.1.2, respectively, and any other polypeptides capable of catalyzing the conversion of an acyl thioester to fatty esters, including, without limitation, thioesterases, ester synthases, acyl-CoA:alcohol transacylases, alcohol O-fatty acid-acyl-transferase, acyltransferases, and fatty acyl-coA:fatty alcohol acyltransferases, or a suitable variant thereof.

In certain embodiments, an endogenous thioesterase of the host cell, if present, is unmodified. In certain other embodiments, the host cell expresses an attenuated level of a thioesterase activity or the thioesterase is functionally deleted. In some embodiments, the host cell has no detectable thioesterase activity. As used herein the term "detectable" means capable of having an existence or presence ascertained. For example, production of a product from a reactant (e.g., production of a certain type of fatty acid esters) is detectable using the methods known in the art or provided herein. In certain embodiments, the host cell expresses an attenuated level of a fatty acid degradation enzyme, such as, for example, an acyl-CoA synthase, or the fatty acid degradation enzyme is functionally deleted. In some embodiments, the host cell has no detectable fatty acid degradation enzyme activity. In particular embodiments, the host cell expresses an attenuated level of a thioesterease, a fatty acid degradation enzyme, or both. In other embodiments, the thioesterase, the fatty acid degradation enzyme, or both, are functionally deleted. In some embodiments, the host cell can convert an acyl-ACP or acyl-CoA into fatty acids and/or derivatives thereof such as esters, in the absence of a thioesterase, a fatty acid derivative enzyme, or both. Alternatively, the host cell can convert a free fatty acid to a fatty ester in the absence of a thioesterase, a fatty acid derivative enzyme, or both. In certain embodiments, the method further includes isolating a fatty ester composition, a fatty ester or a free fatty acid from the host cell or from the host cell culture. In preferred embodiments of the disclosure, the fatty acid derivative composition comprises a high percentage of fatty esters. In certain embodiments, the fatty ester or fatty ester composition is derived from a suitable alcohol substrate such as a short- or long-chain alcohol.

In general, the fatty ester or fatty ester composition is isolated from the extracellular environment of the host cell. In some embodiments, the fatty ester or fatty ester composition is spontaneously secreted, partially or completely, from the host cell. In alternative embodiments, the fatty ester or fatty ester composition is transported into the extracellular environment, optionally with the aid of one or more transport proteins. In still other embodiments, the fatty ester or fatty ester composition is passively transported into the extracellular environment.

In some embodiments, the disclosure comprises a method of producing a fatty acid ester or a fatty acid ester composition which composition may comprise a decreased percentage of beta hydroxy esters and/or free fatty acids by culturing a genetically engineered host cell under conditions that allow expression or overexpression of a mutant or variant '377 polypeptide. In an alternative embodiment, the disclosure comprises a method of producing a fatty acid ester or a fatty acid ester composition which composition may comprise an increased percentage of beta hydroxy esters and/or free fatty acids by culturing a genetically engineered host cell under conditions that allow expression or overexpression of a mutant or variant '377 polypeptide. In some embodiments, the method further comprises culturing the genetically engineered host cell in medium comprising carbon source (such as a carbohydrate) under conditions that permit production of a fatty acid ester or a fatty acid ester composition which may comprise an increased or decreased percentage of beta hydroxy esters and/or free fatty acids. In other embodiments, the disclosure comprises a method of producing a fatty acid ester or a fatty acid ester composition which composition may comprise free fatty acids by culturing a genetically engineered host cell under conditions that allow expression or overexpression of a Ppro polypeptide having ester synthase activity. In some embodiments, the method further comprises culturing the genetically engineered host cell in medium comprising carbon source such as a carbohydrate under conditions that permit production of a fatty acid ester or a fatty acid ester composition which may comprise free fatty acids.

In some embodiments, the disclosure provides an ester synthase polypeptide comprising the amino acid sequence of SEQ ID NO: 2, with one or more amino acid substitutions, additions, insertions, or deletions wherein the polypeptide has ester synthase activity. A mutant or variant '377 polypeptide has greater ester synthase activity than the corresponding wild type '377 polypeptide. For example, a mutant or variant '377 polypeptide is capable, or has an improved capacity, of catalyzing the conversion of thioesters, for example, fatty acyl-CoAs or fatty acyl-ACPs, to fatty acids and/or fatty acid derivatives. In particular embodiments, the mutant or variant '377 polypeptide is capable, or has an improved capacity, of catalyzing the conversion of thioester substrates to fatty acids and/or derivatives thereof, such as fatty esters, in the absence of a thioesterase activity, a fatty acid degradation enzyme activity, or both. For example, a mutant or variant '377 polypeptide can convert fatty acyl-ACP and/or fatty acyl-CoA into fatty esters in vivo, in the absence of a thioesterase or an acyl-CoA synthase activity.

In other embodiments, the disclosure provides a Ppro polypeptide comprising the amino acid sequence of SEQ ID NO: 51, with one or more amino acid substitutions, additions, insertions, or deletions wherein the polypeptide has ester synthase activity. In certain embodiments, a Ppro polypeptide of the disclosure has greater ester synthase activity than the corresponding wild type Ppro polypeptide. For example, a Ppro polypeptide of the disclosure having ester synthase activity is capable, or has an improved capacity, of catalyzing the conversion of thioesters, for example, fatty acyl-CoAs or fatty acyl-ACPs, to fatty acids and/or fatty acid derivatives. In particular embodiments, the Ppro polypeptide having ester synthase activity is capable, or has an improved capacity, of catalyzing the conversion of thioester substrates to fatty acids and/or derivatives thereof, such as fatty esters, in the absence of a thioesterase activity, a fatty acid degradation enzyme activity, or both. For example, a Ppro polypeptide having ester synthase activity can convert fatty acyl-ACP and/or fatty acyl-CoA into fatty esters in vivo, in the absence of a thioesterase or an acyl-CoA synthase activity.

In some embodiments, the mutant or variant '377 polypeptide or mutant or variant Ppro polypeptide comprises one or more of the following conserved amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of residue bearing an amide group; exchange of a basic residue, such as lysine and arginine, with another basic residue; and replacement of an aromatic residue, such as phenylalanine and tyrosine, with another aromatic residue. In some embodiments, the mutant or variant '377 polypeptide or mutant or variant Ppro polypeptide having ester synthase activity has about 1, 2, 3, 4, 5, 6, 7, 8, 9, 10, 15, 20, 30, 40, 50, 60, 70, 80, 90, 100, or more amino acid substitutions, additions, insertions, or deletions. In some embodiments, the polypeptide variant has ester synthase and/or acyltransferase activity. For example, the mutant or variant '377 polypeptide polypeptide or mutant or variant Ppro polypeptide is capable of catalyzing the conversion of thioesters to fatty acids and/or fatty acid derivatives, using alcohols as substrates. In a non-limiting example, the mutant or variant '377 polypeptide polypeptide or mutant or variant Ppro polypeptide is capable of catalyzing the conversion of a fatty acyl-CoA and/or a fatty acyl-ACP to a fatty acid and/or a fatty acid ester, using a suitable alcohol substrate, such as, for instance, a methanol, ethanol, propanol, isopropanol, butanol, pentanol, hexanol, heptanol, octanol, decanol, dodecanol, tetradecanol, or hexadecanol.

EXAMPLES

The following specific examples are intended to illustrate the disclosure and should not be construed as limiting the scope of the claims. The applicants have employed a one-gene-system for production of fatty acid esters in recombinant host cells. This includes expressing in suitable host cells mutant or variant '377 polypeptides that have been engineered to have improved ester synthase activity in order to produce fatty ester compositions at increased titer and yield. The fatty ester compositions obtained include FAME as well as increased and decreased amounts of beta hydroxy esters. The same strategy was used for making Ppro polypeptides with enhanced ester synthase activity for the production of fatty esters at increased titer and yield.

Protocols:

All protocols use 96 well plates, master block, 2 mL (Greiner Bio-One, Monroe, N.C. or Corning, Amsterdam, The Netherlands) for growing cultures and Costar plates for extracting fatty acid species from the culture broth. The protocols below include the fermentation conditions and can be used to evaluate fatty acid species production. Alternative protocols can also be used to evaluate fatty acid species production.

Protocol 1 (FA4P, 32° C.):

From an LB culture growing in 96 well plate: 30 μL LB culture was used to inoculate 270 μL FA2P (Table 4), which was then incubated for approximately 16 hours at 32° C. shaker. 30 μL of the overnight seed was then used to inoculate 300 μL FA4P+2% MeOH+1 mM IPTG (Table 4). The cultures were then incubated at 32° C. shaker for 24 hours, when they were extracted following the standard extraction protocol detailed below (Protocol 5).

Protocol 2 (BP3G2P, 32° C.):

Library glycerol stocks were thawed and 10 μL transferred to 150 μL LB+100 μg/mL spectinomycin in 96-shallow-well plates, which were incubated at 32° C. for 20 hours. L of this culture was used to inoculate 280 μL BS1G4Pmedia (Table 4), which was incubated at 32° C. shaking at 250 rpm for 20 hours. 20 μL of this culture was used to inoculate 380 μL BP3G2P media (Table 4). Cultures were incubated at 32° C. shaking for 24 hours, when they were either subjected to the nile red assay following the standard protocol detailed below or extracted following the standard extraction protocol detailed below (Protocol 5).

Protocol 3 (FA2, 32° C.):

From an LB culture growing in a 96 well plate: 30 μL of LB culture was used to inoculate 270 μL FA2, which was then incubated for approximately 16 hours at 32° C. on a shaker. 30 μL of the overnight seed was then used to inoculate 300 μL FA2+2% MeOH+1 mM IPTG. The cultures were then incubated at 32° C. on a shaker for 24 hours, when they were extracted following the standard extraction protocol detailed below (Protocol 5).

Protocol 4 (FA2P, 32° C.):

From an LB culture growing in 96 well plate: 30 μL LB culture was used to inoculate 270 μL FA2P, which was then incubated for approximately 16 hours at 32° C. shaker. L of the overnight seed was then used to inoculate 300 μL FA2P+2% MeOH+1 mM IPTG. The cultures were then incubated at 32° C. shaker for 24 hours, when they were extracted following the standard extraction protocol detailed below (Protocol 5).

Protocol 5 (Fatty Acid Species Standard Extraction):

To each well to be extracted 40 μL 1M HCl, then 300 μL butyl acetate with 500 mg/L C11-FAME as internal standard was added. The 96 well plate was then heat-sealed using a plate sealer (ALPS-300; Abgene, ThermoScientific, Rockford, Ill.), and shaken for 15 minutes at 2000 rpm using MixMate (Eppendorf, Hamburg, Germany). After shaking, the plate was centrifuged for 10 minutes at 4500 rpm at room temperature (Allegra X-15R, rotor SX4750A, Beckman Coulter, Brea, Calif.) to separate the aqueous and organic layers. 50 μL of the organic layer was transferred to a 96 well plate (96-well plate, polypropylene, Corning, Amsterdam, The Netherlands). The plate was heat sealed then stored at −20° C. until it was evaluated by GC-FID by employing standard automated methods.

Protocol 6 (Fatty Acid Species Standard Nile Red Assay):

After 24 hour fermentation, Nile Red assay was performed by adding 70 μL of fermentation broth to 130 μL of 1.54 μg/mL Nile Red in 84.6% water and 15.4% acetonitrile solution (for a final assay concentration of 1 μg/mL Nile Red) in a Greiner MicrolonFluotrac 200 plate and mixed by pipetting up and down. Relative fluorescence units were measured at excitation of 540 nm and emission of 630 nm using the SpectraMax M2.

Protocol 7 (Building a Saturation Library):

Standard techniques known to those of skill in the art were used to prepare saturation libraries. For example, the vector backbone may be prepared by using restriction endonucleases in the vector, while the creation of diversity in the DNA insert can be generated using degenerate primers. For example, the cloning of the vector backbone and a DNA insert with diversity can be performed using InFusion Cloning System (Clontech Laboratories, Inc., Mountain View, Calif.) according to the manufacturer's protocol.

Protocol 8 (Building a Combination Library):

Mutations identified as beneficial were combined to provide Ppro or 377 variants with further improvements in the production of fatty acid species or FAME. Standard techniques known to those of skill in the art were used to prepare the combination libraries. For example, the vector backbone can be prepared by using restriction endonucleases in the vector, while the creation of diversity in the DNA insert can be generated using primers to introduce the desired mutations. For example, the cloning of the vector backbone and a DNA insert with diversity can be performed using InFusion Cloning System (Clontech Laboratories, Inc., Mountain View, Calif.), according to manufacturer's protocol. For example, combination libraries can be generated using the transfer PCR (tPCR) protocol (Erijman et al., 2011. *J. Structural Bio.* 175, 171-177).

Protocol 9 (Library Screening):

Once the library diversity was generated in a saturation library or combination library, it was screened using one of the methods described above (Protocols 1-4). When screening ester synthase variants, three types of hits were identified: (1) increased fatty acid ester species titer ("FAS" titer); (2) increased amount of FAME produced; e.g., C14-FAME; and/or (3) decreased amount of beta hydroxyl ester produced. The mutations in the '377 variants within each hit were identified by sequencing using standard techniques routinely employed by those of skill in the art. The mutations in the '377 variants within each hit were identified by sequencing using standard techniques routinely employed by those of skill in the art. Tables 1 and 2 list the mutations ("hits") identified as beneficial in saturation libraries and Table 5 lists mutations ("hits") identified as beneficial in combination libraries. When screening Ppro variants, two types of hits were identified (1) increased fatty acid ester species; (2) increase in the amount of FAME produced. The mutations in the Ppro variants within each hit were identified by sequencing and using standard techniques routinely employed by those of skill in the relevant field. Tables 8 through 11 list the mutations ("hits") identified as beneficial in saturation libraries and Tables 12 and 14 list mutations ("hits") identified as beneficial in combination libraries.

Example 1

Saturation Library Prepared Using WS377 as a Template

A full saturation library of the ester synthase from *Marinobacter hydrocarbonoclasticus* ("'377"), was built and screened for variants that showed improvement over the wild type WS377 (Protocol 7). The plasmid used to make the full saturation library was designated pKEV027 which expressed SEQ ID NO: 1 (i.e., the wild type nucleic acid sequence of WS377). The full saturation library was screened in an *E. coli* strain (BD64) that was engineered to block beta oxidation (via deletion of FadE) and overexpress a number of fatty acid biosynthetic pathway enzymes (e.g., FabA, FabB, FabF, FabG, FabI, FabH, FabV, FabZ, accABCD) through standard manipulation techniques. However, any suitable host strain can be used herein. The libraries were screened using one of the standard protocols (Protocols 1-2) described above. The improvements were originally classified as either improving titer of FAME or reducing the fraction of beta hydroxy esters (referred to herein as "β-OH esters" or "β-OH FAME" or "beta-OH" or "beta-hydroxy") without necessarily affecting FAME titer. The results from screening saturation libraries are shown in Tables 1 and 2 below. Table 1 presents results for mutations that all showed increased fatty ester titers when using '377 as the template (SEQ ID NO: 1). Table 2 presents results for mutations that led to a decrease in % β-OH FAME using '377 as the template. Notably, some mutants showed both, an improved titer of FAME as well as a decrease in β-OH FAME, which is beneficial if the final desired product is mostly FAME. Some mutants showed an improved titer of FAME as well as an increase in β-OH FAME. In addition, some mutants resulted in an increase or decrease of short-chain esters.

As can be seen in Table 1 below, mutations from the '377 saturation libraries correlated with improved fatty ester titer in all mutants, while the production of β-OH esters and shorter chain length ester varied from mutant to mutant. For example, a substitution of the amino acid at position 15 (Serine to Glycine) changed the total FAME titer from baseline 1 to 2.402. Thus, the titer increased by 2.4 fold compared to baseline (i.e., wild type). In this particular mutant, β-OH esters increased by about 2.66 fold. The production of esters with a carbon chain length of 14 over esters with a carbon chain length of 16 increased by 1.48 fold over baseline (i.e., wild type). On the other hand, a substitution of the amino acid position 393 (Glutamate to Glycine) increased the FAME titer by 2.3 fold and decreased the β-OH esters to 70% of control while C14/C16 ester production stayed about the same.

TABLE 1

| | Average | | |
|---|---|---|---|
| Mutation | Total FAME | % β-OH | C14/C16 |
| S15G | 2.402 | 2.664 | 1.476 |
| Q26T | 1.356 | 2.233 | 1.163 |
| L39M | 1.64 | 2.82 | 0.936 |
| L39S | 2.228 | 2.368 | 1.127 |
| L39A | 1.876 | 2.412 | 0.94 |
| R40S | 1.328 | 2.587 | 1.259 |
| D41H | 2.225 | 2.344 | 1.312 |
| D41G | 2.031 | 3.474 | 1.217 |
| D41A | 1.792 | 2.38 | 2.074 |
| V43K | 2.109 | 1.617 | 0.421 |
| V43S | 1.768 | 2.283 | 1.053 |
| T44F | 2.007 | 1.577 | 0.872 |
| A73Q | 2.195 | 1.877 | 0.915 |
| V76L | 1.553 | 1.255 | 0.76 |
| D77A | 1.952 | 1.645 | 0.887 |
| K78W | 1.758 | 1.469 | 0.826 |
| K78F | 1.794 | 1.984 | 0.767 |
| 180V | 2.961 | 2.903 | 1.028 |
| R93T | 1.649 | 1.587 | 0.734 |
| G101L | 1.787 | 1.294 | 1.288 |
| I102R | 1.718 | 1.418 | 0.928 |
| N110R | 1.582 | 2.038 | 0.957 |
| P111S | 2.05 | 1.09 | 1.176 |
| P111G | 1.855 | 1.228 | 1.154 |

TABLE 1-continued

| | Average | | |
|---|---|---|---|
| Mutation | Total FAME | % β-OH | C14/C16 |
| G126D | 1.963 | 1.065 | 0.751 |
| R131M | 2.139 | 1.857 | 1.115 |
| V155G | 2.267 | 0.865 | 1.127 |
| N164R | 1.692 | 1.114 | 0.806 |
| V171R | 2.657 | 2.152 | 0.815 |
| V171E | 1.472 | 1.065 | 1.042 |
| R172W | 1.499 | 6.244 | 0.922 |
| D182G | 1.89 | 1.18 | 1.147 |
| E184L | 2.352 | 1.055 | 1.157 |
| E184F | 1.589 | 1.026 | 1.108 |
| E184S | 1.566 | 0.937 | 1.147 |
| E184R | 1.733 | 1.185 | 1.242 |
| E184G | 1.647 | 1.463 | 1.138 |
| A185M | 1.518 | 1.134 | 1.131 |
| A185L | 1.754 | 2.777 | 1.176 |
| P188R | 2.519 | 1.138 | 1.108 |
| A190R | 1.86 | 1.204 | 1.314 |
| A190W | 1.559 | 1.645 | 1.196 |
| S192V | 3.748 | 2.086 | 1.148 |
| S192A | 1.518 | 0.998 | 0.902 |
| Q193R | 1.735 | 1.2 | 1.344 |
| Q201W | 1.748 | 1.357 | 1.176 |
| Q201V | 1.79 | 1.289 | 1.32 |
| Q201A | 1.929 | 1.154 | 1.191 |
| A202L | 2.571 | 1.224 | 1.192 |
| D203R | 1.998 | 1.042 | 1.552 |
| P206F | 1.466 | 1.726 | 1.043 |
| G212L | 1.919 | 1.179 | 1.167 |
| V219L | 2.017 | 1.396 | 0.737 |
| T242R | 1.879 | 0.894 | 1.072 |
| T242K | 1.678 | 2.272 | 1.115 |
| A243R | 2.56 | 1.232 | 0.912 |
| R246Q | 3.571 | 0.692 | 0.412 |
| R246L | 2.083 | 0.746 | 0.711 |
| V272A | 1.984 | 1.511 | 0.78 |
| Q287S | 1.723 | 1.275 | 0.646 |
| D292F | 1.827 | 1.162 | 0.814 |
| P294G | 1.649 | 1.692 | 0.874 |
| G298G | 1.511 | 1.383 | 0.796 |
| I303G | 3.36 | 0.388 | 0.21 |
| I303W | 2.075 | 0.578 | 0.58 |
| R304W | 1.578 | 0.425 | 0.354 |
| F317W | 2.208 | 2.076 | 1.529 |
| I319G | 2.515 | 0.89 | 0.721 |
| A323G | 1.766 | 1.188 | 0.751 |
| D328F | 1.816 | 1.055 | 0.671 |
| Q334S | 1.573 | 0.935 | 0.821 |
| Q348A | 1.442 | 3.247 | 2.463 |
| P351G | 1.875 | 1.211 | 1.312 |
| S353T | 2.123 | 2.007 | 0.957 |
| M360W | 2.303 | 0.634 | 0.582 |
| M360S | 1.502 | 0.397 | 0.394 |
| Y366W | 1.506 | 0.969 | 1.175 |
| Y366G | 1.407 | 1.378 | 0.91 |
| G375A | 1.96 | 1.821 | 1.24 |
| M378A | 1.877 | 1.616 | 0.834 |
| E393G | 2.305 | 0.723 | 0.932 |
| T395E | 1.655 | 1.224 | 0.719 |
| V409L | 2.314 | 0.796 | 0.295 |
| I420V | 1.474 | 1.119 | 0.828 |
| S442G | 1.947 | 1.166 | 1.226 |
| A447C | 1.775 | 1.819 | 1.132 |
| A447L | 1.545 | 1.341 | 1.021 |
| A447I | 1.867 | 1.459 | 1.117 |
| L454V | 1.804 | 1.137 | 0.672 |
| R2S, Q348A | 1.628 | 3.976 | 2.475 |
| R2R, S235S | 1.178 | 1.949 | 1.213 |
| G4R, N331G | 2.262 | 2.431 | 1.324 |
| TSP, S186T | 1.6 | 2.837 | 1.198 |
| TSS, R98D | 2.287 | 2.01 | 1.277 |
| TSP, G310H | 1.711 | 2.141 | 1.217 |
| L6Q, Q193S | 1.529 | 2.069 | 2.878 |
| L6Q, A279V | 1.414 | 3.573 | 1.003 |
| D7N, T170R | 3.163 | 1.079 | 0.853 |
| G33S, S442E | 2.28 | 1.453 | 1.199 |

TABLE 1-continued

| Mutation | Average Total FAME | % β-OH | C14/C16 |
|---|---|---|---|
| R150P, A279G | 1.702 | 1.434 | 0.769 |
| E184G, K472T | 2.619 | 1.022 | 1.269 |
| V187G, *474Y | 1.678 | 1.481 | 1.028 |
| P188R, A197V | 2.944 | 1.078 | 1.146 |
| M195G, A197T | 1.291 | 4.127 | 1.223 |
| R207A, P366P | 1.877 | 1.164 | 0.685 |
| D307V, T470P | 1.858 | 1.094 | 1.026 |
| 24 bp repeat | 1.996 | 2.34 | 0.944 |
| 24bp repeat, R177V | 2.553 | 2.516 | 1.518 |
| 24bp repeat, V171R | 2.724 | 2.338 | 0.821 |

Some mutations in the tables have stars, for example, *474Y, which means that the position has a stop codon.

The applicants discovered a 24 bp repeat in one of the variant mutant nucleic acid sequences (i.e., SEQ ID NO: 28). The 24 bp repeat is a duplication of nucleic acid region ATGAAACGTCTCGGAACCCTGGAC (SEQ ID NO: 27) and located at the start of the gene prior to the ATG start codon. Thus, SEQ ID NO: 28 is a variant '377 nucleic acid sequence (this sequence is the result of SEQ ID NO: 27 and SEQ ID NO: 1 combined with no additional mutations) that codes for the amino acid sequence of SEQ ID NO: 29. SEQ ID NO: 29 gave surprisingly good titer as shown in Table 1. However, two additional mutants were detected that included SEQ ID NO: 29 as a template sequence with additional mutations in it, wherein the mutations increased the titer even further (see Table 1). (The numbering of mutations does not include the 24 bp repeat.) Notably, the 24 bp repeat led to an increase in titer of FAS and % beta-OH FAME, as seen in Table 1 which depicts the titer obtained when expressing SEQ ID NO: 29 in a host strain.

As can be seen in Table 2 below, some of the mutations from the '377 saturation libraries correlated with a decrease in % β-OH FAME while still increasing the total FAME tighter to a lesser degree compared in Table 1 (supra). However, some mutants significantly decreased % β-OH FAME while still significantly increasing total FAME titer.

TABLE 2

| Mutations | Average Total FAME | % β-OH | C14/C16 |
|---|---|---|---|
| T24W | 1.141 | 0.533 | 1.024 |
| V69W | 1.154 | 0.661 | 0.657 |
| S105G | 1.146 | 0.875 | 1.109 |
| P111D | 1.271 | 0.802 | 0.822 |
| D113V | 1.242 | 0.687 | 0.629 |
| D113A | 1.279 | 0.740 | 0.580 |
| S115R | 1.118 | 0.880 | 0.925 |
| C121S | 1.088 | 0.756 | 0.969 |
| H122S | 1.186 | 0.905 | 0.780 |
| L127G | 1.455 | 0.644 | 0.507 |
| L134T | 1.350 | 0.495 | 0.611 |
| T136G | 1.090 | 0.591 | 0.472 |
| I146K | 1.523 | 0.381 | 0.342 |
| I146R | 1.328 | 0.199 | 0.220 |
| S147A | 1.233 | 0.796 | 0.945 |
| T158R | 1.694 | 0.749 | 0.855 |
| M165K | 1.260 | 0.889 | 0.569 |
| V171H | 1.168 | 0.677 | 0.902 |
| V171W | 1.168 | 0.091 | 0.812 |
| R172S | 1.590 | 0.505 | 0.897 |

TABLE 2-continued

| Mutations | Average Total FAME | % β-OH | C14/C16 |
|---|---|---|---|
| P173W | 1.189 | 0.647 | 0.652 |
| S192L | 1.215 | 0.898 | 1.176 |
| A228G | 1.147 | 0.787 | 0.503 |
| V234C | 1.059 | 0.185 | 0.775 |
| H239G | 1.318 | 0.833 | 0.874 |
| Q244G | 1.397 | 0.601 | 0.923 |
| R246W | 1.191 | 0.312 | 0.323 |
| R246Q | 3.571 | 0.692 | 0.412 |
| R246G | 1.660 | 0.669 | 0.431 |
| R246V | 1.130 | 0.454 | 0.838 |
| R246L | 2.083 | 0.746 | 0.711 |
| R246A | 1.470 | 0.757 | 0.559 |
| Q250W | 1.061 | 0.850 | 0.860 |
| Q253G | 1.186 | 0.772 | 0.877 |
| L254R | 1.409 | 0.647 | 0.900 |
| L254T | 1.089 | 0.704 | 0.868 |
| K258R | 1.098 | 0.657 | 0.759 |
| S264D | 1.220 | 0.876 | 0.549 |
| S264V | 1.411 | 0.730 | 0.489 |
| S264W | 1.772 | 0.646 | 0.491 |
| G266S | 1.121 | 0.846 | 0.613 |
| S267G | 1.214 | 0.262 | 0.263 |
| Y274G | 1.115 | 0.789 | 0.556 |
| A285R | 1.273 | 0.864 | 0.893 |
| V301A | 1.500 | 0.755 | 0.440 |
| N302G | 1.355 | 0.254 | 0.182 |
| I303G | 3.360 | 0.388 | 0.210 |
| I303W | 2.075 | 0.578 | 0.580 |
| I303R | 1.257 | 0.373 | 0.857 |
| R304W | 1.578 | 0.425 | 0.354 |
| A306G | 1.103 | 0.808 | 1.164 |
| D307G | 1.079 | 0.645 | 1.095 |
| D307L | 1.197 | 0.817 | 1.279 |
| D307R | 1.537 | 0.679 | 0.848 |
| D307V | 1.273 | 0.585 | 0.984 |
| E309A | 1.190 | 0.544 | 0.775 |
| E309G | 1.392 | 0.735 | 0.667 |
| E309S | 1.249 | 0.730 | 0.768 |
| G310R | 1.801 | 0.886 | 1.146 |
| G310V | 1.098 | 0.732 | 0.879 |
| T311S | 1.163 | 0.634 | 0.297 |
| T313S | 1.208 | 0.587 | 0.903 |
| Q314G | 1.140 | 0.347 | 0.694 |
| I315F | 1.345 | 0.178 | 0.182 |
| S316G | 1.079 | 0.000 | 0.413 |
| A320C | 1.387 | 0.777 | 0.595 |
| A327I | 1.057 | 0.373 | 0.889 |
| K349C | 1.145 | 0.781 | 0.481 |
| K349Q | 1.105 | 0.637 | 0.693 |
| K349H | 1.243 | 0.663 | 0.458 |
| K349A | 1.200 | 0.484 | 0.472 |
| K352I | 1.207 | 0.576 | 0.418 |
| K352N | 1.084 | 0.783 | 0.679 |
| T356W | 1.153 | 0.345 | 0.727 |
| T356G | 1.135 | 0.688 | 1.019 |
| M360R | 1.238 | 0.375 | 0.487 |
| M360S | 1.502 | 0.397 | 0.394 |
| M360W | 2.303 | 0.634 | 0.582 |
| M360Q | 1.062 | 0.735 | 0.865 |
| M363W | 1.218 | 0.000 | 0.497 |
| P365G | 1.102 | 0.611 | 0.376 |
| I367M | 1.274 | 0.704 | 0.768 |
| M371R | 1.297 | 0.073 | 0.554 |
| G373R | 1.440 | 0.720 | 0.436 |
| G375S | 1.146 | 0.609 | 0.816 |
| G375V | 1.429 | 0.770 | 0.833 |
| T385G | 1.215 | 0.875 | 0.609 |
| E393R | 1.290 | 0.234 | 0.478 |
| E393W | 1.768 | 0.817 | 0.852 |

Example 2

Combination Library Prepared Using WS377 as a Template

Figure 4:
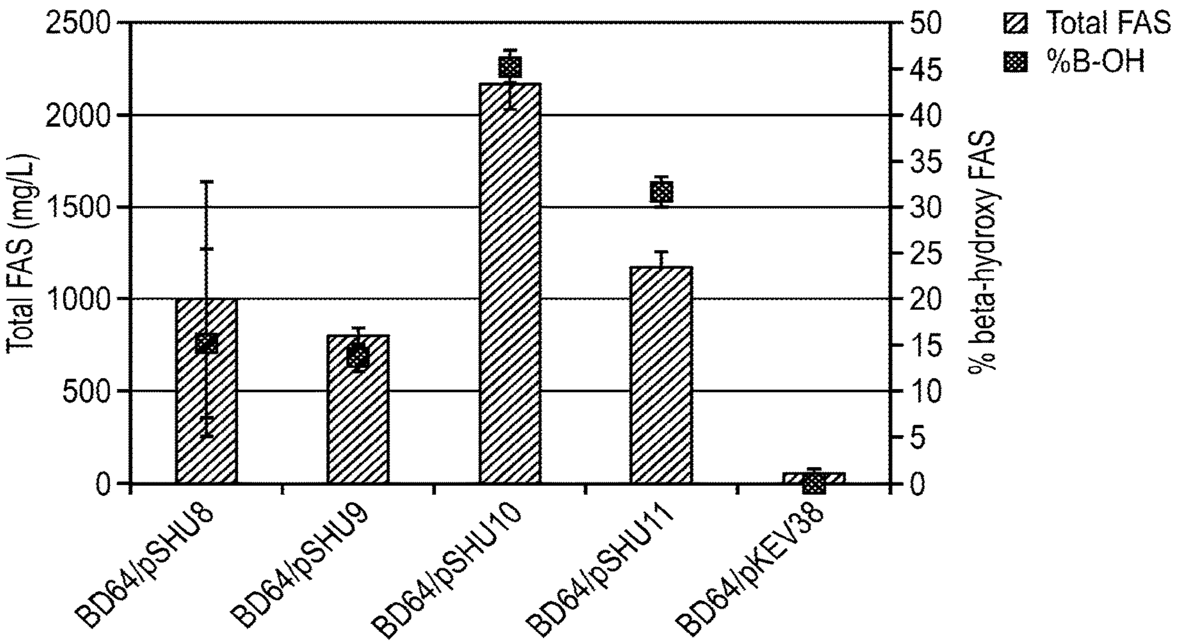
FIG. 4 shows the results of a GC-FID screen from a plate fermentation of combination library hits. The combination library was built using Group 0 primers and pKEV38 as a template, transformed into BD64.

Standard techniques were employed to prepare combination libraries (Protocol 8). The mutations tested in combination libraries (Tables 3A and 3B) were originally identified in the full saturation library of '377 (as described in Example 1). The plasmid used to make the combination libraries was pKEV38, which was constructed by removing the accABCD_birA from pKEV027. Without wanting to be bound by theory, the removal of the accABCD_birA is believed to reduce the intermediate levels of the fatty acids in the biosynthetic pathway such that the affinity of the mutant enzyme for the substrate is more easily detectable. Cells were plated on 2NBT+Nile Red agar (Table 4). Colonies were observed using the Dark Reader DR88X Transilluminator at an excitation range of 400 nm-500 nm and an amber filter permissive at 580-620 nm, handpicked into LB+ 100 μg/mL spectinomycin, grown overnight, and screened using one of the standard protocols (Protocols 1-2) described above. As shown in FIG. 4, one of the variants from this library showed a dramatic increase in FAS over the control (BD64/pKEV038, SEQ ID NO: 2). FIG. 4 shows the results of a plate fermentation of combination library hits. Several library hits outperformed the control (i.e., BD64/pKEV038) showing that '377 variants can support high production of FAS. The plasmid of the highest-producing variant, named pSHU10 (expressing variant '377 of SEQ ID NO: 14), was isolated and used as template for subsequent combination libraries.

The combination libraries were screened in strain BD64 (supra) by using one of the standard protocols (Protocols 1-2; supra). The results from screening '377 combination libraries are shown in Table 5.

Table 3A below shows the amino acid substitutions that were introduced in the first round of combination libraries.

TABLE 3A

| | |
|---|---|
| Mutations | T5S; S15G; G33S; L39S; L39A; D41A; V43K; I102R; P111S; R131M; V171R; P188R; S192V; Q201V; R246Q; R246L; I303W; I303G; F317W; I319G; S353T; E393G; V409L; S442G |

Table 3B below shows the amino acid substitutions that were introduced in the second round of combination libraries.

TABLE 3B

| | | | | | | |
|---|---|---|---|---|---|---|
| K1T | G101L | R172S | D203R | A285R | A327I | T385G |
| K1N | I102R | R172W | P206F | E286H | D328F | E393G |
| G4R | S105G | P173W | R207A | Q287S | N331G | E393R |
| S5P | N110R | R177V | G212L | D292F | Q334S | E393W |
| S5T | S111P | A179V | G212A | P294G | Q348A | T395E |
| L6Q | S111G | D182G | V219L | V301A | Q348R | E404K |
| D7N | S111D | E184L | A228G | N302G | K349C | E404R |
| G15S | D113V | E184G | V234C | I303W | K349Q | L409V |
| T24W | D113A | E184R | H239G | I303G | K349H | S410G |
| Q26T | S115R | E184F | T242R | I303R | K349A | L411A |
| L30H | C121S | E184S | T242K | R304W | P351G | I420V |
| G33S | H122S | A185L | A243R | A306G | K352I | C422G |
| L39A | G126D | A185M | Q244G | D307F | K352N | S424G |
| L39M | L127G | S186T | R246Q | D307N | T353S | S424Q |
| L39S | R131M | V187G | R246L | D307G | T356G | N430G |
| R40S | L134T | V187R | R246G | D307L | T356W | G442S |
| D41A | T136G | R188P | R246W | D307R | Q357V | G442E |
| D41H | I146K | A190R | R246V | D307V | M360R | M443G |
| D41G | I146R | A190P | R246A | E309A | M360W | A447C |
| D41Y | I146L | A190W | Q250W | E309G | M360S | A447L |
| V43K | S147A | S192V | Q253G | E309S | M360Q | A447I |
| V43S | V149L | S192L | L254R | G310R | M363W | L454V |
| T44F | R150P | S192A | L254T | G310H | P365G | D455E |
| V69W | V155G | Q193S | K258R | G310V | Y366W | L457Y |
| A73Q | T158R | Q193R | S264D | T311S | Y366G | E458W |
| V76L | N164R | M195G | S264V | T313S | I367M | I461G |
| D77A | M165K | A197V | S264W | Q314G | M371R | R467T |
| K78W | T170R | A197T | G266S | I315F | G373R | K472T |
| K78F | R171V | L200R | S267G | S316G | G375S | K472* |
| I80V | R171H | Q201V | V272A | W317F | G375V | |
| R93T | R171E | Q201W | Y274G | I319G | G375A | |
| R98D | R171F | Q201A | A279G | A320C | M378A | |
| E99Q | R171W | A202L | A279V | A323G | V381F | |

Table 4 below shows the media names and formulations that were used.

TABLE 4

| Media Name | Formulation | | |
|---|---|---|---|
| 2NBT + Nile Red agar | 1 | X | P-lim Salt Soln w/(NH4)2SO4 |
| | 1 | mg/ml | Thiamine |
| | 1 | mM | MgSO4 |
| | 1 | mM | CaCl2 |
| | 30 | g/L | glucose |
| | 1 | X | TM2 |
| | 5 | g/L | casaminoacids |
| | 15 | g/L | Agarose |
| | 2% | | Methanol |
| | 0.5 | mg/L | Nile Red |
| | 10 | mg/L | Fe Citrate |
| | 100 | mg/L | spectinomycin |
| | 100 | mM | BisTris (pH 7.0) |
| BS1G4P | 1 | X | P-lim Salt Soln w/(NH4)2SO4 |
| | 1 | mg/ml | Thiamine |
| | 1 | mM | MgSO4 |
| | 0.1 | mM | CaCl2 |
| | 10 | g/L | glucose |
| | 1 | X | TM2 |
| | 10 | mg/L | Fe Citrate |
| | 100 | μg/mL | spectinomycin |
| | 100 | mM | BisTris (pH 7.0) |
| BP3G2P | 0.5 | X | P-lim Salt Soln w/(NH4)2S04 |
| | 1 | mg/ml | Thiamine |
| | 1 | mM | MgSO4 |
| | 0.1 | mM | CaCl2 |
| | 50 | g/L | glucose |
| | 1 | X | TM2 |
| | 10 | mg/L | Fe Citrate |
| | 100 | μg/mL | spectinomycin |
| | 100 | mM | BisTris (pH 7.0) |
| | 2.5 | g/L | (NH4)2SO4 |
| | 2% | | MeOH |
| | 1 | mM | IPTG |
| FA2P | 1 | X | P-lim Salt Soln |
| | 2 | g/L | NH4Cl |
| | 1 | mg/ml | Thiamine |
| | 1 | mM | MgSO4 |
| | 0.1 | mM | CaCl2 |
| | 30 | g/L | glucose |
| | 1 | X | TM2 |
| | 10 | mg/L | Fe Citrate |
| | 100 | mM | BisTris (pH 7.0) |
| FA4P | 0.5 | X | P-lim Salt Soln |
| | 2 | g/L | NH4Cl |
| | 1 | mg/ml | Thiamine |
| | 1 | mM | MgSO4 |
| | 0.1 | mM | CaCl2 |
| | 50 | g/L | glucose |
| | 1 | X | TM2 |
| | 10 | mg/L | Fe Citrate |
| | 100 | mM | BisTris (pH 7.0) |
| FA2 (2 g/L NH4Cl) for 96 well plate screen | 1 | X | Salt Soln |
| | 1 | g/L | NH4Cl |
| | 1 | mg/ml | Thiamine |

TABLE 4-continued

| Media Name | Formulation | | |
|---|---|---|---|
| | 1 | mM | MgSO4 |
| | 0.1 | mM | CaCl2 |
| | 30 | g/L | glucose |
| | 1 | X | TM2 |
| | 10 | mg/L | Fe Citrate |
| | 100 | mM | BisTris (pH 7.0) |
| FA2 (2 g/L NH4Cl) with Triton for shake flask validation | 1 | X | Salt Soln |
| | 1 | g/L | NH4Cl |
| | 1 | mg/ml | Thiamine |
| | 1 | mM | MgSO4 |
| | 0.1 | mM | CaCl2 |
| | 30 | g/L | glucose |
| | 1 | X | TM2 |
| | 10 | mg/L | Fe Citrate |
| | 0.05% | | Triton X-100 |
| | 100 | mM | BisTris (pH 7.0) |

Table 5 below depict the secondary screen, showing the mutations over pSHU10 (which contains mutations T5S, S15G, P111S, V171R, P188R, F317W, S353T, V409L, S442G) and the normalized GC-FID results. The results depicted are relative to control (i.e., pSHU10, SEQ ID NO: 14). Each line on the table represents a different combination mutant that was made. All mutants were measured to have distinct properties in that they either affected the total FAME produced, the total FAS produced, the percent FAME produced, or the ester species in the final composition (with C12/C14 or C14/C16 chain length), or a combination of these properties. As can be seen in Table 5, some mutants behaved similar to other mutants in terms of their properties.

For example, as shown on the first line in Table 5 below, the mutant containing mutations A190P, N302G, T313 S, and Q348R produced a higher percent FAME (and reduction of β-OH FAME), and also increased the production of C14/C16 chain length esters, meaning it produced more of C14 esters than C16 esters in the final product. This is desirable since shorter chain esters can be used for many products including biodiesel. The results also show that the applicants were able to alter the final chain length of ester species in the final composition.

The following combinations of mutations relate to the results shown herein; their performance is relative to the control (pSHU10; SEQ ID NO: 14). KASH008 (SEQ ID NO: 16) increased the % FAME by 1.4 fold, while increasing titer by 1.06 fold. KASH032 (SEQ ID NO: 18) increased % FAME by 1.29 fold, while affecting titer. KASH040 (SEQ ID NO: 20) increased % FAME by 1.16 fold, while the titer decreased to 0.91 times the control. KASH078 (SEQ ID NO: 26) increased the % FAME by 1.25 fold, while decreasing titers to 0.76 of control. KASH060 (SEQ ID NO: 22) and KASH061 (SEQ ID NO: 24) are of special interest because they affected not only the % FAME, but they also produced significantly shorter ester chain products, as was shown by an increase in C12/C14 (6.8 fold for KASH060 and 3.1 fold for KASH061) and C14/C16 (4.0 fold for KASH060 and 3.2 fold for KASH061).

TABLE 5

| Mutation | Total FAME | Total FAS | % FAME | C12/C14 | C14/C16 |
|---|---|---|---|---|---|
| A190P, N302G, T313S, Q348R | 0.545 | 0.475 | 1.146 | 0.945 | 1.486 |
| A190P, S264V, A327I, Q348A | 0.444 | 0.807 | 0.556 | 2.441 | 3.171 |
| A197T, V219L, R467L | 0.409 | 0.473 | 0.865 | 1.491 | 1.821 |
| A197V, Q250W, G442S | 0.663 | 0.647 | 1.024 | 1.130 | 1.610 |
| A228G, D328F, L409V | 0.922 | 1.385 | 0.701 | 1.254 | 1.918 |
| A279V, K472T | 0.904 | 1.286 | 0.732 | 0.643 | 1.733 |
| A327I | 0.682 | 0.923 | 0.738 | 1.225 | 2.259 |
| A327I, Q348R, V381F, I420V | 0.473 | 0.974 | 0.485 | 2.536 | 3.363 |
| A73Q, G101L, H122S, R172S, Q201W, Q357V | 0.947 | 0.881 | 1.103 | 0.448 | 1.539 |
| A73Q, G101L, H122S, V187G, Q201V, N331G, A447L | 0.530 | 0.525 | 1.009 | 0.838 | 1.651 |
| A73Q, H122S, V187G, Q201A, V234C, G375S, A447L | 0.484 | 0.390 | 1.242 | 0.647 | 1.231 |
| A73Q, Q201W, I315F, G375V, A447I | 0.437 | 0.350 | 1.242 | 0.081 | 0.951 |
| C121S, A228G, A279V, K472* | 0.912 | 0.989 | 0.962 | 0.799 | 1.389 |
| C121S, H122Q, S147A, L200R | 0.654 | 0.608 | 1.122 | 0.244 | 1.164 |
| C121S, R171H, I303R | 0.901 | 0.805 | 1.199 | 2.550 | 1.812 |
| C121S, S147A | 1.016 | 1.172 | 0.945 | 2.072 | 1.144 |
| D113V, E184F, G212L, H239G, V272A, T395E, N430G | 0.528 | 0.506 | 1.044 | 1.278 | 1.557 |
| D113V, E184F, N430G, I461G | 0.818 | 0.784 | 1.042 | 0.923 | 1.411 |
| D113V, E184R, D203E, D307N, N430G, I461G | 0.918 | 0.957 | 0.965 | 0.867 | 1.652 |
| D307F | 0.991 | 1.122 | 0.886 | 0.835 | 1.563 |
| D307N | 0.379 | 0.393 | 0.973 | 1.675 | 1.700 |
| D328F, K472T | 1.068 | 1.580 | 0.742 | 2.931 | 1.740 |
| D328F, T356G, L409V, A468T, K472T | 0.971 | 1.303 | 0.772 | 0.786 | 1.645 |
| D41G, Q193R, Q244G, G310V, Y366G, S424G | 0.669 | 0.569 | 1.176 | 0.000 | 0.576 |
| D41H, I80V, D182G, Q193S, R207A, S267G, G310V, S424Q | 0.535 | 0.414 | 1.296 | 1.056 | 0.598 |
| D41Y, I80V, A320C | 0.579 | 0.558 | 1.043 | 1.109 | 1.219 |
| D41Y, N110R, Q193S, Y366W | 0.641 | 1.214 | 0.528 | 1.179 | 2.665 |
| D455E | 0.671 | 0.842 | 0.800 | 1.188 | 2.183 |
| D77A, A190W, T242K, N302G, T313S | 0.560 | 0.436 | 1.285 | 2.048 | 0.554 |
| D77A, L127G, V155G, A190R, D455E | 0.304 | 0.237 | 1.292 | 0.670 | 1.216 |
| D77A, L127G, V155G, V381F | 0.699 | 0.646 | 1.084 | 1.291 | 1.415 |
| D77A, N302G, T313S, Q348R, M363W, V381F, I420V | 0.357 | 0.300 | 1.192 | 7.037 | 1.598 |

TABLE 5-continued

| Mutation | Total FAME | Total FAS | % FAME | C12/C14 | C14/C16 |
|---|---|---|---|---|---|
| D77A, S105G, A190P | 0.593 | 0.657 | 0.925 | 1.077 | 1.678 |
| D77A, T170M, R177V, T242R, S264D | 0.832 | 1.206 | 0.689 | 1.095 | 1.851 |
| D77A, V155G, A190P, T242K | 0.640 | 0.589 | 1.088 | 1.105 | 1.726 |
| D7N, D41Y, R207A, G310V, Y366G | 0.762 | 0.649 | 1.174 | 0.886 | 0.767 |
| D7N, N164R, D182G, R207A, G310R, P351G, S424Q, T470A | 0.509 | 0.405 | 1.258 | 0.000 | 0.391 |
| D7N, Q193R, Y366W, E393G, S424Q, E458G | 0.655 | 0.603 | 1.086 | 1.653 | 0.719 |
| D7N, Q193R, Y366W, E393G, S424Q, E458W | 0.658 | 0.561 | 1.172 | 0.637 | 0.538 |
| E184F, A323G, T395E, I461G | 0.960 | 1.009 | 0.952 | 0.868 | 1.404 |
| E184G, I461G | 0.994 | 1.164 | 0.854 | 0.829 | 1.631 |
| E184G, M195G, G212A, T311S, N430G, I461G | 0.870 | 0.933 | 0.932 | 0.809 | 1.705 |
| E184L, M195G, G212A, H239G, T311S, K352I | 0.769 | 0.654 | 1.178 | 0.943 | 1.229 |
| E184R, I461G | 0.375 | 0.438 | 0.857 | 0.930 | 2.234 |
| E184S, G212A, V272A, I367M, I461G | 0.707 | 0.635 | 1.118 | 1.175 | 1.660 |
| E184S, G212L, H239G, K352N, I461G | 0.734 | 0.763 | 0.964 | 1.112 | 1.735 |
| E458W | 0.894 | 1.126 | 0.794 | 1.125 | 1.692 |
| E99Q, A228G, A279G, I303R, L409V, K472T | 0.788 | 0.709 | 1.193 | 2.434 | 1.496 |
| E99Q, C121S, T356G, K472T | 1.360 | 1.552 | 0.946 | 2.043 | 1.292 |
| E99Q, I303W, T356G, K472T | 1.286 | 1.260 | 1.096 | 1.966 | 1.049 |
| E99Q, R171V, M443G | 0.734 | 0.790 | 0.971 | 0.805 | 1.602 |
| E99Q, S147A, R171W, L200R, K472* | 1.019 | 1.540 | 0.696 | 1.224 | 1.863 |
| G101L, G375A, S410G | 0.642 | 0.577 | 1.113 | 0.604 | 0.973 |
| G101L, H122S, V187R, G375S, A447I | 0.280 | 0.237 | 1.187 | 0.520 | 1.544 |
| G101L, Q201V, I315F, G375V, A447L | 0.481 | 0.400 | 1.199 | 0.730 | 1.359 |
| G126D, A202L, A306G, S316G, M360S | 0.528 | 0.410 | 1.286 | 0.248 | 0.549 |
| G126D, A306G, M360W | 0.443 | 0.353 | 1.258 | 0.000 | 0.972 |
| G126D, M378A | 0.489 | 0.456 | 1.076 | 0.364 | 1.146 |
| G126D, R188P, A306G, M360W | 0.526 | 0.439 | 1.207 | 0.000 | 1.109 |
| G15S, D113A, E184G, T395E, N430G, I461G | 0.921 | 0.865 | 1.065 | 0.867 | 1.348 |
| G15S, E184G, G212A, K352N, I461G | 1.006 | 1.045 | 0.962 | 0.856 | 1.465 |
| G15S, E184L, H239G, V272A, I461G | 0.788 | 0.701 | 1.124 | 1.109 | 1.713 |
| G15S, E184L, T311S, K352N, I461G | 0.769 | 0.646 | 1.193 | 1.202 | 1.150 |
| G15S, H239G, I461G | 0.465 | 0.468 | 0.995 | 1.504 | 1.768 |
| G15S, I461G | 1.159 | 1.314 | 0.883 | 0.819 | 1.431 |
| G15S, M165K, E184F, G212A | 0.649 | 0.767 | 0.846 | 1.151 | 1.541 |
| G15S, M165K, E184S, A323G, I367M, N430G, I461G | 0.554 | 0.484 | 1.145 | 1.915 | 1.062 |
| G15S, M195G, H239G, I461G | 0.783 | 0.698 | 1.120 | 1.166 | 1.523 |
| G15S, R93T, T136G, G212L, H239G, I461G | 0.594 | 0.528 | 1.125 | 0.788 | 1.466 |
| G15S, V272A, I461G | 0.536 | 0.468 | 1.144 | 1.304 | 1.875 |
| G212A, D307F, K352N, I461G | 0.794 | 0.693 | 1.146 | 1.172 | 1.432 |
| G33S, I102R | 0.777 | 1.150 | 0.675 | 0.742 | 1.702 |
| G33S, I102R, M360W, M378A | 0.577 | 0.528 | 1.101 | 0.298 | 1.542 |
| G33S, L454V | 0.459 | 0.577 | 0.797 | 0.844 | 2.063 |
| G33S, P173R, R188P, R246P, A306G | 0.414 | 0.354 | 1.168 | 0.449 | 2.310 |
| G33S, R188P, M360S, L454V | 0.466 | 0.378 | 1.232 | 0.139 | 1.564 |
| G33S, R246V, A306G, M360R | 0.597 | 0.457 | 1.306 | 0.000 | 0.599 |
| G33S, T470S | 0.680 | 1.044 | 0.654 | 0.792 | 1.749 |
| G373R | 1.159 | 1.332 | 0.943 | 2.117 | 1.109 |
| G375S, A447I | 0.765 | 0.863 | 0.886 | 0.753 | 1.631 |
| G442E | 0.566 | 0.688 | 0.824 | 0.944 | 1.738 |
| G4R, G33S, G126D, P173S, R188P, R246V, Q334S, M360W, L411P | 0.524 | 0.400 | 1.311 | 0.000 | 0.382 |
| G4R, P173W, Q175E, R246Q, K258R, M360S | 0.171 | 0.133 | 1.286 | 0.000 | 0.434 |
| G4R, R188P, R246Q | 0.603 | 0.500 | 1.209 | 0.000 | 1.093 |
| H122S, G375S | 0.482 | 0.405 | 1.193 | 0.717 | 1.483 |
| H122S, I315F | 0.461 | 0.423 | 1.091 | 0.724 | 1.575 |
| H122S, L254T, N331G | 0.436 | 0.371 | 1.173 | 0.441 | 1.113 |
| H122S, Q201V | 0.522 | 0.898 | 0.590 | 0.741 | 4.476 |
| H122S, R172S, Q201W, A447I | 0.567 | 0.496 | 1.140 | 1.294 | 2.362 |
| H122S, V187R, L254T, N331G | 0.389 | 0.329 | 1.176 | 0.357 | 1.554 |
| H122S, V234C, L254R, I315F | 0.456 | 0.365 | 1.242 | 0.101 | 1.069 |
| H239G, K352I, T395E, I461G | 0.795 | 0.703 | 1.131 | 1.024 | 1.636 |
| H239G, T311S, K352N, I461G | 0.913 | 0.782 | 1.168 | 1.066 | 1.125 |
| I102L, R246W, K258R, A306G, M360R, L411A, L454V | 0.559 | 0.464 | 1.205 | 0.000 | 0.493 |
| I102R, P173W, A202L, Q334S, M360R | 0.495 | 0.405 | 1.225 | 0.175 | 0.795 |
| I102R, R246A, Q334S, M360R | 0.580 | 0.451 | 1.286 | 0.000 | 0.519 |
| I102R, R246L, K258R, A306G, M360R, L411A, L454V | 0.664 | 0.517 | 1.286 | 0.000 | 0.360 |
| I102R, R246Q, K258R, M360S | 0.709 | 0.448 | 1.502 | 0.052 | 0.194 |
| I102R, R246W, L454V | 0.772 | 0.668 | 1.157 | 0.000 | 0.940 |
| I146K, V219L, D307N | 0.357 | 0.305 | 1.170 | 2.470 | 1.551 |

TABLE 5-continued

| Mutation | Total FAME | Total FAS | % FAME | C12/C14 | C14/C16 |
|---|---|---|---|---|---|
| I146K, V219L, D307N, G442S | 0.356 | 0.286 | 1.248 | 3.212 | 0.932 |
| I146L, A185L, D307R, G442S | 0.358 | 0.276 | 1.294 | 2.393 | 0.529 |
| I146L, V219L, D307R, G442S | 0.361 | 0.284 | 1.272 | 4.822 | 0.565 |
| I146R, A197T, D307G | 0.281 | 0.221 | 1.274 | 4.844 | 0.902 |
| I146R, A197T, D307N, G442E | 0.315 | 0.255 | 1.234 | 3.768 | 1.213 |
| I303R, D328F | 0.619 | 0.531 | 1.212 | 1.228 | 1.882 |
| I303W | 1.192 | 1.188 | 1.088 | 1.898 | 1.235 |
| I315F | 0.529 | 0.483 | 1.099 | 0.715 | 1.406 |
| I315F, N331G, G375S, A447C | 0.606 | 0.532 | 1.135 | 0.389 | 1.283 |
| I420V | 0.567 | 0.864 | 0.656 | 1.033 | 2.097 |
| I461G | 0.914 | 1.151 | 0.794 | 0.770 | 1.821 |
| K472T | 0.974 | 1.088 | 0.894 | 1.215 | 1.442 |
| K78F, R131M, S192V, G266S, K349H | 0.754 | 0.540 | 1.327 | 0.660 | 0.537 |
| K78F, S192V, A243R, K349H | 1.501 | 1.055 | 1.417 | 0.695 | 0.629 |
| K78W, S111G, C422G | 0.788 | 0.538 | 1.387 | 0.839 | 0.495 |
| L127G, A190W, D203R, A327I, I420V, D455E | 0.547 | 0.565 | 0.968 | 1.198 | 1.590 |
| L127G, A190W, S264D, V381F | 0.292 | 0.260 | 1.124 | 0.994 | 1.950 |
| L134T | 0.745 | 1.165 | 0.639 | 1.364 | 2.156 |
| L200R, A228G, M443G | 0.537 | 0.569 | 0.980 | 0.610 | 1.696 |
| L200R, A228G, T356W, G373R | 1.224 | 1.167 | 1.126 | 1.326 | 0.904 |
| L200R, I303R, Q314G, T356G | 1.280 | 1.092 | 1.163 | 0.651 | 0.703 |
| L30H, Q201V, V234C, G265D, R304W, G375V | 0.271 | 0.217 | 1.242 | 0.784 | 0.696 |
| L30H, R304W, I315F | 0.507 | 0.397 | 1.282 | 0.626 | 0.650 |
| L30H, V187G, Q201V, L254T, I315F, Q357V, G375V | 0.456 | 0.353 | 1.294 | 0.746 | 0.710 |
| L30H, V234C, S410G, A447L | 0.862 | 1.035 | 0.833 | 1.022 | 1.401 |
| L39A, D77A, S105G, V155G, T242K, V381F, T470S | 0.595 | 0.557 | 1.071 | 4.219 | 1.897 |
| L39A, D77A, T242R, S264D, A327I, M363W, D455E | 0.392 | 0.307 | 1.276 | 0.332 | 0.710 |
| L39A, L127G, A190W, T242R, S264V, V381F, D455E | 0.382 | 0.313 | 1.221 | 0.000 | 1.181 |
| L39A, T313S, Q348R, V381F | 0.434 | 0.547 | 0.794 | 2.921 | 1.846 |
| L39M, D77A, L127G, A190W, T313S | 0.437 | 0.366 | 1.200 | 0.158 | 1.553 |
| L39M, D77A, S105G, V155G, S264V, A327I, Q348R, D455E | 0.542 | 0.628 | 0.862 | 2.186 | 2.129 |
| L39M, L127G, A190R, D203R, Q348R, M363W, I420V | 0.462 | 0.469 | 0.987 | 1.428 | 1.732 |
| L39M, L127G, A190W, V381F, D455E | 0.490 | 0.591 | 0.836 | 1.222 | 2.070 |
| L39M, R177V, A190R, I420V | 0.428 | 0.565 | 0.768 | 1.079 | 1.827 |
| L39M, R177V, A190W, S264D, N302G, A327I | 0.544 | 0.424 | 1.285 | 0.000 | 0.902 |
| L39M, S105G, A190P, T242R, T313S, M363W | 0.954 | 0.819 | 1.163 | 0.549 | 0.790 |
| L39M, S105G, L127G, A190W, D203R, Q348R | 0.480 | 0.525 | 0.917 | 8.297 | 2.700 |
| L39S, A190P, T242R, N302G, T313S, A327I, Q348R | 0.500 | 0.389 | 1.276 | 0.000 | 0.787 |
| L39S, R177V, D203R, T242R, S264D, A327I, M363W | 0.485 | 0.411 | 1.181 | 0.000 | 1.013 |
| L39S, S105G, R177V, N302G, A327I, V381F | 0.324 | 0.255 | 1.269 | 0.000 | 0.980 |
| L39S, V155G, A190P, A327I, Q348R, V381F | 0.239 | 0.287 | 0.837 | 1.552 | 2.340 |
| L39S, V155G, A190R, T242R, S264D, A327I, Q348R | 0.419 | 0.431 | 0.976 | 1.159 | 1.695 |
| L411A | 0.828 | 1.016 | 0.764 | 1.327 | 0.522 |
| L454V | 0.799 | 1.000 | 0.798 | 0.572 | 1.528 |
| L6Q, K78W, S111G, T158R, S192L, E309S, L457Y | 0.167 | 0.104 | 1.526 | 0.000 | 0.282 |
| L6Q, K78W, S111P, R131M, A243R, G266S, C422G | 1.111 | 0.728 | 1.445 | 0.458 | 0.253 |
| L6Q, R40S, S192A, K349Q, T385G, C422G | 0.786 | 0.496 | 1.500 | 0.027 | 0.171 |
| M165K, E184L, I461G | 0.672 | 0.594 | 1.133 | 1.490 | 1.269 |
| M165K, I367M, I461G | 0.544 | 0.471 | 1.155 | 1.572 | 1.386 |
| M360Q | 0.844 | 0.961 | 0.880 | 0.227 | 1.282 |
| M360Q, L454V | 0.259 | 0.219 | 1.236 | 0.000 | 11.652 |
| M360S | 0.596 | 0.548 | 1.090 | 0.159 | 0.956 |
| M360S, M378A, L411A | 0.596 | 0.514 | 1.160 | 0.000 | 1.039 |
| M363W, V381F, D455E | 0.711 | 1.021 | 0.697 | 14.861 | 2.109 |
| M378A | 0.525 | 0.554 | 0.947 | 0.553 | 1.676 |
| M378A, L411A | 0.626 | 0.727 | 0.860 | 0.482 | 1.566 |
| N110R, L134T, N164R, Q193R | 0.526 | 0.805 | 0.655 | 1.535 | 1.835 |
| N164R, G310V, P351G, S424Q, A468T | 0.615 | 0.519 | 1.186 | 1.215 | 0.870 |
| N331G | 0.630 | 0.667 | 0.942 | 0.811 | 1.503 |
| P173W, R246V | 0.515 | 0.393 | 1.311 | 0.000 | 0.880 |
| P294G, G310H, A320C, P351G, E393G, S424G | 0.585 | 0.454 | 1.289 | 1.376 | 0.633 |
| Q193R, G310H, E458W | 0.778 | 0.909 | 0.864 | 1.161 | 1.435 |
| Q193R, P351G, E393W, S424Q, E458W | 0.552 | 0.449 | 1.228 | 0.000 | 0.873 |

TABLE 5-continued

| Mutation | Total FAME | Total FAS | % FAME | C12/C14 | C14/C16 |
|---|---|---|---|---|---|
| Q193S, Q244G, G310H, P351G, E458W | 0.789 | 0.727 | 1.085 | 1.045 | 1.192 |
| Q193S, Q244G, P294G, G310R, S424G | 0.764 | 0.637 | 1.199 | 1.015 | 0.859 |
| Q201A, G375S, S410G, A447L | 0.930 | 0.964 | 0.959 | 0.792 | 1.251 |
| Q201A, I315F, G375A, A447L | 0.527 | 0.464 | 1.139 | 1.059 | 1.250 |
| Q201A, R304W, S410G | 0.508 | 0.402 | 1.265 | 0.708 | 0.831 |
| Q201V, I315F, A447I | 0.622 | 0.591 | 1.047 | 1.053 | 1.398 |
| Q201V, I315F, G375S, A447C | 0.652 | 0.568 | 1.149 | 0.739 | 0.981 |
| Q201W, R304W, S410G | 0.643 | 0.524 | 1.227 | 0.669 | 0.837 |
| Q244G, G310R, A320C, P351G, S424Q | 0.664 | 0.534 | 1.245 | 1.226 | 0.610 |
| Q244G, G310V, P351G, Y366W, E458W | 0.849 | 0.892 | 0.951 | 1.220 | 1.673 |
| Q244G, P294G, G310H, P351G, Y366W, E393W, S424G | 0.507 | 0.457 | 1.108 | 1.205 | 1.023 |
| Q244G, S267G, G310V, A320C, Y366W | 1.052 | 0.905 | 1.161 | 0.820 | 0.649 |
| Q244G, Y366G, S424Q | 0.601 | 0.491 | 1.224 | 0.895 | 0.724 |
| Q26P, R171E, A228G, L268F | 0.540 | 0.964 | 0.635 | 4.918 | 3.527 |
| Q26T, C121S | 0.740 | 0.886 | 0.837 | 0.599 | 1.366 |
| Q26T, C121S, R171F, A228G, K472* | 0.892 | 0.973 | 0.996 | 1.552 | 1.839 |
| Q26T, C121S, R171W, A228G, K472* | 0.542 | 0.553 | 0.983 | 1.047 | 2.189 |
| Q26T, E99Q, R171W, I303W | 0.618 | 0.563 | 1.184 | 0.529 | 1.472 |
| Q26T, E99Q, S147T, R171V, S186T, I303G, K472T | 0.285 | 0.316 | 0.958 | 2.050 | 2.607 |
| Q26T, K472* | 0.826 | 1.343 | 0.618 | 0.880 | 2.071 |
| Q26T, L200R, I303R, K472* | 0.909 | 1.148 | 0.825 | 0.997 | 1.672 |
| Q26T, Q314G | 1.151 | 1.386 | 0.830 | 0.921 | 1.448 |
| Q26T, R171E, I303W, K472T | 0.618 | 0.602 | 1.054 | 0.527 | 1.840 |
| Q26T, R171F, Q253G, T356G | 0.890 | 1.075 | 0.831 | 1.079 | 1.930 |
| Q26T, R171H, S186T, I303G, K472T | 0.709 | 0.697 | 1.064 | 0.780 | 1.558 |
| Q26T, R171V, A228G, I303R, K472T | 0.792 | 0.995 | 0.807 | 1.668 | 2.166 |
| Q26T, S147A, R171E, I303R | 0.632 | 0.614 | 1.027 | 0.844 | 1.988 |
| Q26T, V69L, E99Q, C121S, R171L, A228G, I303W, Q314R, D328F | 0.479 | 0.460 | 1.130 | 0.000 | 1.484 |
| Q26T, V69W, C121S | 0.671 | 0.608 | 1.097 | 0.383 | 1.046 |
| Q26T, V69W, E99Q, A279G, T356G, K472* | 0.771 | 0.712 | 1.077 | 0.454 | 0.984 |
| Q26T, V69W, E99Q, K472* | 0.685 | 0.694 | 1.019 | 0.565 | 1.141 |
| Q26T, V69W, E99Q, R171F, D328F | 0.650 | 0.549 | 1.174 | 0.071 | 1.241 |
| Q26T, V69W, S186T, L200R, I303W | 1.307 | 1.374 | 1.030 | 1.840 | 0.943 |
| Q348R | 0.447 | 0.961 | 0.467 | 2.033 | 3.548 |
| Q348R, M363W | 0.647 | 1.004 | 0.646 | 1.613 | 2.385 |
| R171F, I303W | 0.883 | 0.741 | 1.236 | 0.407 | 1.274 |
| R171F, M443G | 0.557 | 0.450 | 1.228 | 0.494 | 1.719 |
| R171F, Q314G, G373R | 0.710 | 0.573 | 1.251 | 0.424 | 1.208 |
| R171H, S186T, A228G, I303G, D328F | 0.594 | 0.479 | 1.230 | 0.432 | 1.791 |
| R171V, L200R, Q253G, I303W, M443G, K472T | 0.961 | 0.804 | 1.186 | 0.339 | 1.358 |
| R171V, L200R, T356W, G373R, K472T | 0.800 | 0.930 | 0.957 | 2.087 | 1.442 |
| R171W, I303W, K472* | 0.864 | 0.765 | 1.175 | 1.049 | 1.629 |
| R171W, K472T | 0.897 | 1.313 | 0.712 | 0.975 | 2.490 |
| R172S, V187G | 0.557 | 0.609 | 0.945 | 1.058 | 1.874 |
| R172S, V187G, Q201W, R304W | 0.639 | 0.529 | 1.211 | 0.691 | 1.149 |
| R172W, V234C, A447L | 0.544 | 0.848 | 0.646 | 1.245 | 2.495 |
| R188P | 0.583 | 0.648 | 0.897 | 0.491 | 1.794 |
| R188P, A202L, R246G, K258R, Q334S, M360R | 0.416 | 0.317 | 1.311 | 0.000 | 0.512 |
| R188P, A202L, S316G, M360Q | 0.513 | 0.401 | 1.286 | 0.000 | 1.088 |
| R188P, L411A | 0.526 | 0.539 | 0.979 | 0.672 | 1.468 |
| R207A, Q244G, P294G, Y366W, E393W, S424G | 0.873 | 0.751 | 1.161 | 0.932 | 0.952 |
| R246L, K258R, M360R, L454V, A468S | 0.521 | 0.397 | 1.311 | 0.000 | 0.390 |
| R246V, A306G, M360R, L411V, L454V | 0.743 | 0.566 | 1.311 | 0.000 | 0.419 |
| R246V, K258R, M360R | 0.590 | 0.520 | 1.143 | 0.000 | 0.778 |
| R304W, I315F | 0.422 | 0.330 | 1.280 | 0.977 | 0.648 |
| R467T | 0.440 | 0.526 | 0.848 | 1.399 | 1.791 |
| R87W, K349Q, C422G | 0.349 | 0.217 | 1.522 | 0.333 | 0.281 |
| R93T, E184F, I461G | 0.474 | 0.491 | 0.974 | 1.611 | 1.770 |
| R93T, G212A, K352I, I461G | 0.869 | 0.917 | 0.955 | 0.999 | 1.782 |
| R93T, I461G | 1.124 | 1.474 | 0.762 | 0.791 | 1.740 |
| R98D, I146K, T170R, A185L, D307L, R467T | 0.354 | 0.292 | 1.208 | 3.175 | 1.166 |
| R98D, I146L, A185M, A197V, Q250W, D307G | 0.312 | 0.253 | 1.236 | 3.559 | 1.030 |
| R98D, I146R, T170R, D307F, T353S | 0.331 | 0.271 | 1.224 | 3.074 | 1.073 |
| S105G, A190P, Q348R | 0.415 | 0.616 | 0.831 | 1.917 | 2.888 |
| S105G, A190P, S264D, M363W | 0.403 | 0.311 | 1.295 | 0.000 | 1.122 |
| S105G, L127G | 0.413 | 0.358 | 1.155 | 0.438 | 1.411 |
| S105G, L127G, D203R, T242R, A327I, Q348A, V381F | 0.364 | 0.446 | 0.818 | 2.635 | 2.283 |
| S105G, L127G, T242K, Q348A, I420V | 0.320 | 0.313 | 1.024 | 1.097 | 1.840 |
| S105G, V155G, A190P, T242K | 0.555 | 0.446 | 1.244 | 1.520 | 1.507 |

TABLE 5-continued

| Mutation | Total FAME | Total FAS | % FAME | C12/C14 | C14/C16 |
|---|---|---|---|---|---|
| S105G, V155G, R177V, A190W, T242R, Q348A | 0.464 | 0.488 | 0.950 | 3.447 | 1.568 |
| S111G, E309A, C422G | 1.407 | 0.951 | 1.402 | 0.605 | 0.299 |
| S111P, S192L, E309S, K349Q | 1.111 | 0.858 | 1.230 | 0.681 | 0.399 |
| S115R, I146R, D307F, R467T | 0.325 | 0.255 | 1.272 | 5.998 | 0.542 |
| S147A, A228G, A279V, K472* | 0.920 | 1.143 | 0.806 | 0.887 | 1.905 |
| S147A, D328F, G373R, K472T | 0.883 | 0.822 | 1.120 | 0.245 | 1.198 |
| S147A, I303R, D328F, K472* | 0.400 | 0.349 | 1.232 | 2.937 | 2.254 |
| S147A, R171E, A279G, I303W | 0.624 | 0.546 | 1.187 | 1.400 | 1.972 |
| S147A, R171E, I303R, T356G | 0.980 | 1.052 | 1.008 | 4.987 | 2.253 |
| S147A, S186T, I303R, D328F | 0.504 | 0.428 | 1.226 | 0.819 | 1.923 |
| S147A, T356G | 0.669 | 0.751 | 0.901 | 0.660 | 1.404 |
| S186T, A228G, T231S | 0.662 | 0.914 | 0.760 | 0.610 | 2.169 |
| S192A, L457Y | 0.612 | 0.654 | 0.916 | 0.962 | 1.490 |
| S264D, A327I | 0.612 | 0.729 | 0.840 | 1.113 | 1.916 |
| S264D, Q348R, M363W, V381F, D455E | 0.483 | 0.905 | 0.536 | 2.198 | 3.734 |
| S264V, A327I, D455E | 0.768 | 0.960 | 0.800 | 1.008 | 1.472 |
| S264W | 0.690 | 0.804 | 0.855 | 0.584 | 1.686 |
| S316G, L411A, L454V | 0.606 | 0.525 | 1.155 | 0.000 | 0.842 |
| S5P, D77A, S105G, A190P, S264W, N302G, Q348A, I420V | 0.329 | 0.259 | 1.267 | 0.669 | 1.892 |
| S5P, D77A, V155G, A190R, T242K, N302G, A327I, A426V | 0.435 | 0.328 | 1.326 | 0.000 | 0.976 |
| S5P, D77A, V155G, S264D, A327I, I420V | 0.501 | 0.474 | 1.078 | 0.695 | 1.865 |
| S5P, D77A, V155G, S264V, A327I | 0.885 | 1.117 | 0.788 | 1.552 | 1.805 |
| S5P, G15D, L39S, A190R, S264D, Q348R, V381F | 0.482 | 1.085 | 0.444 | 2.533 | 3.606 |
| S5P, L39A, D77A, A190W, D203R, S264W, N302G, A327I, Q348A, I420V | 0.752 | 0.721 | 1.039 | 1.437 | 1.514 |
| S5P, L39A, D77A, V155G, A190P, T242K, L268M | 0.652 | 0.770 | 0.849 | 1.549 | 1.840 |
| S5P, L39A, V155G, A190W, T242R, N302G, T313S, A320C, Q348A | 0.591 | 0.580 | 1.019 | 2.749 | 1.365 |
| S5P, L39A, V155G, Q348R, I420V | 0.496 | 1.177 | 0.421 | 2.953 | 3.910 |
| S5P, L39M, D77A, A190P, T242K, S264D, Q348R, M363W, I420V | 0.610 | 0.602 | 1.013 | 0.874 | 1.485 |
| S6P, L39M, D77A, S105G, A190P, S264W, Q348A | 0.359 | 0.568 | 0.799 | 2.419 | 2.998 |
| S5P, L39M, G50S, D77A, V155G, A190P, T242R, S264D, A327I, V381F, D455E | 0.600 | 0.599 | 0.996 | 1.610 | 1.898 |
| S5P, L39M, S264D, I420V, D455E | 0.604 | 0.643 | 0.939 | 1.494 | 3.014 |
| S5P, L39M, V155G, A190W, D203R, T242R, S264W, N302G, T313S, Q348A, R469L | 0.549 | 0.490 | 1.172 | 3.399 | 1.640 |
| S5P, L39S, D77A, V155G, A190P, T242K, M363W, V381F | 0.486 | 0.393 | 1.238 | 0.000 | 1.277 |
| S5P, L39S, S105G, A190R, N302G, M363W | 0.441 | 0.339 | 1.295 | 0.000 | 0.472 |
| S5P, R177V, D203R, T242R, S264D, N302G, A327I, Q348A, M363W, I420V | 0.592 | 0.498 | 1.182 | 1.497 | 1.203 |
| S5P, S264V, Q348A, I420V | 0.261 | 0.432 | 0.605 | 2.409 | 2.984 |
| S5P, S264W, N302G, T313S | 0.469 | 0.365 | 1.285 | 0.000 | 0.524 |
| S5P, V155G, S264V, G265D | 0.622 | 0.525 | 1.183 | 0.827 | 1.540 |
| S5P, V381F | 0.503 | 1.148 | 0.437 | 15.293 | 3.054 |
| S5T | 0.876 | 1.151 | 0.761 | 2.978 | 1.548 |
| S5T, A190W, T242K, V381F | 0.476 | 0.555 | 0.859 | 2.342 | 1.950 |
| S5T, D77A | 0.722 | 0.804 | 0.899 | 0.508 | 1.186 |
| S5T, D77A, S105G, V155G, A190R, S264D | 0.640 | 0.508 | 1.261 | 9.479 | 1.589 |
| S5T, D77A, V155G, N302G, A327I | 0.399 | 0.306 | 1.303 | 1.174 | 0.961 |
| S5T, L127G, A190R, V381F | 0.405 | 0.382 | 1.080 | 3.787 | 2.108 |
| S5T, L127G, A327I, Q348A, D455E | 0.485 | 0.736 | 0.656 | 2.040 | 2.847 |
| S5T, L39A, A190P, S264D, A327I, Q348A, V381F, D455E | 0.486 | 0.750 | 0.647 | 2.195 | 2.743 |
| S5T, L39A, L127G, A190P, D203R, Q348R | 0.347 | 0.352 | 0.986 | 0.000 | 1.415 |
| S5T, L39A, L127G, D203R | 0.704 | 0.665 | 1.055 | 0.283 | 1.068 |
| S5T, L39M, A190P, D203R, S264W, N302G, I420V | 0.463 | 0.356 | 1.295 | 0.000 | 0.425 |
| S5T, L39M, D77A, S105G, S264W, N302G, T313S, Q348R, V381F | 0.614 | 0.508 | 1.211 | 0.000 | 0.794 |
| S5T, L39M, L127G, A190R, T242K, A327I, Q348R, V381F | 0.442 | 0.477 | 0.922 | 2.084 | 1.958 |
| S5T, L39M, L127G, D203R, T242R, Q348R, V381F | 0.592 | 0.832 | 0.708 | 1.814 | 2.556 |
| S5T, L39M, R177V, A190P, T242R | 0.511 | 0.522 | 0.978 | 2.163 | 3.546 |
| S5T, L39S, D77A, A190P | 0.620 | 0.634 | 0.976 | 0.000 | 1.243 |
| S5T, L39S, D77A, S264V, Q348R, V381F, I420V | 0.476 | 0.483 | 0.978 | 0.000 | 1.463 |
| S5T, L39S, D77A, T313S, Q348A, V381F, I420V | 0.377 | 0.733 | 0.518 | 3.052 | 3.172 |

TABLE 5-continued

| Mutation | Total FAME | Total FAS | % FAME | C12/C14 | C14/C16 |
|---|---|---|---|---|---|
| S5T, L39S, D77A, V155G, A190P, N302G, Q348R, V381F | 0.394 | 0.306 | 1.284 | 0.886 | 1.282 |
| S5T, N302G | 0.621 | 0.490 | 1.269 | 0.166 | 0.692 |
| S5T, S105G, A190P, S264D, Q348A | 0.445 | 0.603 | 0.741 | 2.077 | 2.668 |
| S5T, T242K, N302G, V381F | 0.486 | 0.383 | 1.269 | 0.000 | 0.836 |
| S5T, V155G, N302G, A327I, Q348A, D455E | 0.470 | 0.372 | 1.255 | 3.417 | 1.789 |
| S5T, V155G, N302G, Q348R | 0.497 | 0.391 | 1.269 | 2.115 | 1.577 |
| S5T, V155G, P166S, Q348A, V381F | 0.314 | 0.651 | 0.479 | 6.776 | 3.952 |
| T170R, T353S, E404R | 0.733 | 0.992 | 0.744 | 0.913 | 2.173 |
| T24W, D307N, G442E | 0.353 | 0.331 | 1.067 | 2.003 | 1.690 |
| T24W, D307N, T353S, E404K, G442S | 0.746 | 0.659 | 1.132 | 1.526 | 1.666 |
| T24W, R98D, A185L, A197V, D307V | 0.404 | 0.336 | 1.201 | 2.744 | 1.495 |
| T24W,R98D, A185M, A197T, D307L | 0.363 | 0.329 | 1.102 | 2.617 | 1.579 |
| T24W, R98D, A197T, D307G | 0.426 | 0.363 | 1.172 | 2.189 | 1.579 |
| T24W, R98D, S115R, I146L, A197V, V219L, T353S, G442E, R467T | 0.904 | 0.732 | 1.235 | 2.231 | 1.040 |
| T24W, T170R, A197T, D307L, T311S, G442S | 0.913 | 0.745 | 1.227 | 1.561 | 1.357 |
| T24W, T44F, I146L, D307N | 0.947 | 0.755 | 1.254 | 2.211 | 1.086 |
| T24W, T44F, R98D, A185L, R467T | 0.376 | 0.335 | 1.128 | 2.119 | 1.709 |
| T24W, T44F, R98D, T170R, A185L, V219L, R467T | 0.400 | 0.392 | 1.023 | 2.218 | 1.768 |
| T311S, A323G, I367M | 0.505 | 0.446 | 1.133 | 1.633 | 1.220 |
| T311S, K352N, T395E, N430G, I461G | 0.807 | 0.736 | 1.096 | 1.059 | 1.506 |
| T313S, I420V | 0.800 | 1.036 | 0.772 | 0.877 | 1.459 |
| T44F, D307F | 0.496 | 0.529 | 0.948 | 1.440 | 1.705 |
| T44F, I146R, A197T, G442E, R467T | 0.356 | 0.316 | 1.127 | 2.923 | 1.128 |
| T44F, I146R, Q287S, D307R, G442S | 0.826 | 0.649 | 1.274 | 1.907 | 0.450 |
| T44F, R98D, A185M, G442E | 0.604 | 0.717 | 0.844 | 1.168 | 1.904 |
| T44F, R98D, I146R, A197T, D307G, T311S, T353S, G442E | 0.350 | 0.274 | 1.272 | 4.569 | 0.678 |
| T44F, R98D, S115R, A197T | 0.717 | 0.715 | 1.003 | 1.045 | 1.417 |
| T44F, S115R, A185M, A197V, D307N, E404R | 0.609 | 0.593 | 1.040 | 1.139 | 1.301 |
| T44F, S115R, I146R, A197T, V219L, D307F | 0.266 | 0.205 | 1.294 | 3.144 | 0.518 |
| V149L, I315F, A447C | 0.533 | 0.422 | 1.263 | 0.929 | 1.104 |
| V149L, Q201W, A285R, Q357V, A447C | 0.505 | 0.406 | 1.245 | 0.962 | 0.731 |
| V155G, A190P | 0.517 | 0.471 | 1.097 | 1.254 | 1.680 |
| V155G, A190P, S264V, Q348R, I420V | 0.371 | 0.376 | 0.989 | 17.841 | 2.093 |
| V155G, A190W, S264D, I420V, D455E | 0.802 | 0.851 | 0.943 | 3.273 | 1.703 |
| V155G, D203R, N302G, I420V | 0.792 | 0.608 | 1.295 | 1.038 | 0.969 |
| V155G, M363W | 0.628 | 0.517 | 1.216 | 10.265 | 1.556 |
| V155G, V381F, I420V, D455E | 0.408 | 0.554 | 0.880 | 1.907 | 2.389 |
| V187G, I315F, G375A, A447L | 0.606 | 0.539 | 1.126 | 0.960 | 1.331 |
| V187G, Q201R, V234C, I315F, Q357V, A447I | 0.556 | 0.465 | 1.190 | 0.270 | 1.186 |
| V187G, Q201V, L254R, A285R, S410G, A447L | 0.535 | 0.538 | 1.006 | 0.510 | 1.467 |
| V187G, Q201W, I315F, Q357V, A447I | 0.545 | 0.492 | 1.114 | 0.484 | 1.801 |
| V187R, Q201V, I315F, G375A | 0.377 | 0.305 | 1.229 | 0.161 | 0.809 |
| V187R, Q201V, L254R, R304W, N331G, G375A | 0.516 | 0.413 | 1.242 | 0.376 | 0.768 |
| V219L | 0.327 | 0.347 | 0.952 | 1.786 | 1.657 |
| V234C, I315F, Q357V, G375V | 0.542 | 0.441 | 1.225 | 0.090 | 1.181 |
| V381F, I420V | 0.617 | 1.147 | 0.538 | 1.503 | 2.596 |
| V43S, M165K, E184S, G212A | 0.957 | 1.228 | 0.779 | 0.809 | 1.414 |
| V43S, N430G | 0.888 | 1.429 | 0.623 | 0.800 | 2.242 |
| V43S, R93T, E184S, T395V, I461G | 0.809 | 0.785 | 1.029 | 1.010 | 1.450 |
| V69W | 0.702 | 0.709 | 0.990 | 0.304 | 1.214 |
| V69W, C121S, R171E, K472* | 0.719 | 0.742 | 1.015 | 1.734 | 2.123 |
| V69W, C121S, S147A | 1.407 | 1.333 | 1.131 | 0.448 | 0.887 |
| V69W, C121S, S186T, A279G, K472* | 1.286 | 1.225 | 1.126 | 0.959 | 1.033 |
| V69W, E99Q, Q253G, A279G, K472T | 1.161 | 1.142 | 1.034 | 0.453 | 1.051 |
| V69W, Q314G | 0.684 | 0.593 | 1.200 | 0.298 | 0.847 |
| V69W, R171E, S186T, I303W | 0.915 | 0.763 | 1.190 | 0.691 | 1.652 |
| V69W, R171E, S186T, I303W, K472* | 0.933 | 0.838 | 1.193 | 1.431 | 1.585 |
| V69W, R171W | 1.147 | 1.263 | 0.983 | 3.002 | 1.738 |
| V76L, K258R, S316G, M360R | 0.713 | 0.555 | 1.286 | 0.000 | 0.657 |
| V76L, L454V | 0.736 | 1.056 | 0.698 | 0.814 | 1.770 |
| V76L, R246L, Q334S, M360R | 0.511 | 0.407 | 1.258 | 0.393 | 0.485 |
| Y366G | 0.720 | 0.907 | 0.793 | 1.015 | 1.657 |

Example 3

Ester Synthase Mutant Strains with Beneficial Properties

As described in Examples 1 and 2, a number of variant or mutant forms of '377 were identified with beneficial properties. In this experiment, a particular '377 mutant designated herein as 9B12 (SEQ ID NO: 4), which contains three different mutations over wild-type 377 (D7N, A179V, V381F), was cloned into pKEV027, replacing the wild-type '377 gene (SEQ ID NO: 1) coding for the wild type '377 polypeptide (SEQ ID NO: 2) and creating pKEV018. When transformed into strain BD64 (supra), strain KEV040 was created. The plasmid pKEV018 was further mutated using saturation mutagenesis at codon 348 of the gene (start codon=0) to produce the plasmid pKEV022, which contains four different mutations over wild-type '377 (D7N, A179V, Q348R, V381F). Separately, several previously identified mutations were combined with the pKEV018 plasmid to produce plasmid pKEV028 (which contains eight mutations over wild-type '377 (D7N, R87R "silent mutation", A179V, V187R, G212A, Q357V, V381F, M443G). pKEV022 and pKEV028 were transformed into strain BD64 which resulted in the strains designated KEV075 (SEQ ID NO: 10), and KEV085 (SEQ ID NO: 12), respectively. These mutant strains were observed to produce either a significant increase in FAME titer or a reduction in the percentage of "β-OH" FAME or both (e.g., mutant strains 9B12 and KEV085 achieved both).

Figure 5:
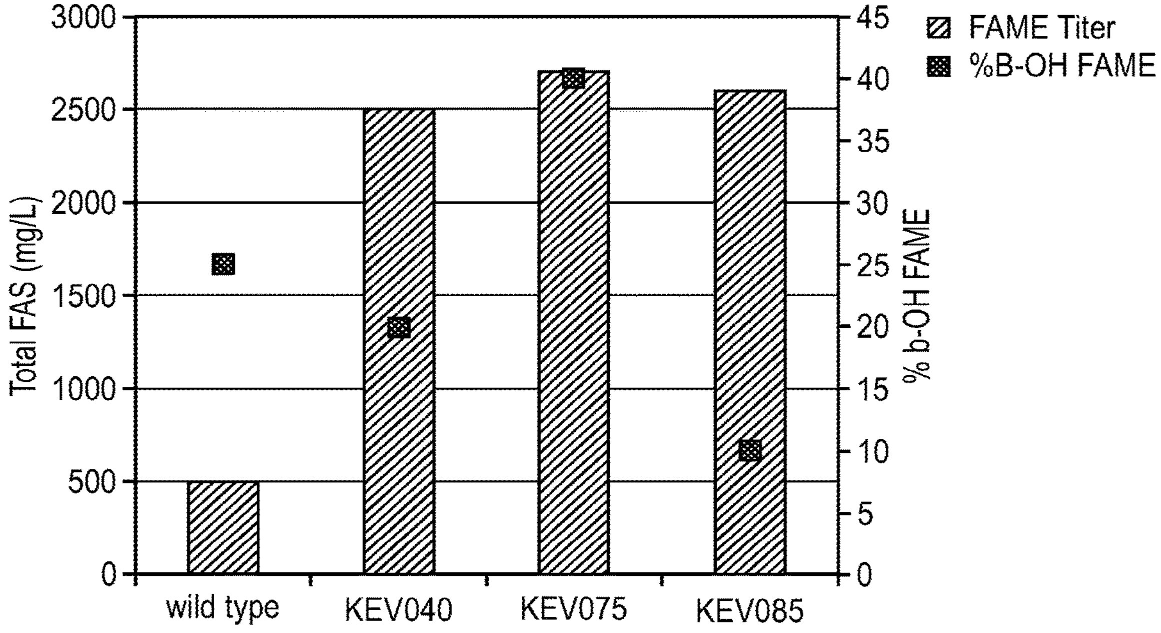
FIG. 5 shows FAME titers and % β-OH FAME produced by mutant strains KEV040, KEV075 and KEV085 compared to a strain which contains wild-type '377 ester synthase.

Strains KEV080 (BD64/pKEV027); KEV040; KEV075 and KEV085 were screened using one of the standard protocols (Protocols 1-2) described above. FIG. 5 shows the relative FAME titers and % β-OH FAME of mutant strains KEV040, KEV075 and KEV085 compared to a strain which contains wild-type '377 ester synthase. Herein, FIG. 5 illustrates that those three variants were observed to have significantly higher titer FAME than the control (wild type); that the % β-OH FAME varied from one variant to another; and that strains 9B12 (KEV040) and KEV085 produced lower % β-OH FAME than the control (wild type).

Example 4

Ester Production by Recombinant Host Cells Engineered to Express a Variant '377 Ester Synthase and a Variant Ppro As demonstrated in Examples 1, 2 and 3, an ester synthase from *Marinobacter hydrocarbonoclasticus* (WS377) was engineered to produce higher levels of fatty acid esters and a lower percentage of β-OH esters. In carrying out the present disclosure, wild type WS377 (SEQ ID NO: 1) was engineered resulting in new strains, such as 9B12, that produce higher levels of FAME directly from acyl-ACP.

The 'tesA of *Photobacterium Profundum* (Ppro) was engineered to have ester synthase activity. One variant of Ppro Vc7P6F9 (SEQ ID NO: 31) in plasmid pBD207 was tested in BD64 (designated herein as becos. 128). Similarly, the 9B12 variant of '377 (SEQ ID NO: 4) in pKEV18 was tested in BD64 (designated herein as KEV040). Cultures of becos. 128 (BD64/pBD207) and KEV040 (BD64/pKEV018) were tested in minimal media with 2% alcohol. After production for about 24 hours, they were extracted and analyzed by GC/FID or GC/MS for identification of the fatty acyl ester (following the protocols listed above).

Figure 6:
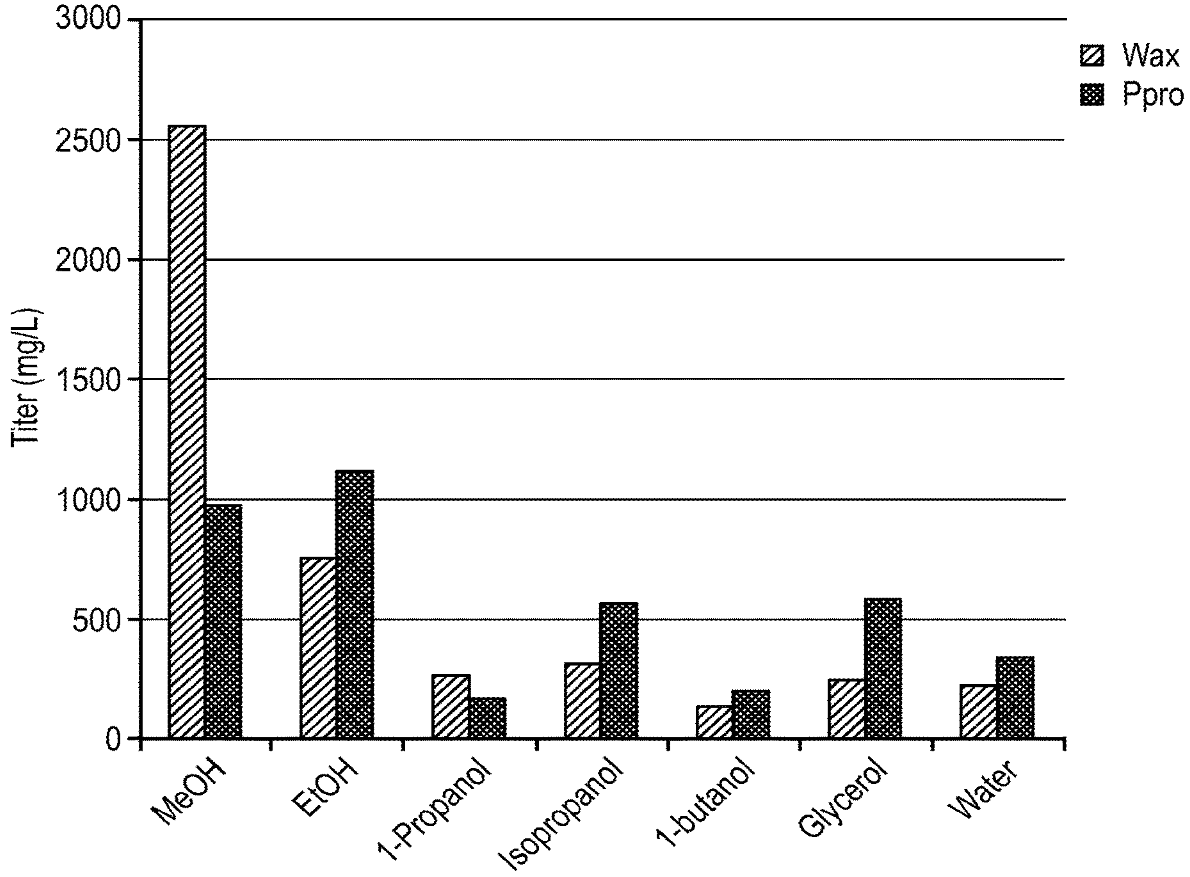
FIG. 6 shows the titer of total fatty acid species produced by KEV040 (Wax) and becos. 128 (Ppro) when methanol, ethanol, 1-propanol, isopropanol, 1-butanol or glycerol was fed to the strains.
Figure 8:
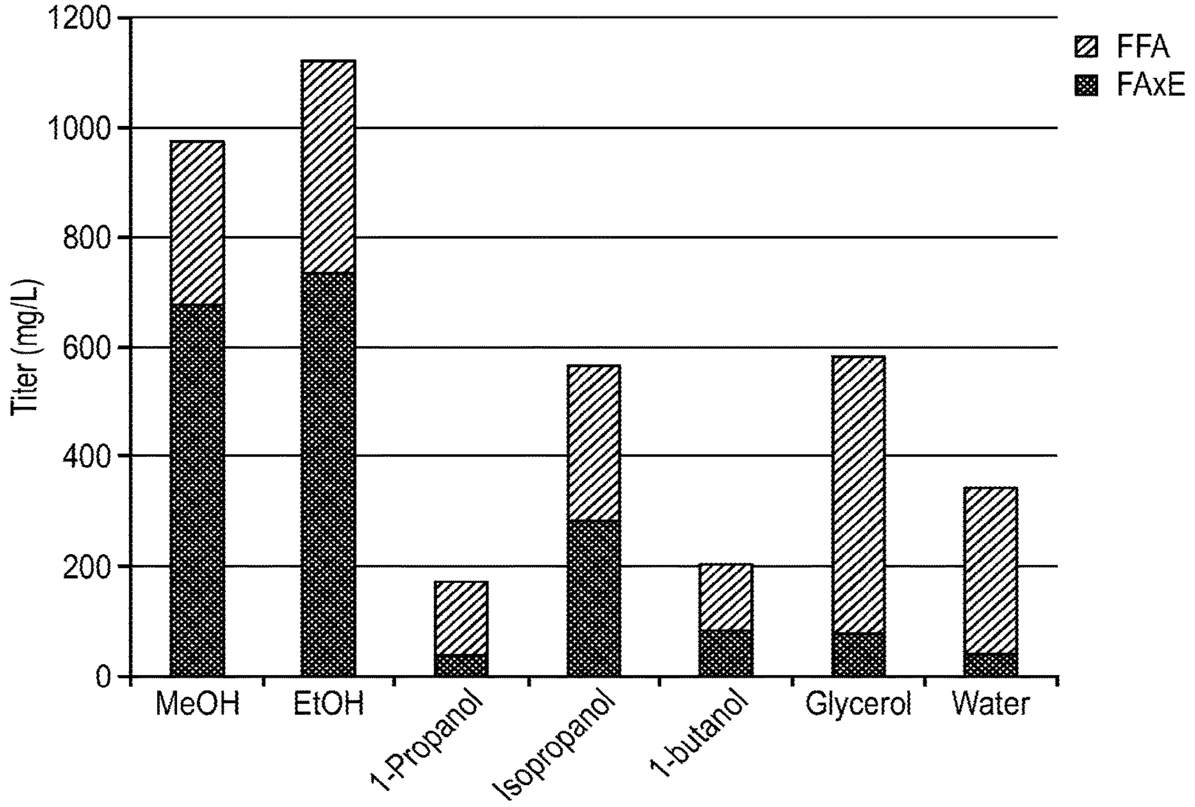
FIG. 8 shows the composition of fatty acid species produced by becos. 128 when cultured in the presence of (fed) methanol, ethanol, 1-propanol, isopropanol, 1-butanol or glycerol. FFA refers to free fatty acid species and FAxE refers to the ester species.

FIG. 6 shows the production of fatty acyl esters from KEV040 (ester synthase from *M. hydrocarbonoclasticus*) (shown as Wax in FIG. 6) and fatty acid species from becos. 128 ('tesA from *P. profundum*) (shown as Ppro in FIG. 6) when fed methanol, ethanol, 1-propanol, isopropanol, 1-butanol or glycerol. As negative control, water was added (lack of exogenous alcohol means that any ester production would rely on endogenous production of alcohol by *E. coli*). While no free fatty acid was produced by KEV040, becos. 128 produced a mixture of fatty acid esters and fatty acids. FIG. 8 shows the amounts of fatty acid esters and fatty acid produced by becos. 128. It should be noted that the in vitro results presented in Holtzapple and Schmidt-Dannert (see Journal of Bacteriology (2007) 189(10):3804-3812) showed that ester synthase from *M. hydrocarbonoclasticus* ('377) has a preference for longer chain alcohols producing primarily waxes. Holtzapple's data suggests that '377 would not be capable of using shorter chain alcohols. In contrast, the applicants work was conducted in vivo and established that the variant '377 enzyme can utilize shorter chain alcohols (C1, C2, C3 and C4), leading to shorter chain esters that can be used for a variety of valuable products (e.g., biodiesel, surfactants, etc.). The applicants used acyl-ACP as a substrate, which is believed to bring about a reduction of the futile cycle involvement (i.e., making the cell more energy efficient). In addition, the applicants showed that not all alcohols needed to have the OH group at position 1, for example, the OH group for propanol could be at position 1 or 2. FIG. 6 shows the production of fatty acyl esters with various chain lengths using a recombinant host cell genetically modified to express a single variant '377 ester synthase. This result was observed for engineered forms of both, a variant of tesA of *P. profundum* (Ppro) and a variant of the '377 ester synthase. It is noteworthy that the engineered mutants can convert not only primary alcohols but also secondary alcohols into a variety of different products, including FAME, FAEE, fatty acyl monoglycerides, and others. Recombinant bacteria, yeast, algae or other host cells can be used for the production of fatty esters.

Example 5

Ester Synthase Mutant Strains Expressing Combination Mutants

Standard techniques known to those of skill in the art were used to prepare combination libraries (Protocol 8). The mutations tested in combination libraries (Tables 3A and 3B) were originally identified in the full saturation library of '377 (as described in Example 1).

The combination libraries were screened in strain GLPH077 which is similar to BD64 but expressed slightly different levels of biosynthetic pathway enzymes (supra) and using one of the standard protocols (Protocols 1-2) (supra). The results from screening pKASH008 (SEQ ID NO: 16) combination libraries are shown in Table 6. As can be seen in Table 6, the resultant '377 ester synthase variants had 24 mutations compared to wild type 377. Two strains, KASH280 (SEQ ID NO: 33) and KASH281 (SEQ ID NO: 35) were used to test the variant '377. However, KASH280 expressed a '377 variant that differed from the one expressed in KASH280 by one substitution mutation. KASH280 expressed a '377 variant where a glutamine at position 348 was exchanged with an arginine (Q348R), allowing the strain to produce a higher titer FAME and a greater number of short chain esters. Conversely, KASH281 expressed a '377 variant where a lysine at position 349 was exchanged with a histidine (K349H), leading the strain to produce a lower titer FAME compared to KASH008. In addition KASH281 produced a lower titer of FAME and lesser number of short chain esters compared to KASH280. Overall, the comparison is to KASH008, which is better than pSHU10, which is better than the wild type (see examples above).

TABLE 7

| AA Position | Mutation | *M. adhaerens* | *M. algicola* | *M.* sp. *ELB17* |
|---|---|---|---|---|
| 24 | T24N | X | X | X |
| 33 | G33D | | | X |
| 33 | G33N | | X | |
| 44 | T44K | | | X |
| 44 | T44A | | X | |

Example 6

TABLE 6

| Strain | Mutations over wild type | # Mutations over wild type | Total FAME | Total FAS | % FAME | C12/C14 | C14/C16 |
|---|---|---|---|---|---|---|---|
| KASH280 | T5S, S15G, K78F, P111S, V171R, P188R, S192V, R207A, A243R, D255E, L257I, N259Q, L260V, H262Q, G265N, A285V, N288D, N289G, F317W, Q348R, S353T, V381F, V409L, S442G | 24 | 1.59 | 0.66 | 0.42 | 1.65 | 2.36 |
| KASH281 | T5S, S15G, K78F, P111S, V171R, P188R, S192V, R207A, A243R, D255E, L257I, N259Q, L260V, H262Q, G265N, A285V, N288D, N289G, F317W, K349H, S353T, V381F, V409L, S442G | 24 | 0.80 | 0.87 | 0.92 | 1.38 | 1.22 |

Ester Synthase Mutant Strains with Beneficial Properties from Natural Diversity

As described in Examples 1 and 2, a number of variant or mutant forms of '377 were identified with beneficial properties. An alignment of the ester synthase polypeptide from different *Marinobacter* organisms, such as *Marinobacter adhaerens* HP15 (YP_005886638.1, SEQ ID NO: 45), *Marinobacter algicola* DG893 (ZP_01893763.1, SEQ ID NO: 47), *Marinobacter* sp. ELB17 (ZP_01736818.1, SEQ ID NO: 49) with the one from *Marinobacter hydrocarbonoclasticus* DSM 8798 (SEQ ID NO: 2) using standard alignment procedures was used to identify mutations that already exist in nature, as this would reveal specific mutations as well as amino acid positions that naturally have diversity and thus could be used to stabilize the variant protein. The alignment was carried out and the analysis identified natural diversity within the ester synthase homologues polypeptides. Table 7 below illustrates a summary of such a group of mutations. When those mutations are combined with an engineered ester synthase from *Marinobacter hydrocarbonoclasticus*, beneficial variants can be observed if they are screened using one of the standard protocols (Protocols 1-2) described above. Examples of such variants are described as SEQ ID NOS: 37, 39, 41 and 43.

Table 7 below shows a list of natural diversity observed by aligning *Marinobacter hydrocarbonoclasticus, M. adhaerens, M. algicola* and *M.* sp. ELB17.

TABLE 7-continued

| AA Position | Mutation | *M. adhaerens* | *M. algicola* | *M.* sp. *ELB17* |
|---|---|---|---|---|
| 48 | E48Q | | | X |
| 48 | E48A | | X | |
| 49 | A49D | | X | |
| 49 | A49T | X | | |
| 58 | Y58C | | | X |
| 58 | Y58L | X | | |
| 70 | I70V | | X | |
| 70 | I70L | X | | X |
| 73 | A73S | | X | |
| 73 | A73T | | | X |
| 73 | A73G | X | | |
| 79 | D79K | X | X | |
| 79 | D79H | | | X |
| 123 | V123I | | X | |
| 123 | V123M | | | X |
| 157 | T157S | | X | X |
| 158 | T158E | | X | |
| 158 | T158K | | | X |
| 161 | E161G | | X | |
| 161 | E161D | X | | X |
| 162 | R162E | | X | X |
| 162 | R162K | X | | |
| 163 | C163I | | X | |
| 163 | C163R | X | | X |
| 164 | N164D | X | | X |
| 166 | P166L | | X | X |
| 170 | T170S | X | X | X |
| 174 | H174E | X | X | X |
| 175 | Q175R | X | X | |
| 175 | Q175S | | | X |
| 176 | R176T | | X | X |
| 179 | A179S | X | X | |
| 179 | A179K | | | X |

TABLE 7-continued

| AA Position | Mutation | *M. adhaerens* | *M. algicola* | *M.* sp. *ELB17* |
|---|---|---|---|---|
| 183 | K183S | X | X | X |
| 189 | A189G | X | | X |
| 191 | V191L | | X | |
| 191 | V191I | | | X |
| 196 | D196E | X | X | X |
| 212 | G212M | | X | |
| 212 | G212S | | | X |
| 216 | V216I | | X | X |
| 236 | V236A | | X | |
| 236 | V236K | X | | X |
| 237 | L237I | X | | X |
| 243 | A243G | X | X | X |
| 255 | D255E | | X | X |
| 257 | L257I | X | X | |
| 257 | L257M | | | X |
| 259 | N259Q | | X | |
| 259 | N259A | | | X |
| 259 | N259E | X | | |
| 260 | L260V | | X | |
| 260 | L260M | | | X |
| 262 | H262Q | | X | |
| 262 | H262R | | | X |
| 263 | A263V | X | | |
| 265 | G265N | | X | |
| 266 | G266S | | | X |
| 266 | G266A | X | | |
| 285 | A285V | | X | |
| 285 | A285L | X | | X |
| 288 | N288D | | X | X |
| 289 | N289G | | X | |
| 289 | N289E | X | | |
| 293 | T293I | | | X |
| 293 | T293A | X | | |
| 306 | A306S | X | X | |
| 331 | N331K | | X | |
| 331 | N331T | X | | X |
| 334 | Q334K | | X | X |
| 335 | Q335S | | X | |
| 335 | Q335C | | | X |
| 335 | Q335N | X | | |
| 338 | T338H | | X | |
| 338 | T338E | | | X |
| 338 | T338A | X | | |
| 353 | S353K | | X | X |
| 393 | E393G | | X | |
| 393 | E393T | | | X |
| 393 | E393Q | X | | |
| 394 | G394E | | X | X |
| 394 | G394R | X | | |
| 402 | R402K | X | | X |
| 413 | A413T | X | | X |
| 461 | I461L | | | X |
| 461 | I461V | | X | |

Example 7

Engineering of 'tesA of *P. profundum* (Ppro)

The 'tesA of *P. profundum* (Ppro) was engineered to act as an ester synthase. When screened in 96 well plates, the wild type Ppro produced about 15-18% FAME of the total acyl products (FAME+free fatty acids). Mutations were identified that increased the FAME content to 42-44% when the variants were tested on 96 well plates. When the same mutants were tested in a shake flask, they produced 62-65% FAME as compared to 30% FAME produced by the wild type enzyme. Mutations were identified based on standard techniques, such as error prone PCR or saturation libraries of Ppro (Protocol 7). The identified mutations were combined generating combination libraries, which were also tested. The libraries were then screened using one of the standard protocols (Protocols 1-4) described above.

Based on the screening of combination libraries, mutations were selected to be either (1) fixed for the next round of combination library screening; (2) re-tested in the next round of combination library screening; or (3) not tested further at that time. Mutations that were identified as beneficial were fixed for future libraries. The process can be carried out by screening using 96 well plates, validation in 96 well plates, and follow-up validation in shake flasks.

The best performers in shake flasks can then be tested in fermenters to verify that there is improvement of the engineered Ppro that is consistent with scale-up. A few of the top hits from the combination libraries can be tested in shake flasks to confirm that the Ppro variants have improved performance at a larger scale than that of 96 well plates. A shake flask validation can be carried out as follows. Desired mutants are streaked on LB+ spectinomycin agar to obtain single colonies and incubated overnight at 37° C. Three single colonies from each mutant are picked into 4 mL LB+ spectinomycin and incubated at 37° C. shaker for approximately 6 hours. 1.5 mL of the LB culture is used to inoculate 15 mL FA2 (2 g/L $NH_4Cl$)+0.05% Triton X-100+ spectinomycin in a baffled 125 mL flask and incubated overnight at 32° C. 3 mL of the overnight culture is used to inoculate 15 mL FA2 (2 g/L $NH_4Cl$)+0.05% Triton X-100+1 mM IPTG, 2% Methanol+spectinomycin in a baffled 125 mL flask and incubated for approximately 24 hours at 32° C. At time of extraction 300 μL of culture is sampled from the flask into a 96 well plate and extracted using a standard extraction protocol (Protocol 5).

A standard extraction protocol was carried out as described above (Protocol 5). The results from screening saturation libraries are shown in Tables 8 through 11. Table 8 presents results for single beneficial mutations found using the wild type as template, i.e, SEQ ID NO: 51. Table 9 presents results for combination mutants found using the wild type as template. Table 10 presents results for single beneficial mutations found using SEQ ID NO: 53 (referred to as PROF 1) as template (SEQ ID NO: 53 already contained two beneficial mutations in its sequence including S46V and Y116H mutations). For PROF1, the S46V and Y116H mutations were "fixed" into the template, such that future rounds of saturation/combination would be starting from that variant rather than from the wild type sequence. Table 11 presents results for double mutations found as beneficial using PROF1 as template. Table 12 presents results for combination mutants found, using the wild type as template. Table 13 presents results for combination mutants found using P1B9v2.0 (SEQ ID NO: 58) as template in BD64.

Table 8 below shows a list of single beneficial mutations found using Ppro wild type (SEQ ID NO: 51) as template.

TABLE 8

| Mutation | Norm FAME | Norm FFA | Norm Titer | Norm % FAME |
|---|---|---|---|---|
| T3L | 0.911 | 0.882 | 0.889 | 1.023 |
| P29A | 1.015 | 1.088 | 1.071 | 0.947 |
| P29F | 0.984 | 0.984 | 0.984 | 1.000 |
| P29G | 1.008 | 1.009 | 1.009 | 0.999 |
| P29S | 1.018 | 1.030 | 1.027 | 0.992 |
| I38Y | 0.765 | 0.592 | 0.632 | 1.211 |
| I45A | 0.420 | 0.304 | 0.320 | 1.317 |
| I45G | 0.311 | 0.109 | 0.137 | 2.242 |
| I45K | 1.205 | 1.145 | 1.154 | 1.046 |
| I45R | 1.313 | 1.257 | 1.265 | 1.038 |
| I45S | 0.398 | 0.242 | 0.264 | 1.509 |
| I45V | 1.162 | 1.096 | 1.105 | 1.050 |

TABLE 8-continued

| Mutation | Norm FAME | Norm FFA | Norm Titer | Norm % FAME |
|---|---|---|---|---|
| I45W | 0.281 | 0.202 | 0.213 | 1.322 |
| S46K | 0.387 | 0.224 | 0.247 | 1.556 |
| S46V | 1.166 | 0.899 | 0.937 | 1.250 |
| S46W | 0.346 | 0.211 | 0.230 | 1.517 |
| D48A | 1.297 | 1.417 | 1.396 | 0.929 |
| D48E | 1.267 | 1.278 | 1.276 | 0.993 |
| D48F | 0.892 | 0.773 | 0.794 | 1.123 |
| D48G | 0.921 | 0.835 | 0.851 | 1.083 |
| D48H | 1.081 | 0.955 | 0.977 | 1.106 |
| D48L | 1.774 | 1.816 | 1.808 | 0.980 |
| D48M | 1.880 | 2.159 | 2.109 | 0.891 |
| D48V | 0.626 | 0.535 | 0.551 | 1.136 |
| D48W | 1.263 | 1.252 | 1.254 | 1.010 |
| T49D | 0.556 | 0.378 | 0.408 | 1.364 |
| T49G | 0.273 | 0.263 | 0.265 | 1.024 |
| T49L | 0.595 | 0.425 | 0.453 | 1.311 |
| T49M | 0.461 | 0.334 | 0.356 | 1.292 |
| T49R | 0.402 | 0.214 | 0.244 | 1.651 |
| T49S | 0.447 | 0.360 | 0.374 | 1.194 |
| T49V | 0.503 | 0.336 | 0.362 | 1.389 |
| T49W | 0.678 | 0.542 | 0.565 | 1.203 |
| G51A | 1.079 | 1.068 | 1.070 | 1.009 |
| G51E | 1.025 | 0.938 | 0.952 | 1.076 |
| G51F | 0.921 | 0.830 | 0.844 | 1.091 |
| G51H | 1.083 | 1.087 | 1.086 | 0.997 |
| G51L | 0.956 | 0.871 | 0.887 | 1.076 |
| G51M | 1.013 | 0.952 | 0.962 | 1.053 |
| G51P | 0.460 | 0.308 | 0.332 | 1.385 |
| G51Q | 1.047 | 1.082 | 1.075 | 0.972 |
| G51R | 1.377 | 1.452 | 1.440 | 0.955 |
| G51S | 1.088 | 1.046 | 1.053 | 1.033 |
| G51T | 1.062 | 1.115 | 1.107 | 0.959 |
| G51V | 1.003 | 1.036 | 1.031 | 0.973 |
| G51Y | 0.852 | 0.833 | 0.837 | 1.016 |
| N52A | 0.970 | 0.856 | 0.883 | 1.099 |
| N52C | 0.825 | 0.676 | 0.710 | 1.161 |
| N52F | 0.797 | 0.668 | 0.697 | 1.141 |
| N52G | 1.026 | 1.093 | 1.078 | 0.951 |
| N52H | 0.959 | 1.035 | 1.017 | 0.943 |
| N52L | 0.974 | 0.848 | 0.877 | 1.110 |
| N52M | 1.040 | 1.045 | 1.044 | 0.996 |
| N52R | 1.405 | 1.641 | 1.587 | 0.885 |
| N52S | 0.903 | 0.810 | 0.832 | 1.084 |
| N52T | 0.874 | 0.785 | 0.806 | 1.084 |
| N52V | 0.812 | 0.699 | 0.725 | 1.118 |
| N76I | 0.518 | 0.285 | 0.326 | 1.584 |
| N76L | 0.366 | 0.160 | 0.200 | 1.834 |
| N76V | 0.642 | 0.336 | 0.395 | 1.624 |
| S92A | 1.001 | 1.054 | 1.042 | 0.960 |
| S92H | 1.026 | 1.106 | 1.087 | 0.943 |
| S92S | 1.002 | 0.972 | 0.979 | 1.022 |
| S92Y | 1.022 | 1.199 | 1.158 | 0.881 |
| I95V | 0.910 | 0.876 | 0.884 | 1.028 |
| Y116A | 0.923 | 0.889 | 0.895 | 1.032 |
| Y116F | 1.077 | 1.035 | 1.042 | 1.034 |
| Y116I | 1.392 | 1.303 | 1.318 | 1.055 |
| Y116L | 1.203 | 1.246 | 1.239 | 0.971 |
| Y116N | 1.430 | 1.424 | 1.425 | 1.003 |
| Y116P | 0.628 | 0.460 | 0.488 | 1.284 |
| Y116R | 1.442 | 1.701 | 1.657 | 0.872 |
| Y116S | 0.876 | 0.757 | 0.777 | 1.127 |
| Y116T | 1.079 | 0.939 | 0.963 | 1.121 |
| Y120R | 0.490 | 0.399 | 0.420 | 1.164 |
| N156A | 1.048 | 1.090 | 1.082 | 0.969 |
| N156C | 0.903 | 0.858 | 0.866 | 1.042 |
| N156G | 0.984 | 1.070 | 1.055 | 0.933 |
| N156L | 0.841 | 0.821 | 0.825 | 1.018 |
| N156R | 1.477 | 1.942 | 1.856 | 0.796 |
| N156W | 0.824 | 0.678 | 0.705 | 1.168 |
| L159G | 0.399 | 0.245 | 0.273 | 1.455 |
| L159M | 1.254 | 1.651 | 1.577 | 0.795 |
| L159N | 0.513 | 0.323 | 0.358 | 1.433 |
| L159R | 0.554 | 0.540 | 0.542 | 1.021 |
| L159S | 0.390 | 0.237 | 0.265 | 1.466 |
| L159Y | 0.476 | 0.318 | 0.347 | 1.368 |

Table 9 below shows a list of combination mutants found using Ppro wild type (SEQ ID NO: 51) as template.

TABLE 9

| Mutation | Mutation | Norm FAME | Norm FFA | Norm Titer | Norm % FAME |
|---|---|---|---|---|---|
| E37D | I45R | 1.189 | 1.255 | 1.246 | 0.953 |
| P29A | Stop_182I | 1.014 | 1.058 | 1.047 | 0.967 |
| I38L | V41I | 0.843 | 0.760 | 0.779 | 1.082 |
| Y116I | Q146H | 1.554 | 1.906 | 1.846 | 0.841 |
| Y116P | E175D | 0.341 | 0.231 | 0.252 | 1.350 |
| Y116Q | G117R | 0.438 | 0.350 | 0.365 | 1.202 |
| G8V | T49S | 0.405 | 0.277 | 0.299 | 1.358 |
| A30T | G51C | 0.566 | 0.483 | 0.499 | 1.134 |
| T49Q | Y116H | 0.383 | 0.247 | 0.269 | 1.417 |
| T49R | Y116H | 0.441 | 0.303 | 0.324 | 1.362 |
| N156K | L159K | 1.456 | 1.955 | 1.862 | 0.782 |
| G158D | L159V | 0.334 | 0.224 | 0.244 | 1.362 |

Table 10 below shows a list of single beneficial mutations found using PROF1 (SEQ ID NO: 53) as template.

TABLE 10

| Mutation | Norm FAME | Norm FFA | Norm Titer | Norm % FAME |
|---|---|---|---|---|
| V41D | 0.394 | 0.310 | 0.330 | 1.195 |
| V41E | 0.891 | 0.855 | 0.863 | 1.033 |
| V41K | 0.999 | 1.016 | 1.012 | 0.989 |
| V41Q | 1.015 | 1.048 | 1.040 | 0.976 |
| V41R | 0.996 | 1.019 | 1.014 | 0.983 |
| V41S | 0.577 | 0.495 | 0.515 | 1.122 |
| V41T | 0.732 | 0.669 | 0.684 | 1.070 |
| V41W | 0.856 | 0.778 | 0.797 | 1.075 |
| F82A | 1.036 | 0.940 | 0.963 | 1.077 |
| F82E | 0.861 | 0.747 | 0.775 | 1.111 |
| F82G | 0.770 | 0.577 | 0.625 | 1.233 |
| F82K | 1.167 | 1.220 | 1.207 | 0.967 |
| F82Q | 0.996 | 0.927 | 0.944 | 1.054 |
| F82R | 1.426 | 1.552 | 1.521 | 0.938 |
| F82V | 0.975 | 0.883 | 0.906 | 1.076 |
| F82W | 1.089 | 1.141 | 1.128 | 0.966 |
| Q84A | 0.989 | 0.936 | 0.949 | 1.043 |
| Q84E | 0.990 | 1.050 | 1.036 | 0.957 |
| Q84G | 0.822 | 0.774 | 0.785 | 1.047 |

Table 11 shows a list of double mutations found as beneficial using PROF1 (SEQ ID NO: 53) as template.

TABLE 11

| Mutation | Mutation | Norm FAME | Norm FFA | Norm Titer | Norm % FAME |
|---|---|---|---|---|---|
| V41L | D48G | 0.684 | 0.601 | 0.621 | 1.103 |
| F82G | T86P | 0.589 | 0.399 | 0.446 | 1.323 |

Figure 7A:
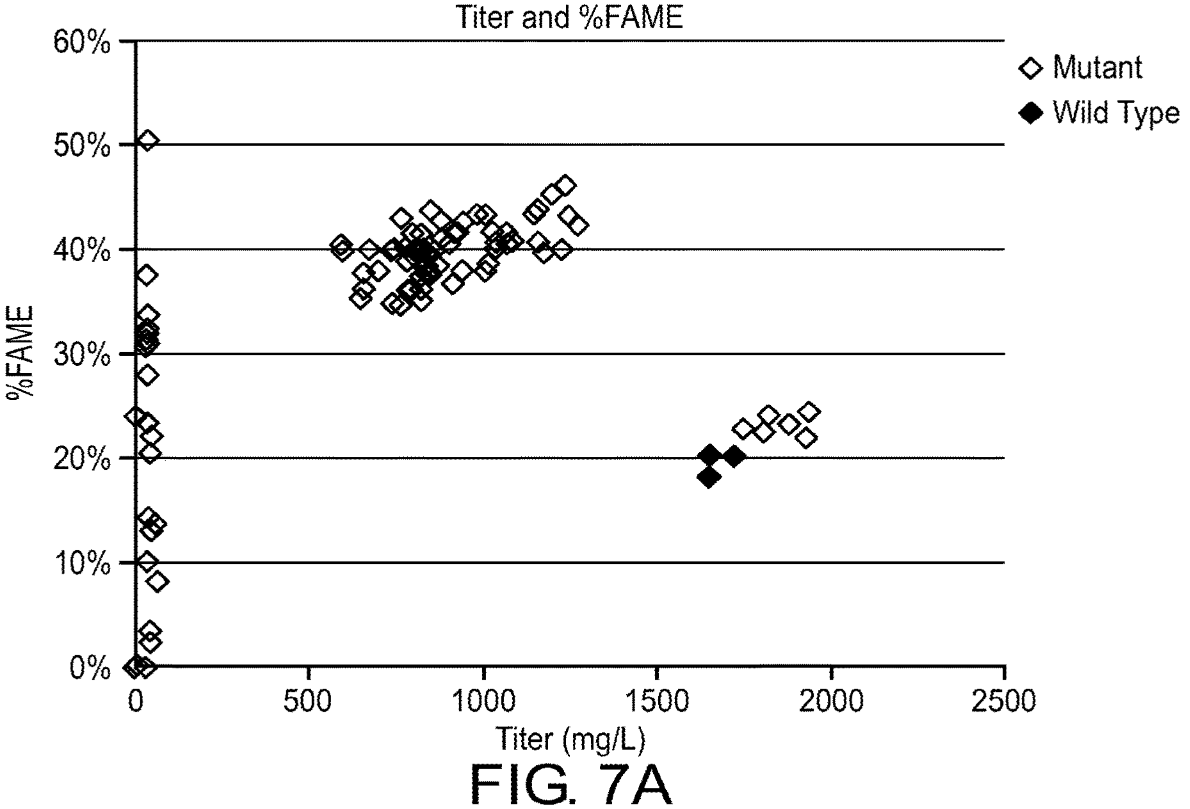
FIGS. 7A and 7B show the titer and % FAME (FIG. 7A) or FAEE (FIG. 7B) produced when a Ppro combination library built was fed methanol to evaluate the ability of Ppro variants to use methanol to make FAME (FIG. 7A) or ethanol to make FAEE (FIG. 7B).
Figure 7B:
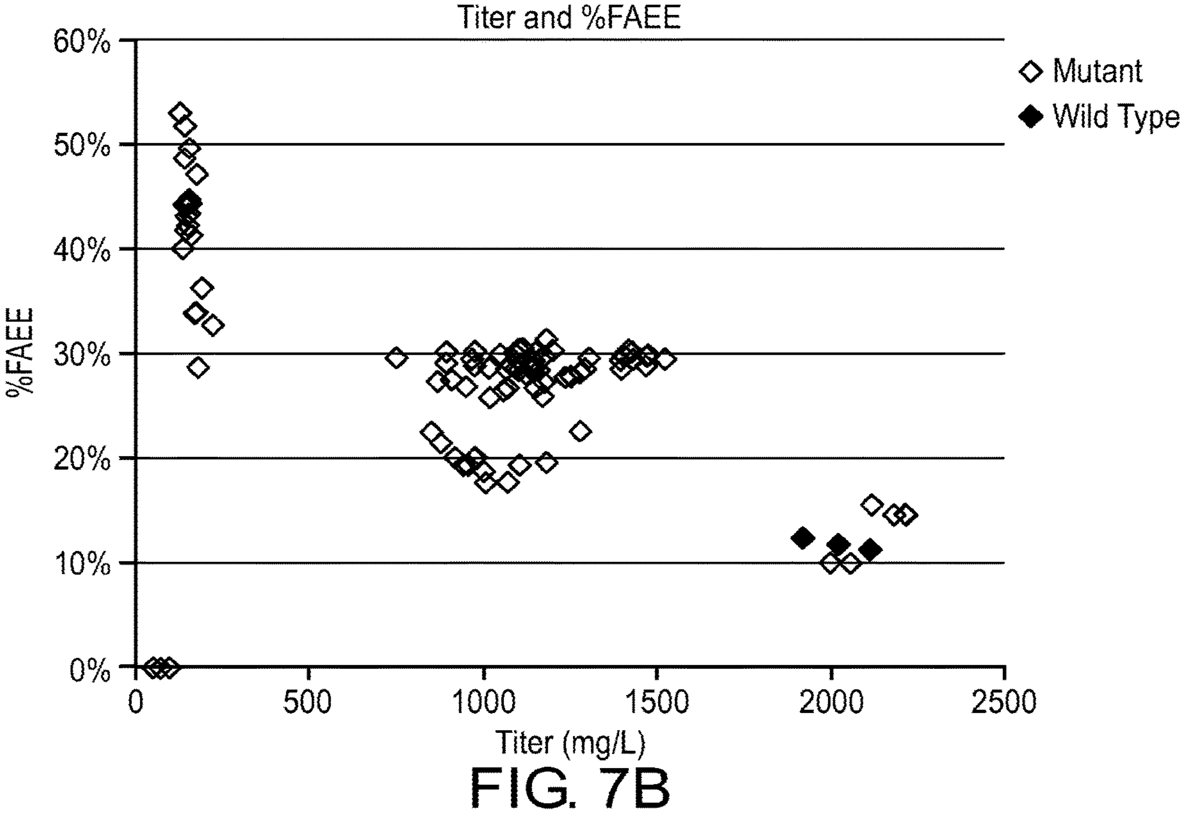

Discussed herein are the results of feeding ethanol to one of the Ppro libraries. One of the combination libraries was fed either methanol or ethanol, in order to test if genes that have improved ester synthase activity using methanol, also show improved ester synthase activity in the presence of ethanol. As can be seen in FIGS. 7A and 7B, the improved ester synthase activity was observed with either methanol or ethanol feeding, though higher percentage esters were obtained using methanol. Table 12 shows a list of combination mutants found using Ppro wild type (SEQ ID NO: 51) as template.

TABLE 12

| Mutations | Norm FAME | Norm FFA | Norm Titer | Norm % FAME |
|---|---|---|---|---|
| D48E, R119C | 1.119 | 1.116 | 1.117 | 1.001 |
| D48E, R88H, Y116H | 1.265 | 1.559 | 1.506 | 0.839 |
| G51R, D102V | 1.012 | 1.026 | 1.023 | 0.988 |
| G51R, R88H, R119C, L159M | 1.597 | 1.818 | 1.778 | 0.897 |
| I45T, D48E, S92R, Y116H | 1.060 | 0.991 | 1.004 | 1.055 |
| I45T, D48E, Y116H | 1.027 | 1.019 | 1.020 | 1.007 |
| I45T, D48E, Y116H, R119C | 0.812 | 0.766 | 0.774 | 1.046 |
| I45T, R88H | 0.643 | 0.490 | 0.518 | 1.237 |
| I45T, S46V, R119C | 0.635 | 0.565 | 0.578 | 1.099 |
| I45T, S46V, Y116H | 1.004 | 0.891 | 0.912 | 1.100 |
| I45T, Y116H | 1.158 | 1.223 | 1.211 | 0.957 |
| K32M, L159M | 1.400 | 1.717 | 1.659 | 0.843 |
| K32M, N156Y, L159M | 1.345 | 1.278 | 1.290 | 1.042 |
| R18C, G51R, N52T, D102V, N115I, P129L, L159M | 1.377 | 1.524 | 1.497 | 0.918 |
| R88H, Y116H | 1.131 | 1.258 | 1.235 | 0.915 |
| S46V, D48E, Y116H | 1.209 | 1.052 | 1.081 | 1.117 |
| S46V, D48E, Y116H, R119C | 1.118 | 0.993 | 1.016 | 1.101 |
| S46V, R88H | 1.086 | 0.820 | 0.868 | 1.249 |
| S46V, T86S, Y116H | 1.401 | 1.092 | 1.149 | 1.219 |
| S46V, Y116H | 1.321 | 1.203 | 1.224 | 1.079 |
| T2_50_T4, R88H, R119C | 0.833 | 0.806 | 0.811 | 1.026 |
| V41I, I45T, Y116H | 1.057 | 1.129 | 1.116 | 0.945 |
| V41L, S46V, R119C | 0.897 | 0.631 | 0.680 | 1.318 |
| Y116H, R119C | 1.107 | 1.277 | 1.246 | 0.888 |
| D48E, G51R, R88H, R119C, L159M | 1.403 | 1.389 | 1.391 | 1.010 |
| D48E, Y116H, R119C | 1.493 | 1.570 | 1.558 | 0.958 |
| G51R, N156Y | 1.097 | 1.133 | 1.127 | 0.972 |
| G51R, R119C, N156Y, L159M | 1.364 | 1.566 | 1.534 | 0.888 |
| G51R, R88H, Y116H, S121R, L159M | 1.562 | 1.631 | 1.621 | 0.962 |
| G51R, V112A, N1151, N156Y | 0.317 | 0.216 | 0.230 | 1.339 |
| G51R, Y116H, R119C | 1.609 | 1.856 | 1.818 | 0.884 |
| H36Q, S46V, R88H, Y116H, R119C, L159M | 0.843 | 0.652 | 0.682 | 1.236 |
| I45N, S46V, D48E, G51R, Y116H, L159M | 1.016 | 0.848 | 0.875 | 1.162 |
| K32M, D48E, R88H, Y116H, N156Y | 0.920 | 0.811 | 0.828 | 1.110 |
| K32M, D48E, Y116H | 1.992 | 1.929 | 1.938 | 1.027 |
| K32M, G51R, Y116H | 1.722 | 1.943 | 1.908 | 0.902 |
| K32M, H36Q, G51R, Y116H, L159M | 1.629 | 1.651 | 1.648 | 0.988 |
| K32M, S46V, D48E, A55T, R119C | 0.710 | 0.518 | 0.547 | 1.294 |
| K32M, S46V, D48E, G51R, Y116H, L159M | 2.067 | 1.562 | 1.634 | 1.264 |
| K32M, S46V, D48E, Y116H, N156Y, L159M | 1.211 | 1.007 | 1.039 | 1.165 |
| K32M, S46V, G51R | 1.305 | 1.144 | 1.169 | 1.115 |
| K32M, S46V, G51R, F82I, Q84L, Y116H, L159M | 2.570 | 2.098 | 2.165 | 1.187 |
| K32M, S46V, G51R, L159M | 1.646 | 1.512 | 1.533 | 1.073 |
| K32M, S46V, G51R, R88H, L159M | 1.730 | 1.552 | 1.579 | 1.097 |
| K32M, S46V, G51R, R88H, Y116H, R119C | 1.516 | 1.397 | 1.415 | 1.072 |
| K32M, S46V, G51R, R88H, Y116H, R119C, S121R | 0.601 | 0.532 | 0.543 | 1.116 |
| K32M, S46V, G51R, Y116H | 2.066 | 1.634 | 1.695 | 1.219 |
| K32M, S46V, G51R, Y116H, N156Y, L159M | 1.992 | 1.859 | 1.880 | 1.060 |
| K32M, S46V, G51R, Y116H, R119C, N156Y, L159M | 1.866 | 1.578 | 1.619 | 1.153 |
| K32M, S46V, G51R, Y116H, S121R, N156Y, L159M | 0.774 | 0.664 | 0.681 | 1.137 |
| K32M, S46V, Y116H | 1.408 | 1.193 | 1.223 | 1.152 |
| K32M, S46V, Y116H, E152*, L159M | 0.441 | 0.385 | 0.394 | 1.136 |
| K32M, S46V, Y116H, L159M | 1.845 | 1.695 | 1.718 | 1.073 |
| K32M, S46V, Y116H, N156Y | 1.261 | 1.061 | 1.093 | 1.156 |
| K32M, Y116H, R119C, L159M | 1.693 | 1.928 | 1.891 | 0.895 |
| P24Q, K32M, S46V, G51R, R88H, L159M | 0.615 | 0.491 | 0.511 | 1.189 |
| R88H, L159M | 1.414 | 1.525 | 1.507 | 0.939 |
| R88H, N89S, Y116H | 1.263 | 1.368 | 1.352 | 0.934 |
| S46V, D48E | 0.975 | 0.755 | 0.790 | 1.234 |
| S46V, D48E, G51R, R119C | 1.160 | 0.946 | 0.979 | 1.181 |
| S46V, D48E, G51R, R119C, L159* | 0.343 | 0.199 | 0.221 | 1.556 |
| S46V, D48E, G51R, R88H, Y116H, L159M | 1.527 | 1.329 | 1.360 | 1.123 |

TABLE 12-continued

| Mutations | Norm FAME | Norm FFA | Norm Titer | Norm % FAME |
|---|---|---|---|---|
| S46V, D48E, G51R, R88H, Y116H, R119C, N156Y | 0.818 | 0.655 | 0.681 | 1.201 |
| S46V, D48E, G51R, Y116H | 1.645 | 1.355 | 1.399 | 1.175 |
| S46V, D48E, G51R, Y116H, L159M | 1.669 | 1.453 | 1.487 | 1.122 |
| S46V, D48E, G51R, Y116H, N156Y, L159M | 1.517 | 1.195 | 1.244 | 1.220 |
| S46V, D48E, G51R, Y116H, S121N | 0.532 | 0.485 | 0.492 | 1.078 |
| S46V, D48E, N156K | 1.411 | 1.112 | 1.159 | 1.217 |
| S46V, D48E, N90K, Y116H, L159M | 0.366 | 0.248 | 0.266 | 1.373 |
| S46V, D48E, R119C | 0.946 | 0.725 | 0.759 | 1.245 |
| S46V, D48E, R88H, Y116H | 1.199 | 1.016 | 1.044 | 1.148 |
| S46V, D48E, Y116H, L159M | 1.534 | 1.232 | 1.279 | 1.198 |
| S46V, D48E, Y116H, N156Y, L159M | 1.265 | 1.007 | 1.048 | 1.206 |
| S46V, G51R | 1.315 | 1.219 | 1.234 | 1.065 |
| S46V, G51R, L791, R88H, Y116H, N156Y, L159M | 1.013 | 0.845 | 0.871 | 1.161 |
| S46V, G51R, N156Y | 1.285 | 1.073 | 1.106 | 1.161 |
| S46V, G51R, R88H, Y116H | 1.561 | 1.389 | 1.416 | 1.103 |
| S46V, G51R, R88H, Y116H, M154K | 0.520 | 0.413 | 0.430 | 1.210 |
| S46V, G51R, R88H, Y116H, N156Y, L159M | 1.677 | 1.571 | 1.588 | 1.055 |
| S46V, G51R, R88H, Y116H, R119C | 1.454 | 1.277 | 1.305 | 1.114 |
| S46V, G51R, R88H, Y116H, R119C, S163F | 0.554 | 0.392 | 0.417 | 1.327 |
| S46V, G51R, Y116H | 1.656 | 1.486 | 1.513 | 1.095 |
| S46V, G51R, Y116H, L159M | 1.989 | 1.875 | 1.893 | 1.050 |
| S46V, G51R, Y116H, N156Y | 1.788 | 1.461 | 1.508 | 1.186 |
| S46V, G51R, Y116H, R119C | 1.869 | 1.480 | 1.535 | 1.216 |
| S46V, G51R, Y116H, R119C, L159M | 2.256 | 2.015 | 2.050 | 1.101 |
| S46V, L159M | 1.487 | 1.300 | 1.329 | 1.118 |
| S46V, N156Y, L159M | 1.360 | 1.113 | 1.148 | 1.184 |
| S46V, R88H, L159M | 1.684 | 1.434 | 1.469 | 1.146 |
| S46V, R88H, Y116H | 1.219 | 1.024 | 1.054 | 1.157 |
| S46V, R88H, Y116H, L159M | 1.647 | 1.439 | 1.471 | 1.119 |
| S46V, R88H, Y116H, N156Y | 1.213 | 0.951 | 0.988 | 1.228 |
| S46V, R88H, Y116H, S125I | 0.685 | 0.501 | 0.530 | 1.290 |
| S46V, R88Y, Y116H, R119C, L159M | 1.254 | 1.119 | 1.140 | 1.101 |
| S46V, Y116H, L159M | 1.671 | 1.510 | 1.534 | 1.089 |
| S46V, Y116H, N156Y | 1.320 | 1.070 | 1.105 | 1.193 |
| S46V, Y116H, R119C | 1.191 | 0.964 | 0.999 | 1.192 |
| S46V, Y116H, R119C, L159M | 1.588 | 1.397 | 1.427 | 1.113 |
| S46V, Y116H, R119C, N156Y | 1.045 | 0.851 | 0.881 | 1.186 |
| S46V, Y116H, R119C, N156Y, L159M | 1.295 | 1.086 | 1.118 | 1.158 |
| V41E, S46V, D48E, R119C | 0.570 | 0.396 | 0.423 | 1.347 |
| V41L, S46V, R88H, L159M | 1.138 | 0.858 | 0.898 | 1.268 |
| Y116H, N156Y, L159M | 1.455 | 1.644 | 1.615 | 0.901 |
| S46V, D48F, G51R, Y116H, E152D, L159M | 1.100 | 0.904 | 0.936 | 1.176 |
| S46V, D48F, G51R, Y116H, G117D, L159M | 0.695 | 0.439 | 0.482 | 1.444 |
| S46V, D48F, G51R, Y116H, L159M | 1.297 | 1.263 | 1.269 | 1.021 |
| S46V, D48F, G51R, N52C, Y116N | 0.304 | 0.163 | 0.187 | 1.632 |
| S46V, D48F, G51R, N52C, N76V, Y116S, N156K | 0.218 | 0.197 | 0.201 | 1.091 |
| S46V, D48F, G51R, N76V, Y116N | 0.656 | 0.291 | 0.350 | 1.882 |
| S46V, D48F, G51R, N76V, Y116H, N156K, L159M | 0.838 | 0.360 | 0.434 | 1.941 |
| S46V, D48F, G51R, P114R, Y116H | 0.636 | 0.518 | 0.536 | 1.194 |
| S46V, D48L, G51R, Y116S, N156K | 0.854 | 0.766 | 0.780 | 1.096 |
| S46V, D48L, G51R, Y116H, M155I, N156S | 0.606 | 0.461 | 0.483 | 1.254 |
| S46V, D48L, G51R, N52C, N76V, Y116H | 1.033 | 0.397 | 0.495 | 2.089 |
| S46V, D48L, G51R, N52F, Y116H, N156K | 1.438 | 1.285 | 1.310 | 1.099 |
| S46V, D48L, G51R, N52F, N76I, Y116N | 0.446 | 0.272 | 0.298 | 1.492 |
| S46V, D48L, G51R, N52F, N76I, Y116N, L149V | 0.536 | 0.279 | 0.321 | 1.667 |
| S46V, D48L, G51R, N52F, N76V, Y116H, L159M | 1.023 | 0.319 | 0.428 | 2.389 |
| S46V, D48L, G51R, N76I, Y116P, L159M | 0.545 | 0.243 | 0.293 | 1.857 |
| S46V, D48L, G51R, N76I, Y116S | 0.398 | 0.238 | 0.265 | 1.501 |
| S46V, D48M, G51R, Y116P | 1.353 | 1.209 | 1.233 | 1.098 |
| S46V, D48M, G51R, N52F, Y116H | 1.951 | 1.559 | 1.620 | 1.204 |

TABLE 12-continued

| Mutations | Norm FAME | Norm FFA | Norm Titer | Norm % FAME |
|---|---|---|---|---|
| S46V, D48M, G51R, N52F, Y116P | 0.864 | 0.659 | 0.692 | 1.247 |
| S46V, D48M, G51R, N52F, Y116H, L159M | 1.432 | 1.225 | 1.260 | 1.136 |
| S46V, D48M, G51R, N76I, Y116N, N156K | 0.913 | 0.362 | 0.447 | 2.042 |
| S46V, D48M, G51R, N76I, Y116S, L159M | 0.971 | 0.387 | 0.481 | 2.012 |
| S46V, D48M, G51R, N76V, Y116P | 1.353 | 0.418 | 0.562 | 2.405 |
| S46V, D48M, G51R, N76V, Y116P, K162R | 1.179 | 0.377 | 0.501 | 2.356 |
| S46V, D48M, G51R, P114R, Y116H, Q151R | 1.481 | 1.318 | 1.345 | 1.102 |
| S46V, G47S, D48L, G51R, N52F, Y116H, N156K | 0.558 | 0.351 | 0.385 | 1.448 |
| S46V, G51R, Y116N, L159M | 2.259 | 1.823 | 1.890 | 1.196 |
| S46V, G51R, Y116N, N156K | 1.798 | 1.818 | 1.814 | 0.992 |
| S46V, G51R, Y116P, N156K | 1.257 | 1.000 | 1.039 | 1.211 |
| S46V, G51R, Y116S, N156K | 1.833 | 1.363 | 1.435 | 1.277 |
| S46V, G51R, N52C, Y116H, L159M | 2.011 | 1.595 | 1.659 | 1.212 |
| S46V, G51R, N52C, Y116H, N156K | 2.141 | 1.869 | 1.913 | 1.119 |
| S46V, G51R, N52C, N76I, Y116H | 0.287 | 0.141 | 0.163 | 1.759 |
| S46V, G51R, N52C, N76V, Y116P | 0.535 | 0.187 | 0.241 | 2.151 |
| S46V, G51R, N52F, Y116H | 1.296 | 1.006 | 1.051 | 1.234 |
| S46V, G51R, N52F, Y116P, N156K, L159M | 0.263 | 0.216 | 0.224 | 1.145 |
| S46V, G51R, N52F, Y116S, L159M | 0.271 | 0.215 | 0.224 | 1.210 |
| S46V, G51R, N76I, Y116H | 0.210 | 0.188 | 0.191 | 1.098 |
| S46V, G51R, N76V, Y116H | 0.740 | 0.331 | 0.397 | 1.865 |
| S46V, G51R, N76V, Y116S | 0.653 | 0.252 | 0.317 | 2.065 |
| S46V, G51R, V112M, Y116N, N156K | 1.384 | 0.949 | 1.016 | 1.363 |
| I38Y, S46V, D48F, G51R, Y116N, L159M | 0.258 | 0.115 | 0.139 | 1.867 |
| I38Y, S46V, D48L, G51R, Y116S | 0.218 | 0.127 | 0.142 | 1.510 |
| I38Y, S46V, D48L, G51R, N76I, Y116H, N156K, L159M | 0.954 | 0.379 | 0.468 | 2.041 |
| I38Y, S46V, D48L, G51R, N76I, R80G, Y116H, N156K, L159M | 0.497 | 0.245 | 0.284 | 1.714 |
| I38Y, S46V, D48M, G51R, N52C, Y116S | 0.441 | 0.305 | 0.327 | 1.348 |
| I38Y, S46V, D48M, G51R, N52F, N76V, Y116H | 1.638 | 0.417 | 0.604 | 2.711 |
| I38Y, S46V, D48M, G51R, N52F, N76V, Y116H, L181S, *182Y | 1.836 | 0.485 | 0.692 | 2.653 |
| I38Y, S46V, D48M, G51R, N76V, Y116N, N156K, L159M | 1.627 | 0.468 | 0.648 | 2.513 |
| I38Y, S46V, G51R, Y116N | 0.764 | 0.551 | 0.585 | 1.305 |
| I38Y, S46V, G51R, Y116H, L159M | 2.024 | 1.801 | 1.835 | 1.103 |
| I38Y, S46V, G51R, N52C, N76I, Y116H, N156K | 0.170 | 0.138 | 0.144 | 1.190 |
| S46V, D48L, G51R, F82I, Q84L, Y116H, L159M | 1.663 | 1.293 | 1.373 | 1.211 |
| S46V, D48L, G51R, N76V, Y116H | 0.678 | 0.340 | 0.413 | 1.639 |
| S46V, D48L, G51R, N76V, F82I, Q84L, Y116N, L159M | 0.846 | 0.375 | 0.484 | 1.745 |
| S46V, D48L, G51R, N76V, Y116N | 0.899 | 0.395 | 0.513 | 1.754 |
| S46V, D48L, G51R, N76V, Y116N, L159M | 0.897 | 0.403 | 0.517 | 1.731 |
| S46V, D48L, G51R, N76V, Y116N, L159M, K162E | 0.721 | 0.342 | 0.430 | 1.675 |
| S46V, D48L, G51R, N76V, Y116N, N156K | 0.888 | 0.382 | 0.492 | 1.805 |
| S46V, D48L, G51R, N76V, Y116N, N156K, L159M | 0.809 | 0.369 | 0.471 | 1.714 |
| S46V, D48L, G51R, N76V, Y116H, L159M | 1.073 | 0.414 | 0.557 | 1.924 |
| S46V, D48L, G51R, N76V, Y116H, N156K | 0.874 | 0.401 | 0.511 | 1.712 |
| S46V, D48L, G51R, N76V, Y116H, N156K, L159M | 0.949 | 0.425 | 0.547 | 1.735 |
| S46V, D48L, G51R, N76V, V112M, Y116N | 0.696 | 0.347 | 0.429 | 1.623 |
| S46V, D48M, G51R, N52Y, N76V, Y116N, L159M | 1.153 | 0.424 | 0.594 | 1.941 |
| S46V, D48M, G51R, N52Y, N76V, Y116H, L159M | 1.157 | 0.437 | 0.605 | 1.914 |
| S46V, D48M, G51R, N76V, Y116H | 1.225 | 0.445 | 0.614 | 1.994 |

TABLE 12-continued

| Mutations | Norm FAME | Norm FFA | Norm Titer | Norm % FAME |
|---|---|---|---|---|
| S46V, D48M, G51R, N76V, Y116N | 1.178 | 0.446 | 0.605 | 1.947 |
| S46V, D48M, G51R, N76V, Y116N, L159M | 1.267 | 0.480 | 0.663 | 1.908 |
| S46V, D48M, G51R, N76V, Y116N, N156K | 1.058 | 0.406 | 0.547 | 1.931 |
| S46V, D48M, G51R, N76V, Y116N, N156K, L159M | 1.176 | 0.490 | 0.650 | 1.811 |
| S46V, D48M, G51R, N76V, Y116H, L159M | 1.312 | 0.529 | 0.711 | 1.845 |
| S46V, D48M, G51R, N76V, Y116H, M155R | 0.799 | 0.352 | 0.449 | 1.779 |
| S46V, D48M, G51R, N76V, Y116H, N156K | 1.254 | 0.532 | 0.700 | 1.791 |
| S46V, D48M, G51R, N76V, Y116H, N156K, L159M | 1.257 | 0.524 | 0.695 | 1.810 |
| S46V, D48M, G51R, R56P, N76V, Y116H, L159M | 0.406 | 0.165 | 0.221 | 1.836 |
| S46V, G51R, N76V, Y116N, L159M | 0.822 | 0.386 | 0.487 | 1.687 |
| S46V, G51R, N76V, Y116N, N156K, L159M | 0.942 | 0.386 | 0.515 | 1.826 |
| S46V, G51R, N76V, Y116N, R119H, N156K, L159M | 0.916 | 0.386 | 0.509 | 1.796 |
| S46V, G51R, N76V, Y116H, L159M | 0.935 | 0.373 | 0.504 | 1.854 |
| S46V, G51R, N76V, Y116H, N156K | 0.834 | 0.340 | 0.447 | 1.864 |
| S46V, G51R, N76V, Y116H, N156K, L159M | 0.965 | 0.381 | 0.508 | 1.900 |
| S46V, G51R, N76V, Y116H, R119L, N156K | 0.761 | 0.326 | 0.420 | 1.809 |
| K32M, S46V, D48L, G51R, F82I, Q84L, Y116H, L159M | 1.724 | 1.281 | 1.377 | 1.251 |
| K32M, S46V, G51R, F82I, Y116H, L159M, | 1.956 | 2.094 | 2.064 | 0.947 |
| K32M, S46V, G51R, F82I, Q84L, Y116H, L159M | 2.066 | 2.023 | 2.032 | 1.016 |
| K32M, S46V, G51R, F82I, Q84L, Y116H, N156K, L159M | 2.050 | 2.348 | 2.284 | 0.897 |
| S46V, T49S, G51R, N76V, Q841, Y116H, N156K, L159M | 0.674 | 0.298 | 0.379 | 1.774 |
| A30E, S46V, D48M, G51R, N76V, F82R, Y116H, I148Y | 0.446 | 0.198 | 0.235 | 1.846 |
| E37A, I45R, S46V, D48M, T49W, G51R, N76V, F82G, Y116H, N156K | 0.625 | 0.318 | 0.367 | 1.704 |
| S46V, D48M, G51R, N76V, F82G, Y116H, A136D, I148Y | 2.627 | 0.613 | 0.913 | 2.878 |
| S46V, D48M, G51R, N76V, F82G, Y116H, I148Y | 2.416 | 0.621 | 0.908 | 2.661 |
| S46V, D48M, G51R, N76V, F82G, Y116H, I148Y, W168C | 0.339 | 0.239 | 0.254 | 1.331 |
| S46V, D48M, G51R, N76V, F82G, Y116H, N156R, L159M | 1.381 | 0.438 | 0.579 | 2.387 |
| S46V, D48M, G51R, N76V, F82G, Q84L, Y116H | 1.602 | 0.483 | 0.650 | 2.467 |
| S46V, D48M, G51R, N76V, F82I, Y116H, N156K, L159K | 1.164 | 0.465 | 0.569 | 2.047 |
| S46V, D48M, G51R, N76V, F82I, Q84L, Y116H, N156R | 1.419 | 0.466 | 0.618 | 2.289 |
| S46V, D48M, G51R, N76V, F82R, Y116H, L159K | 2.760 | 0.734 | 1.035 | 2.661 |
| S46V, D48M, G51R, N76V, F82R, N115A, Y116H, N156K, L159K | 1.874 | 0.582 | 0.788 | 2.375 |
| S46V, D48M, G51R, N76V, F82R, Y116H, N156K, L159K | 1.907 | 0.647 | 0.848 | 2.229 |
| S46V, D48M, G51R, N76V, Y116H, I148Y | 2.793 | 0.796 | 1.114 | 2.505 |
| I45R, S46V, D48M, G51R, N76V, F82I, Y116H, N156K, L159K | 1.335 | 0.491 | 0.626 | 2.125 |
| I45R, S46V, D48M, G51R, N76V, Q84L, Y116H, N156R, L159K | 0.448 | 0.238 | 0.269 | 1.660 |
| I45R, S46V, D48M, T49L, G51R, A67S, N76V, F82G, Y116H, L159K | 0.476 | 0.319 | 0.345 | 1.382 |
| I45R, S46V, D48M, T49L, G51R, N76V, F82G, Y116H, L159K | 0.532 | 0.335 | 0.366 | 1.451 |
| I45R, S46V, D48M, T49L, G51R, N76V, Q84L, Y116H, N156R, L159M | 0.318 | 0.201 | 0.220 | 1.444 |

TABLE 12-continued

| Mutations | Norm FAME | Norm FFA | Norm Titer | Norm % FAME |
|---|---|---|---|---|
| I45R, S46V, D48M, T49R, G51R, N52D, N76V, F82I, Q84L, Y116H, I148Y, N156Y | 1.056 | 0.383 | 0.490 | 2.152 |
| I45R, S46V, D48M, T49W, G51R, N76V, F82I, Q84L, Y116H, I148Y | 0.204 | 0.174 | 0.179 | 1.147 |
| K32M, S46V, D48M, G51R, N76V, F82G, Y116H, N156R, L159M | 1.289 | 0.436 | 0.574 | 2.246 |
| K32M, S46V, D48M, G51R, N76V, F82G, Q84L, Y116H | 1.565 | 0.493 | 0.664 | 2.353 |
| K32M, S46V, D48M, G51R, N76V, F82I, Y116H, L159M | 1.743 | 0.534 | 0.729 | 2.382 |
| K32M, S46V, D48M, G51R, N76V, F82I, Q84L, Y116H, L159M | 1.926 | 0.538 | 0.745 | 2.583 |
| K32M, I45R, S46V, D48M, T49D, G51R, N76V, F82G, Y116H, L159Q | 0.927 | 0.405 | 0.489 | 1.896 |
| K32M, I45R, S46V, D48M, T49D, G51R, N76V, F82I, Y116H, I148Y | 1.884 | 0.599 | 0.806 | 2.335 |
| K32M, S46V, D48M, G51R, N76V, Y116H, L159K | 1.289 | 0.472 | 0.603 | 2.138 |
| K32M, S46V, D48M, N76V, F82G, Q84L, Y116H | 0.902 | 0.353 | 0.441 | 2.045 |
| K32M, S46V, D48M, T49D, G51R, N76V, F82I, Q84L, Y116H | 0.537 | 0.229 | 0.275 | 1.956 |
| K32M, S46V, D48M, T49D, G51R, N76V, Y116H, I148Y | 0.841 | 0.343 | 0.423 | 1.988 |
| K32M, S46V, D48M, T49L, G51R, N76V, F82G, Q84L, Y116H, N156K, L159M | 2.118 | 0.623 | 0.861 | 2.456 |
| K32M, S46V, D48M, T49L, G51R, N76V, F82R, Y116H, L159K | 0.099 | 0.089 | 0.091 | 1.056 |
| K32M, S46V, D48M, T49W, G51R, P58L, L73F, N76V, Q84L, Y116H, N156K, L159K | 0.323 | 0.236 | 0.250 | 1.299 |
| K32M, S46V, D48M, T49W, G51R, N76V, Q84L, Y116H, N156K, L159K | 1.310 | 0.494 | 0.624 | 2.096 |
| S46V, D48M, G51R, N76V, Y116H, N156K, L159M | 2.019 | 0.595 | 0.824 | 2.450 |
| Q34R, I45R, S46V, D48M, T49D, G51R, N76V, F82R, Y116H | 1.421 | 0.492 | 0.642 | 2.214 |
| S46V, D48M, G51R, N76V, Q84L, Y116H, N156K | 1.631 | 0.522 | 0.701 | 2.325 |
| S46V, D48M, T49D, G51R, N76V, F82G, Y116H, L159K | 0.302 | 0.220 | 0.233 | 1.284 |
| S46V, D48M, T49D, G51R, N76V, F82G, Y116H, N156R | 0.596 | 0.267 | 0.319 | 1.871 |
| S46V, D48M, T49D, G51R, N76V, F82I, Y116H, L159M | 0.554 | 0.284 | 0.327 | 1.691 |

TABLE 12-continued

| Mutations | Norm FAME | Norm FFA | Norm Titer | Norm % FAME |
|---|---|---|---|---|
| S46V, D48M, T49D, G51R, N76V, F82R, Y116H, N156R | 0.746 | 0.326 | 0.388 | 1.923 |
| S46V, D48M, T49D, G51R, N76V, F82R, Y116H, N156R, L159I | 0.679 | 0.305 | 0.361 | 1.882 |
| S46V, D48M, T49D, G51R, N76V, F82R, Q84L, Y116H, N156K | 0.822 | 0.358 | 0.427 | 1.927 |
| S46V, D48M, T49D, G51R, N76V, G81C, F82R, Q84L, Y116H, N156K | 0.694 | 0.313 | 0.369 | 1.878 |
| S46V, D48M, T49D, G51R, N76V, Y116H, N156K, L159M | 0.676 | 0.284 | 0.343 | 1.973 |
| S46V, D48M, T49D, G51R, N76V, Y116H, N156R, L159K | 0.563 | 0.284 | 0.329 | 1.711 |
| S46V, D48M, T49D, G51R, N76V, Q84L, Y116H, L159M | 0.545 | 0.289 | 0.330 | 1.653 |
| S46V, D48M, T49L, G51R, N76V, F82I, N156K | 1.486 | 0.505 | 0.662 | 2.242 |
| S46V, D48M, T49L, G51R, N76V, F82I, Y116H, N156K | 1.729 | 0.569 | 0.754 | 2.292 |
| S46V, D48M, T49L, G51R, N76V, F82I, Y116H, N156R, L159K | 0.719 | 0.301 | 0.363 | 1.978 |
| S46V, D48M, T49L, G51R, N76V, F82R, Y116H | 0.854 | 0.345 | 0.427 | 1.998 |
| S46V, D48M, T49L, G51R, N76V, F82R, Q84L, Y116H, I148Y | 0.357 | 0.209 | 0.231 | 1.528 |
| S46V, D48M, T49L, G51R, N76V, Y116H, I148Y | 3.085 | 0.824 | 1.186 | 2.599 |
| S46V, D48M, T49L, G51R, N76V, Y116H, N156K, L159M | 2.230 | 0.621 | 0.877 | 2.543 |
| S46V, D48M, T49L, G51R, N76V, Y116H, N156R | 1.554 | 0.493 | 0.664 | 2.343 |
| S46V, D48M, T49L, G51R, N76V, Q84L, Y116H | 2.723 | 0.748 | 1.063 | 2.563 |
| S46V, D48M, T49L, G51R, N76V, Q84L, Y116H, K150I | 2.411 | 0.699 | 0.972 | 2.480 |
| S46V, D48M, T49W, G51R, N76V, F82G, Q84L, Y116H, I148Y | 1.432 | 0.483 | 0.634 | 2.259 |
| S46V, D48M, T49W, G51R, N76V, F82G, Q84L, Y116H, N156K, L159K | 0.364 | 0.287 | 0.300 | 1.215 |
| S46V, D48M, T49W, G51R, N76V, F82I, Y116H | 0.495 | 0.288 | 0.321 | 1.537 |
| S46V, D48M, T49W, G51R, N76V, F82I, Y116H, N156R, L159M | 0.466 | 0.270 | 0.302 | 1.543 |
| S46V, D48M, T49W, G51R, N76V, F82R, Y116H, L159M | 0.282 | 0.261 | 0.265 | 1.063 |
| S46V, D48M, T49W, G51R, N76V, Q84L, Y116H, N156R, L159K | 1.323 | 0.491 | 0.624 | 2.118 |

Table 13 shows a list of combination mutants found using P1B9v2.0 (SEQ ID NO: 58) as Template in BD64.

TABLE 13

| Mutations | Norm FAME | Norm FFA | Norm Titer | Norm % FAME |
|---|---|---|---|---|
| E37D, S46V, D48M, T49L, G51R, N52K, N76V, F82I, V112L, N115W, Y116H, I148Y, L159M | 3.143 | 2.067 | 2.668 | 1.175 |
| E37D, S46V, D48M, T49L, G51R, N52K, N76V, N115Y, Y116H, I148Y | 3.859 | 1.827 | 2.962 | 1.305 |
| S46V, D48M, T49L, G51R, N76V, F82I, Y116H, I148Y, L159M | 1.088 | 1.211 | 1.143 | 0.953 |
| S46V, D48M, T49L, G51R, N76V, F82I, Y116H, I148Y, L159M, D164T | 1.535 | 1.202 | 1.370 | 1.119 |
| S46V, D48M, T49L, G51R, N76V, F82I, M941, N115C, Y116H, I148Y | 1.422 | 1.177 | 1.303 | 1.091 |
| S46V, D48M, T49L, G51R, N76V, F82I, N115F, Y116H, I148Y | 2.010 | 1.099 | 1.568 | 1.281 |
| 546V, D48M, T49L, G51R, N76V, F82I, V112L, N115F, Y116H, I148Y | 1.216 | 1.030 | 1.128 | 1.079 |
| S46V, D48M, T49L, G51R, N76V, G85S, N115W, Y116H, I148Y, L159M | 1.137 | 1.173 | 1.154 | 0.986 |
| S46V, D48M, T49L, G51R, H64N, N76V, N115F, Y116H, I148Y, D164T | 1.116 | 0.907 | 1.013 | 1.102 |
| S46V, D48M, T49L, G51R, N76V, I87V, V112L, N115W, Y116H, I148Y | 1.776 | 1.022 | 1.405 | 1.266 |

TABLE 13-continued

| Mutations | Norm FAME | Norm FFA | Norm Titer | Norm % FAME |
|---|---|---|---|---|
| K32I, S46V, D48M, T49L, G51R, N52K, N76V, N115F, Y116H, I148Y, L159M | 1.591 | 1.126 | 1.366 | 1.166 |
| S46V, D48M, T49L, G51R, K65M, N76V, F82I, N115W, Y116H, I148Y, N156H | 1.119 | 0.967 | 1.047 | 1.067 |
| S46V, D48M, T49L, G51R, K65M, N76V, F82I, V112L, N115F, Y116H, I148Y | 1.552 | 1.072 | 1.316 | 1.181 |
| S46V, D48M, T49L, G51R, K65M, N76V, G85S, V112L, N115W, Y116H, I148Y, M155K | 0.755 | 0.722 | 0.739 | 1.017 |
| S46V, D48M, T49L, G51R, K65M, N76V, Y116H, I148Y, L159M | 1.025 | 1.035 | 1.030 | 0.995 |
| S46V, D48M, T49L, G51R, K65M, N76V, N115F, Y116H, I148Y | 1.831 | 1.103 | 1.487 | 1.229 |
| S46V, D48M, T49L, G51R, K65M, N76V, N89K, V112L, N115Y, Y116H, I148Y | 1.215 | 1.045 | 1.132 | 1.077 |
| S46V, D48M, T49L, G51R, K65M, N76V, V112L, N115W, Y116H, I148Y | 1.650 | 0.957 | 1.325 | 1.244 |
| S46V, D48M, T49L, G51R, K65M, N76V, V112L, N115Y, Y116H, I148Y | 1.113 | 0.890 | 1.003 | 1.112 |
| S46V, D48M, T49L, G51R, N76V, Y116H, I148Y, L159M, D164T | 1.498 | 1.249 | 1.375 | 1.088 |
| L31M, Q33R, S46V, D48M, T49L, G51R, N52K, N76V, Y116H, I148Y | 1.184 | 1.370 | 1.276 | 0.927 |
| S46V, D48M, T49M, G51R, N52K, N76V, F82I, V112L, N115Y, Y116H, I148Y, D164T | 2.161 | 1.375 | 1.780 | 1.217 |
| S46V, D48M, T49L, G51R, N76V, N115F, Y116H, I148Y, L159M | 1.358 | 1.100 | 1.230 | 1.103 |
| S46V, D48M, T49L, G51R, N76V, N115W, Y116H, I148Y, D164T | 1.337 | 1.013 | 1.184 | 1.126 |
| S46V, D48M, T49L, G51R, N76V, N115W, Y116H, I148Y, L159M | 1.906 | 1.118 | 1.537 | 1.240 |
| S46V, D48M, T49L, G51R, N76V, N115Y, Y116H, I148Y, L159M | 1.267 | 1.013 | 1.155 | 1.096 |
| S46V, D48M, T49L, G51R, N52K, N76V, Y116H, I148Y, D164T | 1.790 | 1.385 | 1.599 | 1.122 |
| 546V, D48M, T49L, G51R, N52K, N76V, F82I, Y116H, I148Y | 4.051 | 2.136 | 3.154 | 1.287 |
| S46V, D48M, T49L, G51R, N52K, N76V, F82I, V112L, N115W, Y116H, I148Y, L159M | 4.148 | 1.636 | 3.039 | 1.359 |
| S46V, D48M, T49L, G51R, N52K, N76V, F82I, V112L, N115Y, Y116H, I148Y, D164T | 2.175 | 1.471 | 1.834 | 1.189 |
| S46V, D48M, T49L, G51R, N52K, K65M, N76V, Y116H, I148Y | 1.733 | 1.303 | 1.525 | 1.136 |
| S46V, D48M, T49L, G51R, N52K, K65M, N76V, N115W, Y116H, I148Y | 4.254 | 1.591 | 2.944 | 1.441 |
| S46V, D48M, T49L, G51R, N52K, K65M, N76V, N891, N115W, Y116H, I148Y | 1.068 | 0.794 | 0.933 | 1.146 |
| S46V, D48M, T49L, G51R, N52K, K65M, N76V, V112L, N115W, Y116H, I148Y, L159M, D164T | 1.721 | 1.094 | 1.426 | 1.205 |
| S46V, D48M, T49L, G51R, N52K, K65M, N76V, V112M, Y116H, I148Y, D164V | 1.112 | 1.085 | 1.099 | 1.011 |
| S46V, D48M, T49L, G51R, N52K, N76V, N115F, Y116H, I148Y, L159M | 2.353 | 1.381 | 1.882 | 1.252 |
| S46V, D48M, T49L, G51R, N52K, N76V, N115W, Y116H, I148Y | 4.639 | 1.722 | 3.264 | 1.424 |
| S46V, D48M, T49L, G51R, N52K, N76V, N115Y, Y116H, I148Y | 4.403 | 2.051 | 3.365 | 1.311 |
| S46V, D48M, T49L, G51R, N52K, N76V, N115Y, Y116H, I148Y, D164T | 4.704 | 1.945 | 3.411 | 1.381 |
| S46V, D48M, T49L, G51R, N52K, N76V, T59A, F82I, V112L, N115W, Y116H, I148Y, L159M | 1.898 | 1.171 | 1.577 | 1.200 |
| S46V, D48M, T49L, G51R, N52K, N76V, V112L, Y116H, I148Y | 3.675 | 2.069 | 2.966 | 1.245 |
| S46V, D48M, T49L, G51R, N52K, N76V, V112L, N115F, Y116H, I148Y, A165V | 1.366 | 1.092 | 1.230 | 1.109 |
| S46V, D48M, T49L, G51R, N52K, N76V, V112L, N115F, Y116H, I148Y, L159M | 3.776 | 2.131 | 2.962 | 1.256 |
| S46V, D48M, T49L, G51R, N52S, N76V, V112L, N115Y, Y116H, I148Y | 1.737 | 1.039 | 1.394 | 1.250 |
| P29R, Q33R, S46V, D48M, T49L, G51R, N52K, N76V, F82I, N115F, Y116H, I148Y, D164T | 3.873 | 2.125 | 3.054 | 1.271 |
| Q28K, Q33R, S46V, D48M, T49L, G51R, N52K, N76V, N115F, Y116H, I148Y, D164T | 4.385 | 2.210 | 3.366 | 1.303 |
| Q28K, Q34R, S46V, D48M, T49L, G51R, N52K, N76V, F82I, V112L, N115W, Y116H, I148Y, L159M | 4.201 | 2.708 | 3.497 | 1.207 |
| Q33A, S46V, D48M, T49L, G51R, N76V, F82I, N115W, Y116H, I148Y, D164T | 1.639 | 1.072 | 1.360 | 1.207 |

TABLE 13-continued

| Mutations | Norm FAME | Norm FFA | Norm Titer | Norm % FAME |
|---|---|---|---|---|
| Q33A, S46V, D48M, T49L, G51R, K65M, N76V, Y116H,K118R, I148Y | 0.987 | 0.985 | 0.986 | 1.003 |
| Q33A, S46V, D48M, T49L, G51R, K65M, N76V, V112L, N115Y, Y116H, I148Y | 1.168 | 0.979 | 1.084 | 1.077 |
| Q33A, S46V, D48M, T49V, G51R, K65M, N76V, N115Y, Y116H, I148Y, L159M | 1.046 | 0.900 | 0.976 | 1.071 |
| Q33A, S46V, D48M, T49L, G51R, N76V, N115Y | 1.565 | 0.994 | 1.313 | 1.191 |
| Q33A, S46V, D48M, T49L, G51R, N76V, N115Y, Y116H, I148Y, L159M | 1.423 | 1.010 | 1.219 | 1.166 |
| Q33A, S46V, D48M, T49L, G51R, N52K, N76V, D77E, F82I, N115F, Y116H, I148Y | 0.885 | 0.791 | 0.844 | 1.047 |
| Q33A, S46V, D48M, T49L, G51R, N52K, N76V, F82I, N115F, Y116H, I148Y, D164Y | 2.639 | 1.713 | 2.230 | 1.187 |
| Q33A, S46V, D48M, T49L, G51R, N52K, N76V, F82I, R88C, N115F, Y116H, I148Y | 4.148 | 2.157 | 3.269 | 1.270 |
| Q33A, S46V, D48M, T49L, G51R, N52K, K65M, N76V, F82I, Y116H, I148Y | 1.807 | 1.632 | 1.730 | 1.047 |
| Q33A, S46V, D48M, T49L, G51R, N52K, K65M, N76V, F82I, Y116H, K118Q, I148Y | 4.314 | 2.663 | 3.585 | 1.204 |
| Q33A, S46V, D48M, T49L, G51R, N52K, N76V, N115F, Y116H, I148Y | 4.458 | 1.534 | 3.079 | 1.447 |
| Q33A, S46V, D48M, T49L, G51R, N52K, T59S, N76V, F82I, N115F, Y116H, I148Y, K162R, D164E | 4.215 | 2.129 | 3.295 | 1.280 |
| Q33A, S46V, D48M, T49L, G51R, T59A, N76V, V112L, Y116H, I148Y, D164T | 1.108 | 1.129 | 1.118 | 0.992 |
| Q33A, S46V, D48M, T49L, G51R, N76V, V112L, Y116H, I148Y, D164T | 1.265 | 1.119 | 1.196 | 1.059 |
| Q33A, S46V, D48M, T49L, G51R, N76V, V112L, N115F, Y116H, I148Y, D164T | 1.823 | 1.108 | 1.486 | 1.229 |
| Q33A, S46V, D48M, T49L, G51R, N76V, V112L, N115F, Y116H, I148Y, K162N, D164T | 1.559 | 0.990 | 1.291 | 1.207 |
| Q33A, S46V, D48M, T49L, G51R, N76V, V112L, N115W, Y116H, I148Y | 1.802 | 1.052 | 1.430 | 1.258 |
| Q33H, S46V, D48M, T49L, G51R, N52K, K65M, N76V, N115W, Y116H, I148Y | 2.564 | 1.315 | 1.949 | 1.318 |
| Q33R, S46V, D48M, T49L, G51R, N76V, F82I, N115W, Y116H, I148Y | 1.587 | 1.198 | 1.404 | 1.131 |
| Q33R, S46V, D48M, T49L, G51R, N76V, F82I, V112L, N115Y, Y116H, I148Y, L159M | 1.432 | 1.351 | 1.396 | 1.017 |
| Q33R, S46V, D48M, T49L, G51R, N76V, M05, N115W, Y116H, I148Y, L159M | 0.983 | 0.920 | 0.952 | 1.030 |
| Q33R, S46V, D48M, T49L, G51R, K65M, N76V, Y116H, I148Y, L159M | 0.986 | 1.054 | 1.019 | 0.965 |
| Q33R, S46V, D48M, T49L, G51R, K65M, N76V, F82I, N115W, Y116H, I148Y | 1.051 | 1.122 | 1.085 | 0.969 |
| Q33R, S46V, D48M, T49L, G51R, K65M, N76V, G81C, N115F, Y116H, I148Y, L159M, D164I | 1.027 | 0.746 | 0.894 | 1.142 |
| Q33R, S46V, D48M, T49L, G51R, K65M, N76V, N115F, Y116H, I148Y, L159M, D164T | 1.846 | 1.048 | 1.469 | 1.254 |
| Q33R, S46V, D48M, T49L, G51R, N76V, L79M, V112L, N115Y, Y116H, I148Y | 0.761 | 0.725 | 0.743 | 1.024 |
| Q33R, S46V, D48M, T49L, G51R, N76V, N115W, Y116H, I148Y | 1.960 | 1.238 | 1.603 | 1.222 |
| Q33R, S46V, D48M, T49L, G51R, N76V, N115W, Y116H, I148Y, L159M | 1.396 | 1.048 | 1.225 | 1.139 |
| Q33R, S46V, D48M, T49L, G51R, N52K, N76V, Y116H, I148Y | 3.939 | 2.752 | 3.352 | 1.175 |
| Q33R, S46V, D48M, T49L, G51R, N52K, N76V, F82I, N115F, Y116H, I148Y, D164T | 3.131 | 2.540 | 2.854 | 1.099 |
| Q33R, S46V, D48M, T49L, G51R, N52K, G53C, N76V, F82I, N115F, Y116H, I148Y, D164T | 1.593 | 1.380 | 1.493 | 1.069 |
| Q33R, S46V, D48M, T49L, G51R, N52K, K65M, N76V, V112L, Y116H, I148Y, L159M | 3.795 | 2.176 | 2.998 | 1.270 |
| Q33R, S46V, D48M, T49L, G51R, N52K, N76V, N115F, Y116H, I148Y | 5.164 | 2.018 | 3.639 | 1.421 |
| Q33R, S46V, D48M, T49L, G51R, N52K, N76V, N115Y, Y116H, I148Y | 4.774 | 1.710 | 3.289 | 1.454 |
| Q33R, S46V, D48M, T49L, G51R, N52K, N76V, N115Y, Y116H, I148Y, L159M, D164T | 2.326 | 1.258 | 1.809 | 1.285 |
| Q33R, S46V, D48M, T49L, G51R, N52K, N76V, V112L, Y116H, I148Y | 4.278 | 2.041 | 3.230 | 1.330 |
| Q33R, S46V, D48M, T49L, G51R, N52K, N76V, V112L, Y116H, I148Y, D164Y | 2.435 | 1.530 | 2.011 | 1.216 |
| Q33R, Q34R, S46V, D48M, T49L, G51R, N52K, N76V, Q63K, Y68C, N115F, Y116H, I148Y | 5.192 | 1.873 | 3.583 | 1.451 |

TABLE 13-continued

| Mutations | Norm FAME | Norm FFA | Norm Titer | Norm % FAME |
|---|---|---|---|---|
| Q33R, S46V, D48M, T49L, G51R, R51S, N52K, K65M, N76V, V112L, Y116H, I148Y, L159M | 1.149 | 1.087 | 1.118 | 1.027 |
| Q33R, S46V, D48M, T49L, G51R, N76V, V112L, N115F, Y116H, I148Y, D164T | 2.316 | 1.030 | 1.714 | 1.351 |
| Q33R, S46V, D48M, T49L, G51R, N76V, V112L, N115Y, Y116H, I148Y | 1.243 | 0.982 | 1.114 | 1.115 |
| Q33R, S46V, D48M, T49L, G51R, Y68S, N76V, F82I, N115W, Y116H, I148Y, D164A | 0.938 | 0.912 | 0.925 | 1.011 |
| Q34L, S46V, D48M, T49L, G51R, N52K, K65M, N76V, N115Y, Y116H, I148Y, D164T | 2.948 | 1.885 | 2.425 | 1.206 |
| Q34R, S46V, D48M, T49L, G51R, N76V, F82I, Y116H, I148Y, D164T | 1.292 | 1.083 | 1.191 | 1.084 |
| Q34R, S46V, D48M, T49L, G51R, N52K, K65M, Y116H, I148Y | 4.561 | 1.912 | 3.277 | 1.391 |
| S46V, D48M, T49L, G51R, N76V, V112L, Y116H, I148Y, L159M | 1.384 | 1.257 | 1.328 | 1.043 |
| S46V, D48M, T49L, G51R, N76V, V112L, N115W, Y116H, I148Y | 2.333 | 1.105 | 1.729 | 1.351 |
| A30T, S46V, D48M, T49L, G51R, N76V, T86P, V112L, N115F, Y116H, I148Y | 1.158 | 0.762 | 0.983 | 1.178 |
| K321, S46V, D48M, T49L, G51R, N52K, N76V, V112L, N115F, Y116H, I148Y | 4.584 | 2.512 | 3.624 | 1.264 |
| K32N, S46V, D48R, T49L, G51R, N52K, N76V, Q84V, N115W, Y116H, I148Y, L149F | 3.361 | 2.327 | 2.888 | 1.164 |
| LSV, S22R, Q33A, S46V, D48M, T49L, G51R, N52K, N76V, I87V, N115F, Y116H, I148Y, L149M | 3.457 | 1.962 | 2.765 | 1.250 |
| N2T, Q34R, S46V, D48M, T49L, G51R, N76V, Q84T, V112L, N115F, Y116H, K118Q, I148Y, L149M | 1.784 | 1.178 | 1.503 | 1.186 |
| S46V, D48M, T49L, G51R, N52K, N76V, G81C, N115W, Y116H, I148Y | 3.148 | 1.848 | 2.546 | 1.236 |
| S46V, D48M, T49L, G51R, N52K, N76V, N115F, Y116H, I148Y | 4.305 | 3.298 | 3.839 | 1.125 |
| S46V, D48M, T49L, G51R, N52K, N76V, N115F, Y116H, K118Q, I148Y | 4.547 | 2.847 | 3.743 | 1.214 |
| S46V, D48M, T49L, G51R, N52K, N76V, Q84A, V112L, N115F, Y116H, I148Y | 4.872 | 2.567 | 3.767 | 1.291 |
| S46V, D48M, T49L, G51R, N52K, N76V, Q84T, N115W, Y116H, I148Y, L149F | 4.840 | 2.692 | 3.809 | 1.270 |
| S46V, D48M, T49L, G51R, N52K, N76V, Q84T, V112L, N115F, Y116H, I148Y | 3.710 | 2.244 | 3.054 | 1.213 |
| S46V, D48M, T49L, G51R, N52K, N76V, Q84V, N115W, Y116H, I148Y, L149F | 2.744 | 1.925 | 2.369 | 1.159 |
| S46V, D48M, T49L, G51R, N52K, N76V, Q84V, V112L, N115F, Y116H, I148Y | 3.042 | 1.847 | 2.518 | 1.208 |
| S46V, D48M, T49L, G51R, N52K, N76V, Q84V, V112L, N115W, Y116H, K118Q, I148Y | 1.944 | 1.219 | 1.608 | 1.208 |
| S46V, D48M, T49L, G51R, N52K, N76V, V112L, N115F, Y116H, I148Y | 4.686 | 2.599 | 3.719 | 1.259 |
| S46V, D48M, T49L, G51R, N52K, N76V, V112L, N115F, Y116H, K118Q, I148Y | 5.314 | 2.799 | 4.163 | 1.276 |
| S46V, D48M, T49L, G51R, N52K, N76V, V112L, N115W, Y116H, I148Y | 4.977 | 2.155 | 3.714 | 1.344 |
| 546V, D48M, T49L, G51R, N52R, N76V, Q84A, V112L, N115W, Y116H, I148Y, L149M | 5.972 | 2.734 | 4.541 | 1.315 |
| P29L, S46V, D48M, T49L, G51R, N52K, N76V, Q84T, V112L, N115F, Y116H, I148Y | 2.850 | 1.792 | 2.377 | 1.200 |
| P29L, Q33A, Q34R, I45M, S46V, D48M, T49L, G51R, N52K, N76V, F82L, R88H, V112L, N115W, Y116H, I148Y | 1.803 | 1.458 | 1.652 | 1.091 |
| Q28H, Q33R, Q34R, S46V, D48M, T49L, G51R, N52K, N76V, Q84T, V112L, N115W, Y116H, I148Y | 3.820 | 1.882 | 2.889 | 1.322 |
| Q33A, S46V, D48M, T49L, G51R, L54M, N76V, Q84V, V112L, N115F | 1.590 | 1.032 | 1.326 | 1.199 |
| Q33A, S46V, D48I, T49L, G51R, N52K, N76V, N115W, Y116H, I148Y, L149M | 1.458 | 1.126 | 1.306 | 1.116 |
| Q33A, S46V, D48M, T49L, G51R, N52K, N76V, N115F, Y116H, I148Y, L149M | 4.373 | 2.843 | 3.664 | 1.193 |
| Q33A, S46V, D48M, T49L, G51R, N52K, N76V, N115F, Y116H, I148Y, L149T | 4.515 | 3.220 | 3.947 | 1.144 |
| Q33A, S46V, D48M, T49L, G51R, N52K, N76V, N115W, Y116H, I148Y, L149M | 4.499 | 2.757 | 3.702 | 1.215 |
| Q33A, S46V, D48M, T49L, G51R, N52K, N76V, Q84A, V112L, N115W, Y116H, K118Q, I148Y, L149T | 2.859 | 1.522 | 2.226 | 1.284 |

TABLE 13-continued

| Mutations | Norm FAME | Norm FFA | Norm Titer | Norm % FAME |
|---|---|---|---|---|
| Q33A, S46V, D48M, T49L, G51R, N52K, N76V, Q84A, V112L, N115W, Y116H, I148Y, L149M | 3.673 | 2.095 | 2.982 | 1.232 |
| Q33A, S46V, D48M, T49L, G51R, N52K, N76V, Q84T, N115W, Y116H, I148Y | 3.231 | 1.937 | 2.610 | 1.235 |
| Q33A, S46V, D48M, T49L, G51R, N52K, N76V, Q84V, V112L, N115W, Y116H, I148Y, L149F | 3.489 | 1.854 | 2.741 | 1.273 |
| Q33A, S46V, D48M, T49L, G51R, N52K, N76V, V112L, N115F, Y116H, I148Y | 4.389 | 2.814 | 3.699 | 1.187 |
| Q33A, S46V, D48M, T49L, G51R, N52R, N76V, Y116H, I148Y, L149T | 3.791 | 3.302 | 3.557 | 1.069 |
| Q33A, S46V, D48M, T49L, G51R, N52S, N76V, Q84V, V112L, N115F, Y116H, I148Y | 1.751 | 0.996 | 1.393 | 1.256 |
| Q33A, Q34R, S46V, D48M, T49L, G51R, N52K, N76V | 4.215 | 4.136 | 4.181 | 1.008 |
| Q33A, Q34R, S46V, D48M, T49L, G51R, N52K, N76V, P83R, Q84A, V112L, N115F, Y116H, K118Q, I148Y | 3.306 | 2.121 | 2.782 | 1.189 |
| Q33A, Q34R, S46V, D48M, T49L, G51R, N52K, N76V, Q84A, V112L, N115F, Y116H, K118Q, I148Y | 4.736 | 3.094 | 4.010 | 1.181 |
| Q33A, Q34R, S46V, D48M, T49L, G51R, N52K, N76V, V112L, N115W, Y116H, I148Y | 5.554 | 3.159 | 4.504 | 1.234 |
| Q33A, Q34R, S46V, D48M, T49L, G51R, N52R, N76V, Y116H, I148Y, L149F | 3.728 | 3.273 | 3.510 | 1.062 |
| Q33A, Q34R, S46V, D48M, T49L, G51R, N52R, N76V, Q84V, V112L, N115W, Y116H, I148Y, L149T | 5.915 | 2.816 | 4.427 | 1.335 |
| Q33A, Q34R, S46V, D48M, T49L, G51R, N52R, N76V, V112L, N115F, Y116H, I148Y, L149F | 4.973 | 2.606 | 3.839 | 1.295 |
| Q33A, Q34R, S46V, D48M, T49L, G51R, N76V, Q84A, N115F, Y116H, I148Y | 1.535 | 0.921 | 1.254 | 1.224 |
| Q33A, Q34R, S46V, D48M, T49L, G51R, N76V, Q84V, V112L, N115W, Y116H, I148Y, L149T | 1.508 | 1.013 | 1.270 | 1.187 |
| Q33A, S46V, D48M, T49L, G51R, N76V, Q84A, V112L, N115W, Y116H, I148Y | 1.676 | 1.063 | 1.407 | 1.192 |
| Q33A, S46V, D48M, T49L, G51R, N76V, Q84T, V112L, N115W, Y116H, I148Y | 1.373 | 0.956 | 1.186 | 1.158 |
| Q33A, S46V, D48M, T49L, G51R, N76V, V112L, N115F, Y116H, K118Q, I148Y, L149T | 2.007 | 1.269 | 1.653 | 1.222 |
| Q33P, S46V, D48M, T49L, G51R, N52R, N76V, V112L, N115F, Y116H, I148Y | 2.207 | 1.365 | 1.804 | 1.238 |
| Q33R, E37D, S46V, D48M, T49L, G51R, N52K, N76V, G81C, Q84A, V112L, N115W, Y116H, I148Y | 3.331 | 1.850 | 2.645 | 1.259 |
| Q33R, S46V, D48M, T49L, G51R, N76V, N115F, Y116H, I148Y | 1.776 | 1.148 | 1.485 | 1.195 |
| Q33R, S46V, D48M, T49L, G51R, N76V, N115F, Y116H, K118Q, I148Y, L149F | 1.966 | 1.146 | 1.599 | 1.230 |
| Q33R, S46V, D48M, T49L, G51R, N52K, N76V, F82V, V112L, N115F, Y116H, I148Y | 3.586 | 2.808 | 3.242 | 1.106 |
| Q33R, S46V, D48M, T49L, G51R, N52K, N76V, G81C, N115F, Y116H, I148Y | 3.470 | 1.980 | 2.780 | 1.248 |
| Q33R, S46V, D48M, T49L, G51R, N52K, N76V, G81C, Q84A, V112L, N115W, Y116H, I148Y, L149M | 3.143 | 1.816 | 2.535 | 1.240 |
| Q33R, S46V, D48M, T49L, G51R, N52K, N76V, L79M, V112L, N115W, Y116H, I148Y, L149T | 2.892 | 1.774 | 2.392 | 1.209 |
| Q33R, S46V, D48M, T49L, G51R, N52K, N76V, N115W, Y116H, I148Y | 3.279 | 2.324 | 2.852 | 1.149 |
| Q33R, S46V, D48M, T49L, G51R, N52K, N76V, Q84A, V112L, N115F, Y116H, I148Y, L149F | 3.751 | 2.345 | 3.134 | 1.197 |
| Q33R, S46V, D48M, T49L, G51R, N52K, N76V, Q84A, V112L, N115F, Y116H, I148Y, L149F, M154I | 1.426 | 1.098 | 1.282 | 1.113 |
| Q33R, S46V, D48M, T49L, G51R, N52K, N76V, Q84A, V112L, N115W, Y116H, I148Y, L149M | 6.010 | 2.759 | 4.521 | 1.329 |
| Q33R, S46V, D48M, T49L, G51R, N52K, N76V, Q84A, V112L, N115W, Y116H, I148H | 1.968 | 1.221 | 1.622 | 1.212 |
| Q33R, S46V, D48M, T49L, G51R, N52K, N76V, Q84K, V112L, N115F, Y116H, I148Y | 2.521 | 1.712 | 2.164 | 1.166 |
| Q33R, S46V, D48M, T49L, G51R, N52K, N76V, Q84T, N115F, Y116H, I148Y, L149M | 3.052 | 2.022 | 2.591 | 1.178 |
| Q33R, S46V, D48M, T49L, G51R, N52K, N76V, Q84T, V112L, N115F, Y116H, I148Y | 3.220 | 1.947 | 2.630 | 1.224 |
| Q33R, S46V, D48M, T49L, G51R, N52K, N76V, Q84T, V112L, N115F, Y116H, K118Q, I148Y, L149T | 4.980 | 2.989 | 4.068 | 1.224 |

TABLE 13-continued

| Mutations | Norm FAME | Norm FFA | Norm Titer | Norm % FAME |
|---|---|---|---|---|
| Q33R, S46V, D48M, T49L, G51R, N52K, N76V, Q84T, V112L, N115W, Y116H, I148Y | 3.012 | 1.832 | 2.490 | 1.210 |
| Q33R, S46V, D48M, T49L, G51R, N52K, N76V, Q84V, V112L, N115F, Y116H, K118Q, I148Y, L149F | 4.921 | 2.656 | 3.834 | 1.283 |
| Q33R, S46V, D48M, T49L, G51R, N52K, N76V, Q84V, V112L, N115W, Y116H, K118Q, I148Y | 2.999 | 1.686 | 2.398 | 1.249 |
| Q33R, S46V, D48M, T49L, G51R, N52K, N76V, Q84V, V112L, N115W, Y116H, I148Y, L149F | 3.750 | 1.961 | 2.931 | 1.279 |
| Q33R, S46V, D48M, T49L, G51R, N52K, N76V, V112L, N115F, Y116H, I148Y | 4.702 | 2.750 | 3.839 | 1.225 |
| Q33R, S46V, D48M, T49L, G51R, N52K, N76V, V112L, N115W, Y116H, I148Y | 5.424 | 2.806 | 4.253 | 1.276 |
| Q33R, S46V, D48M, T49L, G51R, N52K, N76V, V112L, N115W, Y116H, I148Y, L149M | 6.026 | 2.682 | 4.477 | 1.345 |
| Q33R, S46V, D48M, T49L, G51R, N52K, N76V, V112L, N115W, Y116H, I148Y, L149T | 4.563 | 2.572 | 3.672 | 1.242 |
| Q33R, S46V, D48M, T49L, G51R, N52R, N76V, Y116H, I148Y, L149F | 4.017 | 3.432 | 3.736 | 1.075 |
| Q33R, S46V, D48M, T49L, G51R, N52R, N76V, N115W, Y116H, I148Y | 5.463 | 2.558 | 4.068 | 1.343 |
| Q33R, S46V, D48M, T49L, G51R, N52R, N76V, Q84A, N115F, Y116H, I148Y, L149F | 4.830 | 2.877 | 3.893 | 1.241 |
| Q33R, S46V, D48M, T49L, G51R, N52R, N76V, Q84A, V112L, N115F, Y116H, K118Q, I148Y, L149M | 2.939 | 1.666 | 2.381 | 1.235 |
| Q33R, S46V, D48M, T49L, G51R, N52R, N76V, Q84T, V112L, N115F, Y116H, I148Y | 3.105 | 1.992 | 2.607 | 1.191 |
| Q33R, S46V, D48M, T49L, G51R, N52R, N76V, T86P, V112L, N115W, Y116H, I148Y, L149T | 5.372 | 2.835 | 4.251 | 1.265 |
| Q33R, S46V, D48M, T49L, G51R, N52R, N76V, V112L, N115F, Y116H, I148Y | 4.105 | 2.503 | 3.388 | 1.211 |
| Q33R, S46V, D48M, T49L, G51R, N52R, N76V, V112L, N115F, Y116H, K118Q, I148Y, L149M | 3.385 | 2.212 | 2.871 | 1.175 |
| Q33R, S46V, D48M, T49L, G51R, N52R, N76V, V112L, N115W, Y116H, I148Y, L149T | 6.042 | 2.468 | 4.462 | 1.354 |
| Q33R, Q34K, S46V, D48M, T49L, G51R, N76V, Q84V, V112L, N115W, Y116H, I148Y, L149T | 1.484 | 0.957 | 1.231 | 1.205 |
| Q33R, Q34R, S46V, D48I, T49L, G51R, N52K, N76V, N115W | 1.665 | 1.313 | 1.497 | 1.112 |
| Q33R, Q34R, S46V, D48M, T49L, G51R, N52K, A67T, N76V, V112L, N115F, Y116H, I148Y, L149M, M155I | 1.891 | 1.298 | 1.610 | 1.174 |
| Q33R, Q34R, S46V, D48M, T49L, G51R, N52K, N76V, N115W, Y116H, K118Q, I148Y | 4.801 | 2.910 | 3.895 | 1.231 |
| Q33R, Q34R, S46V, D48M, T49L, G51R, N52K, N76V, Q84A, V112L, N115F, Y116H, I148Y, L149F | 5.024 | 2.719 | 4.005 | 1.254 |
| Q33R, Q34R, S46V, D48M, T49L, G51R, N52K, N76V, Q84T, V112L, N115W, Y116H, I148Y | 5.007 | 2.275 | 3.695 | 1.354 |
| Q33R, Q34R, S46V, D48M, T49L, G51R, N52K, N76V, Q84V, N115F, Y116H, I148Y, K133R, L149T | 3.340 | 2.027 | 2.711 | 1.231 |
| Q33R, Q34R, S46V, D48M, T49L, G51R, N52K, N76V, Q84V, N115F, Y116H, I148Y, L149T | 3.305 | 2.106 | 2.730 | 1.210 |
| Q33R, Q34R, S46V, D48M, T49L, G51R, N52K, N76V, V112L, N115F, Y116H, I148Y | 4.894 | 2.294 | 3.645 | 1.343 |
| Q33R, Q34R, S46V, D48M, T49L, G51R, N52K, N76V, V112L, N115F, Y116H, I148Y, L149M | 4.942 | 2.527 | 3.799 | 1.300 |
| Q33R, Q34R, S46V, D48M, T49L, G51R, N52K, N76V, V112L, N115W, Y116H, I148Y, L149F | 6.145 | 2.696 | 4.566 | 1.346 |
| Q33R, Q34R, S46V, D48M, T49L, G51R, N52R, N76V, Q84V, N115W,Y116H, K118Q, I148Y, L149M | 5.301 | 2.946 | 4.223 | 1.255 |
| Q33R, Q34R, S46V, D48M, T49L, G51R, N52R, N76V, V112L, N115W, Y116H, I148Y | 5.818 | 2.358 | 4.270 | 1.363 |
| Q33R, Q34R, S46V, D48M, T49L, G51R, N76V, Q84A, V112L, N115F, Y116H, I148Y, L149F, G158C | 1.854 | 1.113 | 1.527 | 1.215 |

TABLE 13-continued

| Mutations | Norm FAME | Norm FFA | Norm Titer | Norm % FAME |
|---|---|---|---|---|
| Q33R, Q34R, S46V, D48M, T49L, G51H, N52K, N76V, V112L, N115F, Y116H, I148Y | 2.840 | 1.559 | 2.225 | 1.275 |
| Q33R, Q34R, S46V, D48M, T49L, G51R, N76V, V112L, N115W, Y116H, I148Y | 1.685 | 0.926 | 1.346 | 1.253 |
| Q33R, Q34R, S46V, D48M, T49L, G51R, N76V, V112L, N115W, Y116H, K118Q, I148Y | 1.501 | 1.097 | 1.314 | 1.142 |
| Q33R, S46V, D48M, T49L, G51R, N76V, Q84A, N115F, Y116H, I148Y, L149F | 1.737 | 1.143 | 1.452 | 1.196 |
| Q33R, S46V, D48M, T49L, G51R, N76V, Q84A, N115W, Y116H, K118Q, I148Y | 1.967 | 1.441 | 1.726 | 1.140 |
| Q33R, S46V, D48M, T49L, G51R, N76V, Q84A, N89H, N115W, Y116H, K118Q, I148Y | 1.225 | 1.050 | 1.145 | 1.070 |
| Q33R, S46V, D48M, T49L, G51R, N76V, Q84T, V112L, N115F, Y116H, I148Y | 1.695 | 1.019 | 1.382 | 1.226 |
| Q33R, S46V, D48M, T49L, G51R, N76V, Q84V, N115F, Y116H, I148Y, L149T | 1.640 | 1.024 | 1.348 | 1.216 |
| Q33R, S46V, D48M, T49L, G51R, N76V, Q84V, T86P, V112L, N115F, Y116H, I148Y, L149M | 2.225 | 1.168 | 1.717 | 1.295 |
| Q33R, S46V, D48M, T49L, G51R, R56H, N76V, N115F, Y116H, K118Q, I148Y, L149F | 0.986 | 0.818 | 0.911 | 1.083 |
| Q33R, S46V, D48M, T49L, G51R, N76V, V112L, N115F, Y116H, I148Y | 4.155 | 2.220 | 3.289 | 1.262 |
| Q33R, S46V, D48M, T49L, G51R, N76V, V112L, N115F, Y116H, I148Y, L149M | 2.305 | 1.130 | 1.742 | 1.322 |
| Q33R, S46V, D48M, T49L, G51R, N76V, V112L, N115F, Y116H, I148Y, L149T | 1.756 | 1.057 | 1.447 | 1.213 |
| Q33R, S46V, D48M, T49L, G51R, N76V, V112L, N115W, Y116H, I148Y | 1.825 | 1.178 | 1.529 | 1.194 |
| Q33R, S46V, D48M, T49L, G51R, N76V, V112L, N115W, Y116H, I148Y, L149M | 1.821 | 1.164 | 1.530 | 1.190 |
| Q34K, S46V, D48M, T49L, G51R, N52K, N76V, Q84V, V112L, N115F, Y116H, I148Y | 1.571 | 1.126 | 1.376 | 1.142 |
| Q34K, S46V, D48M, T49L, G51R, N52R, N76V, V112L, N115F, Y116H, I148Y | 2.881 | 1.734 | 2.374 | 1.214 |
| Q34L, S46V, D48M, T49L, G51R, N52K, N76V, N115F, Y116H, K118Q, I148Y | 5.058 | 2.819 | 3.998 | 1.264 |
| Q34R, G35A, S46V, D48M, T49L, G51R, N76V, Q84A, V112L, N115F, Y116H, I148Y, L149T | 1.792 | 1.116 | 1.493 | 1.200 |
| Q34R, S46V, D48M, T49L, G51R, N76V, N115W, Y116H, I148Y | 2.409 | 1.476 | 1.961 | 1.205 |
| Q34R, S46V, D48M, T49L, G51R, N52K, N76V, Q84A, V112L, N115F, Y116H, I148Y, L149T | 5.576 | 2.923 | 4.304 | 1.294 |
| Q34R, S46V, D48M, T49L, G51R, N52R, N76V, N115W, Y116H, I148Y | 5.448 | 2.512 | 4.039 | 1.348 |
| Q34R, S46V, D48M, T49L, G51R, N52R, N76V, V112L, N115W, Y116H, I148Y, L149F | 3.948 | 1.967 | 3.080 | 1.282 |
| Q34R, S46V, D48M, T49L, G51R, N76V, Q84A, V112L, N115F, Y116H, I147L, I148Y, L149T | 1.061 | 0.669 | 0.888 | 1.195 |
| Q34R, S46V, D48M, T49L, G51R, N76V, Q84A, V112L, N115F, Y116H, I148Y, L149T | 1.961 | 1.090 | 1.576 | 1.244 |
| Q34R, S46V, D48M, T49L, G51R, N76V, Q84T, V112L, N115W, Y116H, I148Y, L149F | 1.823 | 1.156 | 1.531 | 1.191 |
| Q34R, S46V, D48M, T49L, G51R, N76V, Q84V, V112L, N115W, Y116H, I148Y, L149M | 1.684 | 1.102 | 1.429 | 1.179 |
| 546V, D48M, T49L, G51R, N76V, Q84T, N115W, Y116H, I148Y, L149T | 1.146 | 0.904 | 1.034 | 1.108 |
| S46V, D48M, T49L, G51R, N76V, Q84V, V112L, N115F, Y116H, K118Q, I148Y | 1.599 | 0.886 | 1.257 | 1.271 |
| S46V, D48M, T49L, G51R, N76V, V112L, N115F, Y116H, I148Y | 2.233 | 1.193 | 1.735 | 1.287 |
| S46V, D48M, T49L, G51R, N76V, V112L, N115W, Y116H, K118Q, I148Y, L149F | 1.649 | 1.026 | 1.370 | 1.204 |
| S46V, D48M, T49L, G51R, N76V, V112L, N115W, Y116H, I148Y, L149F | 2.150 | 1.111 | 1.652 | 1.301 |

TABLE 13-continued

| Mutations | Norm FAME | Norm FFA | Norm Titer | Norm % FAME |
|---|---|---|---|---|
| S46V, D48M, T49L, G51R, N76V, V112L, N115W, Y116H, I148Y, L149M | 1.810 | 1.166 | 1.525 | 1.187 |
| S46V, D48M, T49L, G51R, N76V, V112L, N115W, Y116H, I148Y, L149T | 1.657 | 1.059 | 1.395 | 1.188 |

As is apparent to one with skill in the art, various modifications and variations of the above aspects and embodiments can be made without departing from the spirit and scope of this disclosure. Such modifications and variations are within the scope of this disclosure.

We claim:

1. A variant ester synthase polypeptide comprising a variant of SEQ ID NO: 67, wherein said variant ester synthase polypeptide the variant of SEQ ID NO: 67 is genetically engineered to have at least one substitution mutation at an amino acid position selected from the group of G4R, T5P, T5S, D7N, S15G, T24M, T24W, L30H, G33S, L39A, L39M, L39S, R40S, D41A, D41G, D41H, D41Y, V43K, V43S, T44F, A73Q, V76L, D77A, K78F, K78W, I80V, R98D, E99Q, G101L, I102R, P111D, P111G, P111S, H122S, R131M, I146K, I146L, I146R, S147A, V149L, R150P, V155G, N164R, P166S, T170R, V171E, V171F, V171H, V171R, V171W, R172S, R172W, P173W, R177V, A179V, D182G, E184F, E184G, E184L, E184R, E184S, A185L, A185M, S186T, V187G, V187R, P188R, A190P, A190R, A190W, S192A, S192L, S192V, Q193R, Q193S, M195G, A197T, A197V, Q201A, Q201V, Q201W, A202L, D203R, P206F, R207A, G212A, G212L, V219L, V234C, H239G, T242K, T242R, A243R, Q244G, R246A, R246G, R246L, R246Q, R246V, R246W, K258R, S264D, S264V, S264W, S267G, A285R, P294G, V301A, N302G, I303G, I303R, I303W, R304W, A306G, D307F, D307G, D307L, D307N, D307R, D307V, E309A, E309G, E309S, G310H, G310R, G310V, T311S, T313S, Q314G, I315F, S316G, F317W, I319G, A320C, A323G, D328F, Q334S, Q348A, Q348R, K349A, K349C, K349H, K349Q, P351G, K352I, K352N, S353T, T356G, T356W, Q357V, M360Q, M360R, M360S, M360W, Y366G, Y366W, G375A, G375V, G375S, V381F, E393R, E393W, T395E, V409L, L411A, I420V, S424G, S424Q, S442E, S442G, M443G, A447C, A447I, A447L, L454V, D455E, L457Y, E458W, I461G, K466N, A468G, K472T and K472*, wherein said variant ester synthase polypeptide has improved fatty acid ester activity compared to a corresponding wild type polypeptide comprising the amino acid sequence of SEQ ID NO: 67.

* * * * *